(12) United States Patent
Yousef et al.

(10) Patent No.: US 7,022,497 B1
(45) Date of Patent: Apr. 4, 2006

(54) HUMAN KALLIKREIN-LIKE GENES

(75) Inventors: George M. Yousef, Toronto (CA); Eleftherios P. Diamandis, Toronto (CA)

(73) Assignee: Mt. Sinai Hospital, Ontario (CA)

( * ) Notice: Subject to any disclaimer, the term of this patent is extended or adjusted under 35 U.S.C. 154(b) by 0 days.

(21) Appl. No.: 09/936,271

(22) PCT Filed: Mar. 9, 2000

(86) PCT No.: PCT/CA00/00258

§ 371 (c)(1),
(2), (4) Date: Sep. 10, 2001

(87) PCT Pub. No.: WO00/53776

PCT Pub. Date: Sep. 14, 2000

Related U.S. Application Data

(60) Provisional application No. 60/144,919, filed on Jul. 21, 1999, now abandoned, provisional application No. 60/127,386, filed on Apr. 1, 1999, now abandoned, provisional application No. 60/124,260, filed on Mar. 11, 1999, now abandoned.

(51) Int. Cl.
*C12N 15/00* (2006.01)

(52) U.S. Cl. ............... 435/69.1; 536/24.31; 536/23.1; 435/320.1; 435/325

(58) Field of Classification Search ............... 536/23.1, 536/24.31; 435/320.1, 325, 69.1
See application file for complete search history.

(56) References Cited

U.S. PATENT DOCUMENTS

| 5,786,148 | A | 7/1998 | Bandman et al. |
| 5,922,321 | A | 7/1999 | Bandman et al. |
| 5,962,300 | A | 10/1999 | Hillman et al. |
| 6,197,511 | B1 | 3/2001 | Hillman et al. |
| 6,472,195 | B1 | 10/2002 | Hillman et al. |

FOREIGN PATENT DOCUMENTS

| WO | WO 98/20117 A1 | 5/1998 |
| WO | WO-01/04143 A3 | 1/2001 |
| WO | WO-01/51633 A3 | 7/2001 |

OTHER PUBLICATIONS

Hillier et al. accssion No. W73168, Oct. 16, 1998.*
Hillier et al. accession No. N80762, Mar. 29, 1996.*
J. Simmer et al, "Purification, Characterization, and Cloning of Enamel Matrix Serine Proteinase 1", J. Dent. Res., 77(2):377-386 (Feb., 1998).
P. Riegman et al, "Characterization of the Human Kallikrein Locus", Genomics, 14:6-11 (1992).
L. Schedlich et al, "Primary Structure of a Human Glandular Kallikrein Gene", DNA, 6(5):429-437 (1987).
P. Riegman et al, "Characterization of the Prostate-Specific Antigen Gene: a Novel Human Kallikrein-Like Gene", Biochem. Biophys. Res. Comm., 159(1):95-102 (Feb., 1989).
G. Yousef et al, "Prostase/KLK-L1 is a New Member of the Human Kallikrein Gene Family, is Expressed in Prostate and Breast Tissues, and is Hormonally Regulated", Cancer Research, 59:4252-4256 (Sep., 1999).
P. Nelson et al, Molecular Cloning and Characterization of Prostase, an Androgen-Regulated Serine Protease with Prostate-Restricted Expression, Proc. Natl. Acad. Sci. USA, 96(6):3114-3119 (Mar., 1999).
S. Stephenson et al, "Localization of a new Prostate-Specific Antigen-Related Serine Protease Gene, KLK4, is Evidence for an Expanded Human Kallikrein Gene Family Cluster on Chromosome 19q13.3-13.4", J. Biol. Chem., 274 (33): 23210-23214 (Aug., 1999).
E. Diamandis et al, "The New Human Kallikrein Gene Family: Implications in Carcinogenesis", Trends in Endocrinology and Metabolism, 11(2):54-60 (2000).
G. Yousef et al, "Identification of Novel Human Kallikrein-Like Genes on Chromosome 19q13.3-q13.4", Anticancer Research, 19:2843-2852 (Jul., 1999).
B. Dupont et al, "Assignment of Serine Protease 17 (PRSS17) to Human Chromosome Bands 19q13.3-q13.4 by in situ Hybridization", Cytogenet. Cell. Genet., 86:212-213 (Apr., 1999).
B. Evans et al, "Structure and Chromosomal Localization of the Human Renal Kallikrein Gene", Biochemistry, 27(9): 3124-3129 (1988).
J. Clements, "The Glandular Kallikrein Family of Enzymes: Tissue-Specific Expression and Hormonal Regulation", Endocr. Rev., 10(4):393-419 (Nov., 1989).

(Continued)

*Primary Examiner*—Celine Qian
(74) *Attorney, Agent, or Firm*—Howson and Howson

(57) ABSTRACT

The invention relates to nucleic acid molecules, kallikrein-like proteins encoded by such nucleic acid molecules; and use of the proteins and nucleic acid molecules.

8 Claims, 51 Drawing Sheets

OTHER PUBLICATIONS

B. Evans et al, "Mouse Glandular Kallikrein Genes", J. Biol. Chem., 262(17):8027-8034 (Jun., 1987).

C. Drinkwater et al, "Kallikreins, Kinins and Growth Factor Biosynthesis", Trends Biochem. Sci. 13:169-172 (May, 1988).

P. Ashley et al, "Tissue-Specific Expression of Kallikrein-Related Genes in the Rat", Biochemistry, 24(17):4520-4527 (1985).

W. Gerald et al, "Sex Dimorphism and Hormonal Regulation of Rat Tissue Kallikrein mRNA", Biochem. Biophys. Acta., 867(1-2):16-23 (May, 1986) (Abstract only).

A. Anisowicz et al, "A Novel Protease Homolog Differentially Expressed in Breast and Ovarian Cancer", Mol. Med., 2(5):624-636 (Sep., 1996).

S. Little et al, "Zyme, a Novel and Potentially Amyloidogenic Enzyme cDNA Isolated from Alzheimer's Disease Brian", J. Biol. Chem., 272(40):25135-25142 (Oct., 1997).

K. Yamashiro et al, "Molecular Cloning of a Novel Trypsin-Like Serine Protease (Neurosin) Preferentially Expressed in Brain", Biochim. Biophys. Acta., 1350:11-14 (1997).

X. Liu et al, "Identification of a Novel Serine Protease-Like Gene, the Expression of Which is Down-Regulated During Breast Cancer Progression", Cancer Res., 56:3371-3379 (Jul., 1996).

L. Luo et al, "Structural Characterization and Mapping of the Normal Epithelial Cell-Specific 1 Gene", Biochem. Biophys. Res. Commun., 247(3):580-586 (1998).

M. Schachter et al, Pharmacol. Rev., 31:1-17 (1980).

R. Richards et al, "Mouse Glandular Kallikrein Genes", J. Biol. Chem., 257(6):2758-2761 (Mar., 1982).

B. Van Leeuwen et al, "Mouse Glandular Kallikrein Genes—Identification, Structure, and Expression of the Renal Kallikrein Gene", J. Biol. Chem., 261(12):5529-5535 (Apr., 1986).

B. Evans et al, "Genes for the α and γ Subunits of Mouse Nerve Growth Factor are Contiguous", EMBO J., 4(1):133-138 (1985).

I. Rogozin et al, "Gene Structure Prediction Using Information on Homologous Protein Sequence", Comput. Applic. Biosci., 12(3):161-170 (1996).

E. Diamandis, "Prostate-Specific Antigen: Its Usefulness in Clinical Medicine", Trends Endocrinol. Metab., 9(8):310-316 (1998).

E. Diamandis et al, "Detection of Prostate-Specific Antigen Immunoreactivity in Breast Tumors", Breast Cancer Res. Treat.., 32:301-310 (1994).

T. Ishikawa et al, "Expression of α-Fetoprotein and Prostate-Specific Antigen Genes in Several Tissues and Detection of mRNAs in Normal Ciculating Blood by Reverse Transcriptase-Polymerase Chain Reaction", Jpn. J. Clin. Oncol., 28(12):723-728 (1998).

D. Irwin et al, "Structure and Evolution of the Bovine Prothrombin Gene", J. Mol. Biol., 212:31-45 (1988).

J. Goyal et al, "The Role for NES1 Serine Protease as a Novel Tumor Suppressor", Cancer Res., 58(21):4782-4786 (Nov., 1998) (Abstract only).

E. Diamandis et al, "Editorial: New Biological Functions of Prostate-Specific Antigen?", J. Clin. Endocrinol. Metab., 80(5):1515-1517 (1995).

J. Reifenberger et al, "Molecular Genetic Analysis of Oligodendroglial Tumors Shows Preferental Allelic Deletions on 19q and 1p", Am. J. Pathol., 145(5):1174-1190 (Nov., 1994).

Y. Iida, "Quantification Analysis of 5'-Splice Signal Sequences in mRNA Precursors. Mutations in 5'-Splice Signal Sequence of Human β-Globin Gene and β-Thalassemia", J. Theor. Biol., 145:523-533 (1990).

J. Clements, "The Molecular Biology of the Kallikreins and their Roles in Inflammation", in S. Farmer (ed.), The Kinin System, pp. 71-97, New York (1997).

S. Yoshida et al, "Sequence Analysis and Expression of Human Neuropsin cDNA and Gene", Gene, 213:9-16 (1998).

T. Takayama et al, "Characterization of the Precursor of Prostate-Specific Antigen", J. Biol. Chem., 272(34):21582-21588 (Aug., 1997).

M. Dayhoff et al, "Atlas of Protein Sequence and Structure", Natl. Biomed. Res. Found., 5(Suppl 3):79-81 (1978).

M. Kozak, "An Analysis of 5'-Noncoding Sequences from 699 Vertebrate Messenger RNAs", Nucleic Acid Res., 15 (20):8125-8148 (1987).

N. Proudfoot et al, "3' Non-Coding Region Sequences in Eukaryotic Messenger RNA", Nature, 263:211-214 (Sep., 1976).

H. Yu et al, "Prognostic Value of Prostate-Specific Antigen for Women with Breast Cancer: a Large United States Cohort Study", Clin. Cancer Res., 4:1489-1497 (Jun., 1998).

E. Sauter et al, "Prostate-Specific Antigen Levels in Nippple Aspirate Fluid Correlate with Breast Cancer Risk", Cancer Epidermol. Biomarkers Prev., 5:967-970 (Dec., 1996).

A. Fortier et al, "Antiangiogentic Activity of Prostate-Specific Antigen", J. Natl. Cancer Inst., 91(19):1635-1640 (Oct., 1999).

A. Kumar et al, "Expression of Pro Form on Prostate-Specific Antigen by Mammalian Cells and its Conversion to Mature, Active Form by Human Kallikrein 2", Cancer Res., 57:3111-3114 (Aug., 1997).

J. Lovgren et al, "Activation of the Zymogen Form of Prostate-Specific Antigen by Human Glandular Kallikrein 2", Biochem. Biophys. Res. Commun., 238(2):549-555 (1997).

L. Lai et al, "Prostate-Specific Antigen in Breast Cyst Fluid: Possible Role of Prostate-Specific Antigen in Hormone-Dependent Breast Cancer", Int. J. Cancer, 66:743-746 (1996).

H. Rittenhouse et al, "Human Kallikrein 2 (hK2) and Prostate-Specific Antigen (PSA): Two Closley Related, but Distinct, Kallikreins in the Prostate", Crit. Rev. Clin. Lab. Sci., 35(4):275-368 (1998).

L. Hansson et al, "Cloning, Expression, and Characterization of Stratum Corneum Chymotryptic Enzyme", J. Biol. Chem., 269(30):19420-19426 (Jul., 1994).

U. Stenman, "New Ultrasensitive Assays Facilitate Stuides on the Role of Human Glandular Kallikfrien (hK2) as a Marker for Prostatic Disease", Clin. Chem., 45(6):753-754 (1999).

M. Black, "Development of an Ultrasensitive Immunoassay for Human Glandular Kallikrein with No Cross-Reactivity from Prostate-Specific Antigen", Clin. Chem.., 45(6):790-799 (1999).

L. Underwood et al, "Cloning of Tumor-Associated Differentially Expressed Gene-14, a Novel Serine Protease Overexpressed by Ovarian Carcinoma", Cancer Res., 59:4435-4439 (Sep., 1999).

N. Heuze et al, "Molecular Cloning and Expression of an Alternative hKLK3 Transcript Coding for a Variant Protein of Prostate-Specific Antigen", Cancer Res., 59:2820-2824 (Jun., 1999).

P. Riegman et al, "Identification and Androgen-Regulated Expression of Two Major Human Glandular Kallikrein-1 (hGK-1) mRNA Species", Mol. Cell Endocrinol., 76:181-190 (1991).

L. Chen et al, "Molecular Cloning and Characterization of a Novel Kallikrein Transcript in Colon and its Distribution in Human Tissues", Braz. J. Med. Biol. Res., 27:1829-1838 (1994).

S. Mitsui et al, "A Novel Form of Human Neuropsin, a Brain-Related Serine Protease, is Generated by Alternative Splicing and is Expressed Preferentially in Human Adult Brain", Eur. J. Biochem., 260:627-634 (1999).

R. Baffa et al, "A Comparative Analysis of Prostate-Specific Antigen Gene Sequence in Benign and Malignant Prostate Tissue", Urology, 47:795-800 (1996).

P. Henttu et al, "Expression of the Gene Coding for Human Prostate-Specific Antigen and Related hGK-1 in Benign and Malignant Tumors of the Human Prostate", Int. J. Cancer, 45:654-660 (1990).

R. McCormack et al, "Molecular Forms of Prostate-Specific Antigen and the Human Kallikrein Gene Family: a New Era", Urology, 45(5):729-744 (May, 1995).

X. Liu et al, "Identification of Three New Alternate Human Kallikrein 2 Transcripts: Evidence of Long Transcipt and Alternative Splicing", Biochem. Biophys. Res. Commun., 264(3):833-839 (1999).

P. Riegman et al, "Molecular Cloning and Characterization of Novel Prostate Antigen cDNA's", Biochem. Biophys. Res. Commun., 155(1):181-188 (Aug., 1988).

A. Lundwall et al, "Molecular Cloning of Human Prostate Specific Antigen cDNA", FEBS Lett., 214(2):317-322 (Apr., 1987).

N. Zarghami et al, "Steroid Hormone Regulation of Prostate-Specific Antigen Gene Expression in Breast Cancer", Br. J. Cancer, 75(4):579-588 (1997).

Nadeau et al., "Mouse on Human Homology Map", Mouse Genome, 89:31-36 (1991).

Morris et al., "Kallikrein and Renin: Molecular Biology and Biosynthesis", Clin. Sci., 61:351s-353s (Dec. 1981).

Gerald et al., "Sex Dimorphism and Hormonal Regulation of Rat Tissue Kallikrein and mRNA", Biochim. Biophys. Acta, 867:16-23 (May 27, 1986).

Kim et al., "Human Kallikrein Gene 5 (KLK5) Expression is an Indicator of Poor Prognosis in Ovarian Cancer", Brit. J. Cancer, 84(5):643-650 (Mar. 2001).

Obiezu et al., "Higher Human Kallikrein Gene 4 (KLK4) Expression Indicates Poor Prognosis of Ovarian Cancer Patients", Clin. Cancer Res., 7:2380-2386 (Aug. 2001).

Yousef et al., "Identification and Characterization of KLK-L4, a New Kallikrein-like Gene that Appears to be Down-Regulated in Breast Cancer Tissues", J. of Biol. Chem., 275(16):11891-11898 (Apr. 21, 2000).

Yousef et al., "Quantitative Expression of the Human Kallikrein Gene 9 (KLK9) in Ovarian Cancer: A New Independent and Favorable Prognostic Marker", Cancer Res., 61:7811-7818 (Nov. 1, 2001).

Yousef et al., "The New Kallikrein-Like Gene, KLK-L2", J. Biol. Chem.., 274(53): 37511-37516 (Dec. 31, 1999).

Yousef et al., "The Expanded Human Kallikrein Gene Family: Locus Characterization and Molecular Cloning of a New Member, KLK-L3 (KLK9)", Genomics, 65:184-194 (Apr. 15, 2000).

Yousef et al., "The New Human Tissue Kallikrein Gene Family: Structure, Function, and Association to Disease", Endocrine Reviews, 22(2):184-204 (Apr. 2001).

Hu et al., "Characterization of the Mouse and Human PRSS7 Genes, their Relationship to Other Serine Proteases, and the Expression of PRSS17 in Developing Mouse Incisors", Gene, 251:1-8 (Jun. 13, 2000).

Goyal et al., "The Role of NES1 Serine Protease as a Novel Tumor Suppressor", Cancer Res., 58:4782-4786 (Nov. 1, 1998).

Brattsand et al., "Purfication, Molecular Cloning, and Expression of a Human Stratum Corneum Trypsin-Like Serine Protease with Possible Function in Desquamation", J. Biol. Chem., 274(42):30033-30040 (Oct. 15, 1999).

* cited by examiner

FIGURE 4

<u>TGACCCGCTG TACCACCCCA</u> GCATGTTCTG CGCCGGCGGA GGGCAAGACC
AGAAGGACTC CTGCAACGGT GACTCTGGGG GGCCCCTGAT CTGCAACGGG
TACTTGCAGG GCCTTGTGTC TTTCGGAAAA GCCCCGTGTG GCCAAGTTGG
CGTGCCAGGT GCCTACACCA ACCTCTGCAA ATTCACTGAG TGGATAGAGA
AAACCGTCCA GGCCAGTTAA CTCTGGGGAC TGGGAACCCA TGAAATTGAC
CCCCAAATAC ATCCTGCGGA AGGAATTC

FIGURE 7

```
(ATG)GCTACAGCAAGACCCCCCTGGATGTGGGTGCTCTGTGCTCTGATCACAGCCT
  M  A  T  A  R  P  P  W  M  W  V  L  C  A  L  I  T  A
TGCTTCTGGGGGTCACAG[gt]aaccaga---------------intron 1---------------tccc[ag]
  L  L  L  G  V  T
AGCATGTTCTCGCCAACAATGATGTTTCCTGTGACCACCCCTCTAACACCGTGCCC
  E  H  V  L  A  N  N  D  V  S  C  D  H  P  S  N  T  V  P
TCTGGGAGCAACCAGGACCTGGGAGCTGGGGCCGGGGAAGACGCCCGGTCGGAT
  S  G  S  N  Q  D  L  G  A  G  A  G  E  D  A  R  S  D
GACAGCAGCAGCCGCATCATCAATGGATCCGACTGCGATATGCACACCCAGCCGT
  D  S  S  S  R  I  I  N  G  S  D  C  D  M  H  T  Q  P
GGCAGGCCGCGCTGTTGCTAAGGCCCAACCAGCTCTACTGCGGGGCGGTGTTGGT
  W  Q  A  A  L  L  R  P  N  Q  L  Y  C  G  A  V  L  V
GCATCCACAGTGGCTGCTCACGGCCGCCCACTGCAGGAAGA[gt]gagtggga------
  H  P  Q  W  L  L  T  A  A /H\ C  R  K  K
---------------intron 2---------------tcttcctc[ag]AGTTTTCAGAGTCCGTCT
                                                    V  F  R  V  R  L
CGGCCACTACTCCCTGTCACCAGTTTATGAATCTGGGCAGCAGATGTTCCAGGGG
   G  H  Y  S  L  S  P  V  Y  E  S  G  Q  Q  M  F  Q  G
GTCAAATCCATCCCCCACCCTGGCTACTCCCACCCTGGCCACTCTAACGACCTCAT
  V  K  S  I  P  H  P  G  Y  S  H  P  G  H  S  N /D\ L  M
GCTCATCAAACTGAACAGAAGAATTCGTCCCACTAAAGATGTCAGACCCATCAAC
  L  I  K  L  N  R  R  I  R  P  T  K  D  V  R  P  I  N
GTCTCCTCTCATTGTCCCTCTGCTGGGACAAAGTGCTTGGTGTCTGGCTGGGGGAC
  V  S  S  H  C  P  S  A  G  T  K  C  L  V  S  G  W  G  T
AACCAAGAGCCCCCAAGgtgagtgtcca[ggt]---------intron 3---------tgac[ag]
  T  K  S  P  Q
TGCACTTCCCTAAGGTCCTCCAGTGCTTGAATATCAGCGTGCTAAGTCAGAAAAG
  V  H  F  P  K  V  L  Q  C  L  N  I  S  V  L  S  Q  K  R
GTGCGAGGATGCTTACCCGAGACAGATAGATGACACCATGTTCTGCGCCGGTGAC
   C  E  D  A  Y  P  R  Q  I  D  D  T  M  F  C  A  G  D
AAAGCAGGTAGAGACTCCTGCCAG[gtg]aggacacc---------intron 4---------[ ]
ag
  K  A  G  R  D  S  C  Q
GGTGATTCTGGGGGGCCTGTGGTCTGCAATGGCTCCCTGCAGGGACTCGTGTCCT
  G  D /S\ G  G  P  V  V  C  N  G  S  L  Q  G  L  V  S
GGGGAGATTACCCTTGTGCCCGGCCCAACAGACCGGGTGTCTACACGAACCTCTG
  W  G  D  Y  P  C  A  R  P  N  R  P  G  V  Y /T\ N  L  C
CAAGTTCACCAAGTGGATCCAGGAAACCATCCAGGCCAACTC(CTGA)GTCATCC
CA
  K  F  T  K  W  I  Q  E  T  I  Q  A  N  S
GGACTCAGCACACCGGCATCCCCACCTGCTGCAGGGACAGCCCTGACACTCCTTT
CAGACCCTCATTCCTTCCCAGAGATGTTGAGAATGTTCATCTCTCCAGCCCCTGAC
CCCATGTCTCCTGGACTCAGGGTCTGCTTCCCCACATTGGGCTGACCGTGTCTCT
CTAGTTGAACCCTGGGAACAATTTCCAAAACTGTCCAGGGCGGGGGTTGCGTCTC
AATCTCCCTGGGGCACTTTCATCCTCAAGCTCAGGGCCCATCCCTTCTCTGCAGCT
CTGACCCAAATTTAGTCCCAGAAATAAACTGAGAAG
```

FIGURE 9

```
prostase    MATAGNPWGWFLG----YLILGVAGSLVSG------------------------------  26
EMSP        MATAGNPWGWFLG----YLILGVAGSLVSG------------------------------  26
KLK-L2      MATARPPWMWVLCALITALLLGVTEHVLANNDVSCDHPSNTVPSGSNQDLGAGAGEDARS  60
zyme        --------MKKLM-----VVLSLIAAAWA-------------------------------  16
neuropsin   -MGRPRPRAAKTW-----MFLLLLGGAWAGH----------------------------S  26
TLSP        --------MRILQ-----LILLALATGLVG------------------------------  17
PSA         ------MWVPVVF-----LTLSVTWIGAAPL-----------------------------  20
KLK2        ------MWDLVLS-----IALSVGCTGAVPL-----------------------------  20
KLK1        ------MWFLVLC-----LALSLGGTGAAPP-----------------------------  20
trypsinogen -------MNPLLI-----LTFVAAALAAPFD-----------------------------  19
                                           ♣ prostase    --SCSQIINGEDCSPHSQPWQAALVM-ENELFCSGVLVHPQWVLSAAHCFQNSYTIGLGL  83
EMSP        --SCSQIINGEDCSPHSQPWQAALVM-ENELFCSGVLVHPQWVLSAAHCFQNSYTIGLGL  83
KLK-L2      DDSSSRIINGSDCDMHTQPWQAALLLRPNQLYCGAVLVHPQWLLTAAHCRKKVFRVRLGH 120
zyme        -EEQNKLVHGGPCDKTSHPYQAALYT-SGHLLCGGVLIHPLWVLTAAHCKKPNLQVFLGK  74
neuropsin   RAQEDKVLGGHECQPHSQPWQAALFQ-GQQLLCGGVLVGGNWVLTAAHCKKPKYTVRLGD  85
TLSP        --GETRIIKGFECKPHSQPWQAALFE-KTRLLCGATLIAPRWLLTAAHCLKPRYIVHLGQ  74
PSA         --ILSRIVGGWECEKHSQPWQVLVAS-RGRAVCGGVLVHPQWVLTAAHCIRNKSVILLGR  77
KLK2        --IQSRIVGGWECEKHSQPWQVAVYS-HGWAHCGGVLVHPQWVLTAAHCLKKNSQVWLGR  77
KLK1        --IQSRIVGGWECEQHSQPWQAALYH-FSTFQCGGILVHRQWVLTAAHCISDNYQLWLGR  77
trypsinogen --DDDKIVGGYNCEENSVPYQVSLNS--GYHFCGGSLINEQWVVSAGHCYKSRIQVRLGE  75
              ♣  I         I          II    I II+I prostase    HSLEADQEPGSQMVEASLSVRHPEYN----RP-------LLANDLMLIKLDESVS-ESDT 131
EMSP        HSLEADQEPGSQMVEASLSVRHPEYN----RP-------LLANDLMLIKLDESVS-ESDT 131
KLK-L2      YSLSPVYESGQQMFQGVKSIPHPGYS----HP-------GHSNDLMLIKLNRRIR-PTKD 168
zyme        HNLRQ-RESSQEQSSVVRAVIHPDY----DAA-------SHDQDIMLIRLARPAK-LSEL 121
neuropsin   HSLQN-KDGPEQEIPVVQSIPHPCYN-SSDVE-------DHNHDLMLIQLRDQAS-LGSK 135
TLSP        HNLQK-EEGCEQTRTATESFPHPGFNNSLPNK-------DHRNDIMLVKMASPVS-ITWA 125
PSA         HSLFH-PEDTGQVFQVSHSFPHPLYDMSLLKNRFLRPGDDSSHDLMLLRLSEPAE-LTDA 135
KLK2        HNLFE-PEDTGQRVPVSHSFPHPLYNMSLLKHQSLRPDEDSSHDLMLLRLSEPAK-ITDV 135
KLK1        HNLFD-DENTAQFVHVSESFPHPGFNMSLLENHTRQADEDYSHDLMLLRLTEPADTITDA 136
trypsinogen HNIEV-LEGNEQFINAAKIIRHPQYDRKTLNN----------DIMLIKLSSRAV-INAR 122
                                             _____ ♣     I prostase    IRSISIASQCPTAGNSCLVSGWGLLANG--RMPTVLQCVNVSVVSEEVCSKLYDPLYHPS 189
EMSP        IRSISIASQCPTAGNSCLVSGWGLLANG--RMPTVLQCVNVSVVSEEVCSKLYDPLYHPS 189
KLK-L2      VRPINVSSHCPSAGTKCLVSGWGTTKSPQVHFPKVLQCLNISVLSQKRCEDAYPRQIDDT 228
zyme        IQPLPLERDCSANTTSCHILGWGKTADG--DFPDTIQCAYIHLVSREECEHAYPGQITQN 179
neuropsin   VKPISLADHCTQPGQKCTVSGWGTVTSPRENFPDTLNCAEVKIFPQKKCEDAYPGQITDG 195
TLSP        VRPLTLSSRCVTAGTSCLISGWGSTSSPQLRLPHTLRCANITIIEHQKCENAYPGNITDT 185
PSA         VKVMDLPTQEPALGTTCYASGWGSIEPEEFLTPKKLQCVDLHVISNDVCAQVHPQKVTKF 195
KLK2        VKVLGLPTQEPALGTTCYASGWGSIEPEEFLRPRSLQCVSLHLLSNDMCARAYSEKVTEF 195
KLK1        VKVVELPTEEPEVGSTCLASGWGSIEPENFSFPDDLQCVDLKILPNDECKKAHVQKVTDF 196
trypsinogen VSTISLPTAPPATGTKCLISGWGNTASSGADYPDELQCLDAPVLSQAKCEASYPGKITSN 182
                     I       I I           I   I   I prostase    MFCAGGGHDQKDSCNGDSGGPLICNGYLQGLVSFGKAPCGQVGVPGVYTNLCKFTEWIEK 249
EMSP        MFCAGGGHDQKDSCNGDSGGPLICNGYLQGLVSFGKAPCGQVGVPGVYTNLCKFTEWIEK 249
KLK-L2      MFCAG-DKAGRDSCQGDSGGPVVCNGSLQGLVSWGDYPCARPNRPGVYTNLCKFTKWIQE 287
zyme        MLCAGDEKYGKDSCQGDSGGPLVCGDHLRGLVSWGNIPCGSKEKPGVYTNVCRYTNWIQK 239
neuropsin   MVCAGSSK-GADTCQGDSGGPLVCDGALQGITSWGSDPCGRSDKPGVYTNICRYLDWIKK 254
TLSP        MVCASVQEGGKDSCQGDSGGPLVCNQSLQGIISWGQDPCALPERPSLYTKVVHYRKWIQE 245
PSA         MLCAGRWTGGKSTCSGDSGGPLVCNGVLQGITSWGSEPCALPERPSLYTKVVHYRKWIKD 255
KLK2        MLCAGLWTGGKDTCQGDSGGPLVCNGVLQGITSWGPEPCALPEKPAVYTKVVHYRKWIKD 255
KLK1        MLCVGHLEGGKDTCVGDSGGPLMCDGVLQGVTSWGYVPCGTPNKPSVAVRVLSYVKWIED 256
trypsinogen MFCVGFLEGGKDSCQGDSGGPVVCNGQLQGVVSWG-DGCAQKNKPGVYTKVYNYVKWIKN 241
              I   O I II+III       I I         I     I
```

(A)

```
        +------------------------------zyme
   +----5
   !    +------------------------------neuropsin
   !
   !                              +----------PSA
   !                     +-------2
   !    +---------------3         +------KLK2
   !    !               !
 --8----6               +------------------KLK1
   !    !
   !    +----------------------------trypsinogen
   !
   !                                  +prostase (KLK-
L1)
   !         +------------------------------1
   !    +---4                              +EMSP
   !    !   !
   +--7     +------------------KLK-L2
        !
        +---------------------TLSP
```

CACTGGACGGGTGCACGTTCAGGATCCAGGTGCCCAGGGGTC(ATG)AAG CTG GGA CTC
                                                                                                              M  K  L  G  L

CTC TGT GCT CTG CTC TCT CTG CTG GCA G gtga... intron 1 .cag GG CAT GGC
 L   C   A   L   L   S   L   L   A                                                G   H
G TGG GCA GAC ACC CGT GCC ATC GGG GCC GAG GAA TGT CGC CCC AAC TCC CAG
 W   A   D   T   R   A   I   G   A   E   E   C   R   N   S
Q CCT TGG CAG GCC GGC CTC TTC CAC CTT ACT CGG CTC TTC TGT GGG GCG ACC
 P   W   Q   A   G   L   F   H   L   T   R   L   F   C   G   A   T CTC ATC AGT GAC CGC TGG CTG CTC ACA GCT GCC CAC TGC CGC AAG CCgtga......
 L   I   S   D   R   W   L   L   T   A   A   H   C   R   K   P intron 2 ......gcagG TAT CTG TGG GTC CGC CTT GGA GAG CAC CAC CTC TGG AAA
                                    Y   L   W   V   R   L   G   E   H   H   L   W   K TGG GAG GGT CCG GAG CAG CTG TTC CGG GTT ACG GAC TTC TTC CCC CAC CCT
 W   E   G   P   E   Q   L   F   R   V   T   D   F   F   P   H   P GGC TTC AAC AAG GAC CTC AGC GCC AAT GAC CAC AAT GAT GAC ATC ATG CTG
 G   F   N   K   D   L   S   A   N   D   H   N   D   D   I   M   L ATC CGC CTG CCC AGG CAG GCA CGT CTG AGT CCT GCT GTG CAG CCC CTC AAC
 I   R   L   P   R   Q   A   R   L   S   P   A   V   Q   P   L   N CTC AGC CAG ACC TGT GTC TCC CCA GGC ATG CAG TGT CTC ATC TCA GGC TGG
 L   S   Q   T   C   V   S   P   G   M   Q   C   L   I   S   G   W GGG GCC GTG TCC AGC CCC AAG G gtat...... intron     acag CG CTG TTT CCA GTC
 G   A   V   S   S   P   K                                                  A   L   F   P
V ACA CTG CAG TGT GCC AAC ATC AGC ATC CTG GAG AAC AAA CTC TGT CAC TGG
 T   L   Q   C   A   N   I   S   I   L   E   N   K   L   C   H   W GCA TAC CCT GGA CAC ATC TCG GAC AGC ATG CTC TGT GCG GGC CTG TGG GAG
 A   Y   P   G   H   I   S   D   S   M   L   C   A   G   L   W   E GGG GGC CGA GGT TCC TGC CAG gtga...... intron ..acag GGT GAC TCT GGG GGC
 G   G   R   G   S   C   Q                                         G   D   S   G
G CCC CTG GTT TGC AAT GGA ACC TTG GCA GGC GTG GTG TCT GGG GGT GCT GAG
 P   L   V   C   N   G   T   L   A   G   V   V   S   G   G   A   E

FIGURE 15 (CONT'D)

```
CCC TGC TCC AGA CCC CGG CGC CCC GCA GTC TAC ACC AGC GTA TGC CAC
TAC
 P   C   S   R   P   R   R   P   A   V   Y   T   S   V   C   H
 Y
CTT GAC TGG ATC CAA GAA ATC ATG GAG AAC TGA
 L   D   W   I   Q   E   I   M   E   N
GCCCGCGCGCCACGGGGGCACCTTGGAAGACCAAGAGAGGCCGAAGGGCACGGGGTA
GGGGGTTCTCGTAGGGTCCCAGCCTCAATGGTTCCCGCCCTGGACCTCCAGCTGCCCTG
ACTCCCCTCTGGACACTAAGACTCCGCCCCTGAGGCTCCGCCCCCTCACGGGTCAAGCA
AGACACAGTCGCGCCCCCTCGGAACGGAGCAGGGACACGCCCTTCAGAGCCGTCTCTAT
GACGTCACCGACAGCCATCACCTCCTTCTTGGAACAGCACAGCCTGTGGCTCCGCCCCA
AGGAACCACTTACACAAAATAGCTCCGCCCCTCGGAACTTTGCCCAGTGGGACTTCCCC
TCGGGACTCCACCCCTTGTGGCCCCGCCTCCTTCACCAGAGATCTCGCCCCTCGTGATGT
CAGGGGCGCAGTAGCTCCGCCCACGTGGAGCTCGGGCGGTGTAGAGCTCAGCCCTTGTG
GCCCCGTCCTGGGCGTGTGCTGGGTTTGAATCCTGGCGGAGACCTGGGGGGAAATTGAG
GGAGGGTCTGGATACCTTTAGAGCCAATGCAACGGATGATTTTTCAGTAAACGGGGAAA
CCTCA
```

FIGURE 17

```
PSA          ---------MWVPVVFLTLSVTWIGAAPLI-LSRIVGGWECEKHSQPWQVLVASRGRAVC
KLK2         ---------MWDLVLSIALSVGCTGAVPLI-QSRIVGGWECEKHSQPWQVAVYSHGWAHC
KLK1         ---------MWFLVLCLALSLGGTGAAPPI-QSRIVGGWECEQHSQPWQAALYHFSTFQC
trypsinogen  ---------MNPLLILTFVAAALAAPFDD-DDKIVGGYNCEENSVPYQVSLNS-GYHFC
KLK-L3       ---------MKLGLLCALLSLLAGHGWA--DTRAIGAEECRPNSQPWQAGLFHLTRLFC
TLSP         ---------MRI-LQLILLALATGLVGG--ETRIIKGFECKPHSQPWQAALFEKTRLLC
neuropsin    -MGRPRPRAAKTWMFLLLLGGAWAGHSRAQ-EDKVLGGHECQPHSQPWQAALFQGQQLLC
zyme         ---------MKK--LMVVLSLIAAAWAEE-QNKLVHGGPCDKTSHPYQAALYTSGHLLC
HSCCE        ---MARSLLLPLQILLLSLALETAGEEAQG--DKIIDGAPCARGSHPWQVALLSGNQLHC
prostase     ---MA-TAGNPWGWFLGYLILGVAGSLVSGSCSQIINGEDCSPHSQPWQAALVMENELFC PSA          GGVLVHPQWVLTAAHCIRNKSVILLGRHSLFHPEDT-GQVFQVSHSFPHPLYDMSLLKNR
KLK2         GGVLVHPQWVLTAAHCLKKNSQVWLGRHNLFEPEDT-GQRVPVSHSFPHPLYNMSLLKHQ
KLK1         GGILVHRQWVLTAAHCISDNYQLWLGRHNLFDDENT-AQFVHVSESFPHPGFNMSLLENH
trypsinogen  GGSLINEQWVVSAGHCYKSRIQVRLGEHNIEVLEGN-EQFINAAKIIRHPQYDRKTLNN-
KLK-L3       GATLISDRWLLTAAHCRKPYLWVRLGEHHLWKWEGP-EQLFRVTDFFPHPGFNKDLSAN-
TLSP         GATLIAPRWLLTAAHCLKPRYIVHLGQHNLQKEEGC-EQTRTATESFPHPGFNNSLPNK-
neuropsin    GGVLVGGNWVLTAAHCKKPKYTVRLGDHSLQNKDGP-EQEIPVVQSIPHPCYNSSD-VE-
zyme         GGVLIHPLWVLTAAHCKKPNLQVFLGKHNLRQRESS-QEQSSVVRAVIHPDYDAAS----
HSCCE        GGVLVNERWVLTAAHCKMNEYTVHLGSDTLGDRR---AQRIKASKSFRHPGYSTQT----
prostase     SGVLVHPQWVLSAAHCFQNSYTIGLGLHSLEADQEPGSQMVEASLSVRHPEYNRPLLAN- PSA          FLRPGDDSSHDLMLLRLSEPAE-LTDAVKVMDLPTQEPALGTTCYASGWGSIEPEEFLTP
KLK2         SLRPDEDSSHDLMLLRLSEPAK-ITDVVKVLGLPTQEPALGTTCYASGWGSIEPEEFLRP
KLK1         TRQADEDYSHDLMLLRLTEPADTITDAVKVVELPTEEPEVGSTCLASGWGSIEPENFSFP
trypsinogen  ----------DIMLIKLSSRAV-INARVSTISLPTAPPATGTKCLISGWGNTASSGADYP
KLK-L3       ------DHNDDIMLIRLPRQAR-LSPAVQPLNLSQTCVSPGMQCLISGWGAVSSPKALFP
TLSP         ------DHRNDIMLVKMASPVS-ITWAVRPLTLSSRCVTAGTSCLISGWGSTSSPQLRLP
neuropsin    ------DHNHDLMLLQLRDQAS-LGSKVKPISLADHCTQPGQKCTVSGWGTVTSPRENFP
zyme         -------HDQDIMLLRLARPAK-LSELIQPLPLERDCSANTTSCHILGWGKTADG--DFP
HSCCE        -------HVNDLMLVKLNSQAR-LSSMVKKVRLPSRCEPPGTTCTVSGWGTTTSPDVTFP
prostase     ----------DLMLIKLDESVS-ESDTIRSISIASQCPTAGNSCLVSGWGLLANG--RMP PSA          KKLQCVDLHVISNDVCAQVHPQKVTKFMLCAGRWTGGKSTCSGDSGGPLVCNGVLQGITS
KLK2         RSLQCVSLHLLSNDMCARAYSEKVTEFMLCAGLWTGGKDTCGGDSGGPLVCNGVLQGITS
KLK1         DDLQCVDLKILPNDECKKAHVQKVTDFMLCVGHLEGGKDTCVGDSGGPLMCDGVLQGVTS
trypsinogen  DELQCLDAPVLSQAKCEASYPGKITSNMFCVGFLEGGKDSCQGDSGGPVVCNGQLQGVVS
KLK-L3       VTLQCANISILENKLCHWAYPGHISDSMLCAGLWEGGRGSCQGDSGGPLVCNGTLAGVVS
TLSP         HTLRCANITIIEHQKCENAYPGNITDTMVCASVQEGGKDSCQGDSGGPLVCNQSLQGIIS
neuropsin    DTLNCAEVKIFPQKKCEDAYPGQITDGMVCAGSSKG-ADTCQGDSGGPLVCDGALQGITS
zyme         DTIQCAYIHLVSREECEHAYPGQITQNMLCAGDEKYGKDSCQGDSGGPLVCGDHLRGLVS
HSCCE        SDLMCVDVKLISPQDCTKVYKDLLENSMLCAGIPDSKKNACNGDSGGPLVCRGTLQGLVS
prostase     TVLQCVNVSVVSEEVCSKLYDPLYHPSMFCAGGGHDQKDSCNGDSGGPLICNGYLQGLVS PSA          WGSEPCALPERPSLYTKVVHYRKWIKDTIVANP
KLK2         WGPEPCALPEKPAVYTKVVHYRKWIKDTIAANP
KLK1         WGYVPCGTPNKPSVAVRVLSYVKWIEDTIAENS
trypsinogen  WG-DGCAQKNKPGVYTKVYNYVKWIKNTIAANS
KLK-L3       GGAEPCSRPRRPAVYTSVCHYLDWIQEIMEN--
TLSP         WGQDPCAITRKPGVYTKVCKYVDWIQETMKNN-
neuropsin    WGSDPCGRSDKPGVYTNICRYLDWIKKIIGSKG
zyme         WGNIPCGSKEKPGVYTNVCRYTNWIQKTIQAK-
HSCCE        WGTFPCGQPNDPGVYTQVCKFTKWINDTMKKHR
prostase     FGKAPCGQVGVPGVYTNLCKFTEWIEKTVQAS-
```

FIGURE 18

```
            +------TLSP
      +----4
      !     +--------------KLK-L3
   +-13
   !  !    +---------------neuropsin
   !  +-12
+-14     +-----------------------NES 1
!  !
!  !    +-------------zyme
!  +-11
!     +-----------KLK-L4
!
!              +-----PSA
!           +---2
!     +--------3  +---KLK2
!     !       !
!     !       +-------KLK1
-15-10
!     !  +-------------trypsinogen I
!     !  !
!     !  !      +------------------complement factor D
!     +--9   +--6
!        !  +---7  +----------------------granzyme A
!        !  !   !
!        +--8  +---------------------cathepsin G
!           !
!           +----------------------chymotrypsin
!
!              +prostase/KLK-L1
!        +-------------1
+----5            +EMSP
     !
     +----------KLK-L2
```

FIGURE 25

TCAGGCCCCGCCCGCCCTGCCCTCCCCTCCCGATCCCGGAGCC (ATG) TGG CCC CTG GCC
                                                                                        M   W   P    L    A

CTA GTG ATC GCC TCC CTG ACC TTG GCC TTG TCA GGA G...gtaaga.... intron 1 ..... ttaccag
L   V   I    A   S    L    T    L    A   L    S    G GT GTC TCC CAG GAG TCT TCC AAG GTT CTC AAC ACC AAT GGG ACC AGT GGG TTT
G   V   S    Q   E    S    S    K    V   L    N    T    N    G   T    S    G   F CTC CCA GGT GGC TAC ACC TGC TTC CCC CAC TCT CAG CCC TGG CAG GCT GCC
L   P    G   G    Y    T    C    F    P    H   S    Q    P    W   Q    A    A CTA CTA GTG CAA GGG CGG CTA CTC TGT GGG GGA GTC CTG GTC CAC CCC AAA
L   L    V   Q    G    R    L    L    C    G   G    V    L    V    H   P    K TGG GTC CTC ACT GCC GCA CAC TGT CTA AAG GA gtatgt ..... intron 2........ cacag G GGG
W   V    L    T    A    A   [H]  C    L    K                                    E    G CTC AAA GTT TAC CTA GGC AAG CAC GCC CTA GGG CGT GTG AAA GCT GGT GAG
L   K    V   Y    L    G    K    H    A   L    G    R    V    E   A    G    E CAG GTG AGG GAA GTT GTC CAC TCT ATC CCC CAC CCT GAA TAC CGG AGA AGC
Q   V    R   E    V    V    H   S    I    P    H   P    E    Y    R    R   S CCC ACC CAC CTG AAC CAC GAC CAT GAC ATC ATG CTT CTG GAG CTG CAG TCC
P   T    H   L    N    H    D    H   [D]   I    M    L    L    E   L    Q    S CCG GTC CAG CTC ACA GGC TAC ATC CAA ACC CTG CCC CTT TCC CAC AAC AAC CGC
P   V    Q   L    T    G    Y    I    Q   T    L    P    L    S    H   N    N    R CTA ACC CCT GGC ACC ACC TGT CGG GTG TCT GGC TGG GGC ACC ACC ACC AGC
L   T    P    G   T    T    C    R    V    S   G    W   G    T    T    T   S CCC CAG G gtatgcac... intron 3..... tcccc ag TG AAT TAC CCC AAA ACT CTA CAA TGT GCC
P   Q                                              V   N    Y   P    K    T    L    Q    C   A AAC ATC CAA CTT CGC TCA GAT GAG GAG TGT CGT CAA GTC TAC CCA GGA AAG
N   I    Q   L    R    S    D    E    E   C    R    Q   V    Y    P    G    K ATC ACT GAC AAC ATG TTG TGT GCC GGC ACA AAA GAG GGT GGC AAA GAC TCC
I   T    D   N    M   L    C    A    G   T    K    E   G    G    K    D    S TGT GAG gtatgca... intron 4..... aactcag GGT GAC TCT GGG GGC CCC CTG GTC TGT AAC
C   E                                        G   D    [S]   G    G    P    L    V   C    N AGA ACA CTG TAT GGC ATC GTC TCC TGG GGA GAC TTC CCA TGT GGG CAA CCT
R   T    L   Y    G    I    V    S    W   G    D    F   P    C    G    Q    P GAC CGG CCT GGT GTC TAC ACC CGT GTC TCA AGA TAC GTC CTG TGG ATC CGT
D   R    P   G    V    Y    T    R    V   S    R    Y   V    L    W    I    R

FIGURE 25 (CONT'D)

```
GAA ACA ATC CGA AAA TAT GAA ACC CAG CAG CAA AAA TGG TTG AAG GGC CCA
 E   T   I   R   K   Y   E   T   Q   Q   Q   K   W   L   K   G   P

CAA (TAA) AAGTTGAGAAATGTACCGGCTTCCATCCTGTCACCATGACTTCCTCAC
 Q
ATGGTCTGCTTAGCCCTTCTCTGCTCCTTATTCCCAGTGTTCCATTTGAACCAGTGATCCATGTC
CTGAAAAATGCTCAATCTCAGCTAACATTCCATGTTTCAGAAGCATTCAGGCACTGCCAGGCT
TGCAGTCTCCCAGATGTTGCATCCCTGAAACATCTCAACAACCTGAATGTCCCAACCCAGACA
ATGGCCCAGGTCTCTCAACTTCATCAGTGTGGCTTCTATGAGCCCAGATCACCACCTGAACGT
TCTGTCTGTGGCACATTCTTAAATATTTCCATCAGCCCATCTCAACAATATATGTCCTATAAAT
GGACCATCCTTGACA
```

FIGURE 27

```
                      1          15 16           30 31          45 46          60 61          75 76           90
 1 KLK-L1/protease               ---MATAGN PWGWFLG---YLIL GVAG-------- ---------SLVSG ------------- --------SCSQ IINGEDCSPHSQPWQ         45
 2 EMSP                          ---MATAGN PWGWFLG---YLIL GVAG-------- ---------SLVSG ------------- --------SCSQ IINGEDCSPHSQPWQ         45
 3 KLK-L2                        ---MATARP PMMWVLCALITALLL GVTEHVLANNDVSCD HPSNTVPSGSNQDLG AGAGEDARSDDSSSR IINGSDCDMHTQPWQ         81
 4 PSA                           ---------- MWVPVF---LTLSV TWIG-------- ---------AAPLI ------------- --------L-SR IVGGWECEKHSQPWQ         39
 5 KLK2                          ---------- MMDLVLS---IALSV GCTG-------- ---------AVPLI ------------- --------Q--SR IVGGWECEKHSQPWQ         39
 6 KLK1                          ---------- MWFLVLC---LALSL GGTG-------- ---------AAPPI ------------- --------Q--SR IVGGWECEQHSQPWQ         39
 7 trypsinogen                   ---------- -MNPLLI---LTFVA ALA--------- ---------APFDD ------------- --------D--DK IVGGYNCEENSVPYQ         38
 8 zyme/protease M               ---------- -MKKLMV----VLSL IAAA-------- ---------WAEEQNK- ------------- --------- LVHGGPCDKTSHPYQ         36
 9 KLK-L4                        ---------- -MW PLAIVIA----SLTL GETR-------- ---------GVSQESSKV- ------------- --------- LNTNGTSGF LPGGYTCFPHSQPWQ         50
10 TLSP                          ---------- -MR ILQLILLALATGIVG GHSR-------- ---------I------- ------------- --------- -IKGFECKPHSQPWQ         36
11 neuropsin                     -MGRPRPRA AKTWMFLLLLGGAWA AEAA-------- ---------AQEDK-- ------------- --------- VLCGHECQPHSQPWQ         47
12 NES1                          MRAPHLHLSAASGAR ALAKLLPLLMAQLMA ------------- ---------LLPQN-- ------------- --------DTRLDP EAYGAPCARGSQPWQ         60

91         105 106         120 121         135 136         150 151         165 166         180
 1 prostase                      AALVM-ENELFCSGV LVHPQ...   FQ NSYTIGLGLHSLEAD QEPGSQMVEASLSVR HPEYNRPLLAN---- -------DLMLIKLD        123
 2 EMSP                          AALVM-ENELFCSGV LVHPQ...   FQ NSYTIGLGLHSLEAD QEPGSQMVEASLSVR HPEYNRPLLAN---- -------DLMLIKLD        123
 3 KLK-L2                        AALLRPNQLYCGAV LVHPQ...   RK KVFRVRLGHYSLSPV YESGQQMFQGVKSIP HPGYSHPGHSN---- -------DLMLIKLN        150
 4 PSA                           VLVAS-RGRAVCGGV LVHPQ...   IR NKSVLLLGRHSLFHP -EDTGQVFQVSHSFP HPLYDMSLLKNRFLR PGDDSSHDLMLLRLS        127
 5 KLK2                          VAVYS-HGWAHCGGV LVHPQ...   LK KNSQWLGRHNLFEP -EDTGQRVPVSHSFP HPLYNMSLLKHQSLR PDEDSSHDLMLLRLS        127
 6 KLK1                          AALYH-FSTFQCGGI LVHRQ...   IS DNYQLMLGRHNLFDD -ENTAQVRVVSESFP HPGFNMSLLENHTRQ ADEDYSHDLMLLRLT        127
 7 trypsinogen                   VSLNS--GYHFCGGS LINEQ...VS  YK SRIQVRLGEHNIEVL -EGNEQFINAAKIIR HPQYDRKTLNN---- -------DLMLIKLS        114
 8 zyme                          AALYT-SGHLLCGGV LIHPL...   KK PMLQVFLGKRNLRQR -ESSOEQSSVVRAVI HPDYDAA------- -------SHDQDIKNTRLA        113
 9 KLK-L4                        AALLV-QGRLLCGGV LVHPK...   LK EGLKVYLGKHALGRV -EAGEQVREVHSIP HPEYRRSPTHL---- -------NHDHDIKNIAELQ        131
10 TLSP                          AALFE-KTRLLCGAT LIAPR...   LK PRYIVHLGQHNLQKE -EGCEQTRTATESFP HPGFNNSLPNK---- -------DHRNDIMLVKMA        117
11 neuropsin                     AALFQ-GQQLLCGGV LVGGN...   KK PKYTVRLGDHSLQNK -DGPEQEIPVVQSIP HPCVNSSD-VE---- -------DHNHDLMLEQLR        127
12 NES1                          VSLFN-GLSFHCAGV LVDQS...RGN KPLWARVGDDHLLLL Q--GEQLRRTTRSVV HPKYHQGS-GPILPR R--TDEHDLMLKLA        144

181        195 196         210 211         225 226         240 241         255 256         270
 1 prostase                      ESVS-ESDTIRSISI ASQCPTAG-NSCLVS GWGLLANG--RMPTV LQCVNVSVVSEEVCS KLYDPLYHPSMFCAG GGHDQKDSCNGDBCG        209
 2 EMSP                          ESVS-ESDTIRSISI ASQCPTAG-NSCLVS GWGLLANG--RMPTV LQCVNVSVVSEEVCS KLYDPLYHPSMFCAG GGHDQKDSCNGDBCG        209
 3 KLK-L2                        RRIR-PTKDVRPINV SSHCPSAG-TKCLVS GWGTTKSPQVHFPKV LQCLNLSVLSQKRCE DAYPRQIDDTMFCAG DKAG-RDSCQGDBCG        247
 4 PSA                           EPAE-LTDAVKVMDL PTQEPALG-TTCYAS GWSIEPEEFLTPKK LQCVDLHVISNDVCA QVHPQKVTKFMLCAG RWTGGKSTCSGDBCG        215
 5 KLK2                          EPAK-ITDVVKVLGL PTQEPALG-TTCYAS GWSIEPEEFLRPRS LQCVSLHLLSNDMCA RAYSEKVTEFMLCAG LWTGKDTCGGDBCG        215
 6 KLK1                          EPADTITDAVRVVEL PTEEPEVG-STCLAS GWSIEPENFSFPDD LQCVDLKILPNDECK KAHVQKVTDPFMLCVG HLEGGKDTCVGDBCG        216
 7 trypsinogen                   SRAV-INARVSTISL PTAPPATG-TKCLIS GWGNTASSGADYPDE LQCLDAPVLSQAKCE ASYPGKITSNMFCVG FLEGGKDSCQGDBCG        202
 8 zyme                          RPAK-LSELIQPLPL ERDCSANT-TSCHIL GWGKTADQ--DFPDT IQCAYHLVSREECE HAYPGQITQNMLCAG DEKYGKDSCQGDBCG        199
 9 KLK-L4                        SPVQ-LTGYIQTLPL SHNNRLTPGTTCRVS GWGTTTSPQVNYPKT LQCANIQLRSDEECR QVYPGKITDNMLCAG TKEGGKDSCEDBCG        220
10 TLSP                          SPVS-ITWAVRPLTL SSRCVTAG-TSCLIS GWGSTSSPQLRLPHT LRCANITIEHQKCE NAYPGNITDTMVCAS VQEGGKDSCQGDBCG        205
11 neuropsin                     DQAS-LGSKVKPISL ADHCTQPG-QKCTVS GWGTTVTSPRENFPDT LNCAEVKIFPQKKCE DAYPGQITDGMVCAG SSKG-ADTCQGDBCG        214
12 NES1                          RPVVP-GPRVRALQL PYRCAQPG-DOCQVA GWGTTAARRVKYNKG LTCSSITILSPKECE VFYPGVTNNMICAG LDRG-QDPCQSDBGG        231
```

FIGURE 27 (CONT'D)

```
                 271              285 286              300 301              315 316             330 331
 1 prostase      GYLQGLVSFG       KAPCGQVGVPGVYTN       LCKFTEWIEKTVQAS      ---------------    331
 2 EMSP          GYLQGLVSFG       KAPCGQVGVPGVYTN       LCKFTEWIEKTVQAS      ---------------    254
 3 KLK-L2        GSLQGLVSWG       DYPCARPNRPGVYTN       LCKFTKWIQETIQAN      S--------------    254
 4 PSA           GVLQGITSWG       SEPCALPERPSLYTK       VVHYRKWIKDTIVAN      P--------------    293
 5 KLK2          GVLQGITSWG       PEPCALPEKPAVYTK       VVHYRKWIKDTIAAN      P--------------    261
 6 KLK1          GVLQGVTSWG       YVPCGTPNKPSVAVR       VLSYVKWIEDTIAEN      S--------------    261
 7 trypsinogen   GQLQGVVSWG       -DGCAQKNKPGVYTK       VYNYVKWIKNTIAAN      S--------------    262
 8 zyme          GDHLRGLVSWG       NIPCGSKEKPGVYTN       VCRYTNWIQKTIQAK      ---------------    247
 9 KLK-L4        RTLYGIVSWG       DFPCGQPDRPGVYTR       VSRYVLWIRETIRKY      ETQQQKWLKGPQ      244
10 TLSP          QSLQGIISWG       QDPCAITRKPGVYTK       VCKYVDWIQETMKNN      ---------------    277
11 neuropsin     DGALQGITSWG       SDPCGRSDKPGVYTN       ICRYLDWIKKIIGSK      G--------------    250
12 NES1          DETLQGILSWG       VYPCGSAQHPAVYTQ       ICKYMSWINKVIRSN      ---------------    260
```

FIGURE 29

```
                +------TLSP
           +----4
           !    +-------------KLK-L3
      +-13
      !   !   +--------------neuropsin
      !   +-12
 +-14         +-----------------NES1
 !   !
 !   !   +-----------zyme
 !   +-11
 !        +-----------KLK-L4
 !
 !                 +-----PSA
 !              +---2
 !   +---------3   +---KLK2
 !   !          !
 !   !          +--------KLK1
-15-10
 !   !   +-----------trypsinogen I
 !   !   !
 !   !   !       +----------------complement factor D
 !   +--9    +--6
 !       !  +---7  +----------------------granzyme A
 !       !  !   !
 !       +--8   +--------------------cathepsin G
 !       !
 !              +----------------------chymotrypsin
 !
 !                 +prostase/KLK-L1
 !       +-------------1
 +----5            +EMSP
      !
      +----------KLK-L2
```

FIGURE 33

```
GCAGGTAGGTGGACGGAGAGATAGCAGCGACGAGGACAGGCCAAACAGTGACAGCCACG
TAGAGGATCTGGCAGACAAAGAGACAAGGTGAGAAGGAG gtagg.........Intron 1......
.............................................tgacactcccccag ACTTTGGAAGTGACCCACC(ATG)
                                                                    M
GGG CTC AGC ATC TTT TTG CTC CTG TGT GTT CTT G gtgagttctccg
 G   L   S   I   F   L   L   L   C   V   L
gagcagggagagggca........... Intron 2 ...............cctgtctgtctccag GG CTC
                                                                        G   L
AGC CAG GCA GCC ACA CCG AAG ATT TTC AAT GGC ACT GAG TGT GGG
 S   Q   A   A   T   P   K   I   F   N   G   T   E   C   G
CGT AAC TCA CAG CCG TGG CAG GTG GGG CTG TTT GAG GGC ACC AGC
 R   N   S   Q   P   W   Q   V   G   L   F   E   G   T   S
CTG CGC TGC GGG GGT GTC CTT ATT GAC CAC AGG TGG GTC CTC ACA
 L   R   C   G   G   V   L   I   D   H   R   W   V   L   T
GCG GCT CAC TGC AGC GGC AG gtaagtcccttcc............intron3...............
 A   A  |H|  C   S   G   S
.ccgtcgccaccggcag C AGG TAC TGG GTG CGC CTG GGG GAA CAC AGC
                    R   Y   W   V   R   L   G   E   H   S
CTC AGC CAG CTC GAC TGG ACC GAG CAG ATC CGG CAC AGC GGC TTC
 L   S   Q   L   D   W   T   E   Q   I   R   H   S   G   F
TCT GTG ACC CAT CCC GGC TAC CTG GGA GCC TCG ACG AGC CAC GAG
 S   V   T   H   P   G   Y   L   G   A   S   T   S   H   E
CAC GAC CTC CGG CTG CTG CGG CTG CGC CTG CCC GTC CGC GTA ACC
 H  |D|  L   R   L   L   R   L   R   L   P   V   R   V   T
AGC AGC GTT CAA CCC CTG CCC CTG CCC AAT GAC TGT GCA ACC GCT
 S   S   V   Q   P   L   P   L   P   N   D   C   A   T   A
GGC ACC GAG TGC CAC GTC TCA GGC TGG GGC ATC ACC AAC CAC CCA
 G   T   E   C   H   V   S   G   W   G   I   T   N   H   P
CGG A gtaagggcccagggccaggg....................intron 4 ......................
 R
.gaccctgcagcacgcatgttctctctccag AC CCA TTC CCG GAT CTG CTC
                                 N   P   F   P   D   L   L
CAG TGC CTC AAC CTC TCC ATC GTC TCC CAT GCC ACC TGC CAT GGT
 Q   C   L   N   L   S   I   V   S   H   A   T   C   H   G
GTG TAT CCC GGG AGA ATC ACG AGC AAC ATG GTG TGT GCA GGC GGC
 V   Y   P   G   R   I   T   S   N   M   V   C   A   G   G
GTC CCG GGG CAG GAT GCC TGC CAG gtgagcc............ Intron 5 ............
 V   P   G   Q   D   A   C   Q
.aaaacagaaataagatgtctcccttgttcagacagtacttctcttcccttccag GGT
                                                        G
GAT TCT GGG GGC CCC CTG GTG TGT GGG GGA GTC CTT CAA GGT CTG
 D  |S|  G   G   P   L   V   C   G   G   V   L   Q   G   L
GTG TCC TGG GGG TCT GTG GGG CCC TGT GGA CAA GAT GGC ATC CCT
 V   S   W   G   S   V   G   P   C   G   Q   D   G   I   P
GGA GTC TAC ACC TAT ATT TGC AA(G TAT GTG GAC TGG ATC CGG ATG
 G   V   Y   T   Y   I   C   K   Y   V   D   W   I   R   M
ATC ATG AGG AAC AAC (TGA) CCTGTTTCCTCCACCTCCACCCCCACCCCTTAACTT
 I   M   R   N   N
GGGTACCCCTCTGGCCCTCAGAGCACCAATATCTCCTCCATCACTTCCCCTAG)CTCCAC
TCTTGTTGGCCTGGGAACTTCTTGGAACTTTAACTCCTGCCAGCCCTTC(TAA) GACCCACG
AGCGGGGTGAGAGAAGTGTGCAATAGTCTGGAATAAATATAAATGAAGGAGGGGC
```

Figure 36

(Multiple sequence alignment of kallikrein-related peptidases)

Figure 36 cont'd

```
     271              285 286            300 301
 1 PSA       SLITKVVHYRKWIKD TIVANP------------- 261
 2 hK2       AVYTKVVHYRKWIKD TIAANP------------- 261
 3 hK1       SVAVRVLSYVKWIED TIAENS------------- 262
 4 prostase  GVYTNLCKFTEWIEK TVQAS-------------- 254
 5 zyme      GVPFNVCRYTNWIQK TIQAK-------------- 244
 6 TLSP      GVYTKVCKYVDWIQE TMKNN-------------- 250
 7 KLK-L4    GVTTRVSRYVLWIRE TIRKYETQQQKWLKG PQ  277
 8 NES1      AVYTQICKYMSNINK VIRSN-------------- 276
 9 KLK-L5    GVYTYICKYVDWIRM IMRNN-------------- 248
10 neuropsin GVYTNICRYLDWIKK IIGSKG------------- 260
                                ♦
```

FIGURE 41

```
ATCGTGTAAT CACCGCCACA TCCAGTGCAA AGCTGATTCG TCACCACAGA GCAGCTCCCT
CCTGCCACCC CATCCCTGGG TCCCAAGAGA ACCCTTTCTT AAAAGAGGGA GTTCTTGACG
GGTGTGGTGG CTCATGCCTG TAATCCTTGC ACTTTGGGAG GCCAAGGAGG GTGGATCATT
TGAGGTCAGG AGTTTGAGAC CAGACTGGCC AACATGGTGA AACCCTGTCT TTACTAAAAA
TACAAAAAAA TGAGCGGGGC ATGGTGGTGG GTGCCTATAG CCCCAGCTAC TCAGGAGGCT
GAGGCAGGAG AATCGCTTGA ACCCAGGAGG CAGAGGTTGC AGTGAGCCGA GATTGAGCCA
CTGCACTCCA GCCGGGCTA AAGAGTGAGA CTCTGTCTCA AAAAAAAAAA AAAGAAAAAG
AAAAAAAGAA AAAAAAATAA AATAAATAAA TAAATAAAAT AAATTTAAAA ATTTAAAAAT
AAAGAGGGGG TTCTTGTGTT GATGCCGAGC CTGAACCAAG GCAGAGGAGG CCGGGAAGGC
TTCCCAAGGC CTTCAGCTCA AAGCAGGGAG GCCCATAGTT AAACAGAAAC AGTTCAGGAA
TCACAGAAAG GCACCTGGGG AGAGATGGGT GTGTGGCTCC AGATGCAGGT GCCCAGACAG
TGCGTCCCCA GGTGTACAGA CAGACCCAGG CCAAGCTCCA GCTCAAAGAG CCAGCCTAGG
GGGGTGCCGA GGTGGAGGGA GGCTGAGTCA GGCTGAGGCC GGGGAACAGT TGGGGTAGCC
AAGGGAGGCA AGCAGCCTCC TGAGTCACCA CGTGGTCCAG GTACGGGGCT GCCCAGGCCC
AGAGACGGAC ACAAGCACTG GGAATTTAA GGGGCTAGGG GAGGGGCTGA GGAGGGTAGG
CCCTCCCCCA AATGAGGATG GAACCCCCCC AACTCCAGAA CCCCCCTGCA GGCTGGCCAG
AATCCTTCCC CATCTCATTC ACTCTGTCTC TCCTGCTCTC TGCCGTCTCC TATTTTGAAT
TTCCAACCCC GTCTGTTAAG ACTGTCCTTC TGTCTCTGAA TCTCTGTCCC CTTCTCTTTC
TGGGTCTCTC TCCCTCTCCC TCTGGGTCTC TGTCCCCCTC TCTGGGTCTC TGTCACTCTC
TCTTTGCATC TCCAGCTCTC ACTTTGTCTC TGCACCTAGC AGATCCCAAG CTGGGGAATG
CCAGTTCTGG CACCAACCTT CCTGCTCCCT GCTGGGGCCT CTGCTCCCCC ATCTCTCAGG
AGTCGAAAGT GAGAAAGCAA GGTGGGCAGC TCTGCTCCAG GTCCAGGTAT CTCCCGCCCA
CCTCCTGCCC GTCCTCTATC CCACCCCTCC TCTCCATCTC TCCCTGGCGC TGCCATCTCT
CATCTAGGCC TCCGTCTCCT CTGTCATTGT CCCCATCCCC TGTAGGTGCC CATCCTTCCC
GTCTCCCCTC TGCCATCGGC CTGCCTGTCC CATCCTCTTT CTCCCACCAT GTCCCGTTCT
CTTCCACGTC TCATGCCCGC ACTGCCTTCA TCATCATCGC TGTTGTTCTG TGTGTGTTTG
TGGTGAGTGC CGCATGGTGG GGGCGTCTCG GCCTCTCTCC TCTCTCTCCA CTGTTTCTC
TTTCTGTGTG TCTGTTTCCA TTCTATCTCC ACCTTCTTCC CTCCGTCTTT TGCTTTTCTA
TCTCCACTTC TCCACACCCC TCTCTCCCTG CGTCTCTGTG TCTCCCTCTT CCTCTGTCTT
GTTTTTTTCC CACCGTCTGC CTCTTCTGTT CCCTGTCACA TCCAACTTCC ACCGGTTTCT
CCAGCTCTCT CCTCAGTTCC TTCTCTCATG AGCACACCTG CCTCTGTGCT CGTATTCCTG
GACTCCTCTC TCTCCACTGT CATATCTTCT CATTCATTTT CCCAGTCTCT CTCTGTCTCT
TGCTCTCCCC CTCTCTGTCA CTCTGTCTCT GTCTCTCTCT TTCTCTCTCT CTCTCTGTGT
CTCTCTGTCT GGCTCTCTCT CTGTCTCTCT CTCCATCTCT CTCTCTCTCT CCCCCCCGTC
ACCCTGTCTC TGTCTCTCTC TGTCTGTGTG TCTCTCTGTC TTTCTCTCTC TCCATCTCTC
TCTGTCTCTC TCTCTCTCTC TCTCTCTCTC CCTCTCTCCC TCCTCCCGTG ACTCCCTCTC
TCAGTCCATC TCTTCCTCCC TCTCTCAGCC CCTTCGTGCC CTTTCCTCTG ACACTCCCCA
CCCTGGTTTC CTGACTCCAC CACTAGATCC ACCACCTCCA GCAACTGGGA ACCCTCCCCT
GCCCACCCTG CCCTGGGGTC CCCTCCCAGG ATTCCTTCTA GATTATAGCA TCTTCCCTGG
GCGGGTTCTC ATGAACAATT GTGGCTGCTT TTTTGGCCAG ACAGGGGAGG GAGGGGATGG
GATCAGGGAG TCCTGGAATG GAACTAGGC AATAAAAAAA AAAAAATGTC AGAAGCAGGG
CGGCGGGAGG TGGGGCAGG GCCAGCTGTC CTTACCAGGG ATAAAAGGCT TTGCCAGTGT
GACTAGGAAG AGAGACACCT CCCCTCCTTC CTTCATCAAG ACATCAAGGA GGGACCTGTG
CCCTGCTCCA CATCCTCCCA CCTGCCGCCC GCAGAGCCTG CAGGCCCGC CCCCCTCGTC
TCTGGTCCCT ACCTCTCTGC TGTGTCTTCA TGTCCCTGAG GGTCTTGGGC TCTGGGTAAG
TGCCCCTTGC TGTCTCTGCC TCTCAGCCCC CGGTTCTGTT GAAGGTTCCT TCTCTCTCAC
TTTTTCTCTG CATTTGACAG GACCTGGCCC TCAGCCCCTA AAATGTTCCT CCTGCTGACA
GCACTTCAAG TCCTGGCTAT AGGTAAGAGA ACGGTTGGGT ATGACACAAG GGGGTCCCCT
GGAGACTCTG AGAAGAGATG GGGATGGGTC CTTGGGGCCC CTGAACGTGCT ATGGTGACCT
CATAAGAAAG AGCAGGGAGT GGTTTGGGGG TCATGGTGGG GGAACGTGCT GGAGGCCTAA
ATTCCTAGTT GTGGAGGTGC TAGGGAATTG TGGGCCGGG TCCTGAGTGG GTCATAGCAG
CTGGTGCAAA ATACATAAGG AATCTTAGGG AACTATTAGG TCCTGAGTGG GTCATAGCAG
AAAGATCACG GGGCTCTACC TGACTGTGTT AGGAAAGAAA CAATGTCAGA AAGATGTTTT
GTTGTCAGAG GGAAGGTGGA GAAGGATGAT GGGATGGCGG GATCGTGGCA TGGGGTGGCG
GGATCGTGGC ATGGGTGTGT GAGGTGGATG GGGGAGGACA GGGAGGTCCT TGAATGTGTT
CCTTGGGGTC CCACTGAGTG GGAACGTTGG GGAGGACAGG GGAGGTCCT TGAATGTGTT
GGGGAAGGAC TCATTGGGGG GAAATGTGGC ATATTTCGAG AAGTGATCAC AGAAATTATG
GGAGCATAGA GCTAAGGGTC GTAGATGTAG CAAGGCCCTG GATAAGGTGG CCACGGCACA
AATAAGAGA TGCTACGGAG GTGACTTGGG AGGTGAGTCA GAAAGCTCTC CGTGCTGGGG
```

FIGURE 41 (CONT'D)

```
CAATAACGGG GTCAATATTG GGCATGTCTC ACCCTGGGTG GGACAGATAG AGGCGGGCAG
TTTAGGGGTT AGACCAAAAG GAAGGGGATT TGTCAGTTTT GGAATCCTAC AAACTTGTGG
AGTGGAGAGT GTTTGCTCAT CTACTTTCCC CACCCAATCC TGTCCACTCC TAGCCATGAC
ACAGAGCCAA GAGGATGAGA ACAAGATAAT TGGTGGCCAT ACGTGCACCC GGAGCTCCCA
GCCGTGGCAG GCGGCCCTGC TGGCGGGTCC CAGGCGCCGC TTCCTCTGCG GAGGCGCCCT
GCTTTCAGGC CAGTGGGTCA TCACTGCTGC TCACTGCGGC CGCCCGTAAG TGACCCCCTC
CCCTGTCCCT GTACCTAGTG AATTCCAGAG TCTAAAGCCC TAGAGCTGAG CTGAGAACCT
GGATCTCTGT ATAGAACCCA ATGTAGTGGC TGGCTCCTGG TTTGAGGTCT AGAGAAGAGC
CTGGAACAAA AACACAGCTC GGGATGTGGG CTCCTCCATA AATCTCGAAC TCAGCATAGG
TTCTGAAAGC AGATGGGCAG CTTGGAACCC ATGGACCTGC TGAGAACCGA ACATCTGATC
CAGTGATTCT TCCAGAGGCC ACACATTACA TCGAGACCAA GCTTAGCCCA TTCCAGATTG
GTGGCTGAAT TCAGGACCCC GTCTACATTC AGAAACTCAG GACACTACGT AGAACTCAGA
GCCCAGTTCA GGACCTGCAG TCTAGCCATA AATCCAGAAC TAGAACGCTG CTCACAGCTG
GAACATACAA CTCTAAGAAT AGAGGCAAAA CCTGGAGGCT GTTTCACACC CAAGGTTTAG
TTCAGAGTCT AGTCTATAGC TCCGCTATGA GCAGACTTCA ACCCAGTGTT TGAATCCCAG
AATGTGGCGG GTGCGGTGGC TCATGCCTAT AATCCTAGCA CTTTGGGATG CTGAGGCAGG
CAGATCACCT GAGGTCAGGA GTTCGAGACC AGCCTGAGCA ACATAGAGAA ACCCTGTCTC
TACTAAAAAT GCAAAATTAG CCAGGCATGG TGGCACATGC CTGTAATCCC AGCCACTCGG
GAGGCTGAGG CAGGAGAATC ACTTGAACCT GGGAGGCGGA GGTTGCAGTG AGTCAAGATC
GCACCATTGC ACTCCAGGCT AGGCAACAAG AGCGAAACTC CATATCAATC AATCAATCAA
TAAATCCCAG AATGCAGATC CTAATCAGAA GCCCCATATA AAACCTAGAC CCCTCCTAAA
TTCTAGATCT GAACTTACAA CCCAGACCCC AGCCAAGAGG TCAAAATGCC TATAAGCCAT
ATCTATGCCA TAAACAGGTC AGTCTAGAAC CTAGAGATCA AAGCTCAGGC CAGAGTCTAG
AATATAAAGG CCAGAATGCA AACCAGACTC TAGAATCTTG GATCCGGGCC ATAACCTAGA
GCTCCAACTA GAACCCAGAG CCCAACCTGA GGTCAAGGGC TAGGGCCAGA GTCCAGAACC
AAGAGCCCTA TAATCCAATA TGAAACAGAC CTGTAGAGGC TGGGTGCGGT GGCTCACGCC
TGTAATCCCA GCACTTTGGG AGGCTGAGGC GGGAGAATCA CTTGAACTGG GAGTTGGAGG
TCGAGAGTGA GCTGAGATCG TGCCACTGCA CTCCAGCCTA GGTGACAGAG CGAGACTCCA
TCACAAAAAA AAAATAAATA AATAAATCAA GTCATAATCC AGGTTCGATC TAGAATCCTG
ATCTTAGCAT AGAGTCAAAA GTTTAAGATG TCTAGAACTC AGAACCCAGG CTAGAAACAG
AATGGTGCCT ACTCCGGAAT ATCAGTTCCG ATTTAGAGCC TAGACTCATA ACGCAGTTTC
GCTTAGGACT CAATGCACCG AGCCCAGCAC AGACCCTGGC ACGGAGCCAA GCTCTCCCAA
TCATCACCTT CTTCCCAAGC CAGGAGCTGG AGCCCAGCCC AAGAGCGGAA GGAGAGGCAG
CTGGGGCTGG GCCGAGAGAA TGCCCTGGCC ATGGGGAAGG GCACAGGAGG CCAAGAATGC
TCGGCCTGCA GTTAGTGAGA AGCAGGCTAG ACCTCGGGGA AGACTCGTCA CCCGGCCAGG
GAACCGGGCT GGAGGGTGGG GAGGAGTCTC TGGCTCAGAC CCTGAGCAGC GCTTCTCTTG
GGGGTCGTGG CCAGGATCCT TCAGGTTGCC CTGGGCAAGC ACAACCTGAG GAGGTGGGAG
GCCACCCAGC AGGTGCTGCG CGTGGTTCGT CAGGTGACGC ACCCAACTA CAACTCCCGG
ACCCACGACA ACGACCTCAT GCTGCTGCAG CTACAGCAGC CCGCACGGAT CGGGAGGGCA
GTCAGGCCCA TTGAGGTCAC CCAGGCCTGT GCCAGCCCCG GGACCTCCTG CCGAGTGTCA
GGCTGGGGAA CTATATCCAG CCCCATCGGT GAGGACTCCT GCGTCTTGGA AAGCAGGGGA
CTGGGCCTGG GCTCCTGGGT CTCCAGGAGG TGGAGCTGGG GGGACTGGGG CTCCTGGGTC
TGAGGGAGGA GGGGCTGGGC CTGGACTCCT GGGTCTGAGG GAGGAGGGGG CTGAGGCCTG
GACTCCTGGG TCTCAAGGAG GAGGAGCTGG GCCTGGACTC ATACGTCTGA GGGAGGAGGG
GCTGGAGCCT GGACTCCTGG GTCTCAAGGA GGAGGGGCTG GCCTGGACT TCTGGGTCTG
AGGGAGGAGG GGCTGGGGAC CTGGACTCCC GGGTCTGAGG GAGGAGGGAC TGGGGGTCTG
GACTCCTGGG TCTGAGGGAG GAGGGCTGG GGCCTGGAC TCCTGGGTCT GAGGGAGGAG
GTGCTGGGGC TGGACTCCTG GGTCGGAAGG AGGAGGGGCT GGGGGCCTGG ACCCTTGGGT
CTTATGGGAG GGTAGACCCA GTTATAACCC TGCAGTGTCC CCCAGCCAGG TACCCCGCCT
CTCTGCAATG CGTGAACATC AACATCTCCC CGGATGAGGT GTGCCAGAAG GCCTATCCTA
GAACCATCAC GCCTGGCATG GTCTGTGGTAG GATTATTTG GGACTGGGAT TTAAGCAAAT
AGGTAAGGCC CAGGATGGGA GCTGTGGTAG GATTATTTTG GGACTGGGAT TTAAGCAAAT
GATGTCAGGA GCATGGAAGT CTGCAGAGGT CTTCAGAAGA GAGTGAACCG CAGGCACAGA
GAGATTCCGA TAGCCAGGCC ACCCTGCTTC CTAGCCCTGT GCCCCTGGG TAATGGACTC
AGAGCATTCA TGCCTCAGTT TCCTCATCTG TCAGGTGGGA GTAACCCTCT TAGGGTAGTT
GGTGGAATGG GATGAGGCAG GTTGGGGAAA GATCGCAGAG TGGCCTCTGC TCATATGGGT
```

FIGURE 41 (CONT'D)

```
CTGGGAAAGG CTGTGCTGAG GCTTCTAGAA ATCTTAATGC ATCCTTGAGG GAGGCAGAGA
TGGGGAAATA GAAAAAGAGA GACACACAAA TGTTCTACAG TTGGAGCGAA CAGAGAGGGG
CCTGGTGAGA TTCAAGGGAC AGGCAGGTGC ACACAGAGAC AGAGCCAGAC CCAGCGGAGA
GGGAAGGAAG TGCCCCGACC TCCGGGGCTG AGACCTCAGA GCTGGGGCAG GACTGTGTCC
CTAACTGTCC ACCAGTGTCT CTGCCTGTCT CCCTGTGTCT GCTTCTCGGG TTCTCTGTGC
CATGGTGGCT CTGGCTACCT GTCCATCAGT GTCTCCATTT CTGTTCCTCC CCCTCAGGGT
GACTCTGGGG GACCCCTGGT GTGCAGAGGA CAGCTCCAGG GCCTCGTGTC TTGGGGAATG
GAGCGCTGCG CCCTGCCTGG CTACCCGGT GTCTACACCA ACCTGTGCAA GTACAGAAGC
TGGATTGAGG AAACGATGCG GGACAAATGA TGGTCTTCAC GGTGGGATGG ACCTCGTCAG
CTGCCCAGGC CCTCCTCTCT CTACTCAGGA CCCAGGAGTC CAGGCCCCAG CCCTCCTCC
CTCAGACCCA GGAGTCCAGG CCCCAGCCC CTCCTCCCTC AGACCCGGGA GTCCAGGCCC
CCAGCCCCTC CTCCCTCAGA CCCAGGAGTC CAGGCCCCAG CCCTCCTCC CTCAGACCCG
GGAGTCCAGG CCCCCAGCCC CTCCTCCCTC AGACCCAGGA GTCCAGGCCC CAGTCCCTCC
TCCCTCAGAC CCAGGAGTCC AGGCCCCAG CCCTCCTCC CTCAGACCCA GGAATCCAGG
CCCAGCCCCT CCTCCCTCAG ACCCAGGAGC CCAGTCCCC CAGCCCTCC TCCTTGAGAC
CCAGGAGTCC AGGCCCAGCC CCTCCTCCCT CAGACCCAGG AGCCCAGTC CCCAGCATCC
TGATCTTTAC TCCGGCTCTG ATCTCTCCTT TCCAGAGCA GTTGCTTCAG GCGTTTCTC
CCCACCAAGC CCCCACCCTT GCTGTGTCAC CATCACTACT CAAGACCGGA GGCACAGAGG
GCAGGAGCAC AGACCCCTTA AACCGGCATT GTATTCCAAA GACGACAATT TTTAACACGC
TTAGTGTCTC TAAAAACCGA ATAAATAATG ACAATAAAAA TGGAATCATC CTAAATTGTA
TTCATTCATC CATGTGTTTA CTTTTTATTT TTGAGACAA GGTCTTGCTC AGTCTCCTGG
TGAAATGCTG TAACGCAATC ATAGCTCACT GCAACGTGA CCTCCTGGGC TCCAGTGATC
CTCTTACCTC AGCCTCCCGA GTAGCTGGGA CCACAGGTGC CCGTCACCAT GCCCCGCTAC
TTTTTAAATT TTGTGTAGAG ATGAGGTTTC CCTGTGTTGC TCAGGCTGGT CTCGAACACC
TGACCCCAAG CAATCCGCCT ACGTCGGTTT CCCAAAGTGC CGGGATTGCA GGCGTGAGCT
GCCGCGCCCA GCCTTATCCA TCCAATTAAT GACTTCAAGA AACATGTACA CAGTGGCCCC
ACCATGCCAA GCCAGGAGCT GTGTACTGAC AAGTGGCTGC CTCCCTCTTT GCGTGTTTTT
CCTTGGGAGT CCCCCGTCCA CCCCACTGTA TCAGGTTTCT AGACGGAAAC ACCTCAGCCC
TGCAGAGTGA CCTTGAGCAT GACTGCCTTC TACCAGCCTC CTCCCTGGAG CCCCTGTGGT
CCAGGGTAGG GAACTAAGTG CCTTGTTTCC TGGAAAATTC TATGCAAATG AAGATGTCCT
CATTTTCCTA ATCAGATCTC AGGTGAGGAG AGTTGAGTTA ATCACAGGCT TCAGTTCCTG
CCCAGGCAAA GCCCTTCTCT CATTTTATTA ATTTATTTCC ACTCTTCATC TCTGGCTCTG
CTCCCCTCCC TCCCCACAGG CACCGACATA AATGGCTTTG AGTGCCCTGC ATCCTTGGAA
AACAAGGCAG TGTCACAGTG TACTGTTTCT AATTTACATG AAACCATTGT GTTAGGAATC
TCATTCTCTT TCTTACTTTC ACTCATCAAC AGCTATTGAG CACCTACTAC GGGCCAGGCA
TTGGTCTATT TATTAGGCAC CTGCTATACA CCAGGCATTG TTCTGGGTGC TGGAGGAAGA
ACTGTGAGCA AGCCAGTCAG AATCCCTGCC CTCACAGAAC TTATATTCTA GCAGGAGATG
ACAGACAAGA AGCCATAAAC ATAATTTTAA AATAAAGCAG AGTCCCTATG AGTAACGAGG
TCAATAAACT TGGGCTGGGC GGCAGGCCCA ATGTGTGCCA GGGCCAGCTC ATACATGCTC
GCAAGAGTCT ACCAGCAAAT TTTCAGGAAT TTCGAGAACC AGTTGCTAAA TGCAGCCATC
ATTAAAAATT AAATTACATA AGCGTATAAT TACATAATTG ATTAAAAAAA TTGTCAGTAA
ATACTCAAAA CTCAACTGTT GCTAATTATT TCAACTAATA CCTATGCTTG GGAGTGAGAT
ATGTCTCTTG TACTACGTCT GTAATGATGA GTTTCTGCAC ACCTCTTTCC AACTCCCCAA
CTCTGTCTGC ACCAGTAGCT TGACAATAGC CAAAGAAGAA GTATTTACTG CACTGAAATT
GAAAAACACT ATAGATAGGG CTTTGCCGGA CAGTCATTGC TAAACCTTTA CCAGGCACCC
TTGGATGGGT CTGCCTGGGA ATGACCTCAT GATCTTAGTG TCTGTCTTCT CAAAGTTCTG
TGCTTGGATA CTGCAGAGTA TAGCTAAAAT AGAATGTTGT ACTCACCTTA TGTTCTATGG
GGACAGCACA GTATTGGGGA ACCCTAAGGT GGCAGGTCTG GGACATGCAC GAAAGATTGC
TGGGAAGTAG AGGCTCCCTC CTTTTCCTCA TCCTCCCACC CCATCCTCCA GTGTCTGGTA
ACCACCATTC TACTCTCTGC TTCAAGAGT CTGAGTTTTT TAGATTTCAC ATGTAAGTGA
GATCATGCAG TAATTGTCAT TCTGTGTCTG ACCTATTTCA CTTAACACAG TGTCCTCCCG
GTCCATCCAT GTTGTCACAA ATGACAGGAT TTCTTTCTTT TATAAGGCAG AATAATATTA
AATTATACTG ATACTAATAT ATTACATTTC CTTTATCCAT TCATCCATCA ACAGACACAT
```

FIGURE 43

```
                1               15 16              30 31              45 46              60 61              75 76              90
 1  PSA         ---------------    ---------------    ---------------    ---------------    -------RIVGGWECE    KHSQPWQVLVASRG-    -RAVCGGVLVHPQWV     60
 2  hK2         ---------------    ---------------    ---------------    ---------------    -------RIVGGWECE    KHSQPWQVLVAVYHG-    -WAHCGGVLVHPQWV     60
 3  hK1         ---------------    ---------------    ---------------    ---------------    -------RIVGGWECE    QHSQPWQVAVYSHG-    -TFQCGGILVHRQWV     60
 4  HSCCE       --------------M    ARSLLLPLQILLLSL    ALETAGEEAQGD---    ---------------    -------KIIDGAPCA    RGSHPWQVALLSGN-    -QLHCGGVLVNERWV     65
 5  zyme        ---------------    --MKKLMVVLSLIAA    AWAEEQ---------    ---------------    -------NKLVHGPCD    KTSHPYQAALYTSG-    -HLLCGGVLIHPLWV     57
 6  KLK-L6      ---------------    --MFLLLTALQVLAI    AMTQSQEDE------    ---------------    -------NKIIGGHTCT    RSSQPWQAALLAGPR    RRFLCGGALLSGQWV     62
 7  TLSP        ---------------    --MRILQLILLALAT    GLVGGETR-------    ---------------    -------IIKGFECK    PHSQPWQAALFEKT-    -RLLCGATLIAPRWL     57
 8  KLK-L4      ---------------    --MWPLALVIASLTL    ALSGGVSQESSKVLN    TNGTSGFLPGGYTCF    PHSQPWQVLFNGL-    -RLLCGGVLVHPKWV     71
 9  NES1        MRAPHLHLSAASGAR    ALAKLLPLLMAQLWA    AEAALLPQNDTR-L-    ---------------    ------DPEAYGAPCA    RGSQPWQVSLFNGL-    -SFHCAGVLVDQSWV     81
10  KLK-L5      ---------------    -MGLSIFLLLCVLGL    SQAATPKIFN-----    ---------------    ---------GTECG    RNSQPWQVGLFEGT-    -SLRCGGVLIDHRWV     57
11  neuropsin   ---------------    -MGRPR PRAAKTWMFLLLGG    AWAGHSRAQE-----    ---------------    ------DKVLGGHECQ    PHSQPWQAALFQGQ-    -QLLCGGVLVGGNMV     68
12  prostase    ---------------    --MATAGN PWGWFLGYLILGVAG    SLVSGSCS-------    ---------------    ------QIINGEDCS    PHSQPWQAALVMEN-    -ELFCSGVLVHPQWV     66

91              105 106            120 121            135 136            150 151            165 166            180
 1  PSA         LTAAHCIRNKSVILL    GRHSLFHP-EDTGQV    FQVSHSFPHPLYDMS    LLKNRFLRPGDDSSH    DLMLLRLSEPAE-LT    DAVKVMDLPTQ-EPA   147
 2  hK2         LTAAHCLKKNSQVWL    GRHNLFEP-EDTGQR    VPVSHSFPHPLXNMS    LLKHQSLRPDEDSSH    DLMLLRLSEPAK-IT    DVVKVLGLPTQ-EPA   147
 3  hK1         LTAAHCISDNYQLWL    GRHNLFDD-ENTAQF    VHVSESFPHPGFNMS    LLENHTRQADEDYSH    DLMLLRLTEPADTIT    DAVKVVELPTE-EPE   148
 4  HSCCE       LTAAHCKMNEYTVHL    GSDTLGD---RRAQR    IKASKSFRHPGY--S    T--------QTHVN    DLMLVKLNSQAR-LS    SMVKKVRLPSRCEP-   139
 5  zyme        LTAAHCKKPNLQVFL    GKHNLRQR-ESSQEQ    SSVVRAVIHPDYD--    --------AASHDQ    DIMLLRLARPAK-LS    ELIQPLERD-CSA     133
 6  KLK-L6      ITAAHCGRPILQVAL    GKHNLRRW-EATQQV    LRVVRQVTHPNYN--    --------SRTHDN    DLMLLQLQQPAR-IG    RAVRPIEVTQA-CAS   138
 7  TLSP        LTAAHCLKPRYIVHL    GQHNLQKE-EGCEQT    RTATESFPHPGFNNS    L-------PNKDHRN    DIMLVKMASPVS-IT    WAVRPLTLSSR-CVT   137
 8  KLK-L4      LTAAHCLKEGLKVYL    GKHALGRV-EAGEQV    REVHSIPHPEYRRS    P--------THLNHDH    DIMLLELQSPVQ-LT    GYIQTLPLSHNNRLT   152
 9  NES1        LTAAHCGNKPLWARV    GDDHLLLL-QG-EQL    RRTTRSVVHPKYHQG    SGP---ILPRRTDEH    DLMLLKLARPVV-PG    PRVRALQLPYR-CAQ   164
10  KLK-L5      LTAAHCSGSRYWVRL    GEHSLSQL-DWTEQI    RHSGFSVTHPGYLGA    S--------TSHEH    DLRLLRLRLPVR-VT    SSVQPLPLPND-CAT   135
11  neuropsin   LTAAHCKKPKYTVRL    GDHSLQNK-DGPEQE    IPVVQSIPHPCYNSS    D---------VEDHNH    DMLLQLRDQAS-LG    SKVKPISLADH-CTQ   147
12  prostase    LSAAHCFQNSYTIGL    GLHSLEADQEPGSQM    VEASLSVRHPEYN--    ---------RPLLAN    DLMLIKLDESVS-ES    DTIRSISIASQ-CPT   143
```

FIGURE 4.3 (CONT'D)

```
             181        195 196        210 211        225 226        240 241        255 256        270
 1 PSA       LGTTCYASGWGSIEP EEFLTPKKLQCVDLH VISNDVCAQVHPQKV TKFMLCAGRWTGGKS TCSGDSGGPLVCNGV LQGITSWG-SEPCAL  236
 2 hK2       LGTTCYASGWGSIEP EEFLRPRSLQCVSLH LLSNDMCARAYSEKV TEFMLCAGLWTGGKD TCGGDSGGPLVCNGV LQGITSWG-PEPCAL  236
 3 hK1       VGSTCLASGWGSIEP ENFSFPDDLQCVDLK ILPNDECKKAHVQKV TDFMLCVGHLEGGKD TCVGDSGGPLMCDGV LQGVTSWG-YVPCGT  237
 4 HSCCE     PGTTCTVSGWGTTTS PDVTFPSDLMCVDVK LISPQDCTKVYKDLL LVSREECEHAYPGQI ACNGDSGGPLVCRGT LQGLVSWG-TFPCGQ  228
 5 zyme      NTTSCHILGWGKTAD --GDFPDTIQCAYIH LVSREECEHAYPGQI TQNMLCAGDEKYGKD SCQGDSGGPLVCGDH LRGLVSWG-NIPCGS  220
 6 KLK-L6    PGTSCRVSGWGTISS PIARYPASLQCVNIN ISPDEVCQKAYPRTI TPGMVCAGVPQGKD  SCQGDSGGPLVCRGQ LQGLVSWG-MERCAL  227
 7 TLSP      AGTSCLISGWGSTSS PQLRLPHTLRCANIT IIEHQKCENAYPGNI TDTMVCASVQEGGKD SCQGDSGGPLVCNQS LQGIISWG-QDPCAI  226
 8 KLK-L4    PGTTCRVSGWGTTTS PQVNYPKTLQCANIQ LRSDEECRQVYPGKI TDNMLCAGTKEGGKD SCEGDSGGPLVCNRT LYGIVSWG-DFPCGQ  241
 9 NES1      PGDQCQVAGWGTTAA RRVKYNKGLTCSSIT ILSPKECEVFYPGVV TNNMICAGLDR-GQD PCQSDSGGPLVCDET LQGILSWG-VYPCGS  252
10 KLK-L5    AGTECHVSGWGITNH PRNPFPDLLQCLNLS IVSHATCHGVYPGRI TSNMVCAGGVP-GQD ACQGDSGGPLVCGGV LQGLVSWGSVGPCGQ  224
11 neuropsin PGQKCTVSGWGTVTS PRENFPDTLNCAEVK IFPQKKCEDAYPGQI TDGMVCAGSSK-GAD TCQGDSGGPLVCDGA LQGITSWG-SDPCGR  235
12 prostase  AGNSCLVSGWGLLAN --GRMPTVLQCVNVS VVSEEVCSKLYDPLY HPSMFCAGGGHDQKD SCNGDSGGPLICNGY LQGLVSFG-KAPCGQ  230

271        285 286        300 301
 1 PSA       PERPSLYTKVVHYRK WIKDTIVANP----                                                                 261
 2 hK2       PEKPAVYTKVVHYRK WIKDTIAANP----                                                                 261
 3 hK1       PNKPSVAVRVLSYVK WIEDTIAENS----                                                                 262
 4 HSCCE     PNDPGVYTQVCKFTK WINDTMKKHR----                                                                 253
 5 zyme      KEKPGVYTNVCRYTN WIQKTIQAK-----                                                                 244
 6 KLK-L6    PGYPGVYTNLCKYRS WIEETMRDK-----                                                                 251
 7 TLSP      TRKPGVYTKVCKYVD WIQETMKNN-----                                                                 250
 8 KLK-L4    PDRPGVYTRVSRYVL WIRETIRKYETQQQK WLKGPQ                                                         277
 9 NES1      AQHPAVYTQICKYMS WINKVIRSN-----                                                                 276
10 KLK-L5    DGIPGVYTYICKYVD WIRMIMRNN-----                                                                 248
11 neuropsin SDKPGVYTNICRYLD WIKKIIGSKG----                                                                 260
12 prostase  VGVPGVYTNLCKFTE WIEKTVQAS-----                                                                 254
                                           315 316        330 331        345 346        360
```

HUMAN KALLIKREIN-LIKE GENES

CROSS-REFERENCE TO RELATED APPLICATIONS

This is a 371 of PCT/CA00/00258, filed Mar. 9, 2000, which claims the benefit of the priorities of U.S. Patent Application No. 60/144,919, filed Jul. 21, 1999, now abandoned, U.S. Patent Application No. 60/127,386, filed Apr. 1, 1999, now abandoned, and U.S. Patent Application No. 60/124,260, filed Mar. 11, 1999, now abandoned.

FIELD OF THE INVENTION

The invention relates to nucleic acid molecules, proteins encoded by such nucleic acid molecules; and use of the proteins and nucleic acid molecules.

BACKGROUND OF THE INVENTION

Kallikreins and kallikrein-like proteins are a subgroup of the serine protease enzyme family and exhibit a high degree of substrate specificity (1). The biological role of these kallikreins is the selective cleavage of specific polypeptide precursors (substrates) to release peptides with potent biological activity (2). In mouse and rat, kallikreins are encoded by large multigene families. In the mouse genome, at least 24 genes have been identified (3). Expression of 11 of these genes has been confirmed; the rest are presumed to be pseudogenes (4). A similar family of 15–20 kallikreins has been found in the rat genome (5) where at least 4 of these are known to be expressed (6).

Three human kallikrein genes have been described, i.e. prostatic specific antigen (PSA or KLK3) (7), human glandular kallikrein (KLK2) (8) and tissue (pancreatic-renal) kallikrein (KLK1) (9). The PSA gene spans 5.8 Kb of sequence which has been published (7); the KLK2 gene has a size of 5.2 Kb and its complete structure has also been elucidated (8). The KLK1 gene is approximately 45 Kb long and the exon sequences and the exon/intron junctions of this gene have been determined (9).

The mouse kallikrein genes are clustered in groups of up to 11 genes on chromosome 7 and the distance between the genes in the various clusters can be as small as 3–7 Kb (3). All three human kallikrein genes have been assigned to chromosome 19q13.2–19q13.4 and the distance between PSA and KLK2 has been estimated to be 12 Kb (9).

A major difference between mouse and human kallikreins is that two of the human kallikreins (KLK2 and KLK3) are expressed almost exclusively in the prostate while in animals none of the kallikreins is localized in this organ. Other candidate new members of the human kallikrein gene family include protease M (10) (also named Zyme (11) or neurosin (12) and the normal epithelial cell-specific gene-1 (NES1) (13). Both genes have been assigned to chromosome 19q13.3 (10,14) and show structural homology with other serine proteases and the kallikrein gene family (1114).

SUMMARY OF THE INVENTION

In efforts to precisely define the relative genomic location of PSA, KLK2, Zyme and NES1 genes, an area spanning approximately 300 Kb of contiguous sequence on human chromosome 19 (19q13.3–q13.4) was examined. The present inventors were able to identify the relative location of the known kallikrein genes and, in addition, they identified other kallikrein-like genes which exhibit both location proximity and structural similarity with the known members of the human kallikrein family. The novel genes exhibit homology with the currently known members of the kallikrein family and they are co-localized in the same genomic region. These new genes, like the already known kallikreins have utility in various cancers including those of the breast, testicular, and prostate.

The kallikrein-like proteins described herein are individually referred to as "KLK-L1, KLK-L2, KLK-L3, KLK-L4, KLK-L5, or KLK-L6", and collectively as "kallikrein-like proteins" or "KLK-L Proteins". The genes encoding the proteins are referred to as "klk-11, klk-12, klk-13, klk-14, klk-15, or klk-16", and collectively as "kallikrein-like genes" or "klk-1 genes".

Broadly stated the present invention relates to an isolated nucleic acid molecule which comprises:
(i) a nucleic acid sequence encoding a protein having substantial sequence identity with an amino acid sequence of KLK-L1, KLK-L2, KLK-L3, KLK-L4, KLK-L5, or KLK-L6 as shown in SEQ.ID.NO. 2, 3, 14, 22, 23, 44, 45, 57, 58, 59, 60, 66, or 67, respectively;
(ii) a nucleic acid sequence encoding a protein comprising an amino acid sequence of KLK-L1, KLK-L2. KLK-L3, KLK-L4, KLK-L5, or KLK-L6 as shown in SEQ.ID.NO. 2, 3, 14, 22, 23, 44, 45, 57, 58, 59, 60, 66, or 67, respectively;
(iii) nucleic acid sequences complementary to (i);
(iv) a degenerate form of a nucleic acid sequence of (i);
(v) a nucleic acid sequence capable of hybridizing under stringent conditions to a nucleic acid sequence in (i), (ii) or (iii);
(vi) a nucleic acid sequence encoding a truncation, an analog, an allelic or species variation of a protein comprising an amino acid sequence of KLK-L1, KLK-L2, KLK-L3, KLK-L4, KLK-L5, or KLK-L6 as shown in SEQ.ID.NO. 2, 3, 14, 22, 23, 44, 45, 57, 58, 59, 60, 66, or 67, respectively; or
(vii) a fragment, or allelic or species variation of (i), (ii) or (iii).

Preferably, a purified and isolated nucleic acid molecule of the invention comprises:
(i) a nucleic acid sequence comprising the sequence of SEQ.ID.NO. 1, 13, 21, 43, 56, or 65 wherein T can also be U;
(ii) nucleic acid sequences complementary to (i), preferably complementary to the full nucleic acid sequence of SEQ.ID.NO. 1, 13, 21, 43, 56, or 65;
(iii) a nucleic acid capable of hybridizing under stringent conditions to a nucleic acid of (i) or (ii) and preferably having at least 18 nucleotides; or
(iv) a nucleic acid molecule differing from any of the nucleic acids of (i) to (iii) in codon sequences due to the degeneracy of the genetic code.

The invention also contemplates a nucleic acid molecule comprising a sequence encoding a truncation of a KLK-L Protein, an analog, or a homolog of a KLK-L Protein or a truncation thereof. (KLK-L Proteins and truncations, analogs and homologs of KLK-L Proteins are also collectively referred to herein as "KLK-L Related Proteins").

The nucleic acid molecules of the invention may be inserted into an appropriate expression vector, i.e. a vector that contains the necessary elements for the transcription and translation of the inserted coding sequence. Accordingly, recombinant expression vectors adapted for transformation of a host cell may be constructed which comprise a nucleic acid molecule of the invention and one or more transcription and translation elements linked to the nucleic acid molecule.

The recombinant expression vector can be used to prepare transformed host cells expressing KLK-L Related Proteins. Therefore, the invention further provides host cells containing a recombinant molecule of the invention. The invention also contemplates transgenic non-human mammals whose germ cells and somatic cells contain a recombinant molecule comprising a nucleic acid molecule of the invention, in particular one which encodes an analog of a KLK-L Protein, or a truncation of a KLK-L Protein.

The invention further provides a method for preparing KLK-L Related Proteins utilizing the purified and isolated nucleic acid molecules of the invention. In an embodiment a method for preparing a KLK-L Related Protein is provided comprising (a) transferring a recombinant expression vector of the invention into a host cell; (b) selecting transformed host cells from untransformed host cells; (c) culturing a selected transformed host cell under conditions which allow expression of the KLK-L Related Protein; and (d) isolating the KLK-L Related Protein.

The invention further broadly contemplates an isolated KLK-L Protein comprising an amino acid sequence as shown in SEQ.ID.NO. 2, 3, 14, 22, 23, 44, 45, 57, 58, 59, 60, 66, or 67.

The KLK-L Related Proteins of the invention may be conjugated with other molecules, such as proteins, to prepare fusion proteins. This may be accomplished, for example, by the synthesis of N-terminal or C-terminal fusion proteins.

The invention further contemplates antibodies having specificity against an epitope of a KLK-L Related Protein of the invention. Antibodies may be labeled with a detectable substance and used to detect proteins of the invention in tissues and cells.

The invention also permits the construction of nucleotide probes which are unique to the nucleic acid molecules of the invention and/or to proteins of the invention. Therefore, the invention also relates to a probe comprising a nucleic acid sequence of the invention, or a nucleic acid sequence encoding a protein of the invention, or a part thereof. The probe may be labeled, for example, with a detectable substance and it may be used to select from a mixture of nucleotide sequences a nucleic acid molecule of the invention including nucleic acid molecules coding for a protein which displays one or more of the properties of a protein of the invention.

The invention still further provides a method for identifying a substance which binds to a protein of the invention comprising reacting the protein with at least one substance which potentially can bind with the protein, under conditions which permit the formation of complexes between the substance and protein and detecting binding. Binding may be detected by assaying for complexes, for free substance, or for non-complexed protein. The invention also contemplates methods for identifying substances that bind to other intracellular proteins that interact with a KLK-L Related Protein. Methods can also be utilized which identify compounds which bind to KLK-L gene regulatory sequences (e.g. promoter sequences).

Still further the invention provides a method for evaluating a compound for its ability to modulate the biological activity of a KLK-L Related Protein of the invention. For example a substance which inhibits or enhances the interaction of the protein and a substance which binds to the protein may be evaluated. In an embodiment, the method comprises providing a known concentration of a KLK-L Related Protein, with a substance which binds to the protein and a test compound under conditions which permit the formation of complexes between the substance and protein, and removing and/or detecting complexes.

Compounds which modulate the biological activity of a protein of the invention may also be identified using the methods of the invention by comparing the pattern and level of expression of the protein of the invention in tissues and cells, in the presence, and in the absence of the compounds.

The proteins of the invention and substances and compounds identified using the methods of the invention, and peptides of the invention may be used to modulate the biological activity of a KLK-L Related Protein of the invention, and they may be used in the treatment of conditions such as cancer (e.g. breast, testicular, and prostate cancer). Accordingly, the substances and compounds may be formulated into compositions for administration to individuals suffering from cancer.

Therefore, the present invention also relates to a composition comprising one or more of a protein of the invention, a peptide of the invention, or a substance or compound identified using the methods of the invention, and a pharmaceutically acceptable carrier, excipient or diluent. A method for treating or preventing cancer is also provided comprising administering to a patient in need thereof, a KLK-L Related Protein of the invention, or a composition of the invention.

Other objects, features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which:

FIG. 4 shows the sequence of PCR product (SEQ ID NO: 4) obtained with cDNA from female breast tissue using prostase/KLK-L1 primers. Primer sequences (nt 1–12 of SEQ ID NO:4 and nt 259–278 of SEQ ID NO: 4) are underlined. The sequence is identical to the sequence obtained from prostatic tissue.

FIG. 7 shows the genomic organization and partial genomic sequence (nucleotides 2221–11570 of SEQ ID NO: 13) of the KLK-L2 gene. Intronic sequences are not shown except for the splice junctions. Introns are shown with lower case letters and exons with capital letters (SEQ ID NO: 96). The start and stop codons are encircled and the exon-intron junctions are boxed. The translated amino acids of the coding region (SEQ ID NO: 14) are shown underneath by a single letter abbreviation. The catalytic residues are inside triangles. Putative polyadenylation signal is underlined.

FIG. 9 shows the alignment of the deduced amino acid sequence of KLK-L2 with members of the kallikrein multigene family. Genes are (from top to bottom): Prostase/KLK-L1, enamel matrix serine proteinase 1 (EMSP1) (GenBank accession # NP_004908), KLK-L2, zyme (GenBank accession # Q92876), neuropsin (GenBank accession # BAA28673), trypsin-like serine protease (TLSP) (GenBank accession # BAA33404), PSA (GenBank accession # P07288), KLK2 (GenBank accession # P20151), KLK1 (GenBank accession # NP_002248), and trypsinogen (GenBank accession # P07477). (See SEQ ID. Nos. 68–77) Dashes represent gaps to bring the sequences to better alignment. The residues of the catalytic triad are represented by (✤) and the 29 invariant serine protease residues by (❙ or ✜). Conserved areas around the catalytic triad are boxed. The predicted cleavage sites are indicated by (▲). The dotted area represents the kallikrein loop sequence. The trypsin like cleavage pattern is indicated by (○).

FIG. 15 shows the genomic organization and partial genomic sequence of the KLK-L3 gene. Intronic sequences are not shown except for the splice junctions. Introns are shown with lower case letters and exons with capital letters. For the full sequence, see SEQ.ID. NO. 21. The start and stop codons are encircled and the exon-intron junctions are boxed. The translated amino acids of the coding region are shown underneath by a single letter abbreviation. The catalytic residues are inside triangles. Putative polyadenylation signal is underlined.

FIG. 17 is an alignment of the deduced amino acid sequence of KLK-L3 with members of the kallikrein multigene family. Genes are (from top to bottom and in brackets is the GenBank accession #): PSA (P07288), KLK2 (P20151), KLK1 (NP002248), trypsinogen (P07477), KLK-L3 (AF135026), trypsin-like serine protease (TLSP) (BAA33404), neuropsin (BAA28673), zyme (Q92876), human stratum corneum chymotryptic enzyme (HSCCE) (AAD49718), and/prostase/KLK-L1 (AAD21581). (See SEQ.ID. NOs. 78 to 84). Dashes represent gaps to bring the sequences to better alignment. The residues of the catalytic triad are bold and in italics, and the 29 invariant serine protease residues are denoted by (♦). Cysteine residues are marked by (●). Conserved areas around the catalytic triad are highlited in black. The arrow heads (▲) represent the potential cleavage sites. The dotted area represents the kallikrein loop sequence.

FIG. 18 is a dendrogram of the predicted phylogenetic tree for some serine proteases and kallikrein genes. Neighbor-joining/UPGMA method was used to align KLK-L3 with other members of the kallikrein gene family. Gene names and accession numbers are listed in FIG. 17. The tree grouped the classical kallikreins (KLK1, KLK2, and PSA) together and aligned the KLK-L3 gene in one group with TLSP, neuropsin, and NES 1 genes. KLK-L4 (SEQ.ID.NO. 43) lies further telomeric to TLSP (21).

KLK2, neuropsin, NES1, and KLK-L3 genes. Exons are shown by black boxes and introns by the connecting lines. Arrowheads show the start codon, and arrows show the stop codon. Letters above boxes indicate relative positions of the catalytic triad; H denotes histidine, D aspartic acid and S serine. Roman numbers indicate intron phases. The intron phase refers to the location of the intron within the codon; I denotes that the intron occurs after the first nucleotide of the codon, II the intron occurs after the second nucleotide, 0 the intron occurs between codons. Numbers inside boxes indicate exon lengths in base pairs.

Figure 22:
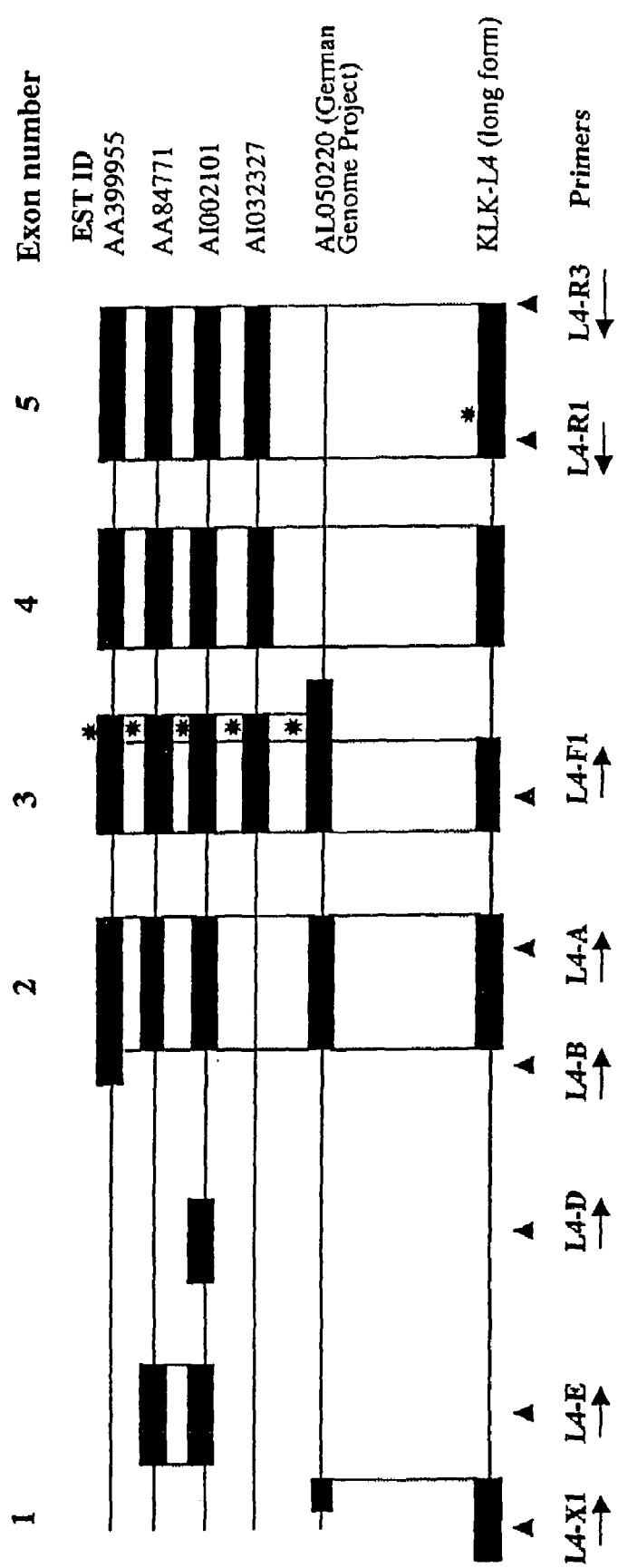

FIG. 22 shows a comparative genomic structure of the ESTs (Table 16), the clone from The German Genome Project, and the long form of KLK-L4. Exons are represented by solid bars and introns by the connecting lines. Exon numbers on top of solid bars refer to GenBank submission #AF135024. The EST IDs represent GenBank accession numbers. Asterisks represent the positions of stop codons. Horizontal arrows indicate the direction of the PCR primers (described in Table 15) and arrowheads their position along the exons. Vertical dotted lines show alignment of identical fragments.

Figure 23:
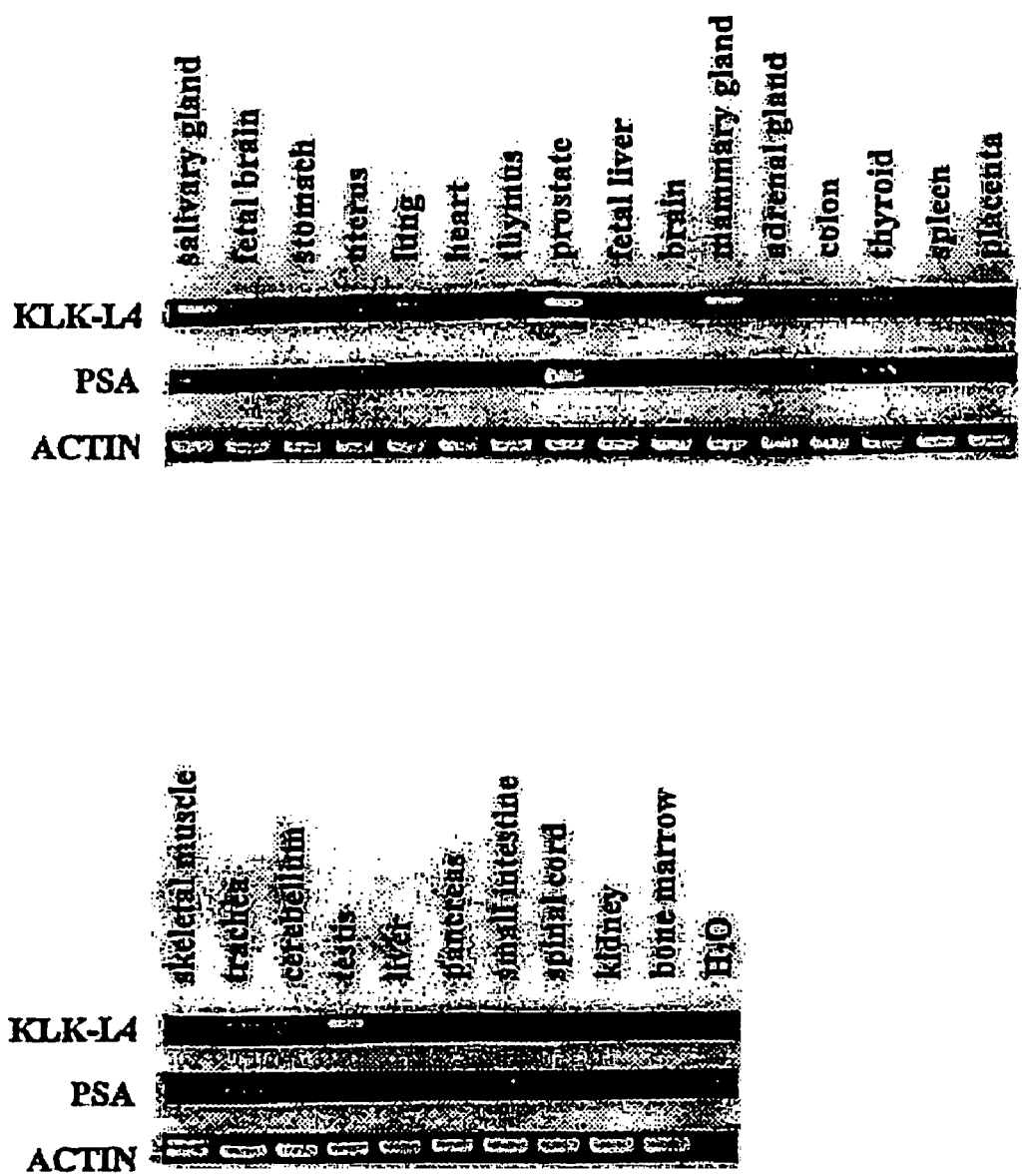

FIG. 23 shows tissue expression of the KLK-L4 gene as determined by RT-PCR. Actin and PSA are control genes. KLK-L4 is highly expressed in breast, prostate, salivary gland and testis.

Figure 24:

FIG. 24 in the Upper Panel is a Diagram showing the comparative genomic structure of the long KLK-L4 form and the short KLK-L4 variant. Exons are represented by boxes and introns by the connecting lines. Exon numbers refer to SEQ. ID. NO. 43 and GenBank Accession No. AF135024. The black region indicates the extra fragment (214 bp) that is found in the long, but not in the short form of the gene. The positions of the stop codons of the two forms are marked with asterisks. Frame shifting occurs as a result of utilization of an alternative splice site, and a stop codon is generated at the beginning of exon 4 in the short form. The Lower Panel shows PCR products of the amplification of the KLK-L4 gene using L4-R1 and L4-X1 primers (FIG. 22 and Table 15). Note the predominant long form and a minor band representing the short form of KLK-L4 mRNA. (M); Markers with sizes in bp shown on the left. Tissues used: (1), salivary gland; (2), mammary gland; (3), prostate; (4), testis; (5), uterus; (6), breast cancer tissue; (7), negative control.

FIG. 25 shows the genomic organization and partial genomic sequence of the KLK-L4 gene. Intronic sequences are not shown except for the splice junction areas. Introns are shown with lower case letters and exons with capital letters. For full sequence, see SEQ. ID. NO.43 or GenBank Accession #AF135024. The start and stop codons are encircled and the exon-intron junctions are underlined. The translated amino acids of the coding region are shown underneath by a single letter abbreviation. The catalytic residues are boxed. The putative polyadenylation signal is underlined.

Figure 26:
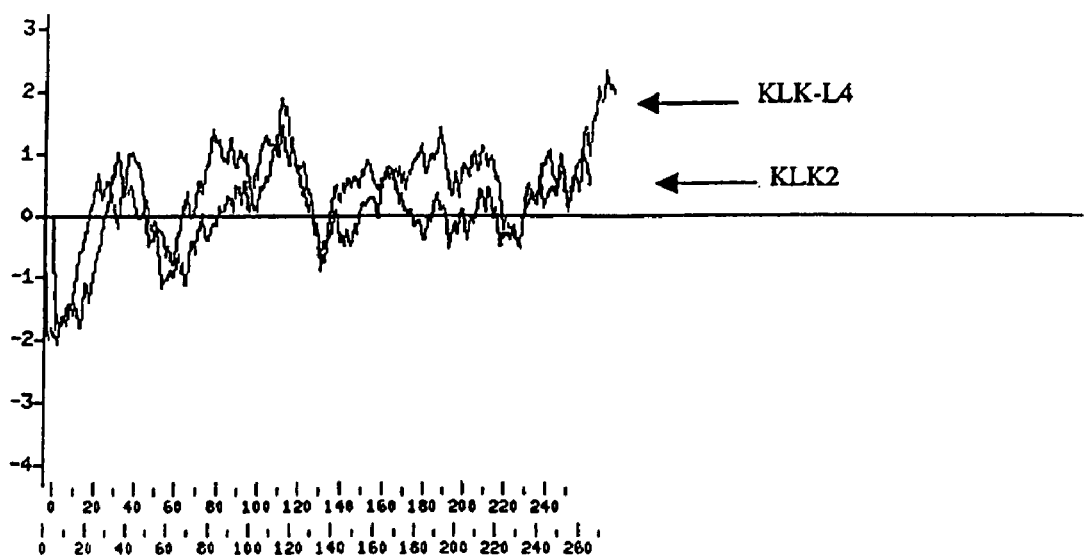

FIG. 26 is a plot of hydrophobicity and hydrophilicity of the KLK-L4 protein, as compared with the glandular kallikrein gene 2 (KLK2). Note the hydrophobic region at the amino terminus, suggesting presence of a signal peptide.

FIG. 27 shows an alignment of the deduced amino acid sequence of KLK-L4 with members of the kallikrein multigene family. Genes are (from top to bottom, and in brackets are the GenBank accession #): KLK-L1/prostase (AAD21581). enamel matrix serine proteinase 1 (EMSP) (NP_004908). KLK-L2 (AF135028). PSA (P07288), KLK2 (P20151). KLK1 (NP_002248), trypsinogen (P07477), zyme (Q92876), KLK-L4 (AF135024), trypsin-like serine protease (TLSP) (BAA33404), KLK-L3 (AF135026), neuropsin (BAA28673), and the normal epithelial cell-specific 1 gene (NES1) (O43240). (See SEQ.ID. NOs. 78–88). Dashes represent gaps to bring the sequences to better alignment. The residues of the catalytic triad are typed in bold, and conserved motifs around them are highlighted in grey. The 29 invariant serine protease residues are denoted by (●), and the cysteine residues by (◆). The predicted cleavage sites are indicated by (▲). The dotted area represents the kallikrein loop sequence. The trypsin-like cleavage pattern of KLK-L4 with the D residue, is indicated by (○).

Figure 28:
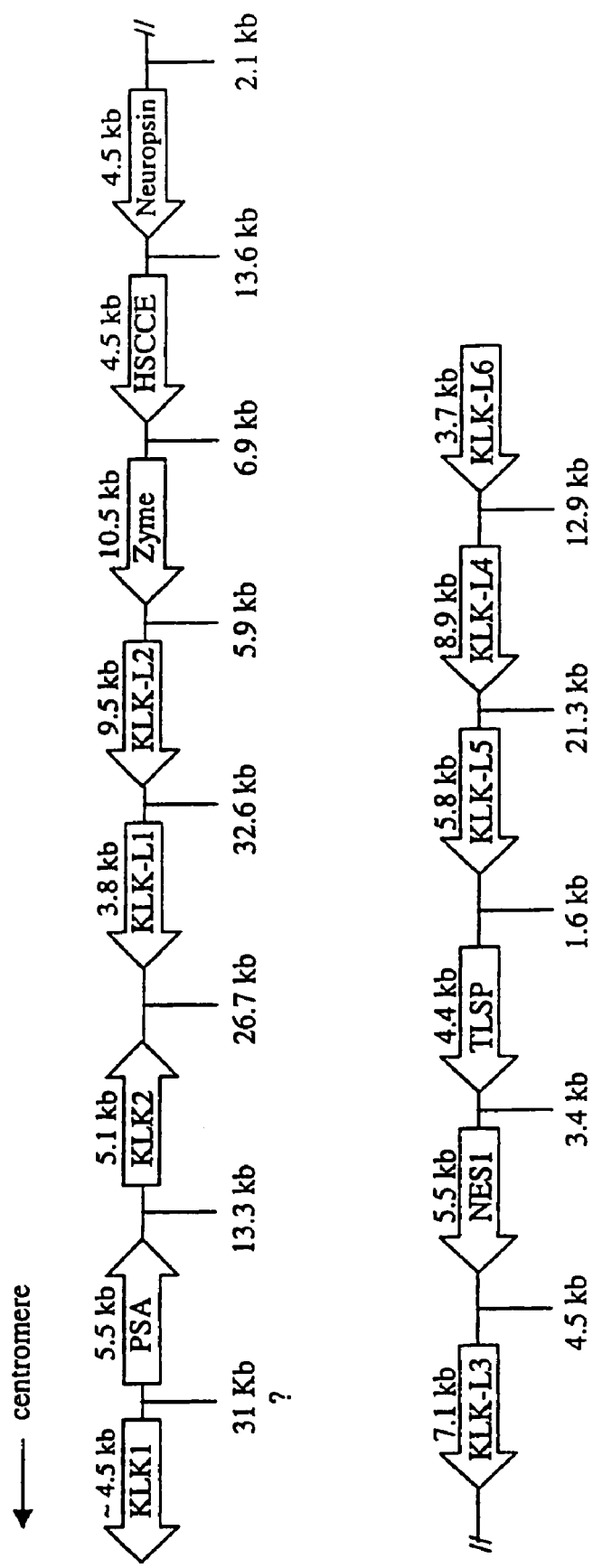

FIG. 28 shows an approximate 300 Kb region of almost contiguous genomic sequence around chromosome 19q13.3–q13.4. Genes are represented by horizontal arrows denoting the direction of the coding sequence. Their lengths are shown on top of each arrow. Distances between genes are mentioned in base pairs below the arrows. The distance between KLK1 and PSA is not accurately known. For gene names, see under abbreviations.

FIG. 29 shows is a dendrogram of the predicted phylogenetic tree for some kallikrein and serine protease genes. The neighbor-joining/UPGMA method was used to align KLK-L4 with other serine proteases and members of the kallikrein gene family. The tree grouped the classical kallikreins (KLK1, KLK2, and PSA) together and aligned the KLK-L4 gene in one group with zyme, NES1, neuropsin, KLK-L3, and TLSP. Other serine proteases were aligned in different groups, as shown.

Figure 30:
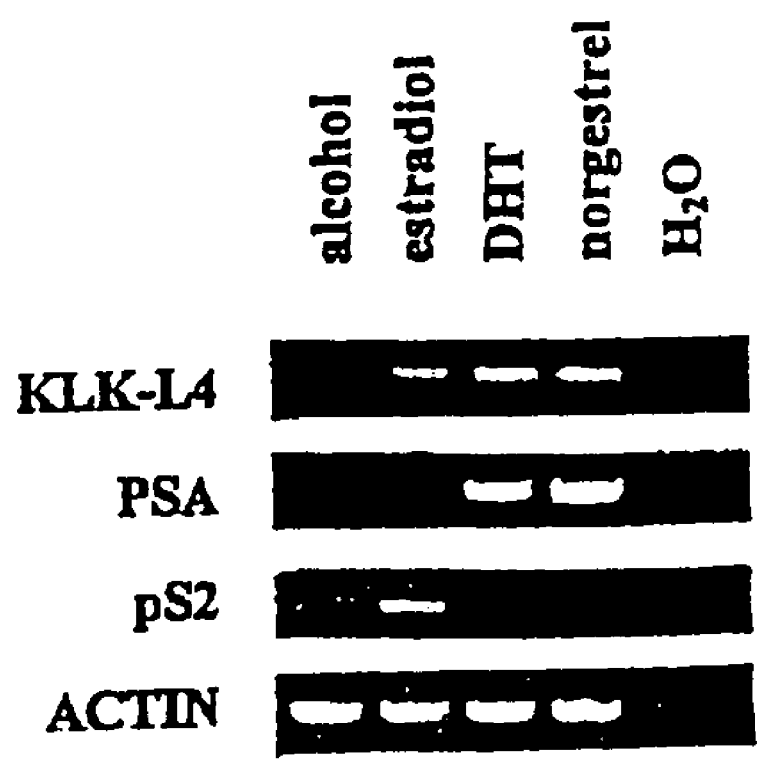

FIG. 30 is a blot showing the hormonal regulation of the KLK-L4 gene in the BT-474 breast carcinoma cell line. DHT=dihydrotestosterone. Steroids were added at $10^{-8}$ M final concentrations. Actin (not regulated by steroid hormones), pS2 (up-regulated by estrogens) and PSA (upregulated by androgens and progestins) are control genes. KLK-L4 is up-regulated by androgens and progestins and to a lesser extent by estrogens. $H_2O$ was used to check for PCR specificity in all PCR reactions. For more details, see text.

Figure 31:
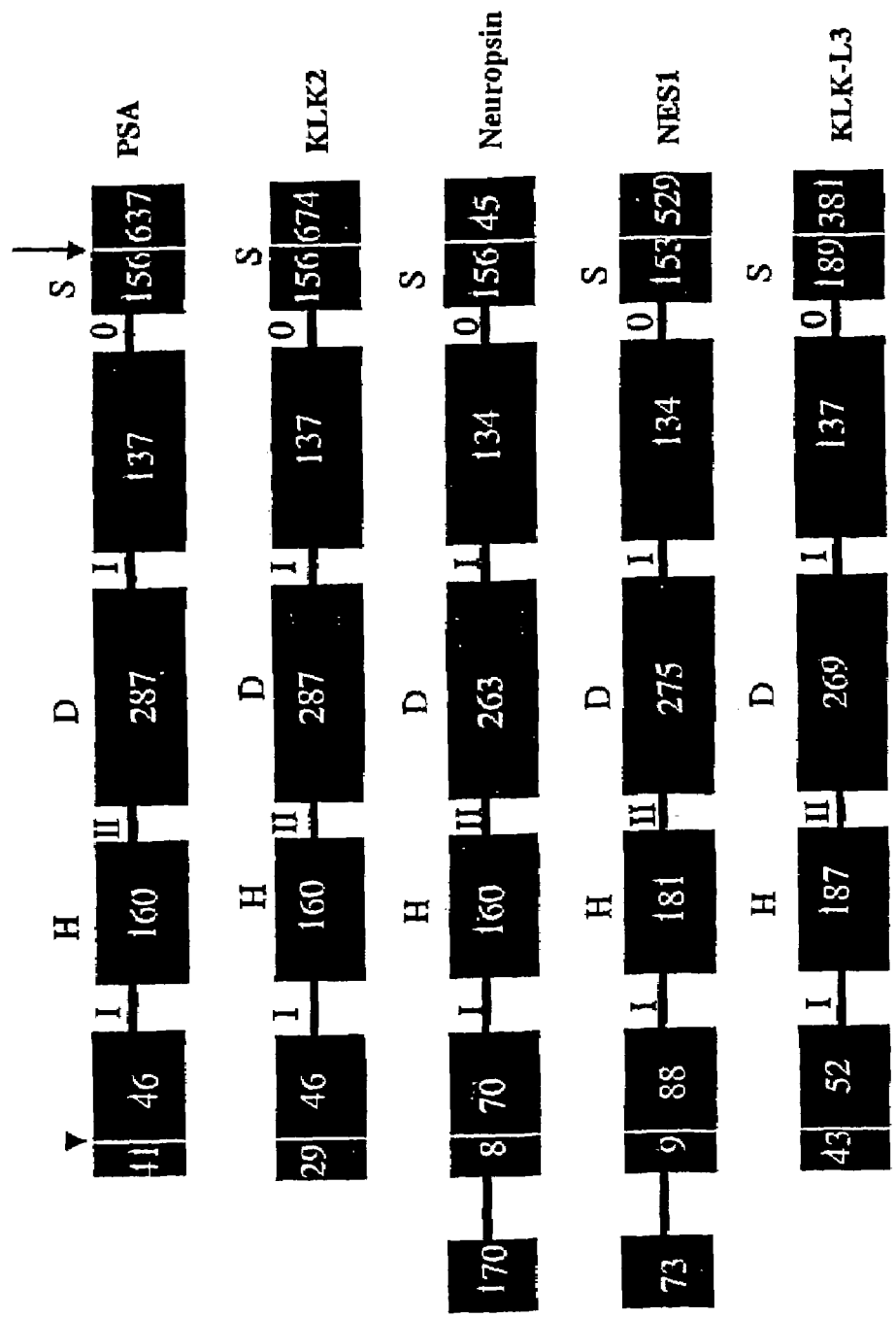

FIG. 31 is a schematic diagram showing the comparison of the genomic structure of PSA, KLK2, neuropsin, NES1, and KLK-L4 genes. Exons are shown by black boxes and introns by the connecting lines. The arrowhead shows the start codons and the arrow the stop codons. Letters above boxes indicate the relative positions of the amino acids of the catalytic triad; H denotes histidine, D aspartic acid and S serine. Roman numbers indicate intron phases. The intron phase refers to the location of the intron within the codon; I, the intron occurs after the first nucleotide of the codon, II the intron occurs after the second nucleotide, 0 the intron occurs between codons. Numbers inside boxes indicate exon lengths in base pairs. The question mark indicates the possibility of more untranslated bases.

Figure 32:
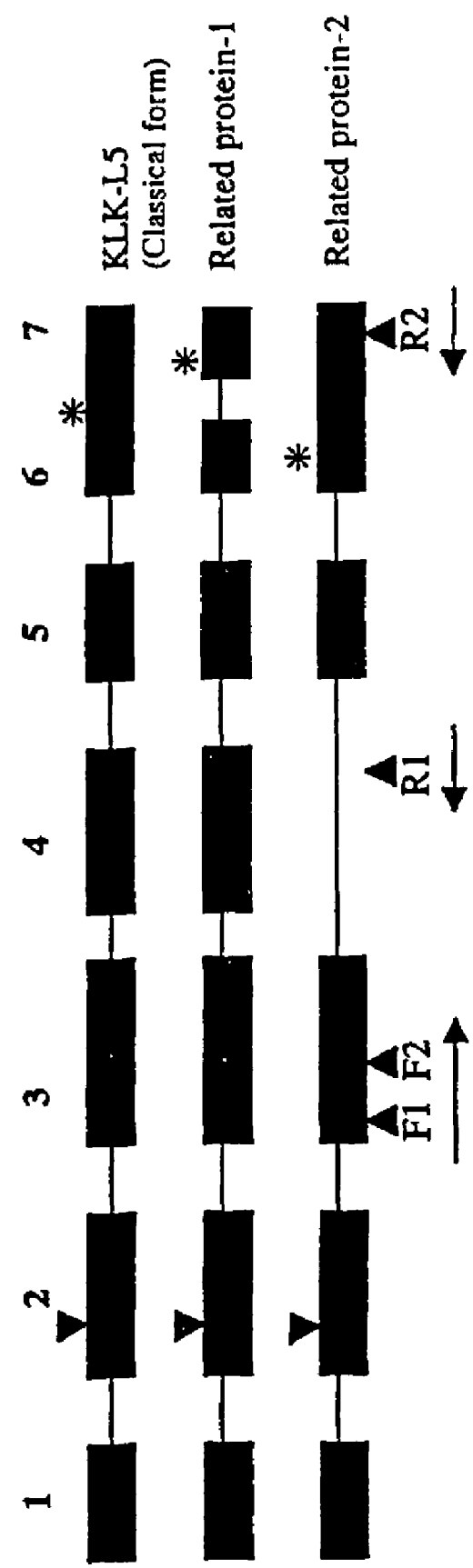

FIG. 32 is a diagram showing the comparative genomic structure of the three splice forms of KLK-L5; the classical kallikrein form, related protein-1, and related protein-2. Exons are represented by solid bars and introns by the connecting lines. Exon numbers refer to SEQ.ID. NO.56 and GenBank Accession #AF135025. Start codons are represented by the inverted arrowhead (▼) and stop codons are represented by asterisks (*). Primer locations are represented by vertical arrowheads (▲) and their directions by horizontal arrows. For primer sequences and codes see Table 17 and SEQ.ID. NOs. 61–64, and 9–12.

FIG. 33 shows the genomic organization and partial genomic sequence of the KLK-L5 gene. Intronic sequences are not shown except for short sequences around the splice junctions. Introns are shown with lower case letters and exons with capital letters. For full sequence, see SEQ.ID.NO. 56. The start and stop codons are encircled and the exon-intron junctions are underlined. The translated amino acids of the coding region are shown underneath by a single letter abbreviation. The catalytic residues are boxed. Putative polyadenylation signal is underlined. The extra intron of the related protein-1 form is represented by non-bold capital letters between brackets. When this intron is spliced, the frame continues with codon AAC (asparagine, N, instead of lysine, K) until it encounters the stop codon TAA (encircled).

Figure 34:
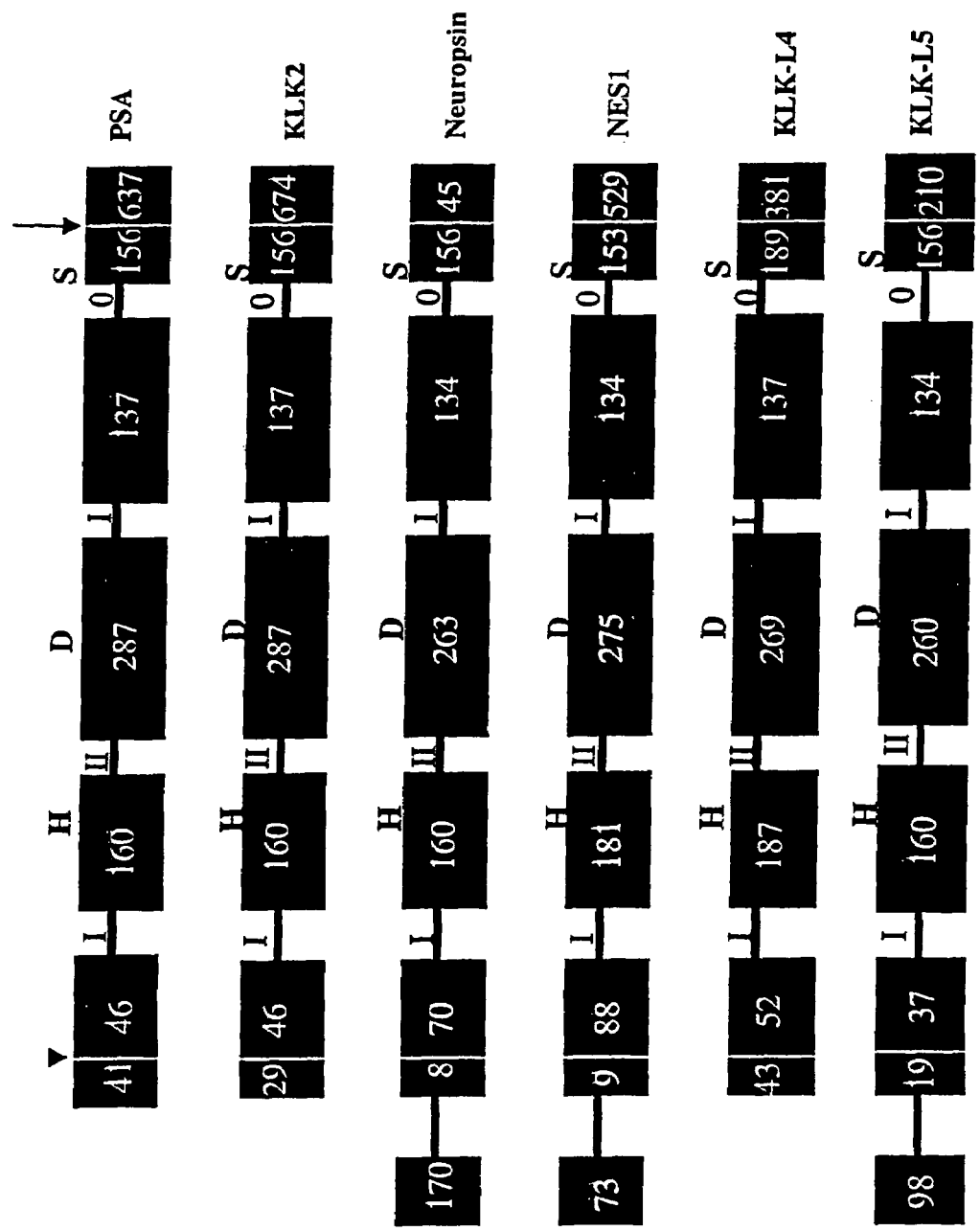

FIG. 34 is a schematic diagram showing the comparison of the genomic structure of PSA, KLK2, neuropsin, NES1, KLK-L4 and KLK-L5 genes. Exons are shown by solid bars and introns by the connecting lines. Arrowhead marks the site of the start codon, and the arrow represents the stop codon. Letters above boxes indicate relative positions of the catalytic triad; H denotes histidine, D aspartic acid and S serine. Roman numbers indicate intron phases. The intron phase refers to the location of the intron within the codon; I denotes that the intron occurs after the first nucleotide of the codon, II the intron occurs after the second nucleotide, 0 the intron occurs between codons. Numbers inside boxes indicate exon lengths in base pairs. Question marks indicate that exact length is not accurately known.

Figure 35:
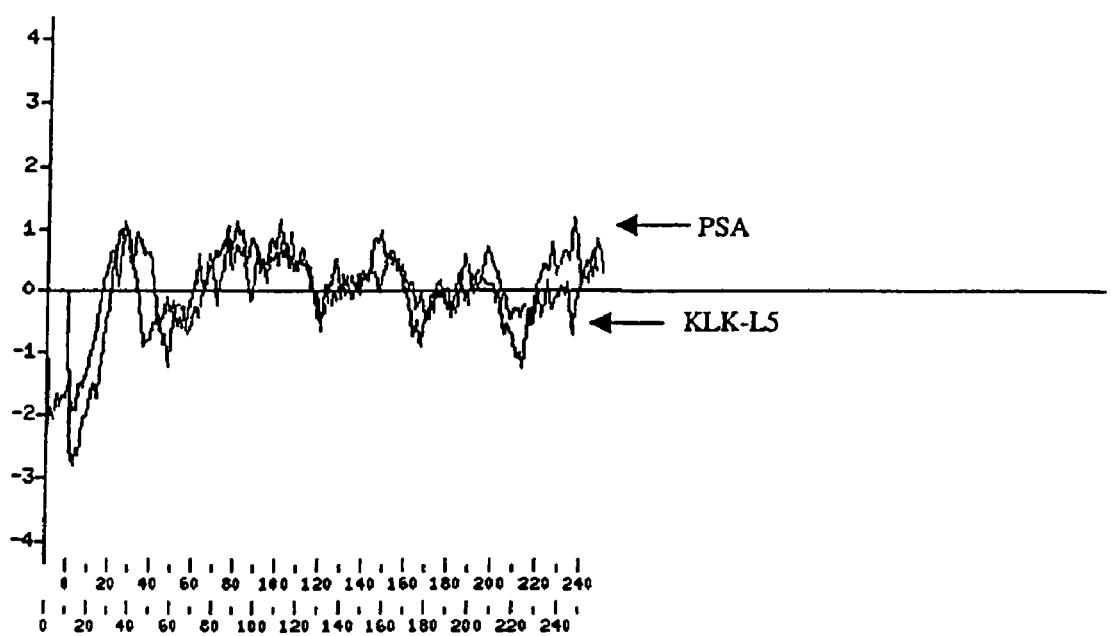

FIG. 35 is a plot of hydrophobicity and hydrophilicity of KLK-L5 protein compared to prostate specific antigen (PSA). The hydrophobic N-terminus may harbor a signal and activation peptide.

Figure 36:
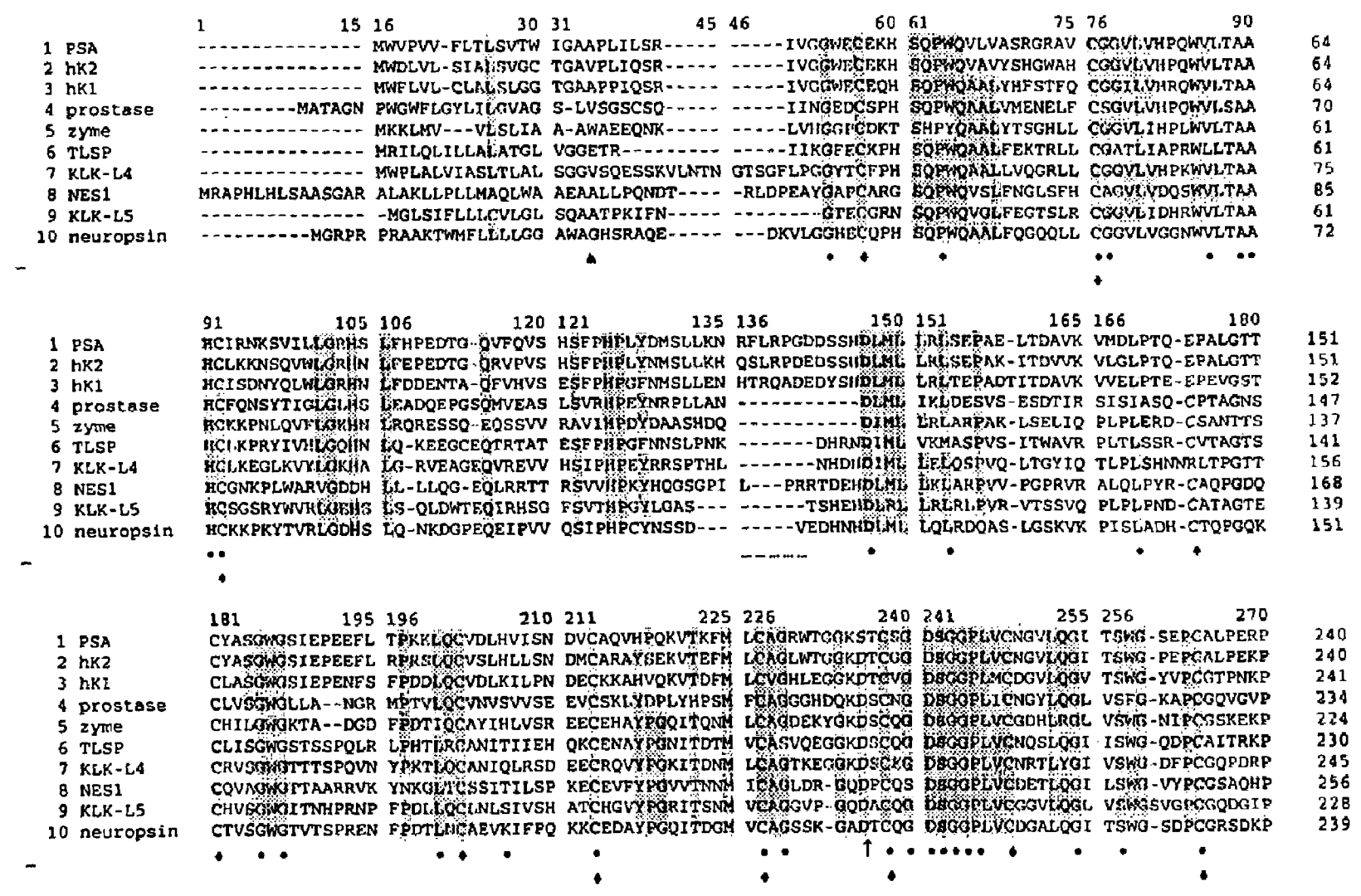

FIG. 36 shows an alignment of the deduced amino acid sequence of KLK-L5 with members of the kallikrein multigene family. (See SEQ.ID. NOs. 78–81, 83, 84). Dashes represent gaps to bring the sequences to better alignment. The residues of the catalytic triad are represented by bold letters, and the 29 invariant serine protease residues are marked with (•). The cysteine residues are marked by (♦). Conserved areas are highlighted in grey. The predicted cleavage sites in signal peptide are indicated by (▲). The dotted area represents the kallikrein loop sequence. A vertical arrow marks the trypsin like cleavage site.

Figure 37:
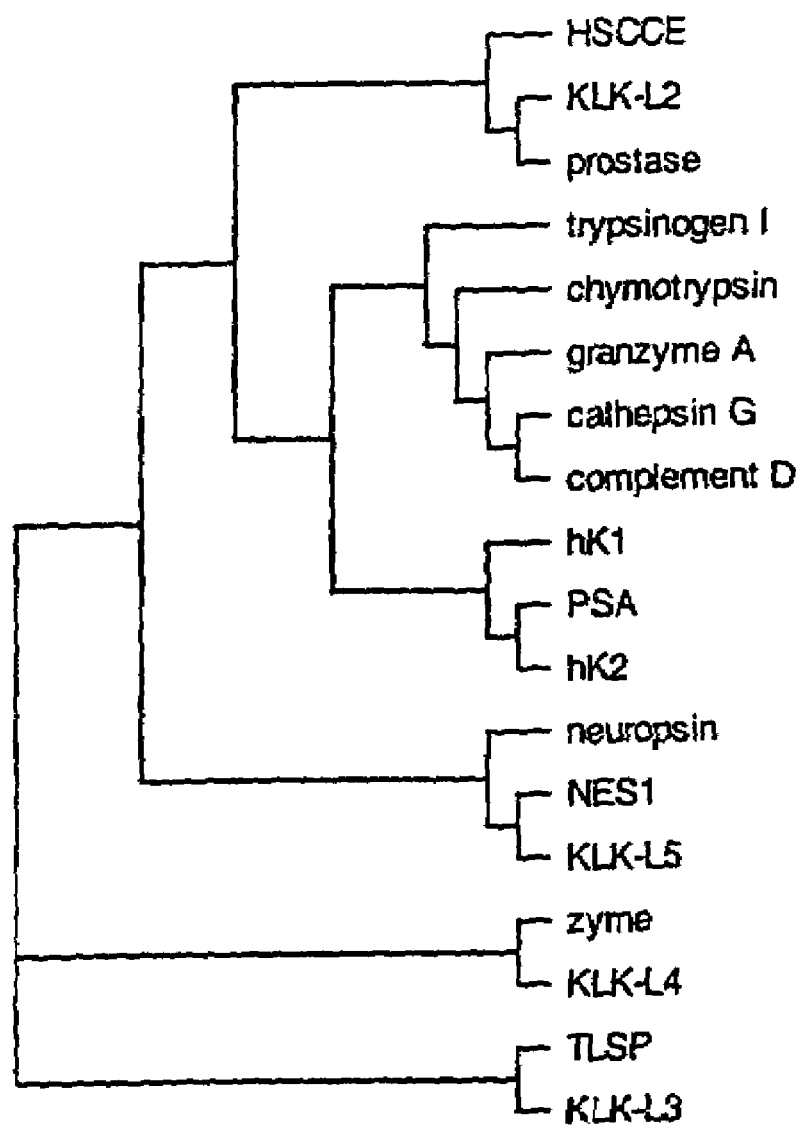

FIG. 37 is a dendrogram of the predicted phylogenetic tree for some serine proteases and other kallikrein proteins. Neighbor-joining/UPGMA method was used to align KLK-L5 with other serine proteases and members of the kallikrein gene family. The tree grouped the classical kallikreins (hK1, hK2, and PSA) together and aligned the KLK-L5 protein in one group with NES1 and neuropsin. Other serine proteases were aligned in different groups.

Figure 38:
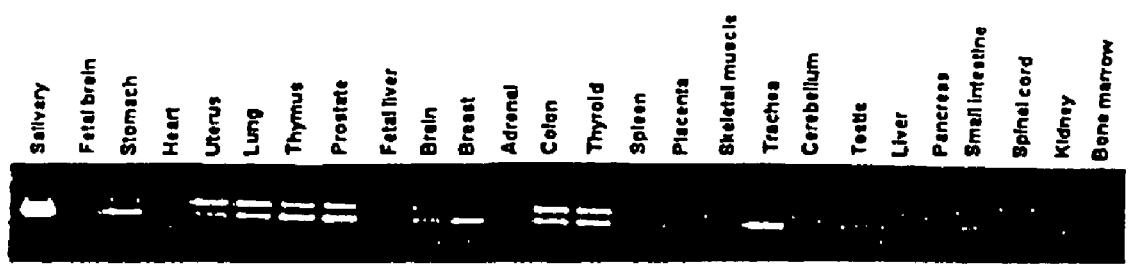

FIG. 38 shows tissue expression of the KLK-L5 gene as determined by RT-PCR. The upper band (905 base pairs, bp) is the classical form (see FIG. 32, the middle (776 bp) the related protein-1, and the lower band (644 bp) the related protein-2. For splice variant discussion see text. The primers used were L5-F2 and L5-R2, as shown in Table 17.

Figure 39:
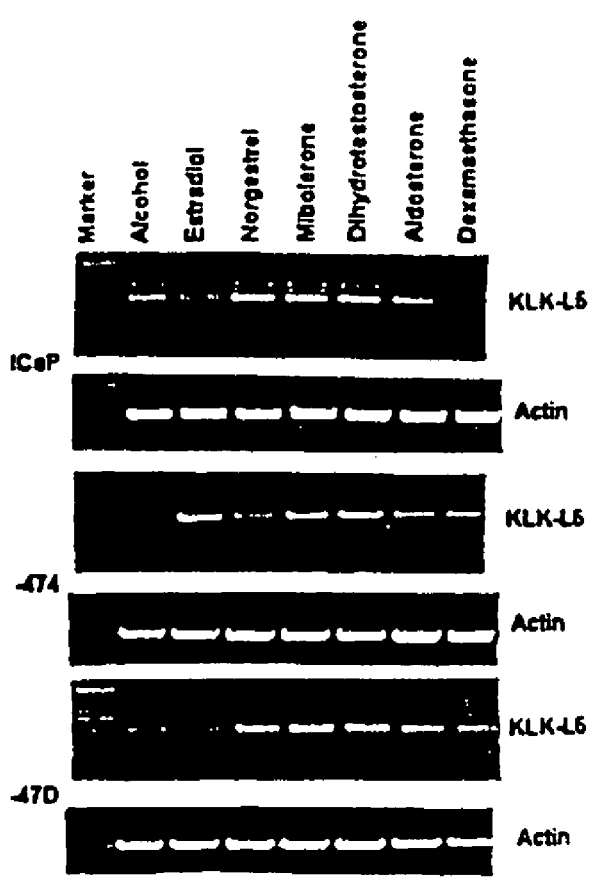

FIG. 39 shows hormonal regulation of the KLK-L5 gene in the LnCaP prostatic carcinoma cell line, BT-474 and T-47D breast carcinoma cell lines. Steroids were at $10^{-8}$ M final concentration. Actin (not regulated by steroid hormones) was used as a control gene. Note detection of three isoforms only in LNCaP.

Figure 40:
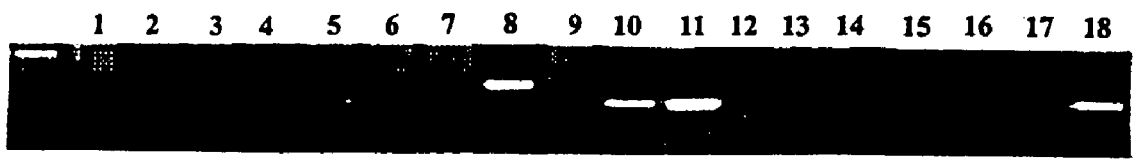

FIG. 40 shows the expression of the KLK-L5 gene in breast cancer (1–17) and normal (18) tissues. Note complete absence of expression in 12 cancer tissues. For isoforms see also FIG. 38.

Figure 42:
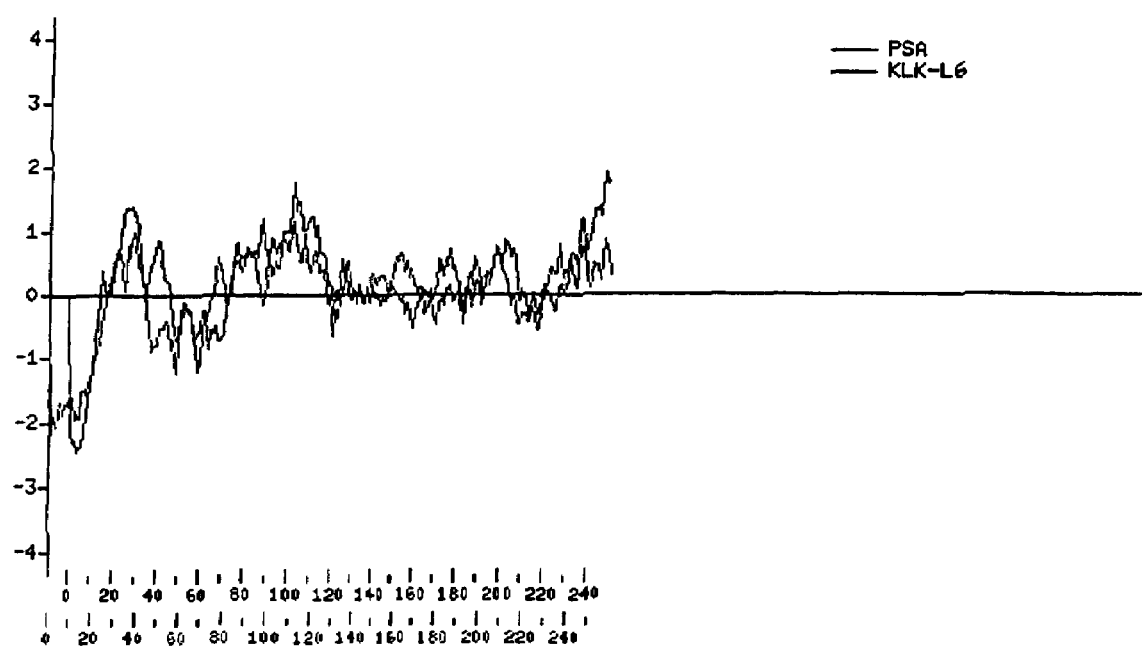

FIG. 41 shows the full structure of a KLK-L6 nucleic acid molecule (SEQ ID NO: 96);

FIG. 42 is a plot of hydrophobicity and hydrophilicity of KLK-L6 protein compared to prostate specific antigen (PSA).

FIG. 43 shows an alignment of the deduced amino acid sequence of KLK-L6 with members of the kallikrein multigene family. (See SEQ.ID. NOs. 78–81, 83, 84). Dashes represent gaps to bring the sequences to better alignment.

Figure 44:
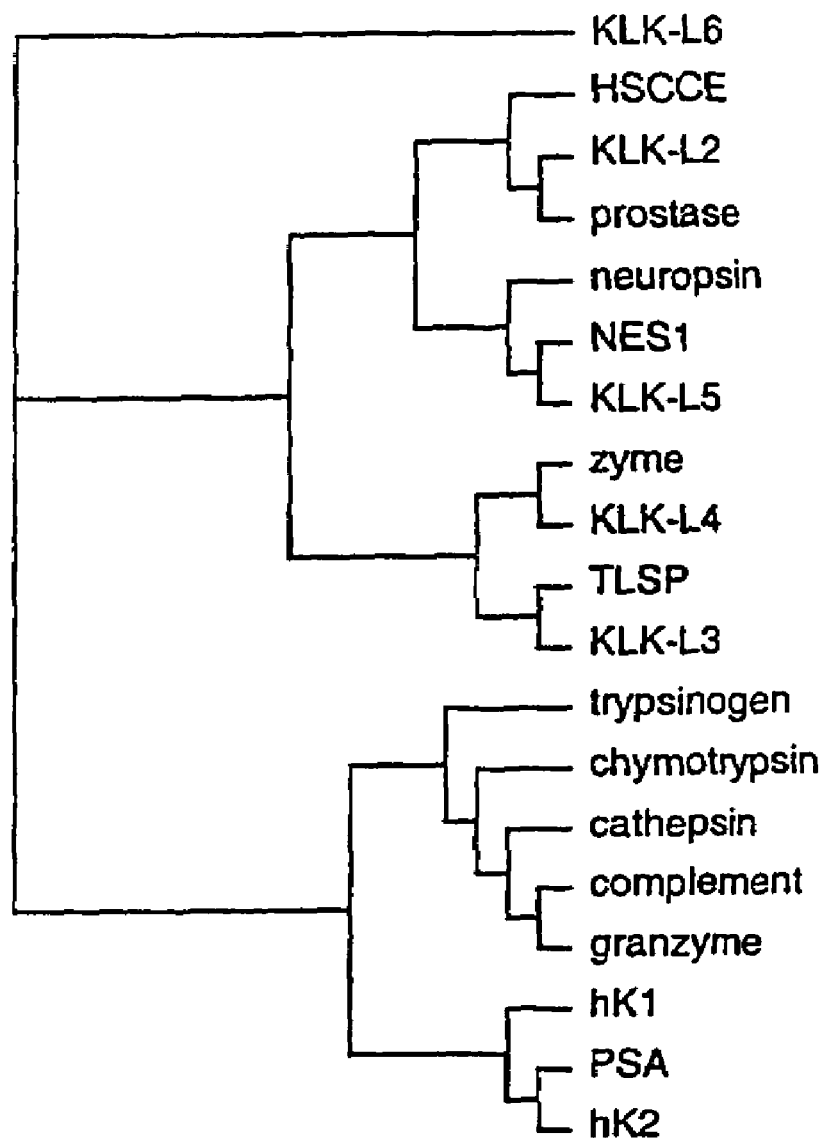

FIG. 44 is a dendrogram of the predicted phylogenetic tree for some serine proteases and other kallikrein proteins. Neighbor-joining/UPGMA method was used to align KLK-L6 with other serine proteases and members of the kallikrein gene family.

DETAILED DESCRIPTION OF THE INVENTION

In accordance with the present invention there may be employed conventional molecular biology, microbiology, and recombinant DNA techniques within the skill of the ant. Such techniques are explained fully in the literature. See for example. Sambrook, Fritsch, & Maniatis, Molecular Cloning: A Laboratory Manual, Second Edition (1989) Cold Spring Harbor Laboratory Press, Cold Spring Harbor, N.Y.); DNA Cloning: A Practical Approach, Volumes I and II (D. N. Glover ed. 1985); Oligonucleotide Synthesis (M. J. Gait ed. 1984); Nucleic Acid Hybridization B. D. Hames & S. J. Higgins eds. (1985); Transcription and Translation B. D. Hames & S. J. Higgins eds (1984); Animal Cell Culture R. I. Freshney, ed. (1986); Immobilized Cells and enzymes IRL Press, (1986); and B. Perbal, A Practical Guide to Molecular Cloning (1984).

1. Nucleic Acid Molecules of the Invention

As hereinbefore mentioned, the invention provides an isolated nucleic acid molecule having a sequence encoding a KLK-L Protein. The term "isolated" refers to a nucleic acid substantially free of cellular material or culture medium when produced by recombinant DNA techniques, or chemical reactants, or other chemicals when chemically synthesized. An "isolated" nucleic acid may also be free of sequences which naturally flank the nucleic acid (i.e., sequences located at the 5' and 3' ends of the nucleic acid molecule) from which the nucleic acid is derived. The term "nucleic acid" is intended to include DNA and RNA and can be either double stranded or single stranded. In an embodiment, a nucleic acid molecule encodes a KLK-L Protein comprising an amino acid sequence as shown in SEQ.ID.NO. 2, 3, 14, 22, 23, 44, 45, 57, 58, 59, 60, 66, or 67, preferably a nucleic acid molecule comprising a nucleic acid sequence as shown in SEQ.ID.NO. 1, 13, 21, 43, 56, or 65.

The invention includes nucleic acid sequences complementary to a nucleic acid encoding a KLK-L Protein comprising an amino acid sequence as shown in SEQ.ID.NO. 2, 3, 14, 22, 23, 44, 45, 57, 58, 59, 60, 66, or 67, preferably the nucleic acid sequences complementary to a full nucleic acid sequence shown in SEQ.ID.NO. 1, 13, 21, 43, 56, or 65.

The invention includes nucleic acid molecules having substantial sequence identity or homology to nucleic acid sequences of the invention or encoding proteins having substantial identity or similarity to the amino acid sequence shown in in SEQ.ID.NO. 2, 3, 14, 22, 23, 44, 45, 57, 58, 59, 60, 66, or 67. Preferably, the nucleic acids have substantial sequence identity for example at least 30%, 35%, 40%, 45%, 50%, 55%, 60%, 65%, 70%, 75%, 80%, or 85% nucleic acid identity; more preferably 90% nucleic acid identity; and most preferably at least 95%, 96%, 97%, 98%, or 99% sequence identity. "Identity" as known in the art and used herein, is a relationship between two or more amino acid sequences or two or more nucleic acid sequences, as determined by comparing the sequences. It also refers to the degree of sequence relatedness between amino acid or nucleic acid sequences, as the case may be, as determined by the match between strings of such sequences. Identity and similarity are well known terms to skilled artisans and they can be calculated by conventional methods (for example see Computational Molecular Biology, Lesk, A. M. ed., Oxford University Press, New York, 1988; Biocomputing: Informatics and Genome Projects, Smith, D. W. ed., Academic Press, New York, 1993; Computer Analysis of Sequence Data, Part 1, Griffin, A. M. and Griffin, H. G. ads., Humana Press, New Jersey, 1994; Sequence Analysis in Molecular Biology, von Heinje, G. Acadmeic Press, 1987; and Sequence Analysis Primer, Gribskov, M. and Devereux, J. eds. M. Stockton Press, New York, 1991, Carillo, H. and Lipman, D., SIAM J. Applied Math. 48:1073, 1988). Methods which are designed to give the largest match between the sequences are generally preferred. Methods to determine identity and similarity are codified in publicly available computer programs including the GCG program package (Devereux J. et al., Nucleic Acids Research 12(1): 387, 1984); BLASTP, BLASTN, and FASTA (Atschul, S. F. et al. J. Molec. Biol. 215: 403–410, 1990). The BLAST X program is publicly available from NCBI and other sources (BLAST Manual, Altschul, S. et al. NCBI NLM NIH Bethesda, Md. 20894; Altschul, S. et al. J. Mol. Biol. 215: 403–410, 1990).

Isolated nucleic acid molecules encoding a KLK-L Protein, and having a sequence which differs from a nucleic acid sequence of the invention due to degeneracy in the genetic code are also within the scope of the invention. Such nucleic acids encode functionally equivalent proteins (e.g., a KLK-L Protein) but differ in sequence from the sequence of a KLK-L Protein due to degeneracy in the genetic code. As one example, DNA sequence polymorphisms within the nucleotide sequence of a KLK-L Protein may result in silent mutations which do not affect the amino acid sequence. Variations in one or more nucleotides may exist among individuals within a population due to natural allelic variation. Any and all such nucleic acid variations are within the scope of the invention. DNA sequence polymorphisms may also occur which lead to changes in the amino acid sequence of a KLK-L Protein. These amino acid polymorphisms are also within the scope of the present invention.

Another aspect of the invention provides a nucleic acid molecule which hybridizes under stringent conditions, preferably high stringency conditions to a nucleic acid molecule which comprises a sequence which encodes a KLK-L Protein having an amino acid sequence shown in SEQ.ID.NO. 2, 3, 14, 22, 23, 44, 45, 57, 58, 59, 60, 66, or 67. Appropriate stringency conditions which promote DNA hybridization are known to those skilled in the art, or can be found in Current Protocols in Molecular Biology, John Wiley & Sons, N.Y. (1989), 6.3.1–6.3.6. For example, 6.0× sodium chloride/sodium citrate (SSC) at about 45° C. followed by a wash of 2.0×SSC at 50° C. may be employed. The stringency may be selected based on the conditions used in the wash step. By way of example, the salt concentration in the wash step can be selected from a high stringency of about 0.2×SSC at 50° C. In addition, the temperature in the wash step can be at high stringency conditions, at about 65° C.

It will be appreciated that the invention includes nucleic acid molecules encoding a KLK-L Related Protein including truncations of a KLK-L Protein, and analogs of a KLK-L Protein as described herein. It will further be appreciated that variant forms of the nucleic acid molecules of the invention which arise by alternative splicing of an mRNA corresponding to a cDNA of the invention are encompassed by the invention. (See for example, splice variants of KLK-L5, SEQ.ID.NO. 58, 59, and 60.)

An isolated nucleic acid molecule of the invention which comprises DNA can be isolated by preparing a labelled nucleic acid probe based on all or part of a nucleic acid sequence of the invention. The labeled nucleic acid probe is used to screen an appropriate DNA library (e.g. a cDNA or genomic DNA library). For example, a cDNA library can be used to isolate a cDNA encoding a KLK-L Related Protein by screening the library with the labeled probe using standard techniques. Alternatively, a genomic DNA library can be similarly screened to isolate a genomic clone encompassing a gene encoding a KLK-L Related Protein. Nucleic acids isolated by screening of a cDNA or genomic DNA library can be sequenced by standard techniques.

An isolated nucleic acid molecule of the invention which is DNA can also be isolated by selectively amplifying a nucleic acid encoding a KLK-L Related Protein using the polymerase chain reaction (PCR) methods and cDNA or genomic DNA. It is possible to design synthetic oligonucleotide primers from the nucleotide sequence of the invention for use in PCR. A nucleic acid can be amplified from cDNA or genomic DNA using these oligonucleotide primers and standard PCR amplification techniques. The nucleic acid so amplified can be cloned into an appropriate vector and characterized by DNA sequence analysis. cDNA may be prepared from mRNA, by isolating total cellular mRNA by a variety of techniques, for example, by using the guanidinium-thiocynate extraction procedure of Chirgwin et al., Biochemistry, 18, 5294–5299 (1979). cDNA is then synthesized from the mRNA using reverse transcriptase (for example, Moloney MLV reverse transcriptase available from Gibco/BRL, Bethesda, Md., or AMV reverse transcriptase available from Seikagaku America, Inc., St. Petersburg, Fla.).

An isolated nucleic acid molecule of the invention which is RNA can be isolated by cloning a cDNA encoding a KLK-L Related Protein into an appropriate vector which allows for transcription of the cDNA to produce an RNA molecule which encodes a KLK-L Related Protein. For example, a cDNA can be cloned downstream of a bacteriophage promoter, (e.g. a T7 promoter) in a vector, cDNA can be transcribed in vitro with T7 polymerase, and the resultant RNA can be isolated by conventional techniques.

Nucleic acid molecules of the invention may be chemically synthesized using standard techniques. Methods of chemically synthesizing polydeoxynucleotides are known, including but not limited to solid-phase synthesis which, like peptide synthesis, has been fully automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373,071).

Determination of whether a particular nucleic acid molecule encodes a KLK-L Related Protein can be accomplished by expressing the cDNA in an appropriate host cell by standard techniques, and testing the expressed protein in the methods described herein. A cDNA encoding a KLK-L Related Protein can be sequenced by standard techniques, such as dideoxynucleotide chain termination or Maxam-Gilbert chemical sequencing, to determine the nucleic acid sequence and the predicted amino acid sequence of the encoded protein.

The initiation codon and untranslated sequences of a KLK-L Related Protein may be determined using computer software designed for the purpose, such as PC/Gene (IntelliGenetics Inc., Calif.). The intron-exon structure and the transcription regulatory sequences of a gene encoding a KLK-L Related Protein may be confirmed by using a nucleic acid molecule of the invention encoding a KLK-L Related Protein to probe a genomic DNA clone library. Regulatory elements can be identified using standard techniques. The function of the elements can be confirmed by using these elements to express a reporter gene such as the lacz gene which is operatively linked to the elements. These constructs may be introduced into cultured cells using conventional procedures or into non-human transgenic animal models. In addition to identifying regulatory elements in DNA, such constructs may also be used to identify nuclear proteins interacting with the elements, using techniques known in the art.

In a particular embodiment of the invention, the nucleic acid molecules isolated using the methods described herein are mutant klk-1 gene alleles. The mutant alleles may be isolated from individuals either known or proposed to have a genotype which contributes to the symptoms of for example, cancer (e.g. breast, testicular, brain, colon, and prostate cancer). Mutant alleles and mutant allele products may be used in therapeutic and diagnostic methods described herein. For example, a cDNA of a mutant klk-1 gene may be isolated using PCR as described herein, and the DNA sequence of the mutant allele may be compared to the normal allele to ascertain the mutation(s) responsible for the loss or alteration of function of the mutant gene product. A genomic library can also be constructed using DNA from an individual suspected of or known to carry a mutant allele, or a cDNA library can be constructed using RNA from tissue known, or suspected to express the mutant allele. A nucleic acid encoding a normal klk-1 gene or any suitable fragment thereof, may then be labeled and used as a probe to identify the corresponding mutant allele in such libraries. Clones containing mutant sequences can be purified and subjected to sequence analysis. In addition, an expression library can be constructed using cDNA from RNA isolated from a tissue of an individual known or suspected to express a mutant klk-1 allele. Gene products made by the putatively mutant tissue may be expressed and screened, for example using antibodies specific for a KLK-L Related Protein as described herein. Library clones identified using the antibodies can be purified and subjected to sequence analysis.

The sequence of a nucleic acid molecule of the invention, or a fragment of the molecule, may be inverted relative to its normal presentation for transcription to produce an antisense nucleic acid molecule. An antisense nucleic acid molecule may be constructed using chemical synthesis and enzymatic ligation reactions using procedures known in the art.

2. Proteins of the Invention

An amino acid sequence of a KLK-L Protein comprises a sequence as shown in Tables 1 to 5 or SEQ.ID.NO. 2, 3, 14, 22, 23, 44, 45, 57, 58, 59, 60, 66, or 67.

In addition to proteins comprising an amino acid sequence as shown in Tables 1 to 5 or SEQ.ID.NO. 2, 3, 14, 22, 23, 44, 45, 57, 58, 59, 60, 66, or 67, the proteins of the present invention include truncations of a KLK-L Protein, analogs of a KLK-L Protein, and proteins having sequence identity or similarity to a KLK-L Protein, and truncations thereof as described herein (i.e. included in KLK-L Related Proteins). Truncated proteins may comprise peptides of between 3 and 70 amino acid residues, ranging in size from a tripeptide to a 70 mer polypeptide.

The truncated proteins may have an amino group (—NH2), a hydrophobic group (for example, carbobenzoxyl, dansyl, or T-butyloxycarbonyl), an acetyl group, a 9-fluorenylmethoxy-carbonyl (PMOC) group, or a macromolecule including but not limited to lipid-fatty acid conjugates, polyethylene glycol, or carbohydrates at the amino terminal end. The truncated proteins may have a carboxyl group, an amido group, a T-butyloxycarbonyl group, or a macromolecule including but not limited to lipid-fatty acid conjugates, polyethylene glycol, or carbohydrates at the carboxy terminal end. The proteins of the invention may also include analogs of a KLK-L Protein, and/or truncations thereof as described herein, which may include, but are not limited to a KLK-L Protein, containing one or more amino acid substitutions, insertions, and/or deletions. Amino acid substitutions may be of a conserved or non-conserved nature. Conserved amino acid substitutions involve replacing one or more amino acids of a KLK-L Protein amino acid sequence with amino acids of similar charge, size, and/or hydrophobicity characteristics. When only conserved substitutions are made the resulting analog is preferably functionally equivalent to a KLK-L Protein. Non-conserved substitutions involve replacing one or more amino acids of the KLK-L Protein amino acid sequence with one or more amino acids which possess dissimilar charge, size, and/or hydrophobicity characteristics.

One or more amino acid insertions may be introduced into a KLK-L Protein. Amino acid insertions may consist of single amino acid residues or sequential amino acids ranging from 2 to 15 amino acids in length.

Deletions may consist of the removal of one or more amino acids, or discrete portions from a KLK-L Protein sequence. The deleted amino acids may or may not be contiguous. The lower limit length of the resulting analog with a deletion mutation is about 10 amino acids, preferably 20 to 40 amino acids.

The proteins of the invention include proteins with sequence identity or similarity to a KLK-L Protein and/or truncations thereof as described herein. Such KLK-L Proteins include proteins whose amino acid sequences are comprised of the amino acid sequences of KLK-L Protein regions from other species that hybridize under selected hybridization conditions (see discussion of stringent hybridization conditions herein) with a probe used to obtain a KLK-L Protein. These proteins will generally have the same regions which are characteristic of a KLK-L Protein. Preferably a protein will have substantial sequence identity for example, about 30%, 35%, 40%, 45%, 50%, 60%, 65%, 70%, 75%, 80%, or 85% identity, preferably 90% identity, more preferably at least 95%, 96%, 97%, 98%, or 99% identity, and most preferably 98% identity with an amino acid sequence shown in Tables 1 to 5 or SEQ.ID.NO. 2, 3, 14, 22, 23, 44, 45, 57, 58, 59, 60, 66, or 67.

A percent amino acid sequence homology, similarity or identity is calculated as the percentage of aligned amino acids that match the reference sequence using known methods as described herein.

The invention also contemplates isoforms of the proteins of the invention. An isoform contains the same number and kinds of amino acids as a protein of the invention, but the isoform has a different molecular structure. Isoforms contemplated by the present invention preferably have the same properties as a protein of the invention as described herein.

The present invention also includes KLK-L Related Proteins conjugated with a selected protein, or a marker protein (see below) to produce fusion proteins. Additionally, immunogenic portions of a KLK-L Protein and a KLK-L Protein Related Protein are within the scope of the invention.

A KLK-L Related Protein of the invention may be prepared using recombinant DNA methods. Accordingly, the nucleic acid molecules of the present invention having a sequence which encodes a KLK-L Related Protein of the invention may be incorporated in a known manner into an appropriate expression vector which ensures good expression of the protein. Possible expression vectors include but are not limited to cosmids, plasmids, or modified viruses (e.g. replication defective retroviruses, adenoviruses and adeno-associated viruses), so long as the vector is compatible with the host cell used.

The invention therefore contemplates a recombinant expression vector of the invention containing a nucleic acid molecule of the invention, and the necessary regulatory sequences for the transcription and translation of the inserted protein-sequence. Suitable regulatory sequences may be derived from a variety of sources, including bacterial, fungal, viral, mammalian, or insect genes (For example, see the regulatory sequences described in Goeddel, Gene Expression Technology: Methods in Enzymology 185, Academic Press, San Diego, Calif. (1990). Selection of appropriate regulatory sequences is dependent on the host cell chosen as discussed below, and may be readily accomplished by one of ordinary skill in the art. The necessary regulatory sequences may be supplied by the native KLK-L Protein and/or its flanking regions.

The invention further provides a recombinant expression vector comprising a DNA nucleic acid molecule of the invention cloned into the expression vector in an antisense orientation. That is, the DNA molecule is linked to a regulatory sequence in a manner which allows for expression, by transcription of the DNA molecule, of an RNA molecule which is antisense to the nucleic acid sequence of a protein of the invention or a fragment thereof. Regulatory sequences linked to the antisense nucleic acid can be chosen which direct the continuous expression of the antisense RNA molecule in a variety of cell types, for instance a viral promoter and/or enhancer, or regulatory sequences can be chosen which direct tissue or cell type specific expression of antisense RNA.

The recombinant expression vectors of the invention may also contain a marker gene which facilitates the selection of host cells transformed or transfected with a recombinant molecule of the invention. Examples of marker genes are genes encoding a protein such as G418 and hygromycin which confer resistance to certain drugs, β-galactosidase, chloramphenicol acetyltransferase, firefly luciferase, or an immunoglobulin or portion thereof such as the Fc portion of an immunoglobulin preferably IgG. The markers can be introduced on a separate vector from the nucleic acid of interest.

The recombinant expression vectors may also contain genes which encode a fusion moiety which provides increased expression of the recombinant protein; increased solubility of the recombinant protein; and aid in the purification of the target recombinant protein by acting as a ligand in affinity purification. For example, a proteolytic cleavage site may be added to the target recombinant protein to allow separation of the recombinant protein from the fusion moiety subsequent to purification of the fusion protein. Typical fusion expression vectors include pGEX (Amrad Corp., Melbourne, Australia), pMAL (New England Biolabs, Beverly, Mass.) and pRIT5 (Pharmacia, Piscataway, N.J.) which fuse glutathione S-transferase (GST), maltose E binding protein, or protein A, respectively, to the recombinant protein.

The recombinant expression vectors may be introduced into host cells to produce a transformant host cell. "Transformant host cells" include host cells which have been transformed or transfected with a recombinant expression vector of the invention. The terms "transformed with", "transfected with", "transformation" and "transfection" encompass the introduction of a nucleic acid (e.g. a vector) into a cell by one of many standard techniques. Prokaryotic cells can be transformed with a nucleic acid by, for example, electroporation or calcium-chloride mediated transformation. A nucleic acid can be introduced into mammalian cells via conventional techniques such as calcium phosphate or calcium chloride co-precipitation, DEAE-dextran-mediated transfection, lipofectin, electroporation or microinjection. Suitable methods for transforming and transfecting host cells can be found in Sambrook et al. (Molecular Cloning: A Laboratory Manual, 2nd Edition, Cold Spring Harbor Laboratory press (1989)), and other laboratory textbooks.

Suitable host cells include a wide variety of prokaryotic and eukaryotic host cells. For example, the proteins of the invention may be expressed in bacterial cells such as *E. coli*, insect cells (using baculovirus), yeast cells, or mammalian cells. Other suitable host cells can be found in Goeddel, Gene Expression Technology: Methods in Enzymology 185, Academic Press, San Diego, Calif. (1991).

A host cell may also be chosen which modulates the expression of an inserted nucleic acid sequence, or modifies (e.g. glycosylation or phosphorylation) and processes (e.g. cleaves) the protein in a desired fashion. Host systems or cell lines may be selected which have specific and characteristic mechanisms for post-translational processing and modification of proteins. For example, eukaryotic host cells including CHO, VERO, BHK, HeLA, COS, MDCK, 293, 3T3, and W138 may be used. For long-term high-yield stable expression of the protein, cell lines and host systems which stably express the gene product may be engineered.

Host cells and in particular cell lines produced using the methods described herein may be particularly useful in screening and evaluating compounds that modulate the activity of a KLK-L Related Protein.

The proteins of the invention may also be expressed in non-human transgenic animals including but not limited to mice, rats, rabbits, guinea pigs, micro-pigs, goats, sheep, pigs, non-human primates (e.g. baboons, monkeys, and chimpanzees) [see Hammer et al. (Nature 315:680–683, 1985), Palmiter et al. (Science 222:809–814, 1983). Brinster et al. (Proc Natl Acad. Sci USA 82:44384442, 1985), Palmiter and Brinster (Cell. 41:343–345, 1985) and U.S. Pat. No. 4,736,866)]. Procedures known in the art may be used to introduce a nucleic acid molecule of the invention encoding a KLK-L Related Protein into animals to produce the founder lines of transgenic animals. Such procedures include pronuclear microinjection, retrovirus mediated gene transfer into germ lines, gene targeting in embryonic stem cells, electroporation of embryos, and sperm-mediated gene transfer.

The present invention contemplates a transgenic animal that carries the KLK-L gene in all their cells, and animals which carry the transgene in some but not all their cells. The transgene may be integrated as a single transgene or in concatamers. The transgene may be selectively introduced into and activated in specific cell types (See for example, Lasko et al, 1992 Proc. Natl. Acad. Sci. USA 89:6236). The transgene may be integrated into the chromosomal site of the endogenous gene by gene targeting. The transgene may be selectively introduced into a particular cell type inactivating the endogenous gene in that cell type (See Gu et al Science 265: 103–106).

The expression of a recombinant KLK-L Related Protein in a transgenic animal may be assayed using standard techniques. Initial screening may be conducted by Southern Blot analysis, or PCR methods to analyze whether the transgene has been integrated. The level of mRNA expression in the tissues of transgenic animals may also be assessed using techniques including Northern blot analysis of tissue samples, in situ hybridization, and RT-PCR. Tissue may also be evaluated immunocytochemically using antibodies against KLK-L Protein.

Proteins of the invention may also be prepared by chemical synthesis using techniques well known in the chemistry of proteins such as solid phase synthesis (Merrifield, 1964, J. Am. Chem. Assoc. 85:2149–2154) or synthesis in homogenous solution (Houbenweyl, 1987, Methods of Organic Chemistry, ed. E. Wansch, Vol. 15 I and II, Thieme, Stuttgart).

N-terminal or C-terminal fusion proteins comprising a KLK-L Related Protein of the invention conjugated with other molecules, such as proteins, may be prepared by fusing, through recombinant techniques, the N-terminal or C-terminal of a KLK-L Related Protein, and the sequence of a selected protein or marker protein with a desired biological function. The resultant fusion proteins contain KLK-L Protein fused to the selected protein or marker protein as described herein. Examples of proteins which may be used to prepare fusion proteins include immunoglobulins, glutathione-S-transferase (GST), hemagglutinin (HA), and truncated myc.

3. Antibodies

KLK-L Related Proteins of the invention can be used to prepare antibodies specific for the proteins. Antibodies can be prepared which bind a distinct epitope in an unconserved region of the protein. An unconserved region of the protein is one that does not have substantial sequence homology to other proteins. A region from a conserved region such as a well-characterized domain can also be used to prepare an antibody to a conserved region of a KLK-L Related Protein. Antibodies having specificity for a KLK-L Related Protein may also be raised from fusion proteins created by expressing fusion proteins in bacteria as described herein.

The invention can employ intact monoclonal or polyclonal antibodies, and immunologically active fragments (e.g. a Fab, (Fab)$_2$ fragment, or Fab expression library fragments and epitope-binding fragments thereof), an antibody heavy chain, and antibody light chain, a genetically engineered single chain Fv molecule (Ladner et al, U.S. Pat. No. 4,946,778), or a chimeric antibody, for example, an antibody which contains the binding specificity of a murine antibody, but in which the remaining portions are of human origin. Antibodies including monoclonal and polyclonal antibodies, fragments and chimeras, may be prepared using methods known to those skilled in the art.

4. Applications of the Nucleic Acid Molecules. KLK-L Related Proteins, and Antibodies of the Invention The nucleic acid molecules, KLK-L Related Proteins, and antibodies of the invention may be used in the prognostic and diagnostic evaluation of cancer (e.g. breast, testicular, and prostate cancer) or other conditions, and the identification of subjects with a predisposition to cancer (Section 4.1.1 and 4.1.2). Methods for detecting nucleic acid molecules and KLK-L Related Proteins of the invention, can be used to monitor conditions including cancer, by detecting KLK-L Related Proteins and nucleic acid molecules encoding KLK-L Related Proteins. It would also be apparent to one skilled in the art that the methods described herein may be used to study the developmental expression of KLK-L Related Proteins and, accordingly, will provide further insight into the role of KLK-L Related Proteins. The applications of the present invention also include methods for the identification of compounds that modulate the biological activity of KLK-L or KLK-L Related Proteins (Section 4.2). The compounds, antibodies etc. may be used for the treatment of cancer (Section 4.3).

4.1 Diagnostic Methods

A variety of methods can be employed for the diagnostic and prognostic evaluation of conditions including cancer (e.g. breast, testicular, and prostate cancer), and the identification of subjects with a predisposition to such conditions. Such methods may, for example, utilize nucleic acid molecules of the invention, and fragments thereof, and antibodies directed against KLK-L Related Proteins, including peptide fragments. In particular, the nucleic acids and antibodies may be used, for example, for: (1) the detection of the presence of KLK-L mutations, or the detection of either over- or under-expression of KLK-L mRNA relative to a non-disorder state or the qualitative or quantitative detection of alternatively spliced forms of KLK-L transcripts which may correlate with certain conditions or susceptibility toward such conditions; and (2) the detection of either an over- or an under-abundance of KLK-L Related Proteins relative to a non-disorder state or the presence of a modified (e.g., less than full length) KLK-L Protein which correlates with a disorder state, or a progression toward a disorder state.

The methods described herein may be performed by utilizing pre-packaged diagnostic kits comprising at least one specific KLK-L nucleic acid or antibody described herein, which may be conveniently used, e.g., in clinical settings, to screen and diagnose patients and to screen and identify those individuals exhibiting a predisposition to developing a disorder.

Nucleic acid-based detection techniques are described, below, in Section 4.1.1. Peptide detection techniques are described, below, in Section 4.1.2. The samples that may be analyzed using the methods of the invention include those which are known or suspected to express KLK-L or contain KLK-L Related Proteins. The samples may be derived from a patient or a cell culture, and include but are not limited to biological fluids, tissue extracts, freshly harvested cells, and lysates of cells which have been incubated in cell cultures.

Oligonucleotides or longer fragments derived from any of the nucleic acid molecules of the invention may be used as targets in a microarray. The microarray can be used to simultaneously monitor the expression levels of large numbers of genes and to identify genetic variants, mutations, and polymorphisms. The information from the microarray may be used to determine gene function, to understand the genetic basis of a disorder, to diagnose a disorder, and to develop and monitor the activities of therapeutic agents.

The preparation, use, and analysis of microarrays are well known to a person skilled in the art. (See, for example, Brennan, T. M. et al. (1995) U.S. Pat. No. 5,474,796; Schena, et al. (1996) Proc. Natl. Acad. Sci. 93:10614–10619; Baldeschweiler et al. (1995), PCT Application WO95/251116; Shalon, D. et al. (1995) PCT application WO95/35505; Heller, R. A. et al. (1997) Proc. Natl. Acad. Sci. 94:2150–2155; and Heller, M. J. et al. (1997) U.S. Pat. No. 5,605,662.)

4.1.1 Methods for Detecting Nucleic Acid Molecules of the Invention

The nucleic acid molecules of the invention allow those skilled in the art to construct nucleotide probes for use in the detection of nucleic acid sequences of the invention in samples. Suitable probes include nucleic acid molecules based on nucleic acid sequences encoding at least 5 sequential amino acids from regions of a KLK-L Protein, preferably they comprise 15 to 30 nucleotides. A nucleotide probe may be labeled with a detectable substance such as a radioactive label which provides for an adequate signal and has sufficient half-life such as $^{32}P$, $^{3}H$, $^{14}C$ or the like. Other detectable substances which may be used include antigens that are recognized by a specific labeled antibody, fluorescent compounds, enzymes, antibodies specific for a labeled antigen, and luminescent compounds. An appropriate label may be selected having regard to the rate of hybridization and binding of the probe to the nucleotide to be detected and the amount of nucleotide available for hybridization. Labeled probes may be hybridized to nucleic acids on solid supports such as nitrocellulose filters or nylon membranes as generally described in Sambrook et al, 1989, Molecular Cloning, A Laboratory Manual (2nd ed.). The nucleic acid probes may be used to detect genes, preferably in human cells, that encode KLK-L Related Proteins. The nucleotide probes may also be useful in the diagnosis of cancer; in monitoring the progression of cancer; or monitoring a therapeutic treatment.

The probe may be used in hybridization techniques to detect genes that encode KLK-L Related Proteins. The technique generally involves contacting and incubating nucleic acids (e.g. recombinant DNA molecules, cloned genes) obtained from a sample from a patient or other cellular source with a probe of the present invention under conditions favorable for the specific annealing of the probes to complementary sequences in the nucleic acids. After incubation, the non-annealed nucleic acids are removed, and the presence of nucleic acids that have hybridized to the probe if any are detected.

The detection of nucleic acid molecules of the invention may involve the amplification of specific gene sequences using an amplification method such as PCR, followed by the analysis of the amplified molecules using techniques known to those skilled in the art. Suitable primers can be routinely designed by one of skill in the art.

Genomic DNA may be used in hybridization or amplification assays of biological samples to detect abnormalities involving klk-1 structure, including point mutations, insertions, deletions, and chromosomal rearrangements. For example, direct sequencing, single stranded conformational polymorphism analyses, heteroduplex analysis, denaturing gradient gel electrophoresis, chemical mismatch cleavage, and oligonucleotide hybridization may be utilized.

Genotyping techniques known to one skilled in the art can be used to type polymorphisms that are in close proximity to the mutations in a klk-1 gene. The polymorphisms may be used to identify individuals in families that are likely to carry mutations. If a polymorphism exhibits linkage disequalibrium with mutations in a klk-1 gene, it can also be used to screen for individuals in the general population likely to carry mutations. Polymorphisms which may be used include restriction fragment length polymorphisms (RFLPs), single-base polymorphisms, and simple sequence repeat polymorphisms (SSLPs).

A probe of the invention may be used to directly identify RFLPs. A probe or primer of the invention can additionally be used to isolate genomic clones such as YACs, BACs, PACs, cosmids, phage or plasmids. The DNA in the clones can be screened for SSLPs using hybridization or sequencing procedures.

Hybridization and amplification techniques described herein may be used to assay qualitative and quantitative aspects of klk-1 expression. For example, RNA may be isolated from a cell type or tissue known to express klk-1 and tested utilizing the hybridization (e.g. standard Northern analyses) or PCR techniques referred to herein. The techniques may be used to detect differences in transcript size which may be due to normal or abnormal alternative splicing. The techniques may be used to detect quantitative differences between levels of full length and/or alternatively splice transcripts detected in normal individuals relative to those individuals exhibiting cancer symptoms or other disease conditions.

The primers and probes may be used in the above described methods in situ i.e directly on tissue sections (fixed and/or frozen) of patient tissue obtained from biopsies or resections.

4.1.2. Methods for Detecting KLK-L Related Proteins

Antibodies specifically reactive with a KLK-L Related Protein, or derivatives, such as enzyme conjugates or labeled derivatives, may be used to detect KLK-L Related Proteins in various samples (e.g. biological materials). They may be used as diagnostic or prognostic reagents and they may be used to detect abnormalities in the level of KLK-L Related Proteins expression, or abnormalities in the structure, and/or temporal, tissue, cellular, or subcellular location of a KLK-L Related Protein. Antibodies may also be used to screen potentially therapeutic compounds in vitro to determine their effects on cancer, and other conditions. In vitro immunoassays may also be used to assess or monitor the efficacy of particular therapies. The antibodies of the invention may also be used in vitro to determine the level of KLK-L expression in cells genetically engineered to produce a KLK-L Related Protein.

The antibodies may be used in any known immunoassays which rely on the binding interaction between an antigenic determinant of a KLK-L Related Protein and the antibodies. Examples of such assays are radioimmunoassays, enzyme immunoassays (e.g. ELISA), immunofluorescence, immunoprecipitation, latex agglutination, hemagglutination, and histochemical tests. The antibodies may be used to detect and quantify KLK-L Related Proteins in a sample in order to determine its role in particular cellular events or pathological states, and to diagnose and treat such pathological states.

In particular, the antibodies of the invention may be used in immuno-histochemical analyses, for example, at the cellular and sub-subcellular level, to detect a KLK-L Related Protein, to localize it to particular cells and tissues, and to specific subcellular locations, and to quantitate the level of expression.

Cytochemical techniques known in the art for localizing antigens using light and electron microscopy may be used to detect a KLK-L Related Protein. Generally, an antibody of the invention may be labeled with a detectable substance and a KLK-L Related Protein may be localised in tissues and cells based upon the presence of the detectable substance. Examples of detectable substances include, but are not limited to, the following: radioisotopes (e.g., 3H, $^{14}$C, $^{35}$S, $^{125}$I, $^{131}$I), fluorescent labels (e.g., FITC, rhodamine, lanthanide phosphors), luminescent labels such as luminol, enzymatic labels (e.g., horseradish peroxidase, beta-galactosidase, luciferase, alkaline phosphatase, acetylcholinesterase), biotinyl groups (which can be detected by marked avidin e.g., streptavidin containing a fluorescent marker or enzymatic activity that can be detected by optical or calorimetric methods), predetermined polypeptide epitopes recognized by a secondary reporter (e.g., leucine zipper pair sequences, binding sites for secondary antibodies, metal binding domains, epitope tags). In some embodiments, labels are attached via spacer arms of various lengths to reduce potential steric hindrance. Antibodies may also be coupled to electron dense substances, such as ferritin or colloidal gold, which are readily visualised by electron microscopy.

The antibody or sample may be immobilized on a carrier or solid support which is capable of immobilizing cells, antibodies etc. For example, the carrier or support may be nitrocellulose, or glass, polyacrylamides, gabbros, and magnetite. The support material may have any possible configuration including spherical (e.g. bead), cylindrical (e.g. inside surface of a test tube or well, or the external surface of a rod), or flat (e.g. sheet, test strip). Indirect methods may also be employed in which the primary antigen-antibody reaction is amplified by the introduction of a second antibody, having specificity for the antibody reactive against KLK-L Related Protein. By way of example, if the antibody having specificity against a KLK-L Related Protein is a rabbit IgG antibody, the second antibody may be goat anti-rabbit gamma-globulin labeled with a detectable substance as described herein.

Where a radioactive label is used as a detectable substance, a KLK-L Related Protein may be localized by radioautography. The results of radioautography may be quantitated by determining the density of particles in the radioautographs by various optical methods, or by counting the grains.

4.2 Methods for Identifying or Evaluating Substances/Compounds

The methods described herein are designed to identify substances that modulate the biological activity of a KLK-L Related Protein including substances that bind to KLK-L Related Proteins, or bind to other proteins that interact with a KLK-L Related Protein, to compounds that interfere with, or enhance the interaction of a KLK-L Related Protein and substances that bind to the KLK-L Related Protein or other proteins that interact with a KLK-L Related Protein. Methods are also utilized that identify compounds that bind to KLK-L regulatory sequences.

The substances and compounds identified using the methods of the invention include but are not limited to peptides such as soluble peptides including Ig-tailed fusion peptides, members of random peptide libraries and combinatorial chemistry-derived molecular libraries made of D- and/or L-configuration amino acids, phosphopeptides (including members of random or partially degenerate, directed phosphopeptide libraries), antibodies [e.g. polyclonal, monoclonal, humanized, anti-idiotypic, chimeric, single chain antibodies, fragments, (e.g. Fab, F(ab)$_2$, and Fab expression library fragments, and epitope-binding fragments thereof)], and small organic or inorganic molecules. The substance or compound may be an endogenous physiological compound or it may be a natural or synthetic compound.

Substances which modulate a KLK-L Related Protein can be identified based on their ability to bind to a KLK-L Related Protein. Therefore, the invention also provides methods for identifying substances which bind to a KLK-L Related Protein. Substances identified using the methods of the invention may be isolated, cloned and sequenced using conventional techniques. A substance that associates with a polypeptide of the invention may be an agonist or antagonist of the biological or immunological activity of a polypeptide of the invention.

The term "agonist", refers to a molecule that increases the amount of, or prolongs the duration of, the activity of the polypeptide. The term "antagonist" refers to a molecule which decreases the biological or immunological activity of the polypeptide. Agonists and antagonists may include proteins, nucleic acids, carbohydrates, or any other molecules that associate with a polypeptide of the invention.

Substances which can bind with a KLK-L Related Protein may be identified by reacting a KLK-L Related Protein with a test substance which potentially binds to a KLK-L Related Protein, under conditions which permit the formation of substance-KLK-L Related Protein complexes and removing and/or detecting the complexes. The complexes can be detected by assaying for substance-KLK-L Related Protein complexes, for free substance, or for non-complexed KLK-L Related Protein. Conditions which permit the formation of substance-KLK-L Related Protein complexes may be selected having regard to factors such as the nature and amounts of the substance and the protein.

The substance-protein complex, free substance or non-complexed proteins may be isolated by conventional isolation techniques, for example, salting out, chromatography, electrophoresis, gel filtration, fractionation, absorption, polyacrylamide gel electrophoresis, agglutination, or combinations thereof. To facilitate the assay of the components, antibody against KLK-L Related Protein or the substance, or labeled KLK-L Related Protein, or a labeled substance may be utilized. The antibodies, proteins, or substances may be labeled with a detectable substance as described above.

A KLK-L Related Protein, or the substance used in the method of the invention may be insolubilized. For example, a KLK-L Related Protein, or substance may be bound to a suitable carrier such as agarose, cellulose, dextran. Sephadex, Sepharose, carboxymethyl cellulose polystyrene, filter paper, ion-exchange resin, plastic film, plastic tube, glass beads, polyamine-methyl vinyl-ether-maleic acid copolymer, amino acid copolymer, ethylene-maleic acid copolymer, nylon, silk, etc. The carrier may be in the shape of, for example, a tube, test plate, beads, disc, sphere etc. The insolubilized protein or substance may be prepared by reacting the material with a suitable insoluble carrier using known chemical or physical methods, for example, cyanogen bromide coupling.

The invention also contemplates a method for evaluating a compound for its ability to modulate the biological activity of a KLK-L Related Protein of the invention, by assaying for an agonist or antagonist (i.e. enhancer or inhibitor) of the binding of a KLK-L Related Protein with a substance which binds with a KLK-L Related Protein. The basic method for evaluating if a compound is an agonist or antagonist of the binding of a KLK-L Related Protein and a substance that binds to the protein, is to prepare a reaction mixture containing the KLK-L Related Protein and the substance under conditions which permit the formation of substance-KLK-L Related Protein complexes, in the presence of a test compound. The test compound may be initially added to the mixture, or may be added subsequent to the addition of the KLK-L Related Protein and substance. Control reaction mixtures without the test compound or with a placebo are also prepared. The formation of complexes is detected and the formation of complexes in the control reaction but not in the reaction mixture indicates that the test compound interferes with the interaction of the KLK-L Related Protein and substance. The reactions may be carried out in the liquid phase or the KLK-L Related Protein, substance, or test compound may be immobilized as described herein. The ability of a compound to modulate the biological activity of a KLK-L Related Protein of the invention may be tested by determining the biological effects on cells.

It will be understood that the agonists and antagonists i.e. inhibitors and enhancers that can be assayed using the methods of the invention may act on one or more of the binding sites on the protein or substance including agonist binding sites, competitive antagonist binding sites, non-competitive antagonist binding sites or allosteric sites.

The invention also makes it possible to screen for antagonists that inhibit the effects of an agonist of the interaction of KLK-L Related Protein with a substance which is capable of binding to the KLK-L Related Protein. Thus, the invention may be used to assay for a compound that competes for the same binding site of a KLK-L Related Protein.

The invention also contemplates methods for identifying compounds that bind to proteins that interact with a KLK-L Related Protein. Protein-protein interactions may be identified using conventional methods such as co-immunoprecipitation, crosslinking and co-purification through gradients or chromatographic columns. Methods may also be employed that result in the simultaneous identification of genes which encode proteins interacting with a KLK-L Related Protein. These methods include probing expression libraries with labeled KLK-L Related Protein.

Two-hybrid systems may also be used to detect protein interactions in vivo. Generally, plasmids are constructed that encode two hybrid proteins. A first hybrid protein consists of the DNA-binding domain of a transcription activator protein fused to a KLK-L Related Protein, and the second hybrid protein consists of the transcription activator protein's activator domain fused to an unknown protein encoded by a cDNA which has been recombined into the plasmid as part of a cDNA library. The plasmids are transformed into a strain of yeast (e.g. *S. cerevisiae*) that contains a reporter gene (e.g. lacZ, luciferase, alkaline phosphatase, horseradish peroxidase) whose regulatory region contains the transcription activator's binding site. The hybrid proteins alone cannot activate the transcription of the reporter gene. However, interaction of the two hybrid proteins reconstitutes the functional activator protein and results in expression of the reporter gene, which is detected by an assay for the reporter gene product.

It will be appreciated that fusion proteins may be used in the above-described methods. In particular, KLK-L Related Proteins fused to a glutathione-S-transferase may be used in the methods.

The reagents suitable for applying the methods of the invention to evaluate compounds that modulate a KLK-L Related Protein may be packaged into convenient kits providing the necessary materials packaged into suitable containers. The kits may also include suitable supports useful in performing the methods of the invention.

4.3 Compositions and Treatments

The proteins of the invention, substances or compounds identified by the methods described herein, antibodies, and antisense nucleic acid molecules of the invention may be used for modulating the biological activity of a KLK-L Related Protein, and they may be used in the treatment of conditions such as cancer (e.g. prostate, testicular, brain, uterine, thymus, ovarian, colon, ovarian, or breast cancer). Accordingly, the substances, antibodies, peptides, and compounds may be formulated into pharmaceutical compositions for administration to subjects in a biologically compatible form suitable for administration in vivo. By "biologically compatible form suitable for administration in vivo" is meant a form of the active substance to be administered in which any toxic effects are outweighed by the therapeutic effects. The active substances may be administered to living organisms including humans, and animals. Administration of a therapeutically active amount of a pharmaceutical composition of the present invention is defined as an amount effective, at dosages and for periods of time necessary to achieve the desired result. For example, a therapeutically active amount of a substance may vary according to factors such as the disease state, age, sex, and weight of the individual, and the ability of antibody to elicit a desired response in the individual. Dosage regima may be adjusted to provide the optimum therapeutic response. For example, several divided doses may be administered daily or the dose may be proportionally reduced as indicated by the exigencies of the therapeutic situation.

The active substance may be administered in a convenient manner such as by injection (subcutaneous, intravenous, etc.), oral administration, inhalation, transdermal application, or rectal administration. Depending on the route of administration, the active substance may be coated in a material to protect the substance from the action of enzymes, acids and other natural conditions that may inactivate the substance.

The compositions described herein can be prepared by per se known methods for the preparation of pharmaceutically acceptable compositions which can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985). On this basis, the compositions include, albeit not exclusively, solutions of the active substances in association with one or more pharmaceutically acceptable vehicles or diluents, and contained in buffered solutions with a suitable pH and iso-osmotic with the physiological fluids.

Based upon their homology to genes encoding kallikrein, nucleic acid molecules of the invention may be also useful in the treatment of conditions such as hypertension, cardiac hypertrophy, arthritis, inflammatory disorders, neurological disorders, and blood clotting disorders.

Vectors derived from retroviruses, adenovirus, herpes or vaccinia viruses, or from various bacterial plasmids, may be used to deliver nucleic acid molecules to a targeted organ, tissue, or cell population. Methods well known to those skilled in the art may be used to construct recombinant vectors which will express antisense nucleic acid molecules of the invention. (See, for example, the techniques described in Sambrook et al (supra) and Ausubel et al (supra)).

The nucleic acid molecules comprising full length cDNA sequences and/or their regulatory elements enable a skilled artisan to use sequences encoding a protein of the invention as an investigative tool in sense (Youssoufian H and H F Lodish 1993 Mol Cell Biol 13:98–104) or antisense (Eguchi et al (1991) Annu Rev Biochem 60:631–652) regulation of gene function. Such technology is well known in the art, and sense or antisense oligomers, or larger fragments, can be designed from various locations along the coding or control regions.

Genes encoding a protein of the invention can be turned off by transfecting a cell or tissue with vectors which express high levels of a desired KLK-L-encoding fragment. Such constructs can inundate cells with untranslatable sense or antisense sequences. Even in the absence of integration into the DNA, such vectors may continue to transcribe RNA molecules until all copies are disabled by endogenous nucleases.

Modifications of gene expression can be obtained by designing antisense molecules, DNA, RNA or PNA, to the regulatory regions of a gene encoding a protein of the invention, ie, the promoters, enhancers, and introns. Preferably, oligonucleotides are derived from the transcription initiation site, eg, between −10 and +10 regions of the leader sequence. The antisense molecules may also be designed so that they block translation of mRNA by preventing the transcript from binding to ribosomes. Inhibition may also be achieved using "triple helix" base-pairing methodology. Triple helix pairing compromises the ability of the double helix to open sufficiently for the binding of polymerases, transcription factors, or regulatory molecules. Therapeutic advances using triplex DNA were reviewed by Gee J E et al (In: Huber B E and B I Carr (1994) Molecular and Immunologic Approaches, Futura Publishing Co, Mt Kisco N.Y.).

Ribozymes are enzymatic RNA molecules that catalyze the specific cleavage of RNA. Ribozymes act by sequence-specific hybridization of the ribozyme molecule to complementary target RNA, followed by endonucleolytic cleavage. The invention therefore contemplates engineered hammerhead motif ribozyme molecules that can specifically and efficiently catalyze endonucleolytic cleavage of sequences encoding a protein of the invention.

Specific ribozyme cleavage sites within any potential RNA target may initially be identified by scanning the target molecule for ribozyme cleavage sites which include the following sequences, GUA, GUU and GUC. Once the sites are identified, short RNA sequences of between 15 and 20 ribonucleotides corresponding to the region of the target gene containing the cleavage site may be evaluated for secondary structural features which may render the oligonucleotide inoperable. The suitability of candidate targets may also be determined by testing accessibility to hybridization with complementary oligonucleotides using ribonuclease protection assays.

Methods for introducing vectors into cells or tissues include those methods discussed herein and which are suitable for in vivo, in vitro and ex vivo therapy. For ex vivo therapy, vectors may be introduced into stem cells obtained from a patient and clonally propagated for autologous transplant into the same patient (See U.S. Pat. Nos. 5,399,493 and 5,437.994). Delivery by transfection and by liposome are well known in the art.

The nucleic acid molecules disclosed herein may also be used in molecular biology techniques that have not yet been developed, provided the new techniques rely on properties of nucleotide sequences that are currently known, including but not limited to such properties as the triplet genetic code and specific base pair interactions.

The invention also provides methods for studying the function of a polypeptide of the invention. Cells, tissues, and non-human animals lacking in expression or partially lacking in expression of a nucleic acid molecule or gene of the invention may be developed using recombinant expression vectors of the invention having specific deletion or insertion mutations in the gene. A recombinant expression vector may be used to inactivate or alter the endogenous gene by homologous recombination, and thereby create a deficient cell, tissue, or animal.

Null alleles may be generated in cells, such as embryonic stem cells by deletion mutation. A recombinant gene may also be engineered to contain an insertion mutation that inactivates the gene. Such a construct may then be introduced into a cell, such as an embryonic stem cell, by a technique such as transfection, electroporation, injection etc. Cells lacking an intact gene may then be identified, for example by Southern blotting, Northern Blotting, or by assaying for expression of the encoded polypeptide using the methods described herein. Such cells may then be fused to embryonic stem cells to generate transgenic non-human animals deficient in a polypeptide of the invention. Germline transmission of the mutation may be achieved, for example, by aggregating the embryonic stem cells with early stage embryos, such as 8 cell embryos, in vitro; transferring the resulting blastocysts into recipient females and; generating germline transmission of the resulting aggregation chimeras. Such a mutant animal may be used to define specific cell populations, developmental patterns and in vivo processes, normally dependent on gene expression.

The invention thus provides a transgenic non-human mammal all of whose germ cells and somatic cells contain a recombinant expression vector that inactivates or alters a gene encoding a KLK-L Related Protein. In an embodiment the invention provides a transgenic non-human mammal all of whose germ cells and somatic cells contain a recombinant expression vector that inactivates or alters a gene encoding a KLK-L Related Protein resulting in a KLK-L Related Protein associated pathology. Further the invention provides a transgenic nonhuman mammal which doe not express a KLK-L Related Protein of the invention. In an embodiment, the invention provides a transgenic non-human mammal which doe not express a KLK-L Related Protein of the invention resulting in a KLK-L Related Protein associated pathology. A KLK-L Related Protein pathology refers to a phenotype observed for a KLK-L Related Protein homozygous mutant.

A transgenic non-human animal includes but is not limited to mouse, rat, rabbit, sheep, hamster, dog, guinea pig, micro-pig, pig, cat, goat, and non-human primates, preferably mouse.

The invention also provides a transgenic non-human animal assay system which provides a model system for testing for an agent that reduces or inhibits a pathology associated with an KLK-L Related Protein, preferably a KLK-L Related Protein associated pathology, comprising:

(a) administering the agent to a transgenic non-human animal of the invention; and (b) determining whether said agent reduces or inhibits the pathology (e.g. KLK-L Related Protein associated pathology) in the transgenic non-human animal relative to a transgenic non-human animal of step (a) which has not been administered the agent.

The agent may be useful in the treatment and prophylaxis of conditions such as cancer as discussed herein. The agents may also be incorporated in a pharmaceutical composition as described herein.

The activity of the proteins, substances, compounds, antibodies, nucleic acid molecules, agents, and compositions of the invention may be confirmed in animal experimental model systems. Therapeutic efficacy and toxicity may be determined by standard pharmaceutical procedures in cell cultures or with experimental animals, such as by calculating the $ED_{50}$ (the dose therapeutically effective in 50% of the population) or $LD_{50}$ (the dose lethal to 50% of the population) statistics. The therapeutic index is the dose ratio of therapeutic to toxic effects and it can be expressed as the $ED_{50}/LD_{50}$ ratio. Pharmaceutical compositions which exhibit large therapeutic indices are preferred.

The following non-limiting examples are illustrative of the present invention:

EXAMPLES

Example 1

Materials and Methods

Identification of Positive Pac and Bac Genomic Clones from a Human Genomic DNA Library The sequence of PSA, KLK1, KLK2, NES1 and Zyme genes is already known. Polymerase chain reaction (PCR)-based amplification protocols have been developed which allowed generation of PCR products specific for each one of these genes. Using these PCR products as probes, labeled with $^{32}$P, a human genomic DNA PAC library and a human genomic DNA BAC library was screened for the purpose of identifying positive clones of approximately 100–150 Kb long. The general strategies for these experiments have been published elsewhere (14). The genomic libraries were spotted in duplicate on nylon membranes and positive clones were further confirmed by Southern blot analysis as described (14).

DNA Sequences on Chromosome 19

The Lawrence Livermore National Laboratory participates in the sequencing of the human genome project and focuses on sequencing chromosome 19. Large sequencing information on this chromosome is available at the website of the Lawrence Livermore National Laboratory (http://www-bio.llnl.gov/genome/gemnome.html).

Figure 1:
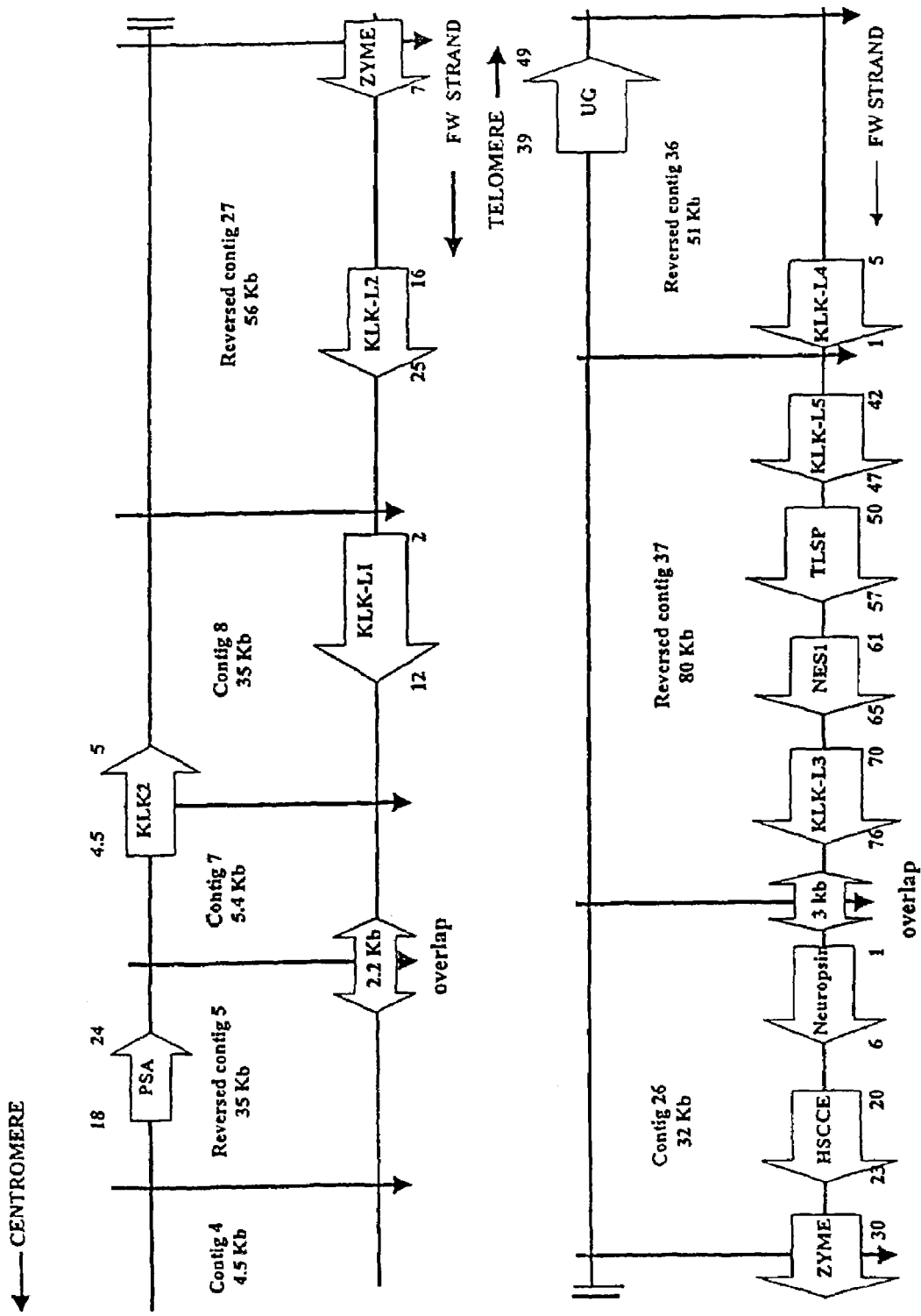
FIG. 1 shows an approximate 300 Kb of contiguous genomic sequence around chromosome 19q13.3–q13.4 represented by 8 contigs, each one shown with its length in Kb. The contig numbers refer to those reported in the Lawrence Livermore National Laboratory website. Note the localization of the seven known genes (PSA, KLK2, Zyme, NES1, HSCCE, neuropsin and TLSP) (see abbreviations for full names of these genes). All genes are represented with arrows denoting the direction of transcription. The gene with no homology to human kallikreins is termed UG (unknown gene). The five new kallikrein-like genes (KLK-L1 to KLK-L5) were numbered from the most centromeric to the most telomeric. Numbers just below or just above the arrows indicate appropriate Kb lengths in each contig. Gene lengths and distances between genes are rounded to the nearest 6.5 kb. The site of the gap is marked with an asterisk.

Approximately 300 Kb of genomic sequences were obtained from that website, encompassing a region on chromosome 19q13.3–13.4, where the known kallikrein genes are localized. This 300 Kb of sequence is represented by 8 contigs of variable lengths. By using a number of different computer programs, an almost contiguous sequence of the region was established as shown diagramatically in FIG. 1 and FIG. 28. Some of the contigs were reversed as shown in FIG. 1 in order to reconstruct the area on both strands of DNA.

By using the published sequences of PSA, KLK2, NES1 and Zyme and the computer software BLAST 2, using alignment strategies, the relative positions of these genes on the contiguous map were identified (FIG. 28). These known genes served as hallmarks for further studies. An EcoR1 restriction map of the area is also available at the website of the Lawrence Livermore National Laboratory. Using this restriction map and the computer program WebCutter (http://www.firstmarket.com/cutter/cut2.html), a restriction study analysis of the available sequence was performed to further confirm the assignment and relative positions of these contigs along chromosome 19. The obtained configuration and the relative location of the known genes are presented in FIG. 1.

Gene Prediction Analysis

For exon prediction analysis of the whole genomic area, a number of different computer programs were used. All the programs were initially tested using known genomic sequences of the PSA, Zyme, and NES1 genes. The more reliable computer programs, GeneBuilder (gene prediction), GeneBuilder (exon prediction), Grail 2 and GENEID-3 were selected for further use.

Protein Homology Searching

Putative exons of the new genes were first translated to the corresponding amino acid sequences. BLAST homology searching for the proteins encoded by the exons of the putative new genes were performed using the BLASTP program and the Genbank databases.

Results

Relative Position of PSA, KLK2, Zyme and NES1 on Chromosome 19

Screening of the human BAC library identified two clones which were positive for the Zyme gene (clones BAC 288H1 and BAC 76F7). These BACs were further analyzed by PCR and primers specific for PSA, NES1, KLK1 and KLK2. These analyses indicated that both BACs were positive for Zyme, PSA and KLK2 and negative for KLK1 and NES1 genes.

Screening of the human PAC genomic library identified a PAC clone which was positive for NES1 (clone PAC 34B1). Further PCR analysis indicated that this PAC clone was positive for NES1 and KLK1 genes and negative for PSA, KLK2 and Zyme. Combination of this information with the EcoR1 restriction map of the region allowed establishment of the relative positions of these four genes. PSA is the most centromeric, followed by KLK2, Zyme and NES1. Further alignment of the known sequences of these genes with the 300 Kb contig enabled precise localization of all four genes and determination of the direction of transcription, as shown by the arrows in FIG. 1. The KLK1 gene sequence was not identified on any of these contigs and appears to be further telomeric to NES1 (since it is co-localized on the same PAC as NES1).

Identification of New Genes

A set of rules was used to consider the presence of a new gene in the genomic area of interest as follows:

1. Clusters of at least 3 exons should be found.
2. Only exons with high prediction score ("good" or "excellent" quality, as indicated by the searching programs) were considered for the construction of the putative new genes.
3. Exons predicted were reliable only if they were identified by at least two different exon prediction programs.

By using this strategy, eleven putative new genes were identified of which three were found on subsequent homology analysis to be known genes not previously mapped i.e. the human stratum corneum chymotrypsin enzyme (HSCCE), human neuropsin, and trypsin-like serine protease (TLSP). Their relative location is shown in FIG. 1. The five genes all have variable homologies with known human or animal kallikrein proteins and/or other known serine proteases (depicted as KLK-L1, KLK-L2, KLK-L3, KLK-L4 and KLK-L5 in FIG. 1 and KLK-L1 to KLK-L6 in FIG. 28).

In Tables 1 to 5, the preliminary exon structure and partial protein sequence for each one of the newly identified genes is shown. In Table 6, some proteins are presented which appear, on preliminary analysis, to be homologous to the proteins encoded by the putative new genes. SEQ. ID. NOs. 2, 3, 14, 22, 23, 44, 45, 57, 58, 59, 60, 66, and 67 show amino acid sequences of KLK-L1–KLK-L6, and SEQ. ID. NOs. 1, 13, 21, 43, 56, and 65 show nucleic acid sequences of the genes encoding KLK-L1–KLK-L6.

Discussion

Prediction of protein-coding genes in newly sequenced DNA becomes very important after the establishment of large genome sequencing projects. This problem is complicated due to the exon-intron structure of the eukaryotic genes which interrupts the coding sequence in many unequal parts. In order to predict the protein-coding exons and overall gene structure, a number of computer programs were developed. All these programs are based on the combination of potential functional signals with the global statistical properties of known protein-coding regions (15). However, the most powerful approach for gene structure prediction is to combine information about potential functional signals (splice sites, translation start or stop signal etc.) together with the statistical properties of coding sequences (coding potential) along with information about homologies between the predicted protein and known protein families (16).

In mouse and rat, kallikreins are encoded by large multigene families and these genes tend to cluster in groups with a distance as small as 3.3–7.0 Kb (3). A strong conservation of gene order between human chromosome 19q13.1–q13.4 and 17 loci in a 20-cM proximal part of mouse chromosome 7, including the kallikrein locus, has been documented (17).

In humans, only a few kallikrein genes were identified. In fact, only KLK1, KLK2 and KLK3 (PSA) are considered to represent the human kallikrein gene family (9), The work described herein provides strong evidence that a large number of kallikrein-like genes are clustered within a 300 Kb region around chromosome 19q13.2–q13.4. The three established human kallikreins (KLK1, KLK2, KLK3), Zyme and NES1, as well as the stratum corneum chymotryptic enzyme, neuropsin, and TLSP (trypsin-like serine protease) and another five new genes KLK-L1 to KLK-L5, may constitute a large gene family. This will bring the total number of kallikrein or kallikrein-like genes in this region of chromosome 19 to thirteen.

The human stratum corneum chymotryptic enzyme (19), neuropsin (20) and trypsin-like serine protease (TLSP) (21) are three previously characterized genes which have many structural similarities with the kallikreins and other members of the serine protease family. However, they have not been mapped in the past. Their precise mapping in the region of the kallikrein gene family indicates that these three genes, along with the ones that were newly identified, or are already known, constitute a family that likely originated by duplication of an ancestral gene. The relative localization of all these genes is depicted in FIG. 1.

Kallikrein genes are a subfamily of serine proteases, traditionally characterized by their ability to liberate lysyl-bradykinin (kallidin) from kininogen (18). More recently, however, a new, structural concept has emerged to describe kallikreins. From accumulated sequence data, it is now clear that the mouse has many genes with high homology to kallikrein coding sequences (19–20). Richard and co-workers have contributed to the concept of a "kallikrein multi-gene family" to refer to these genes (21–22). This definition is not based much on specific enzymatic function of the gene product, but more on its sequence homology and their close linkage on mouse chromosome 7. In humans, only KLK1 meets the functional definition of a kallikrein. KLK2 has trypsin-like enzymatic activity and KLK3 (PSA) has very weak chymotrypsin-like enzymatic activity. These activities of KLK2 and KLK3 are not known to liberate biologically active peptides from precursors. Based on the newer definition, members of the kallikrein family include, not only the gene for the kallikrein enzyme, but also genes encoding other homologous proteases, including the enzyme that processes the precursors of the nerve growth factor and epidermal growth factor (8). Therefore, it is important to note the clear distinction between the enzyme kallikrein and a kallikrein or a kallikrein-like gene.

In carrying out the study only exons were considered which were predicted with "good" or "excellent" quality and only exons were considered which were predicted by at least two different programs. Moreover, the presence of a putative gene was only considered when at least three exons clustered coordinately in that region. Additional evidence that these new genes are indeed homologous to the known kallikreins and other serine proteases comes from comparison of the intron phases. As published previously (14), trypsinogen, PSA and NES1 have 5 coding exons of which the first has intron phase I (the intron occurs after the first nucleotide of the codon), the second has intron phase 11 (the intron occurs after the second nucleotide and the codon), the third has intron phase I and the fourth has intron phase 0 (the intron occurs between codons). The fifth exon contains the stop codon. The intron phases of the predicted new kallikrein-like genes follow these rules and are shown in the respective tables. Further support comes from the identification in the new genes, of the conserved amino acids of the catalytic domain of the serine proteases, as presented in Tables 1–5.

In order to test the accuracy of the computer programs, known genomic areas containing the PSA, Zyme and KLK2 genes were tested. Two of these programs (Grail 2 and GeneBuilder) were able to detect about 95% of the tested known genes. Matches with expressed sequence tag sequences (EST) can also be employed for gene structure prediction in the GeneBuilder program and this can significantly improve the power of the program especially at high stringency (e.g. >95% homology).

In mouse, ten of the kallikrein genes appear to be pseudogenes (9).

Example 2

PROSTASE/KLK-L1 in Prostate and Breast Tissues

The fine mapping of the prostase/KLK-L1 gene and its chromosomal localization in relation to a number of other homologous genes also mapping to the same region are described. In addition, extensive tissue expression studies were carried out that demonstrate that, in addition to prostate (which shows the highest expression), that prostase/KLK-L1 is also expressed in female breasts, testis, adrenals, uterus, colon, thyroid, brain, spinal cord and salivary glands. Furthermore, the gene is up-regulated by androgens and progestins in the breast carcinoma cell line BT-474.

Materials and Methods

DNA Sequences on Chromosome 19

Large DNA sequencing data for chromosome 19 is available at the web site of the Lawrence Livermore National Laboratory (LLNL) (http://www-bio.llnl.gov/genome/genome.html). Approximately 300 Kb of genomic sequence was obtained from that web site, encompassing a region on chromosome 19q13.3–13.4, where the known kallikrein genes are localized. This sequence is represented by 9 contigs of variable lengths. By using the sequences of PSA, KLK2, NES1 and protease M and the alignment program BLAST 2 (37), the relative positions of these genes on the contiguous map were located.

Gene Prediction Analysis

For exon prediction analysis of the whole genomic area, a number of different computer programs were used. Originally all these programs were tested using the known genomic sequences of the PSA, protease M and NES1 genes. The most reliable computer programs GeneBuilder (gene prediction)[http://125.itba.mi.cnr.it/~webgene/genebuilder.html] GeneBuilder (exon prediction) [http://125.itba.mi.cnr.it/~webgene/genebuilder.html], Grail 2 [http://compbio.ornl.gov], and GENEID-3 [http://apolo.imim.es/geneid.htmll] were selected for further use.

Protein Homology Searching

Putative exons of the newly identified gene were first translated to the corresponding amino acid sequences. BLAST homology searching for the proteins encoded by the exons were performed using the BLASTP program and the GenBank databases (37).

Searching Expressed Sequence Tags (ESTs)

Sequence homology searching was performed using the BLASTN alogrithm (37) on the National Center for Biotechnology Information web server (http://www ncbi.nim.nih.gov/BLAST/) against the human EST database (dbEST). Clones with >95% homology were obtained from the I.M.A.G.E. (38) consortium through Research Genetics Inc. Huntsville, Ala. and from The Institute for Genomic Research (TIGR) (http://WWW.TIGR.ORG/tdb/tdb.html) (Table 7). Clones were propagated, purified and then sequenced from both directions with an automated sequencer, using insert-flanking vector primers.

Breast Cancer Cell Line and Stimulation Experiments

The breast cancer cell line BT-474 was purchased from the American Type Culture Collection (ATCC), Rockville, Md. BT474 cells were cultured in RPMI media (Gibco BRL, Gaithersburg, Md.) supplemented with glutamine (200 mmol/L), bovine insulin (10 mg/L), fetal bovine serum (10%), antibiotics and antimycotics, in plastic flasks, to near confluency. The cells were then aliquoted into 24-well tissue culture plates and cultured to 50% confluency. 24 hours before the experiments, the culture media were changed into phenol red-free media containing 10% charcoal-stripped fetal bovine serum. For stimulation experiments, various steroid hormones dissolved in 100% ethanol were added into the culture media, at a final concentration of $10^{-8}$ M. Cells stimulated with 100% ethanol were included as controls. The cells were cultured for 24 hours, then harvested for mRNA extraction.

Reverse Transcriptase Polymerase Chain Reaction

Total RNA was extracted from the breast cancer cells using Trizol reagent (Gibco BRL) following the manufacturer's instructions. RNA concentration was determined spectrophotometrically. 2 μg of total RNA was reverse transcribed into first strand cDNA using the Superscript™ preamplification system (Gibco BRL). The final volume was 20 μl. Based on the combined information obtained from the predicted genomic structure of the new gene and the EST sequences, two gene-specific primers were designed (Table 8), PCR was carried out in a reaction mixture containing 1 μl of cDNA, 10 mM Tris-HCl (pH 8.3), 50 mM KCl, 1.5 mM $MgCl_2$, 200 μM dNTPs (deoxynucleoside triphosphates), 150 ng of primers and 2.5 units of AmpliTaq Gold DNA polymerase (Roche Molecular Systems, Branchburg, N.J., USA) on a Perkin-Elmer 9600 thermal cycler. The cycling conditions were 94° C. for 9 minutes to activate the Taq Gold DNA polymerase, followed by 43 cycles of 94° C. for 30 s, 63° C. for 1 minute and a final extension at 63° C. for 10 min. Equal amounts of PCR products were electrophoresed on 2% agarose gels and visualized by ethidium bromide staining. All primers for RT-PCR spanned at least 2 exons to avoid contamination by genomic DNA.

Tissue Expression of KLK-L1

Total RNA isolated from 26 different human tissues was purchased from Clontech, Palo Alto, Calif. cDNA was prepared as described above for the tissue culture experiments and used for PCR reactions with the primers described in Table 8 (SEQ. ID. Nos 5–12). Tissue cDNAs were amplified at various dilutions.

Cloning and Sequencing of the PCR Products

To verify the identity of the PCR products, they were cloned into the pCR 2.1-TOPO vector (Invitrogen, Carlsbad, Calif., USA) according to the manufacturer's instructions. The inserts were sequenced from both directions using vector-specific primers, by an automated DNA sequencer.

Results

Identification of the Prostase/KLK-L1 Gene

The exon prediction strategy of the 300 Kb DNA sequences around chromosome 19q13.3–q13.4 identified a novel gene with a structure reminiscent of a serine protease. The major features of this gene were its homology, at the amino acid and DNA level, with other human kallikrein genes; the conservation of the catalytic triad (histidine, aspartic acid, and serine), the number of exons and the complete conservation of the intron phases.

EST Sequence Homology Search

EST sequence homology search of the putative exons obtained from the gene prediction programs (as described above) against the human EST database (dbEST) revealed five expressed sequence tags (ESTs) with >95% identity to the putative exons of the gene (Table 7). Positive clones were obtained and the inserts were sequenced from both directions. Alignment was used to compare between the EST sequences and the exons predicted by the computer programs, and final selection of the exon-intron splice sites was made according to the EST sequences. Furthermore, many of the ESTs were overlapping, further ensuring the accuracy of the data.

The coding sequence of the klk-L2 gene is shown in SEQ. ID. NO. 1 and GenBAnk Accession # AF135023. The exons of the gene are as follows: exon 1 (939–999); exon 2 (2263–2425); exon 3 (2847–3097); exon 4 (3181–3317); and exon 5 (4588–4740). The amino acid sequence of KLK-L2 proteins are shown in SEQ. ID. Nos. 2 and 3.

Mapping and Chromosomal Localization of Prostase/KLK-L1 Gene

Alignment of the prostase/KLK-L1 sequence and the sequences of other known kallikrein genes within the 300

Figure 2:
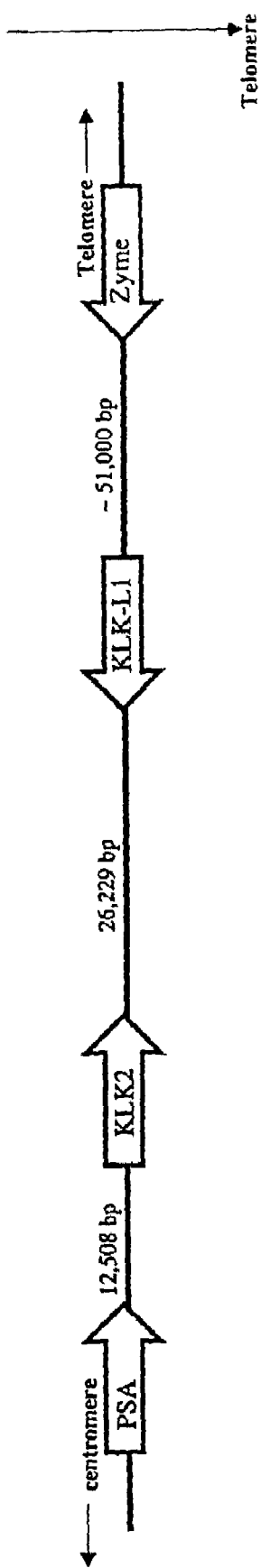
FIG. 2 shows a contiguous genomic sequence around chromosome 19q13.3–q13.4. Genes are represented by horizontal arrows denoting the direction of the coding sequence. Distances between genes are in base pairs.

Kb area of the contigs constructed at the Lawrence Livermore National Laboratory enabled precise localization of all genes and to determine the direction of transcription, as shown in FIG. 2. The distance between PSA and KLK2 genes was calculated to be 12,508 bp. The prostase/KLK-L1 gene is 26,229 bp more telomeric to KLK2 and transcribes in the opposite direction. The zyme gene is about 51 Kb more telomeric to the prostase gene and transcribes in the same direction. The human stratum corneum chymotryptic enzyme gene, the neuropsin gene and the NES 1 gene are all further telomeric to zyme and all transcribe in the same direction as zyme.

Tissue Expression of the Prostase/KLK-L1 Gene

The tissues that express the prostase/KLK-L1 gene were assessed by RT-PCR. The experiments were performed at various dilutions of the cDNAs to obtain some information about the relative levels of expression. RT-PCR for actin was used as a positive control and RT-PCR for the PSA cDNA was used as another positive control with tissue restricted specificity. Positive ESTs for prostase/KLK-L1 were used as controls for the PCR procedure. The PSA gene was found to be highly expressed in the prostate, as expected, and to a lower extent in mammary and salivary glands as also expected from recent literature reports (24, 25). Very low expression of PSA in the thyroid gland, trachea and testis was also found, a finding that accords with recent RT-PCR data by others (26).

Figure 3:
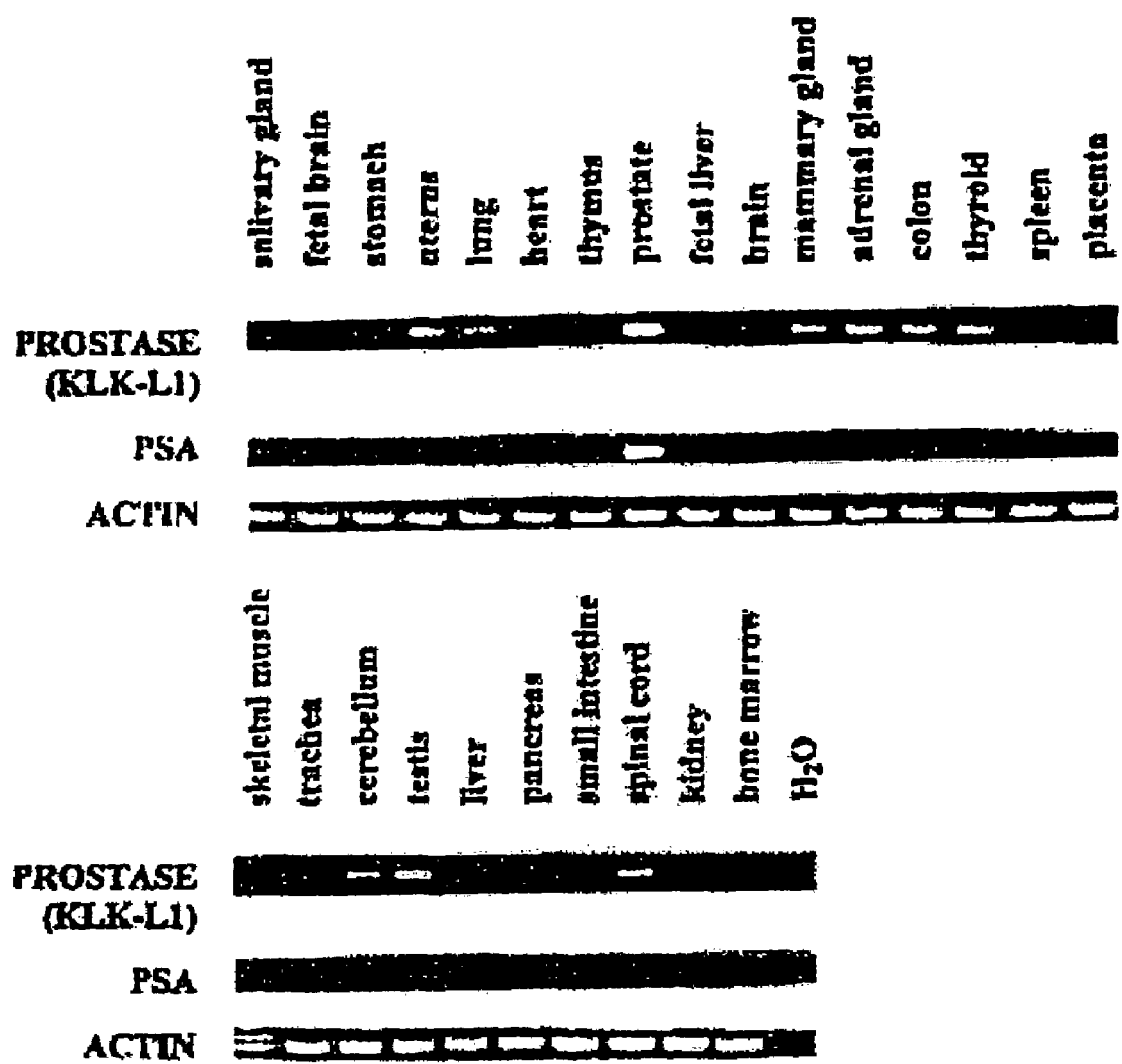
FIG. 3 shows tissue expression of the prostase/KLK-L1 gene as determined by RT-PCR. Actin and PSA are control genes. Interpretations are presented in Table 9.

The tissue expression of prostase/KLK-L1 is summarized in Table 9 and FIG. 3. This protease is primarily expressed in the prostate, testis, adrenals, uterus, thyroid, colon, central nervous system and mammary tissues, and, at much lower levels in other tissues. The specificity of the RT-PCR procedure was verified for prostase/KLK-L1 by cloning the PCR products from mammary, testicular and prostate tissues and sequencing them. One example with mammary tissue is shown in FIG. 4. All cloned PCR products were identical in sequence to the cDNA sequence reported for the prostase/KLK-L1.

Hormonal Regulation of the Prostase/KLk-L1 Gene

Figure 5:
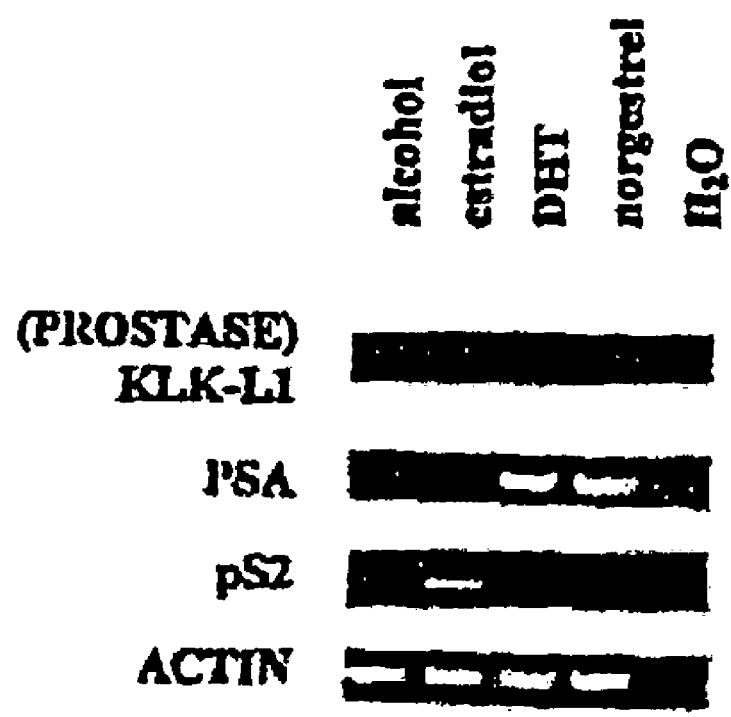
FIG. 5 is a blot showing the results of experiments for hormonal regulation of the prostase/KLK-L1 gene in the BT-474 breast carcinoma cell lines. DHT=dihydrotestosterone. Steroids were added at $10^{-8}$ M final concentrations. Actin (not regulated by steroid hormones), pS2 (up-regulated by estrogens) and PSA (up-regulated by androgens and progestins), are control genes. Prostase/KLK-L1 is up-regulated by androgens and progestins.

The steroid hormone receptor-positive breast carcinoma cell line BT-474 was used as a model system to evaluate whether prostase/KLK-L1 expression is under steroid hormone regulation. As shown in FIG. 5, the controls worked as expected i.e., actin positivity without hormonal regulation in all cDNAs, only estrogen up-regulation of the pS2 gene and up-regulation of the PSA gene by androgens and progestins. Prostase/KLK-L1 is up-regulated primarily by androgens and progestins, similarly to PSA. This up-regulation was dose-dependent and it was evident at steroid hormone levels $\geq 10^{-10}$ M.

Discussion

The KLK3 gene encodes for PSA, a protein that currently represents the best tumor marker available (24). Since in rodents there are so many kallikrein genes, the restriction of this family to only 3 genes in humans was somewhat surprising. More recently, new candidate kallikrein genes in humans have been discovered, including NES1 (13) and zyme/protease M/neurosin (10–12). The known kallikreins and the newly discovered kallikrein-like genes share the following similarities: (a) they encode serine proteases (b) they have five coding exons (c) they share significant DNA and protein homologies with each other (d) they map in the same locus on chromosome 19q13.3–q13.4, a region that is structurally similar to an area on mouse chromosome 7, where all the mouse kallikrein genes are localized (e) they appear to be regulated by steroid hormones. Prostase/KLK-L1 is a member of the same family since these common characteristics are also shared by the newly discovered gene.

The exact localization of the KLK-L1 gene and its position in relation to other genes in the area (FIG. 2) was determined. Prostase/KLK-L1 lies between KLK2 and zyme.

Figure 6:
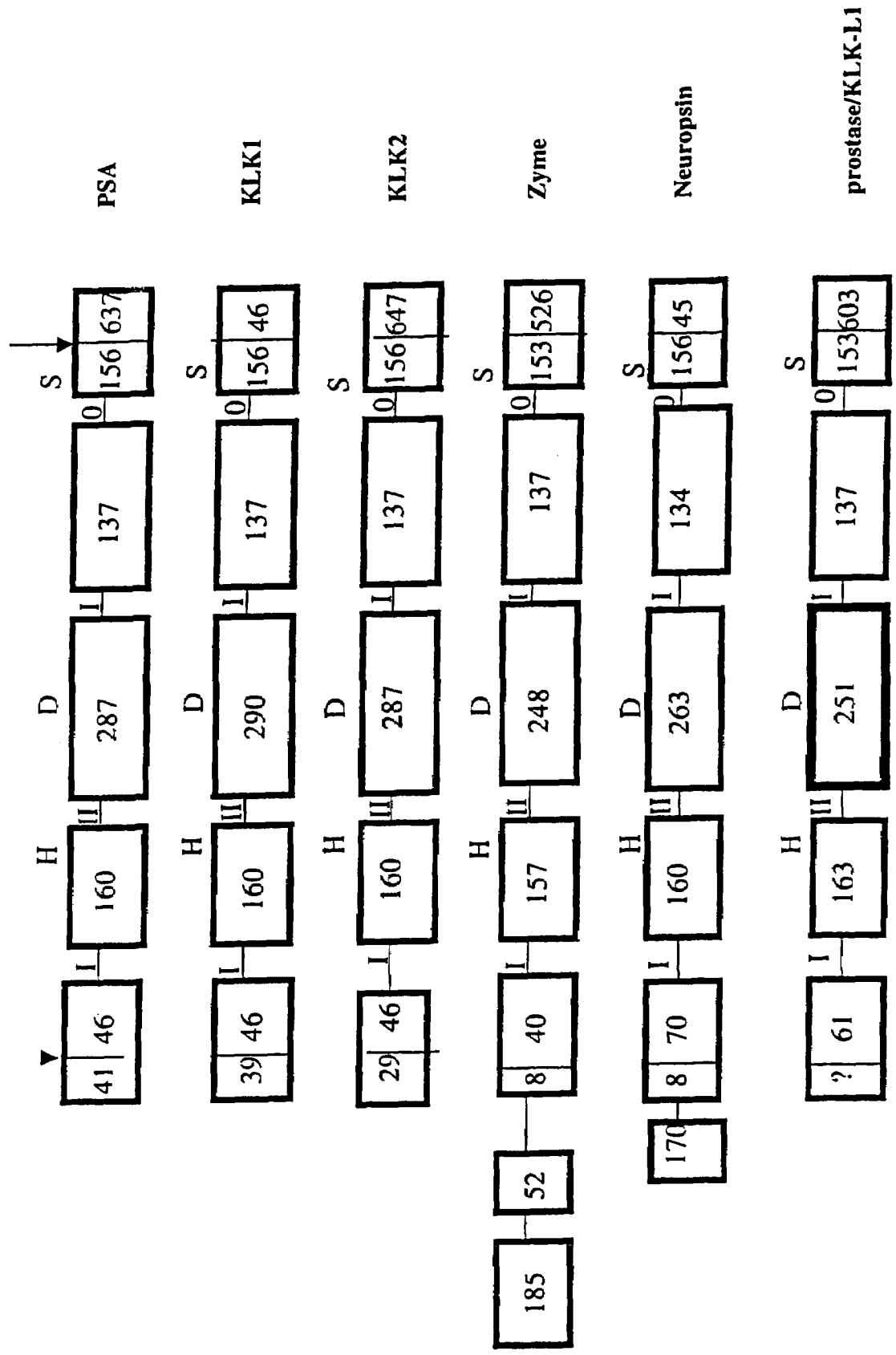
FIG. 6 is a schematic diagram showing comparison of the genomic structure of PSA, KLK1, KLK2, zyme, neuropsin and prostase/KLK-L1 genes. Exons are shown by open boxes and introns by the connecting lines. Arrow head shows the start codons and the vertical arrow represents stop codons. Letters above boxes indicate relative positions of the catalytic triad; H denotes histidine, D aspartic acid and S serine. Roman numbers indicate intron phases. The intron phase refers to the location of the intron within the codon; I denotes that the intron occurs after the first nucleotide of the codon, II the intron occurs after the second nucleotide, 0 the intron occurs between codons. Numbers inside boxes indicate exon lengths in base pairs.

Irwin et al. (27) have proposed that the serine protease genes can be classified into five different groups according to intron position. The established kallikreins (KLK1, KLK2, and PSA), trypsinogen and chymotrypsinogen belong to a group that has: (1) an intron just downstream from the codon for the active site histidine residue, (2) a second intron downstream from the exon containing the codon for the active site aspartic acid residue, and (3) a third intron just upstream from the exon containing the codon for the active site serine residue. As seen in FIG. 6, the genomic organization of prostase/KLK-L1 gene is very similar to this group of genes. The lengths of the coding parts of exons 1–5 are 61,163, 263, 137 and 153 bp, respectively, which are close or identical to the lengths of the exons of the kallikrein genes and also, similar or identical to those of other newly discovered genes in the same chromosomal region like the NES1(14), zyme/protease M/neurosin (10–12) and neuoropsin (28) genes.

The sensitive RT-PCR protocol reveals that the KLK-L1 enzyme is expressed in prostatic tissue and it is also expressed in significant amounts in other tissues, including testis, female mammary gland, adrenals, uterus, thyroid, colon, brain, lung and salivary glands (FIG. 3 and Table 9). The specificity of the RT-PCR primers was verified by sequencing the obtained PCR products, with one example shown in FIG. 4 (SEQ.ID.NO. 4). Tissue culture studies with the breast carcinoma cell line BT-474 further confirm not only the ability of these cells to produce prostase/KLK-L1 but also its hormonal regulation (FIG. 5).

An interesting theme is now developing involving the group of homologous genes on chromosome 19q13.3(PSA, KLK2, prostase, zyme, and NES 1). The combined data suggest that all of them are expressed in prostate and breast tissues, and all of them are hormonally regulated. All these genes may be part of a cascade pathway that plays a role in cell proliferation, differentiation or apoptosis by regulating (positively or negatively) growth factors or their receptors or cytokines, through proteolysis (30). Also interesting is the linkage of locus 19q13 to solid tumors and gliomas (31) which raises the possibility that some of the genes in the region may be disrupted by rearrangements.

The KLK-1L gene encodes for a serine protease that shows homology with other members of the kallikrein gene family and maps to the same chromosomal location. Many structural features of the kallikreins are conserved in prostase/KLK-L1. The precise mapping of this gene between the two known genes KLK2 and zyme is presented. It is further demonstrated that prostase/KLK-L1 is expressed in many tissues, in addition to the prostate, including the female breast. This gene is also herein referred to as 'prostase'. It has been further demonstrated, using breast carcinoma cell lines, that prostase/KLK-L1 can be produced by these cells and that its expression is significantly up-regulated by androgens and progestins. Based on information for other homologous genes in the area (PSA, zyme, and NES1), prostase/KLK-L1 may be involved in the pathogenesis and/or progression of prostate, breast and possibly other cancers.

Example 3

Identification of the KLK-L2 Gene

Materials and Methods

DNA Sequence on Chromosome 19

Sequencing data of approximately 300 Kb of nucleotides on chromosome 19q13.3–q13.4 was obtained from the web site of the Lawrence Livermore National Laboratory (LLNL) (http://www-bio.llnl.gov/genome/genome.html). This sequence was in the form of 9 contigs of different lengths. A restriction analysis study of the available sequences was performed using the "WebCutter" computer program (http://www.firstmarket.com.cutter/cut2.html) and with the aid of the EcoR1 restriction map of this area (also available from the LLNL web site) an almost contiguous stretch of genomic sequences was constructed. The relative positions of the known kallikrein genes: PSA (GenBank accession # X14810), KLK2 (GenBank accession # M18157), and zyme (GenBank accession # U60801) was determined using the alignment program BLAST 2 (37).

New Gene Identification

A number of computer programs were used to predict the presence of putative new genes in the genomic area of interest. These programs were initially tested using the known genomic sequences of the PSA, protease M and NES 1 genes. The most reliable computer programs GeneBuilder (gene prediction) (http://125.itba.mi.cnr.it/~webgene/genebuilder.html) GeneBuilder (exon prediction) (http://125.itba.mi.cnr.it~webgene/genebuilder.html), Grail 2 (http://compbio.ornl.gov) and GENEID-3 (http://apolo.imim.es/geneid.html) were selected for further use.

Expressed Sequence Tag (EST) Searching

The predicted exons of the putative new gene were subjected to homology search using the BLASTN algorithm (37) on the National Center for Biotechnology Information web server (http://www ncbi.nim.nih.gov/BLAST/) against the human EST database (dbEST). Clones with >95% homology were obtained from the I.M.A.G.E. consortium (38) through Research Genetics Inc. Huntsville, Ala. (Table 10). The clones were propagated, purified and sequenced from both directions with an automated sequencer, using insert-flanking vector primers.

Rapid Amplification of cDNA Ends (5' RACE)

According to the EST sequence data and the predicted structure of the gene, two gene-specific primers were designed (R1 & R2) (Table 11). Two rounds of RACE reactions (nested PCR) were performed with 5 µl Marathon Ready™ cDNA of human testis (Clontech, Palo Alto, Calif., USA) as a template. The reaction mix and PCR conditions were conducted according to the manufacturer's recommendations. In brief, denaturation was done for 5 min at 94° C. followed by 94° C. for 5 sec followed by 72° C. for 2 min for 5 cycles, then 94° C. for 5 sec followed by 70° C. for 2 min for 5 cycles then 94° C. for 5 sec followed by 65° C. for 2 min for 30 cycles for the first reaction and 25 cycles for the nested PCR reaction.

Tissue Expression

Total RNA isolated from 26 different human tissues was purchased from Clontech, Palo Alto, Calif. cDNA was prepared as described below for the tissue culture experiments and used for PCR reactions with the primers described in Table 11 (SEQ. ID. Nos 9–12, 15–20). Tissue cDNAs were amplified at various dilutions.

Breast Cancer Cell Line and Hormonal Stimulation Experiments

The breast cancer cell line BT-474 was purchased from the American Type Culture Collection (ATCC), Rockville, Md. Cells were cultured in RPMI media (Gibco BRL, Gaithersburg, Md.) supplemented with glutamine (200 mmol/L), bovine insulin (10 mg/L), fetal bovine serum (10%), antibiotics and antimycotics, in plastic flasks, to near confluency. The cells were then aliquoted into 24-well tissue culture plates and cultured to 50% confluency. 24 hours before the experiments, the culture media were changed into phenol red-free media containing 10% charcoal-stripped fetal bovine serum. For stimulation experiments, various steroid hormones dissolved in 100% ethanol were added into the culture media, at a final concentration of $10^{-8}$ M. Cells stimulated with 100% ethanol were included as controls. The cells were cultured for 24 hours, then harvested for mRNA extraction.

Reverse Transcriptase Polymerase Chain Reaction

Total RNA was extracted from the breast cancer cells using Trizol reagent (Gibco BRL) following the manufacturer's instructions. RNA concentration was determined spectrophotometrically. 2 µg of total RNA was reverse-transcribed into first strand cDNA using the Superscript™ preamplification system (Gibco BRL). The final volume was 20 µl. Based on the combined information obtained from the predicted genomic structure of the new gene and the EST sequences, two gene-specific primers were designed (Table 11) and PCR was carried out in a reaction mixture containing 1 µl of cDNA, 10 mM Tris-HCl (pH 8.3), 50 mM KCl, 1.5 mM $MgCl_2$, 200 µM dNTPs (deoxynucleoside triphosphates), 150 ng of primers and 2.5 units of AmpliTaq Gold DNA polymerase (Roche Molecular Systems. Branchburg, N.J., USA) on a Perkin-Elmer 9600 thermal cycler. The cycling conditions were 94° C. for 9 minutes to activate the Taq Gold DNA polymerase, followed by 43 cycles of 94° C. for 30 s. 63° C. for 1 minute and a final extension at 63° C. for 10 min. Equal amounts of PCR products were electrophoresed on 2% agarose gels and visualized by ethidium bromide staining. All primers for RT-PCR spanned at least 2 exons to avoid contamination by genomic DNA.

To verify the identity of the PCR products, they were cloned into the pCR 2.1-TOPO vector (Invitrogen, Carlsbad. CA. USA) according to the manufacturer's instructions. The inserts were sequenced from both directions using vector-specific primers, with an automated DNA sequencer.

Structure Analysis

Multiple alignment was performed using the Clustal X software package available at: ftp://ftp.ebi.ac.uk/pub/software/dos/clustalw/clustalx/ (clustalx 1.64b.msw.exe) and the multiple alignment program available from the Baylor College of Medicine (BCM), Houston, Tex., USA (kiwi.imoen.bcm.tmc. edu:8808/search-L4 uncher/launcher/html). Phylogenetic studies were performed using the Phylip software package available at: http://evolution.genetics.washington.edu/phylip/getme.html. Distance matrix analysis was performed using the "Neighbor-Joining/UPGMA" program and parsimony analysis was done using the "Protpars" program. Hydrophobicity study was performed using the BCM search launcher programs (http://dot.imgen.bcm.tmc.edu:9331/seq-search/struc-predict.html). Signal peptide was predicted using the "SignalP" server (http://www.cbs-.dtu.dk/services/signal). Protein structure analysis was performed by "SAPS" (structural analysis of protein sequence) program (http://dot.imgen.bcm.tmc.edu:9331/seq-search/struc-predict.html).

Results

Computer analysis of the genomic sequence predicted a putative new gene consisting of four exons. This gene was detected by all programs used and all exons had high prediction scores. EST sequence homology search of the putative exons against the human EST database (dbEST) revealed nine expressed sequence tag (EST) clones from different tissues with >95% identity to the putative exons of the gene (Table 10). Positive clones were obtained and the inserts were sequenced from both directions. The "Blast 2 sequences" program was used to compare the EST sequences with the predicted exons, and final selection of the exon-intron splice sites was done according to the EST sequences. The presence of many areas of overlap between the various EST sequences allowed further verification of the structure of the new gene. The coding sequence of the gene is shown in SEQ. ID. NO. 13 and GenBank Accession #AF135028. The 3' end of the gene was verified by the presence of poly A stretches that are not present in the genomic sequence at the end of two of the sequenced ESTs. One of the sequenced ESTs revealed the presence of an additional exon at the 5' end. The nucleotide sequence of this exon matches exactly with the genomic sequence. To further identify the 5' end of the gene, 5' RACE was performed but no additional sequence could be obtained. However, as is the case with other kallikreins, the presence of further up-stream untranslated exon(s) could not be excluded. The amino acid sequence of KLK-L2 is shown in SEQ. ID. No. 14.

Mapping and Chromosomal Localization of the KLK-L2 Gene

Figure 8:
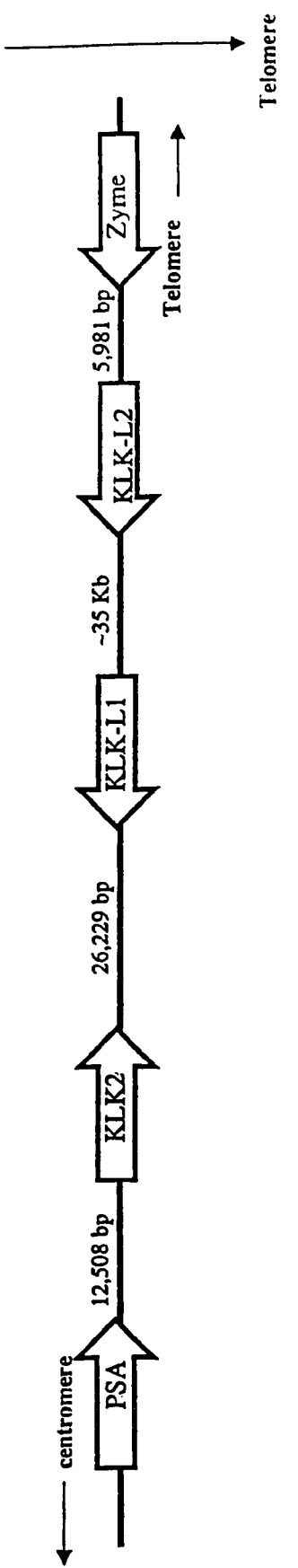
FIG. 8 shows an approximate 300 Kb region of almost contiguous genomic sequence around chromosome 19q13.3–q13.4. Genes are represented by horizontal arrows denoting the direction of the coding sequence. Distances between genes are mentioned in base pairs.

Alignment of KLK-L2 gene and the sequences of other known kallikrein genes within the 300 Kb area of interest enabled precise localization of all genes and determination of the direction of transcription, as shown by the arrows in FIG. 8. The PSA gene was found to be the most centromeric, separated by 12,508 base pairs (bp) from KLK2, and both genes are transcribed in the same direction (centromere to telomere). The prostase/KLK-L1 gene is 26.229 bp more telomeric and transcribes in the opposite direction, followed by KLK-L2. The distance between KLK-L1 and KLK-L2 is about 35 Kilobases (Kb). The zyme gene is 5,981 bp more telomeric and the latter 3 genes are all transcribed in the same direction (FIG. 8).

Structural Characterization of the KLK-L2 Gene and its Protein Product

The KLK-L2 gene, as presented in FIG. 7, is formed of 5 coding exons and 4 intervening introns, spanning an area of 9,349 bp of genomic sequence on chromosome 19q13.3–q13.4. The lengths of the exons are 73, 262, 257,134, and 156 bp, respectively. The intron/exon splice sites (mGT . . . AGm) and their flanking sequences are closely related to the consensus splicing sites (-mGTAAGT . . . CAGm-) (32). The presumptive protein coding region of the KLK-L2 gene is formed of 879 bp nucleotide sequence (SEQ ID NO: 96) encoding a deduced 293-amino acid polypeptide (SEQ ID NO: 14) with a predicted molecular weight of 32 KDa. There are two potential translation initiation codons (ATG) at positions 1 and 25 of the predicted first exon (numbers refer to SEQ. ID. NO.13 and GenBank Accession #AF135028). It is assumed that the first ATG will be the initiation codon, since: (1) the flanking sequence of that codon (GCGGCCATGG SEQ ID NO: 89) matches closely with the Kozak consensus sequence for initiation of translation (GCC A/G CCATGG SEQ ID NO: 90) (33) and is exactly the same as that of the homologous zyme gene. At this initiation codon, the putative signal sequence at the N-terminus is similar to other trypsin-like serine proteases (prostase and EMSP) (FIG. 9). The cDNA ends with a 328 bp of 3' untranslated region containing a conserved poly adenylation signal (AATAAA) located 11 bp up-stream of the poly A tail (at a position exactly the same as that of the zyme poly A tail)(11).

A hydrophobicity study of the KLK-L2 gene shows a hydrophobic region in the N-terminal region of the protein (FIG. 10), suggesting that a presumed signal peptide is present. By computer analysis, a 29-amino acid signal peptide is predicted with a cleavage site at the carboxyl end of $Ala^{29}$. For better characterization of the predicted structural motif of the KLK-L2 protein, it was aligned with other members of the kallikrein multi-gene family, (FIG. 9), and the predicted signal peptide cleavage site was found to match with the predicted signal cleavage sites of zyme (11), KLK1(1), KLK2 (8), and KLK-L1. Also, sequence alignment supports, by analogy, the presence of a cleavage site at the carboxyl end of $Ser^{66}$, which is the exact site predicted for cleavage of the activation peptide of all the other kallikreins aligned in FIG. 9. Interestingly, the starting amino acid sequence of the mature protein (I I N G (S) D C) is conserved in the prostase and enamel matrix serine proteinase I (EMSP) genes. Thus, like other kallikreins, KLK-L2 is likely also synthesized as a preproenzyme that contains an N-terminal signal peptide (prezymogen) followed by an activation peptide and the enzymatic domain.

The presence of aspartate (D) in position 239 suggests that KLK-L2 will possess a trypsin-like cleavage pattern like most of the other kallikreins (e.g., KLK1, KLK2, TLSP, neuropsin, zyme, prostase, and EMSP) but different from PSA which has a serine (S) residue in the corresponding position, and is known to have a chymotrypsin like activity (FIG. 9). The dotted region in FIG. 9 indicates an 11-amino acid loop characteristic of the classical kallikreins (PSA, KLK1, and KLK2) but not found in KLK-L2 or other members of the kallikrein-like gene family (11).

Homology with the Kallikrein Multi-Gene Family

The mature 227-amino acid sequence of the predicted protein was aligned against the GenBank database and the known kallikreins using the "BLASTP" and "BLAST 2 sequence" programs. KLK-L2 is found to have 54% amino acid sequence identity and 68% similarity with the enamel matrix serine proteinase 1 (EMSP1) gene, 50% identity with both trypsin like serine protease (TLSP) and neuropsin genes and 47%, 46%, and 42% identity with trypsinogen, zyme, and PSA genes, respectively. The multiple alignment study shows that the typical catalytic triad of serine proteases is conserved in the KLK-L2 gene ($H^{108}$, $D^{153}$, and $S^{245}$) and, as the case with all other kallikreins, a well conserved peptide motif is found around the amino acid residues of the catalytic triad [i.e., histidine (WLLTAAHC SEQ ID NO: 91), serine (GDSGGP SEQ ID NO: 92), and aspartate (DLMLI SEQ ID NO: 93)] (10, 11).

Twelve cysteine residues are present in the putative mature KLK-L2 protein, ten of them are conserved in all the serine proteases that are aligned in FIG. 9, and would be expected to form disulphide bridges. The other two cysteines ($C^{178}$ and $C^{279}$) are not found in PSA, KLK1, KLK2 or trypsinogen, however, they are found in similar positions in prostase, EMSP1, zyme, neuropsin, and TLSP genes and are expected to form an additional disulphide bond. Twenty nine "invariant" amino acids surrounding the active site of serine proteases have been described (39). Of these, twenty-six are conserved in KLK-L2. One of the non-conserved amino acids ($Ser^{210}$ instead of Pro) is also found in prostase and EMSP1 genes, the second (Leu$^{103}$ instead of Val) is also found in TLSP gene, and the third (Val$^{174}$ instead of Leu) is also not conserved in prostase or EMSP1 genes. According to protein evolution studies, each of these amino acid changes represents a conserved evolutionary substitution to a protein of the same group (39).

Evolution of the KLK-L2 Gene

Figure 10:
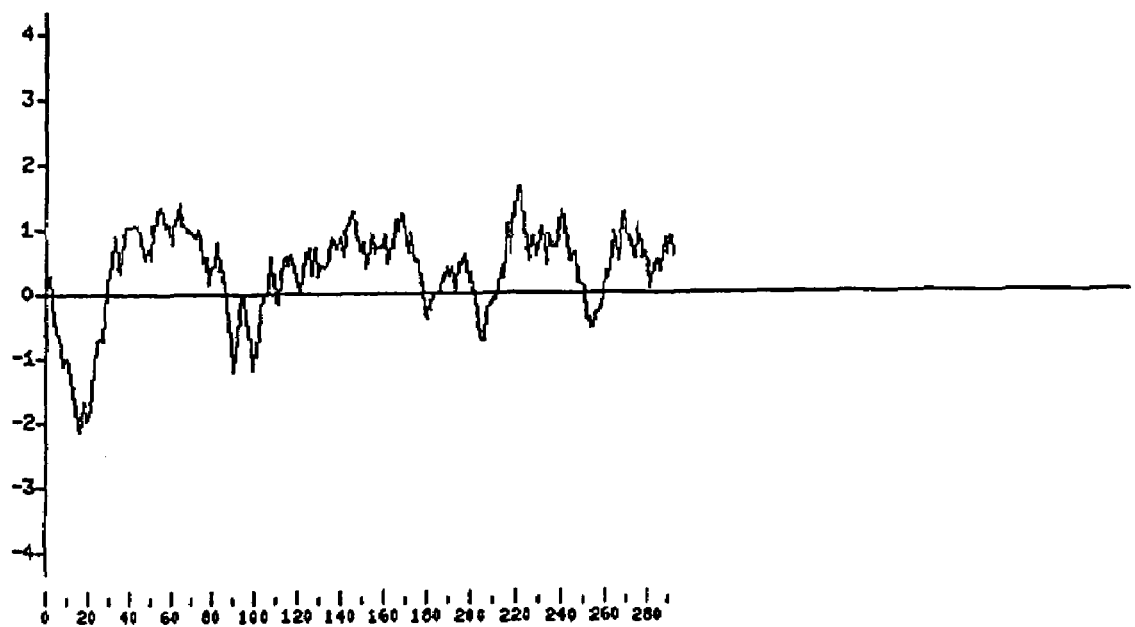
FIG. 10(A) shows a dendrogram of the predicted phylogenetic tree for some kallikrein genes. Neighbor-joining/UPGMA method was used to align KLK-L2 with other members of the kallikrein gene family. Gene names and accession numbers are listed in FIG. 9. The tree grouped the classical kallikreins (KLK1, KLK2, and PSA) together and aligned the KLK-L2 gene in one group with EMSP, prostase, and TLSP. (B) Plot of hydrophobicity and hydrophilicity of KLK-L2.

To predict the phylogenetic relatedness of the KLK-L2 gene with other serine proteases, the amino acid sequences of the kallikrein genes were aligned together using the "Clustal X" multiple alignment program and a distance matrix tree was predicted using the Neighbor-joining/UP-GMA method (FIG. 10). Phylogenetic analysis separated the classical kallikreins (KLK1, KLK2, and PSA) and grouped the KLK-L2 with KLK-L1, EMSP1, and TLSP (40, 41).

Tissue Expression of the KLK-L2 Gene

Figure 11:
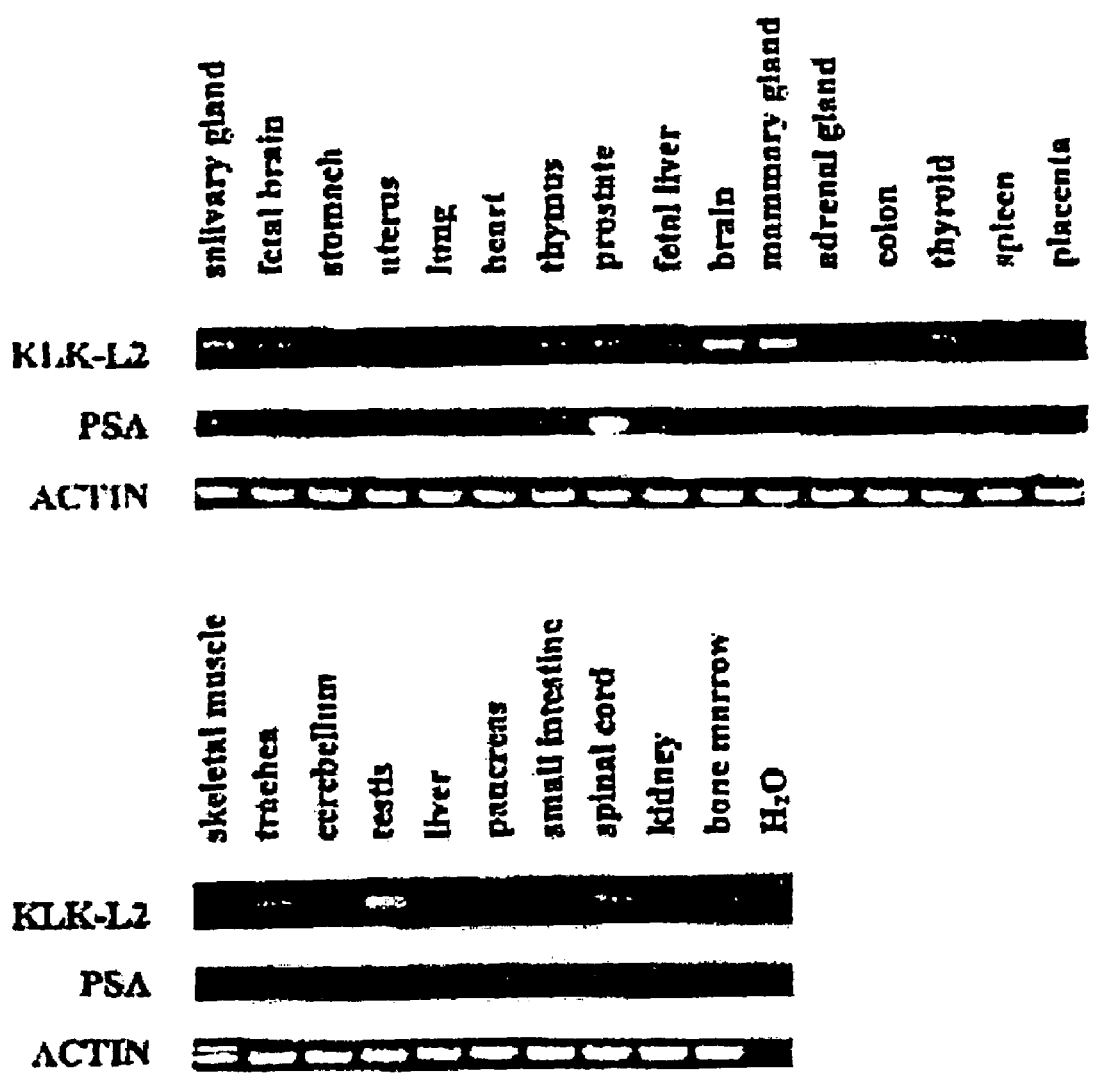
FIG. 11 is a blot showing tissue expression of KLK-L2 gene as determined by RT-PCR. Actin and PSA are control genes. Interpretations are presented in Table 12.

As shown in Table 12 and FIG. 11, the KLK-L2 gene is primarily expressed in the brain, mammary gland, and testis but lower levels of expression are found in many other tissues. In order to verify the RT-PCR specificity, the PCR products were cloned and sequenced.

Hormonal Regulation of the KLK-L2 Gene

Figure 12:
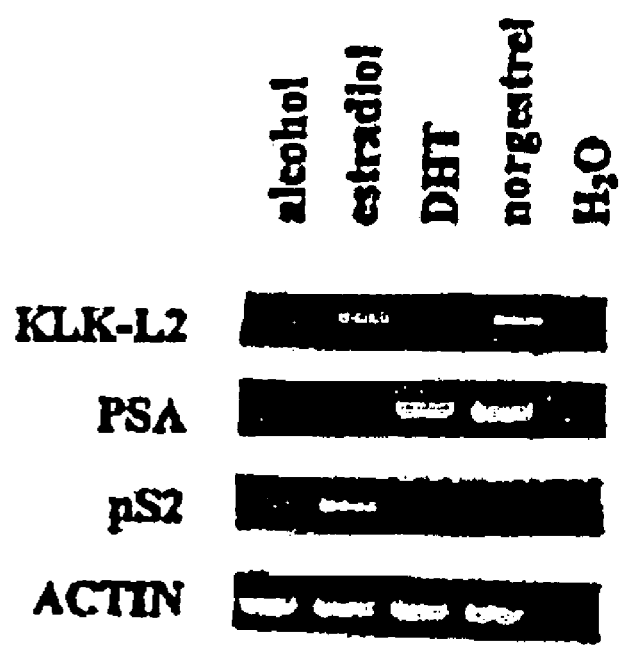
FIG. 12 is a blot showing hormonal regulation of the KLK-L2 gene in BT-474 breast carcinoma cell lines. DHT=dihydrotestosterone. Steroids were at $10^{-8}$ M final concentrations. Actin (not regulated by steroid hormones), pS2 (up-regulated by estrogens) and PSA (upregulated by androgens and progestins), are control genes. KLK-L2 is upregulated by estrogens and progestins.

A steroid hormone receptor positive breast cancer cell line (BT-474) was used as a model to verify whether the KLK-L2 gene is under steroid hormone regulation. PSA was used as a control known to be upregulated by androgens and progestins and pS2 as an estrogen upregulated control. The results indicate that KLK-L2 is up-regulated by estrogens and progestins (FIG. 12).

Expression of KLK-L2 in Ovarian Tissues

Figure 13:
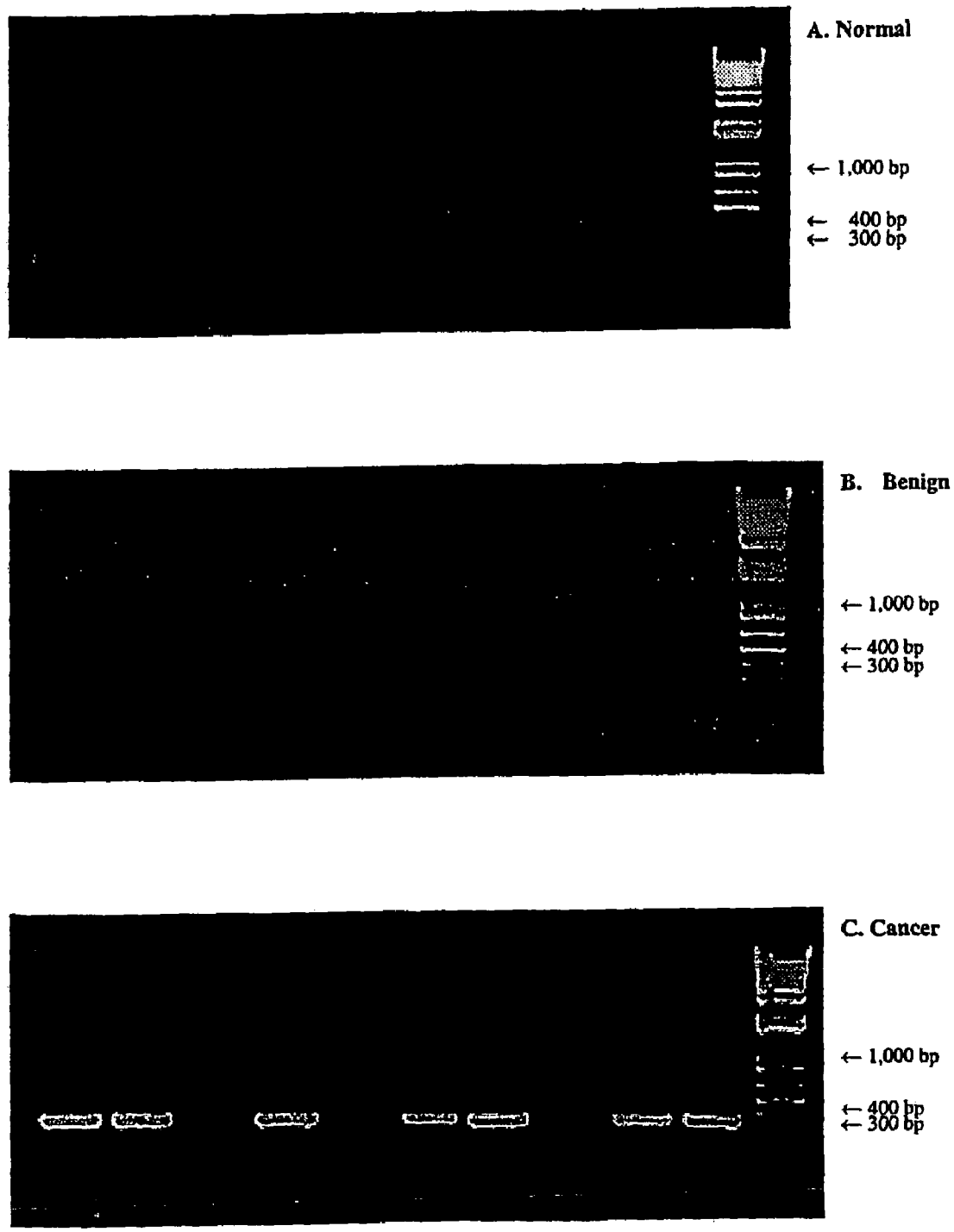
FIG. 13(A–C) are blots of EtBr-stained agarose gels. Total RNA was extracted from normal, benign, and cancer tissues and used to generate cDNA. PCR was performed on cDNA.

KLK-L2 is up-regulated (overexpressed) in ovarian tumors (FIG. 13).

Discussion

With the aid of computer programs for gene prediction and the available EST database, a new gene, named KLK-L2 (for kallikrein like gene 2) was identified. The 3' end of the gene was verified by the presence of "poly A" stretches in the sequenced ESTs which were not found in the genomic sequence, and the start of translation was identified by the presence of a start codon in a well conserved consensus Kozak sequence.

As is the case with other kallikreins, the KLK-L2 gene is composed of 5 coding exons and 4 intervening introns and, except for the second coding exon, the exon lengths are comparable to those of other members of the kallikrein gene family (FIG. 6). The exon-intron splice junctions were identified by comparing the genomic sequence with the EST sequence and were further confirmed by the conservation of the consensus splice sequence (-mGT . . . AGm-) (32), and the fully conserved intron phases, as shown in FIG. 6. Furthermore, the position of the catalytic triad residues in relation to the different exons is also conserved (FIG. 6). As is the case with most other kallikreins, except PSA and HSCCE, KLK-L2 is more functionally related to trypsin than to chymotrypsin (34). The wide range of tissue expression of KLK-L2 should not be surprising since, by using the more sensitive RT-PCR technique instead of Northern blot analysis, many kallikrein genes were found to be expressed in a wide variety of tissues including salivary gland, kidney, pancreas, brain, and tissues of the reproductive system (uterus, mammary gland, ovary, and testis) (34). KLK-L2 is highly expressed in the brain. Another kallikrein, neuropsin, was also found to be highly expressed in the brain and has been shown to have important roles in neural plasticity in mice (35). Also, the zyme gene is highly expressed in the brain and appears to have amyloidogenic potential (11). Taken together, these data point to a possible role of KLK-L2 in the central nervous system.

It was initially thought that each kallikrein enzyme has one specific physiological substrate. However, the increasing number of substrates, which purified proteins can cleave in vitro, has led to the suggestion that they may perform a variety of functions in different tissues or physiological circumstances. Serine proteases encode protein cleaving enzymes that are involved in digestion, tissue remodeling, blood clotting etc., and many of the kallikrein genes are synthesized as precursor proteins that must be activated by cleavage of the propeptide. The predicted trypsin-like cleavage specificity of KLK-L2 makes it a candidate activator of other kallikreins or it may be involved in a "cascade" of enzymatic reactions similar to those found in fibrinolysis and blood clotting (36).

In conclusion, a new member of the human kallikrein gene family, KLK-L2 was characterized. This gene is hormonally regulated and it is mostly expressed in the brain, mammary gland and testis. KLK-L2 may be useful as a tumor marker.

Example 4

Materials and Methods

Strategy for New Gene Discovery

Sequencing data of approximately 300 kb, around chromosome 19q13.3–q13.4, was obtained from the web site of the Lawrence Livermore National Laboratory (LLNL) (http://www-bio.llnl.gov/genome/genome.html). Different computer programs were used for putative new gene prediction, as previously described.

RT-PCR for KLK-L3 cDNA

Total RNA isolated from 26 different human tissues was purchased from Clontech, Palo Alto, CA. cDNA was prepared as described below and used for PCR amplification. A primer set (L3-F1 and L3-R1) was used to identify the presence of the gene in tissues, and the reverse primer (L3-R1) was used with another primer (L3-F2) to amplify and clone the full cDNA of the gene. These primer sequences are shown in Table 13 (SEQ. ID. Nos. 9–12, 24–26). Tissue cDNAs were amplified at various dilutions.

Reverse Transcriptase Polymerase Chain Reaction.

2 μg of total RNA was reverse-transcribed into first strand cDNA using the Superscript™ preamplification system (Gibco BRL, Gaithersburg, Md.). The final volume was 20 μl. Based on the combined information obtained from the predicted genomic structure of the new gene and the EST sequence, two gene-specific primers (L3-F1 and L3-R1) were designed (Table 13, SEQ. ID. Nos. 9–12, 24–26) and PCR was carried out in a reaction mixture containing 1 μl of cDNA. 10 mM Tris-HCl (pH 8.3), 50 mM KCl, 1.5 mM MgCl$_2$, 200 μM dNTPs (deoxynucleoside triphosphates), 150 ng of primers and 2.5 units of AmpliTaq Gold DNA polymerase (Roche Molecular Systems, Branchburg, N.J., USA) on a Perkin-Elmer 9600 thermal cycler. The cycling conditions were 94° C. for 9 minutes, followed by 43 cycles of 94° C. for 30 s, 63° C. for 1 minute, and a final extension . . . 63° C. for 10 minutes. Equal amounts of PCR products were electrophoresed on 2% agarose gels and visualized by ethidium bromide staining. All primers for RT-PCR spanned at least 2 exons to avoid contamination by genomic DNA.

Breast Cancer Cell Line and Hormonal Stimulation Experiments

The breast cancer cell line BT-474 was purchased from the American Type Culture Collection (ATCC), Rockville, Md. Cells were cultured in RPMI media (Gibco BRL, Gaithersburg, Md.) supplemented with glutamine (200 mmol/L), bovine insulin (10 mg/L), fetal bovine serum (10%), antibiotics and antimycotics, in plastic flasks, to near confluency. The cells were then aliquoted into 24-well tissue culture plates and cultured to 50% confluency. 24 hours before the experiments, the culture media were changed into phenol red-free media containing 10% charcoal-stripped fetal bovine serum. For stimulation experiments, various steroid hormones dissolved in 100% ethanol were added into the culture media, at a final concentration of $10^{-8}$ M. Cells stimulated with 100% ethanol were included as controls. The cells were cultured for 24 hours, then harvested for total RNA extraction by the Trizol method (Gibco-BRL). cDNA was prepared and amplified as described above. Control genes (PSA, pS2, and actin) were amplified as previously described herein.

Cloning and Sequencing of the PCR Products.

To verify the identity of the PCR products, they were cloned into the pCR 2.1-TOPO vector (Invitrogen, Carlsbad, Calif., USA) according to the manufacturer's instructions. The inserts were sequenced from both directions using vector-specific primers, with an automated DNA sequencer.

Identification of Positive PAC and BAC Genomic Clones from Human Genomic DNA Libraries The PCR product generated with primer set ZIS and ZIAS (Table 14, SEQ.ID.NOS. 27–42), was purified and then labeled with $^{32}P$ by the random primer method (Sambrook, supra) and used as a probe to screen a human genomic DNA BAC library, spotted in duplicate on nylon membranes, for identification of positive clones. The filters were hybridized in 15% formamide, 500 mM $Na_2HPO_4$, 7% SDS, 1% BSA (w/v) at 65° C. overnight, then washed sequentially with 2×SSC, 1×SSC, 0.2×SSC, containing 0.1% SDS at 65° C., and then exposed to X-ray film as described (Sambrook, supra). Positive clones were obtained, plated on selective LB medium, and then a single colony was transferred into LB broth for overnight cultures. A PAC clone positive for NES1 was identified by a similar methodology as described elsewhere (14). PAC and BAC libraries were constructed by de Jong and associates (42). Purification of BAC and PAC DNA was done by a rapid alkaline lysis miniprep method, which is a modification of the standard Qiagen-Tip method. Positive clones were further confirmed by Southern blot analysis as described (Sambrook, supra).

5' Rapid Amplification of cDNA Ends (5' RACE)

According to the EST sequences and the computer-predicted structure of the KLK-L3 gene, two gene specific primers were designed. Two rounds of RACE reactions (nested PCR) were performed with 5 μlMarathon Ready™ cDNA of human testis (Clontech) as a template. The reaction mix and PCR conditions were selected according to the manufacturer's recommendations. Positive bands were gel-purified using Qiagen Gel Purification kits according to manufacturer's recommendations.

Gene-Specific Amplification of Other Genes from Genomic DNA

According to the published sequence of prostatic specific antigen (PSA), human renal kallikrein (KLK1), human glandular kallikrein (KLK2), normal epithelial cell-specific 1gene (NES1), KLK-L1, KLK-L2 and zyme genes, gene-specific primers were designed for each of these genes (Table 14) and developed polymerase chain reaction (PCR)-based amplification protocols which allowed us to generate specific PCR products with genomic DNA as a template. The PCR reactions were carried out as described above but by using an annealing/extension temperature of 65° C.

Structure Analysis Studies.

A putative new gene, formed of three exons, was predicted by computer analysis of the genomic sequence. The predicted exons were subjected to sequence homology search against the human EST database (dbEST) and revealed an EST clone (GenBank accession # AA583908) which exhibited 99% homology with the putative gene. This EST was obtained, purified and sequenced and the sequence was aligned by BLAST software (37) against the genomic area that contains the putative gene. An additional exon, downstream of the predicted structure, was identified. The 3' end of the gene was verified by: (a) The presence of the serine residue (S) of the catalytic triad in a well-conserved region. This highly conserved motif (GDSGGP SEQ ID NO: 92) always occurs at the beginning of the last exon in all known kallikreins. (b) The presence of a stop codon that is in frame with the predicted amino acid sequence. (c) The presence of a 19-poly A stretch at the end of the EST that was not found in the genomic sequence.

Results:

Construction of a Contiguous Map of the Human Kallikrein Locus on Chromosome 19Q13.3–Q13.4

Sequence information around the human chromosome 19q13.3–q13.4 locus (the proposed kallikrein locus) is available at the Lawrence Livermore National Laboratory web site. Sequences of approximately 300 kb in length were obtained. These sequences were in the form of contigs of different lengths. A restriction analysis study of the contigs was performed using various computer programs. With the aid of the EcoR1 restriction map of this area which is also available at the LLNL web site, the relative positions of these contigs was defined in relation to each other. Some contigs were overlapping, enabling construction of a contiguous segment; however, three gaps were present. <BLAST> analysis of these segments against the GenBank database (37) enabled the precise location of two classical kallikreins, namely PSA and KLK2 to be defined. Other newly discovered serine proteases were localized which are homologous with the kallikrein genes, namely protease M/zyme/neurosin (10, 11, 12), human stratum corneum chymotryptic enzyme (HSSCE) (55), neuropsin (28), normal epithelial cell-specific 1 gene (NES1) (13), trypsin-like serine protease (TLSP) (GenBank accession # AF164623), KLK-L1 (SEQ.ID.NO. 1) and KLK-L2 (SEQ.ID.NO. 13). The gaps in the 300 kb genomic sequence were partially filled as follows:

(a) The margins of the first gap were found to contain the 5' and 3' ends of the KLK2 gene; this gap was filled with the genomic structure of the KLK2 gene (GenBank Accession # M18157).

(b) The margins of the third gap (gaps are numbered from centromere to telomere) were found to have the 3' and 5' ends of the zyme gene mRNA sequence; thus, a radiolabeled probe specific for the zyme gene was used to screen a human BAC library and two positive clones were obtained. Restriction analysis was performed, followed by Southern blotting and a fragment containing the zyme gene was obtained and sequenced, thus filling this gap.

Figure 14:
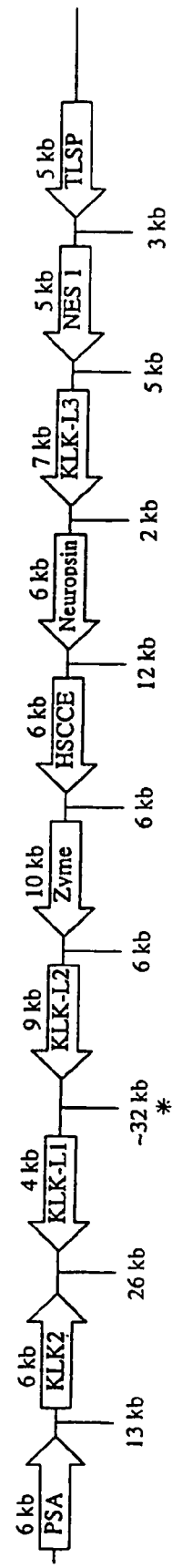
FIG. 14 shows an approximate 300 Kb region of almost contiguous genomic sequence around chromosome 19q13.3–q13.4. Genes are represented by horizontal arrows denoting the direction of the coding sequence. Gene lengths and distances between genes are rounded to the nearest 0.5 kb. The site of the gap is marked with an asterisk. Telomeric to TLSP there are likely another three kallikrein-like genes.

(c) The second gap (between KLK-L1 and KLK-L2 genes) still exists and the EcoRI restriction map of this area was used to approximately define its length (FIG. 14).

Further support for the relative locations of these genes was obtained by performing PCR reactions with gene-specific primers to screen genomic DNA clones. The most centromeric group of genes (PSA, KLK2, KLK-L1, KLK-L2 and zyme) were found to be clustered in one genomic BAC clone, and the next group (HSCCE, neuropsin, KLK-L3 and NES1) were found to be clustered together in another clone, as expected from the data of FIG. 14.

Cloning of the KLK-L3 Gene

A putative new gene, formed of three exons, was predicted by computer analysis of the genomic sequence. The predicted exons were subjected to sequence homology search against the human EST database (dbEST) and revealed an EST clone (GenBank accession # AA583908) which exhibited 99% homology with the putative gene. This EST was obtained, purified and sequenced and the sequence was aligned by BLAST software (37) against the genomic area that contains the putative gene. An additional exon, downstream of the predicted structure, was identified. The 3' end of the gene was verified by: (a) The presence of the serine residue (S) of the catalytic triad in a well-conserved region. This highly conserved motif (GDSGGP) always occurs at the beginning of the last exon in all known kallikreins. (b) The presence of a stop codon that is in frame with the predicted amino acid sequence. (c) The presence of a 19-poly A stretch at the end of the EST that was not found in the genomic sequence.

To verify the accuracy of the cDNA sequence of the gene, PCR reactions were performed using gene-specific primers for the first and last exons of the predicted structure of the gene (L3-F2 and L3-R1) with cDNA isolated from different human tissues as putative templates. A positive band of the expected size was isolated from testis cDNA and fully sequenced. Its sequence was aligned by BLAST against the genomic sequence to unequivocally define the exon/intron boundaries. For further characterization of the 5' end of the gene. 5'RACE reaction was performed using Marathon Ready cDNA from testis as a template. This allowed identification of an additional exon that contains the start codon and 5' untranslated region. The full sequence of the gene is shown in SEQ. ID. NO. 21 (GenBank Accession # AF135026) and the amino acid sequences of KLK-L3 proteins are shown in SEQ. ID. Nos. 22 and 23.

Structural Characterization of the KLK-L3 Gene:

As shown in FIG. 15, the KLK-L3 gene is formed of 5 coding exons and 4 intervening introns, although, as with other kallikreins, the presence of further upstream untranslated exon(s) could not be ruled out (14, 28). All of the exon/intron splice sites conform to the consensus sequence for eukaryotic splice sites (32). The gene further follows strictly the common structural features of the human kallikrein multigene family, as described below.

The predicted protein-coding region of the gene is formed of 753 bp, encoding a deduced amino acid polypeptide with a predicted molecular weight of 27.5 kDa. A potential translation initiation codon is found at position 28 of the predicted first exon (numbers of nucleotides refer to SEQ. ID. NO. 21 or GenBAnk Accession # AF135026. This codon does not match well with the consensus Kozak sequence (33), however, it has a purine at position (−3) which occurs in 97% of vertebrate mRNAs (43), and it is almost identical to the sequence of the zyme gene flanking the start codon. It should also be noted that most kallikreins do not have the consensus G nucleotide in position (+4).

Nucleotides 6803–6808 (AGTAAA) closely resemble a consensus polyadenylation signal (44) and are followed by a stretch of 19 poly A nucleotides not found in genomic DNA, after a space of 14 nucleotides. No other potential polyadenylation signals were discernable in the 3' untranslated region, suggesting that the above motif is indeed the polyadenylation signal. The same polyadenylation signal motif was predicted for the KLK1 and KLK2 genes.

Figure 16:
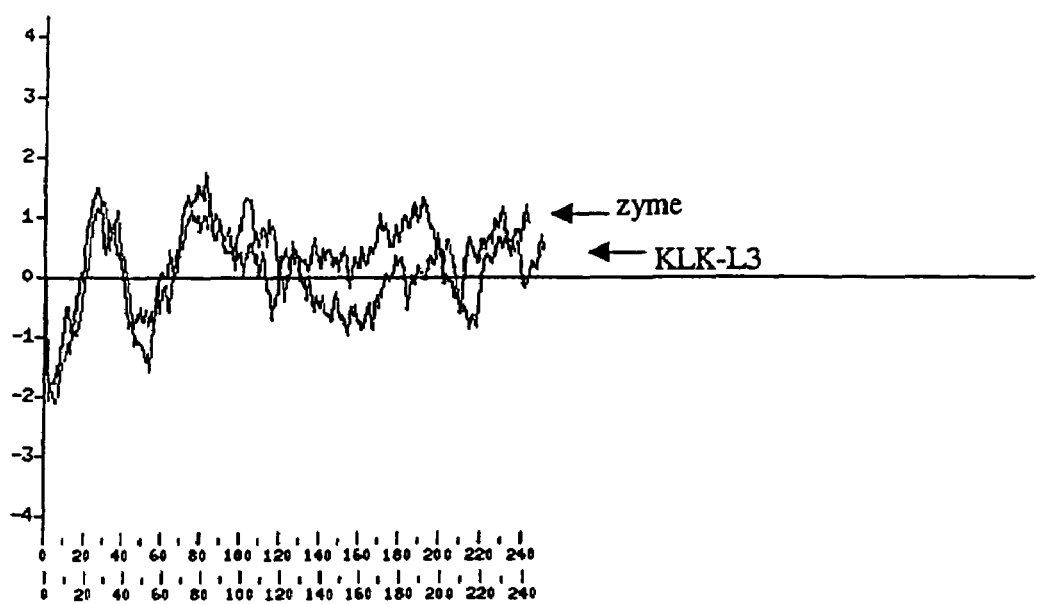
FIG. 16 is a plot of hydrophobicity and hydrophilicity, comparing the pattern of the KLK-L3 with that of the zyme gene. Note the hydrophobic region around the first twenty amino acids, likely representing the signal peptide.

Although the KLK-L3 protein sequence is unique, comparative analysis revealed that it is highly homologous to other members of the kallikrein multigene family. KLK-L3 shows 40% protein identity with the TLSP gene product and 38% and 33% identity with the KLK-L2 and KLK1 proteins, respectively. Hydrophobicity analysis revealed that the imino-terminal region is quite hydrophobic (FIG. 16), consistent with the possibility that this region may harbor a signal sequence, analogous to other serine proteases. Computer analysis of the aminoacid sequence of KLK-L3 predicted a cleavage site between amino acids 19 and 20 (GWA-DT). Sequence alignment (FIG. 17) also revealed a potential cleavage site ($Arg^{22}$), at a site homologous to other serine proteases (lysine (K) or arginine (R) is present in most cases). Several evenly distributed hydrophobic regions throughout the KLK-L3 polypeptide are consistent with a globular protein, similar to other kallikreins and serine proteases. The dotted region in FIG. 17 indicates an 11-amino acid loop characteristic of the classical kallikreins (PSA, KLK1, and KLK2) but not found in KLK-L3 or other members of the kallikrein multi-gene family (11, 41).

Twenty nine "invariant" amino acids surrounding the active site of serine proteases have been described. Of these, twenty-six are conserved in KLK-L3. One of the unconserved amino acids ($Ser^{168}$ instead of Pro) is also found in prostase, KLK-L2 and enamel matrix serine proteinase (EMSP1) genes. The second ($Leu^{58}$ instead of Val) is also found in TLSP and KLK-L2 genes, and the third is $Ala^{26}$ instead of Gly. According to protein evolution studies, each of these changed amino acids represents a conserved evolutionary change to a protein of the same group (45). Twelve cysteine residues are present in the putative mature KLK-L3 protein, ten of them are conserved in all the serine proteases that are aligned in FIG. 17, and would be expected to form disulphide bridges. The other two ($C^{136}$ and $C^{238}$) are not found in PSA, KLK1, KLK2 or trypsinogen; however, they are found in similar positions in prostase, HSCCE, zyme neuropsin, and TLSP genes and are expected to form an additional disulphide bond.

To predict the phylogenetic relatedness of the KLK-L3 gene with other serine proteases, the amino acid sequences of the kallikrein genes were aligned together using the "Clustal X" multiple alignment program and a distance matrix tree was predicted using the Neighbor-joining/UP-GMA method (FIG. 18). Phylogenetic analysis separated the classical kallikreins (KLK1, KLK2, and PSA) and grouped KLK-L3 with TLSP, neuropsin, zyme, HSCCE and prostase/KLK-L1, consistent with previously published studies (11, 41).

Tissue Expression and Hormonal Regulation of the KLK-L3 Gene

Figure 19:
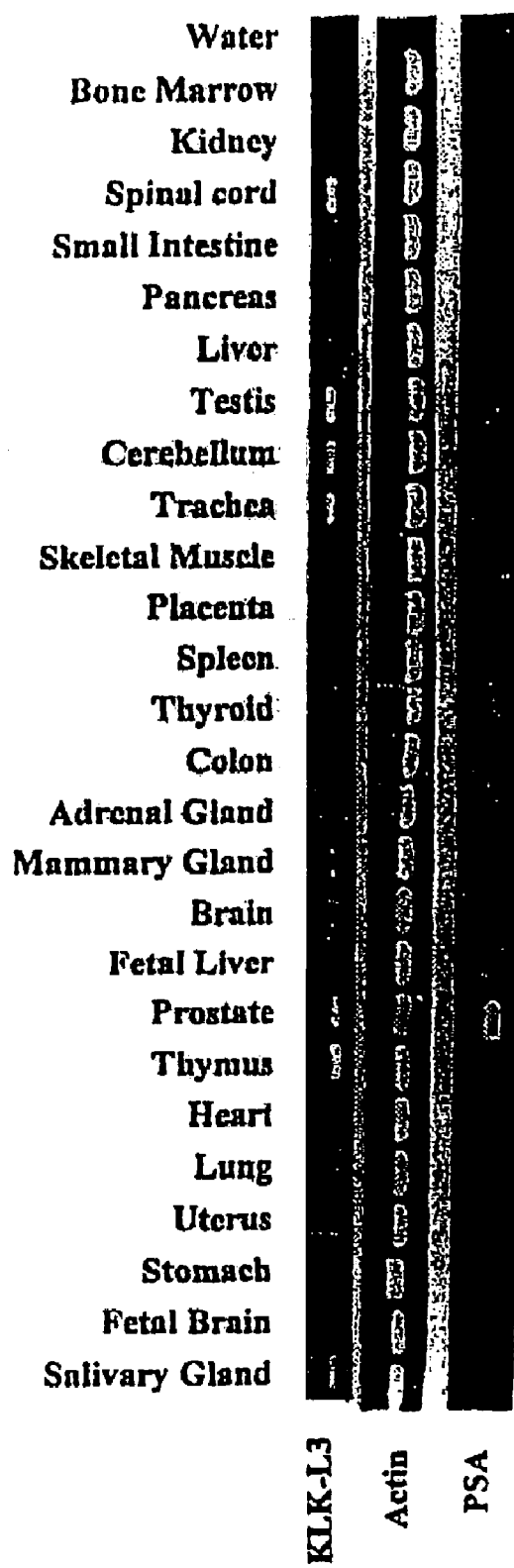
FIG. 19 is a blot showing tissue expression of the KLK-L3 gene as determined by RT-PCR. Actin and PSA are control genes.

As shown in FIG. 19, the KLK-L3 gene is primarily expressed in thymus, testis, spinal cord, cerebellum, trachea, mammary gland, prostate, brain, salivary gland, ovary and skin (the latter two tissues are not shown in the figure).

Figure 20:
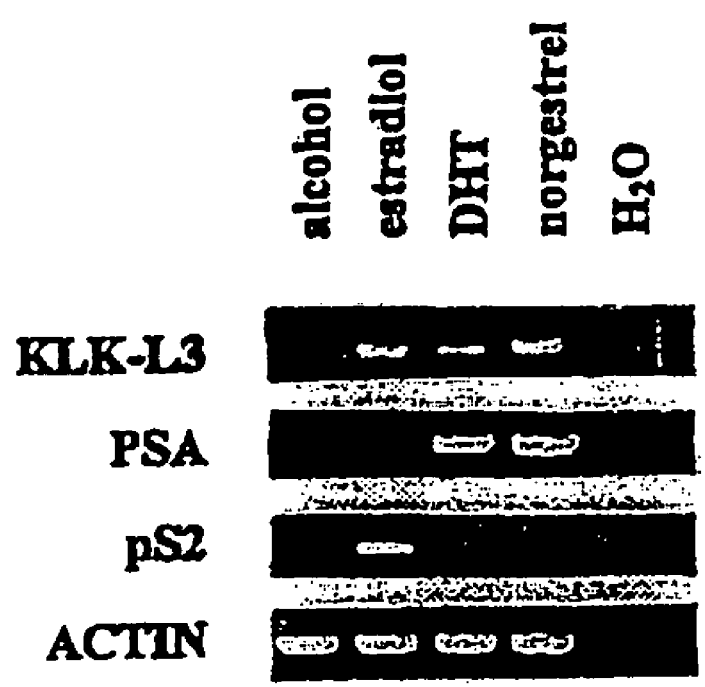
FIG. 20 shows hormonal regulation of the KLK-L3 gene in the BT-474 breast carcinoma cell line. DHT=dihydrotestosterone. Steroids were at $10^{-8}$ M final concentrations. Actin (not regulated by steroid hormones), pS2 (up-regulated by estrogens) and PSA (upregulated by androgens and progestins), are control genes. KLK-L3 is upregulaled by progestins, estrogens and androgens, in that order.

Lower levels of expression are seen in fetal brain, stomach, lung, thyroid, placenta, liver, small intestine, and bone marrow. No expression was seen in uterus, heart, fetal liver, adrenal gland, colon, spleen, skeletal muscle, pancreas, and kidney. In order to verify the RT-PCR specificity, representative PCR products were cloned and sequenced. FIG. 20 shows that KLK-L3 gene is regulated by steroid hormones in the human breast cancer cell line BT-474.

Discussion

A human kallikrein gene locus has been defined, and the first detailed map describing the relative positions of the kallikreins and other kallikrein-like genes has been constructed (FIG. 14). This map is consistent with previous reports on the localization of the classical kallikreins and the approximate mapping of some new kallikreins by radiation hybrid and FISH techniques (9, 14, 67). It should be noted, however, that the lengths of certain segments of this map (as depicted in FIG. 14) are dependent on the EcoR I restriction map of the area and are measured in terms of approximate kb units. Also, the measure of intervals between genes may change slightly in the future, since some kallikreins may have extra 5' exon(s) that have not as yet been identified. Kallikreins with verified 5'-untranslated exons include NES1 (14), zyme, and neuropsin (35). This map is also directional; it indicates that PSA and KLK2 genes are transcribed in the same direction (centromere to telomere) and that the rest of the kallikrein-like genes are transcribed in the reverse direction (FIG. 14).

An early report indicated that KLK1 is located approximately 31 kb centromeric to PSA (9). The map described extends only 24 kb centromeric to PSA, and for this reason, KLK1 was not precisely localized. Thus, the exact location of the KLK1 gene is still to be defined from linear chromosome 19 sequencing data. The possibility still exists that this locus is extended further, and that other kallikrein-like genes may be located upstream of PSA or downstream from TLSP.

Traditionally, kallikreins are characterized by their ability to liberate lysyl-bradykinin (kallidin) from kininogen (2). In humans, only KLK1 meets this "functional" definition. KLK2 and KLK3 are assigned to the same family based on the strong structural similarities of the genes and proteins and the close localization of these genes on the same chromosomal region (20). More recently, a new structural concept has emerged to describe kallikreins. Richards and co-workers introduced the concept of a "kallikrein multigene family" in mice, to refer to these genes (20, 21). This definition is not based much on the specific enzymatic function of the gene product, but more on its sequence homology and its close linkage on mouse chromosome 7.

Figure 21:
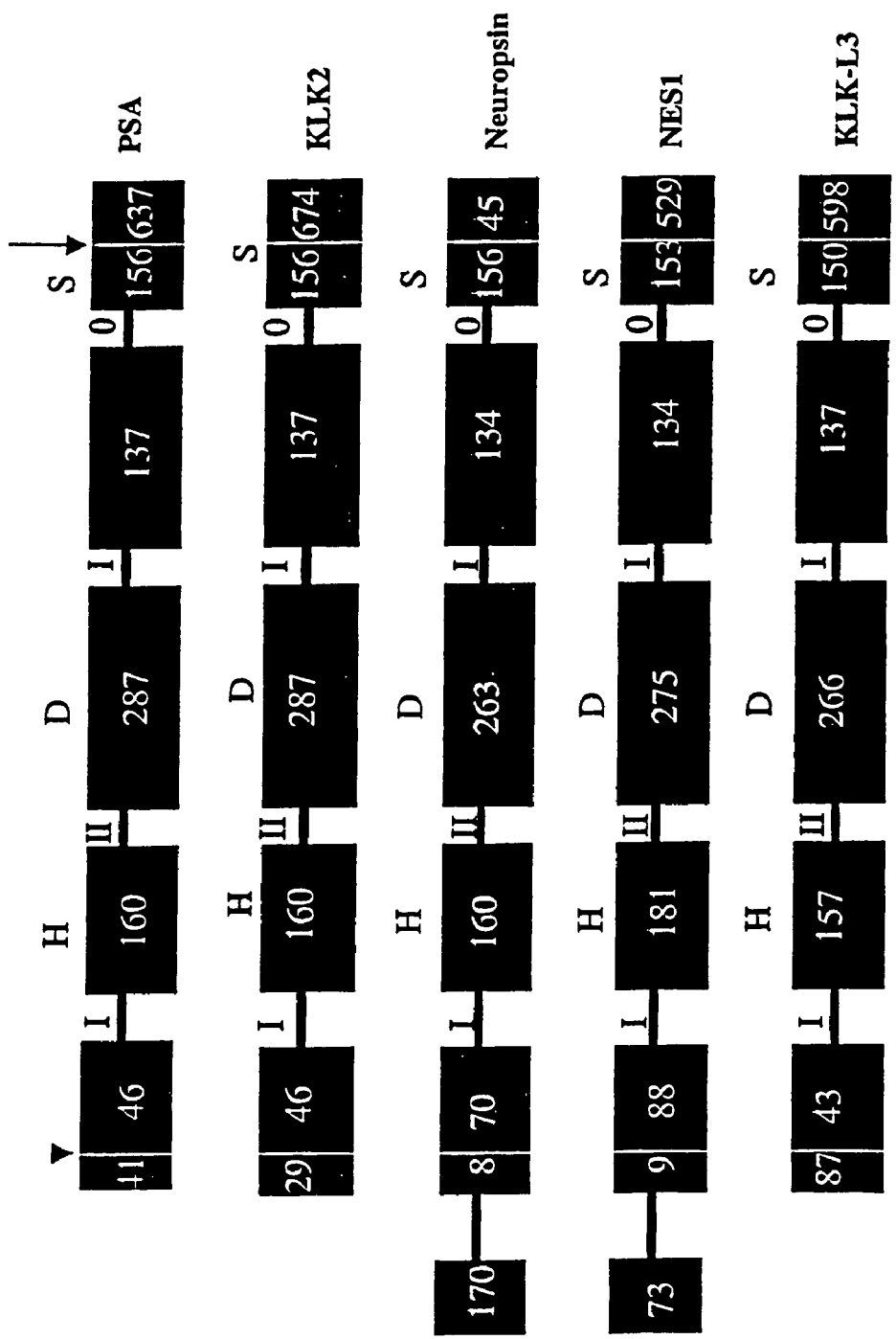
FIG. 21 is a schematic diagram showing the comparison of the genomic structure of PSA.

Irwin et al. (27) proposed that the serine protease genes can be classified into five different groups according to intron position as discussed above. The results indicate the presence of some more common structural features that are found in all kallikreins (including the newly identified KLK-L3 gene): (1) All genes are formed of 5 coding exons and 4 intervening introns (with the possibility that some genes may have extra 5' untranslated exon(s) (24, 31, 35) (FIG. 21). (2) The exon lengths are usually comparable. (3) The intron phases are always conserved (I-II-I-O) (see FIG. 21 for description of intron phases). (4) These genes are clustered in the same chromosomal region, apparently without any intervening non kallikrein-like genes (FIG. 14). Thus, all the recently identified serine proteases that are present in this region (zyme. HSCCE, neuropsin. NES1, prostas KLK-L1, KLK-L2 and TLSP), together with the newly identified kallikrein-like gene (KLK-L3), could be considered members of the expanded human kallikrein multigene family.

The chromosomal band 19q13 is nonrandomly rearranged in a variety of human solid tumors including ovarian cancers (46), and the currently available data indicate that the kallikrein gene locus is related to many malignancies. At least three kallikrein genes (PSA, zyme and NES1) are down regulated in breast cancer (10, 13, 47, 48), and NES1 appears to be a novel tumor suppressor gene (29). Furthermore, PSA exhibits potent antiangiogenic activity (49). It is possible that some of these kallikreins are involved in a cascade pathway, similar to the coagulation or apoptotic process, whereby pro-forms of proteolytic enzymes are activated and then act upon downstream substrates. Such activity was found for the KLK2 gene product which acts upon and activates pro PSA (50, 51).

The expanded human kallikrein gene family has similar number of members as the rodent family of genes. Some new compelling data have raised the possibility that at least some of these genes behave as tumor suppressors (29), as negative regulators of cell growth (52), as antiangiogenic (49) and apoptotic (53) molecules. The paramount diagnostic value of some members is also well-established (24, 54). For these reasons, it is important to check all members of this family of genes as potential diagnostic or prognostic markers or as candidate therapeutic targets.

The newly identified KLK-L3 gene is expressed in many tissues, including skin, thymus, central nervous system, breast, prostate, and testis. The wide range of tissue expression of KLK-L3 should not be surprising since, by using the more sensitive RT-PCR technique, many kallikrein genes were found to be expressed in a wide variety of tissues. For example, PSA, KLK2, prostase/KLK-L1, and KLK-L2 are now known to be expressed in breast and many other tissues (30, 54).

Like many other kallikreins. KLK-L3 is regulated by steroid hormones but in a more complex fashion than PSA and KLK2 which are up-regulated by androgens and progestins (71). In the breast carcinoma cell line studied, KLK-L3 appears to be up-regulated by progestins>estrogens>androgens (FIG. 20).

Example 5

Materials and Methods

DNA Sequence on Chromosome 19 and Prediction of New Genes

Sequencing data of approximately 300 Kb of nucleotides, around chromosome 19q13.3–q13.4, was obtained from the web site of the Lawrence Livermore National Laboratory (LLNL) (http://www http://www-bio.llnl.gov/genome/genome.html) and an almost contiguous stretch of genomic sequences was constructed. A number of computer programs were used to predict the presence of putative new genes in this genomic area.

Expressed Sequence Tag (EST) Searching

The predicted exons of the putative new gene were subjected to homology search using the BLASTN algorithm (37) on the National Center for Biotechnology Information web server (http://www ncbi.nim.nih.gov/BLAST/) against the human EST database (dbEST). Clones with >95% homology were obtained from the I.M.A.G.E. consortium (38) through Research Genetics Inc, Huntsville, Ala. The clones were propagated, purified and sequenced from both directions with an automated sequencer, using insert-flanking vector primers.

Rapid Amplification of cDNA Ends (3' RACE)

According to the EST sequence data and the predicted structure of the gene, two gene-specific primers were designed and two rounds of RACE reactions (nested PCR) were performed with 5 μl Marathon Ready™ cDNA of human testis (Clontech, Palo Alto, Calif., USA) as a template. The reaction mix and PCR conditions used were according to the manufacturer's recommendations.

Tissue Expression

Total RNA isolated from 26 different human tissues was purchased from Clontech. cDNA was prepared as described below, and used for PCR reactions with different sets of primers (Table 15, SEQ.ID.NOs. 46–55, 9–12). Tissue cDNAs were amplified at various dilutions.

Breast Cancer Cell Line and Hormonal Stimulation Experiments

The breast cancer cell line BT-474 was purchased from the American Type Culture Collection (ATCC), Rockville, Md. Cells were cultured in RPMI media (Gibco BRL, Gaithersburg, Md.) supplemented with glutamine (200 mmol/L), bovine insulin (10 mg/L), fetal bovine serum (10%), antibiotics and antimycotics, in plastic flasks, to near confluency. The cells were then aliquoted into 24-well tissue culture plates and cultured to 50% confluency. 24 hours before the experiments, the culture media were changed into phenol red-free media containing 10% charcoal-stripped fetal bovine serum. For stimulation experiments, various steroid hormones dissolved in 100% ethanol were added into the culture media, at a final concentration of $10_{-8}$ M. Cells stimulated with 100% ethanol were included as controls. The cells were cultured for 24 hours, then harvested for mRNA extraction.

Reverse Transcriptase Polymerase Chain Reaction

Total RNA was extracted from the breast cancer tissues and cell lines using Trizol™ reagent (Gibco BRL) following the manufacturer's instructions. RNA concentration was determined spectrophotometrically. 2 μg of total RNA was reverse-transcribed into first strand cDNA using the Superscript™ preamplification system (Gibco BRL). The final volume was 20 μl. Based on the combined information obtained from the predicted genomic structure of the new gene and the EST sequences, two gene-specific primers were designed (LA-F1 and L4-R1 see Table 15, SEQ.ID.NOs. 46 and 47) and PCR was carried out in a reaction mixture containing 1 μl of cDNA, 10 mM Tris-HCl (pH 8.3), 50 mM KCl, 1.5 mM $MgCl_2$, 200 μM dNTPs (deoxynucleoside triphosphates), 150 ng of primers and 2.5 units of AmpliTaq Gold DNA polymerase (Roche Molecular Systems, Branchburg, N.J., USA) on a Perkin-Elmer 9600 thermal cycler. The cycling conditions were 94° C. for 9 minutes to activate the Taq Gold DNA polymerase, followed by 43 cycles of 94° C. for 30 s, 63° C. for 1 minute and a final extension at 63° C. for 10 min. Equal amounts of PCR products were electrophoresed on 2% agarose gels and visualized by ethidium bromide staining. All primers for RT-PCR spanned at least 2 exons to avoid contamination by genomic DNA.

To verify the identity of the PCR products, they were cloned into the pCR 2.1-TOPO vector (Invitrogen, Carlsbad, Calif. USA) according to the manufacturer's instructions. The inserts were sequenced from both directions using vector-specific primers, with an automated DNA sequencer.

Normal and Malignant Breast Tissues

Normal breast tissues were obtained from women undergoing reduction mammoplasties. Breast tumor tissues were obtained from female patients at participating hospitals of the Ontario Provincial Steroid Hormone Receptor Program. The normal and tumor tissues were immediately frozen in liquid nitrogen after surgical resection and stored in this manner until extracted. The tissues were pulverized with a hammer at dry ice temperature and RNA was extracted as described above, using Trizol reagent.

Structure Analysis

Multiple alignment was performed using the Clustal X software package available at: ftp://ftp.ebi.ac.ukl/pub/software/dos/clustalw/clustalx/[clustalx1.64b.msw.exe] and the multiple alignment program available from the Baylor College of Medicine (BCM), Houston, Tex., USA [kiwi.imgen.bcm.tmc. edu:8808/search-launcher/launcher/html]. Phylogenetic studies were performed using the Phylip software package available at: http://evolution.genetics. washington.edu/phylip/getme.html. Distance matrix analysis was performed using the "Neighbor-Joining/UPGMA" program and parsimony analysis was done using the "Protpars" program. Hydrophobicity study was performed using the BCM search launcher programs [http://dot.imgen.bcm.tmc.edu:933/seq-search/struc-predict.html]. Signal peptide was predicted using the "SignalP" server [http://www.cbs. dtu.dk/services/signal]. Protein structure analysis was performed by the "SAPS" (structural analysis of protein sequence) program [http://dot.imgen.bcm.tmc.edu: 9331/seq-search/struc-predict.html].

Results

Cloning of the KLK-L4 Gene

Computer analysis of the genomic sequence around chromosome 19 q13.3–q13.4 predicted a putative new gene formed of at least 3 exons. To experimentally verify the existence of this gene, the putative exons were subjected to sequence homology search against the human expressed sequence tag (EST) database (dbEST), and four EST clones with >97% homology were identified (Table 16). All ESTs were cloned from testicular tissue. These clones were obtained and inserts were sequenced from both directions. Sequences were then compared with the computer-predicted structure and final selection of the intron/exon splice sites was made according to the EST sequences.

As shown in FIG. 22, three ESTs match almost perfectly with the predicted 3 exons (exons 3, 4, 5) of the gene and one EST matches perfectly with predicted exons 3 and 5. However, each of the ESTs extends further upstream with different exonic patterns, suggesting the presence of different splice variants. Attempts to translate these clone sequences demonstrated the presence, in some ESTs, of interrupting stop codons in all three possible reading frames. A homology search of the three common exons against the GenBank database revealed a cDNA sequence from the German Human Genome Project. This clone has an identical exon 2 as the long form of KLK-L4 gene [this form will be described below] but has an extended exon 3 that ends with a stop codon (FIG. 22). This clone was isolated from uterine tissue and is translated by software into a truncated protein product of 196 amino acids which is followed by a 3' untranslated region [GenBank accession # AL050220].

Screening of cDNAs from 26 different tissues by RT-PCR, using gene-specific primers for exons 3 and 5 [L4-F1 and L4-R1] (Table 15 & FIG. 22) revealed that this gene is expressed in many tissues. Four tissues that show the highest level of expression [salivary gland, mammary gland, prostate, and testis] (FIG. 23) and uterus [the EST clone AL050220 was isolated from this tissue] were selected for identification of the full structure of the gene. Different PCR reactions were performed using one reverse primer (L4-R1) together with each of the forward primers located in upstream exons that were found in the different EST clones [primers L4-B, L4-D, L4-E] (Table 15 & FIG. 22). The PCR reactions were performed under different experimental conditions, using the EST clones as positive controls, and the PCR products were sequenced. None of these forms were found in any of the tissues, except in testis where all three forms were found.

By RT-PCR of the KLK-L4 gene using primers L4-R1 and L4-F1, it was found that the gene is expressed in a wide variety of tissues (FIG. 23). In order to obtain the structural forms that exist in these tissues, a homology study was performed. Aligning the predicted polypeptide of the KLK-L4 gene with all other kallikreins and kallikrein-like genes, suggested, by homology, that at least two more exons should be present upstream of the predicted three exons. The genomic fragment upstream of the third exon was subjected to further computer analysis for gene prediction, and exon 2 was identified based on: a) a consensus exon/intron splice site b) preservation intron phase II after this exon, in agreement to intron phases of all other known kallikreins c) presence of the histidine residue of the catalytic triad ($H^{76}$) surrounded by a well-conserved peptide motif [see below] just before the end of this exon d) comparable exon length to other kallikrein genes. A potential first exon was also predicted from the upstream genomic sequence, based on the preserved intron phase (phase 1), and the existence of an in-frame start codon that is located at a comparable distance [in relation to other kallikreins] from the end of this exon. To verify this predicted structure, a PCR reaction was performed using one reverse primer (L4-R1) together with another forward primer that is located in the predicted first exon (primer L4-X1) (Table 15 & FIG. 22). Two main PCR bands were obtained from the tissues examined; the expected 819 bp band (predominant) and an additional minor band of about 650 bp (FIG. 24). Cloning and sequencing of these two bands revealed that the gene exists in two main forms in these tissues; the long form [SEQ. ID. No. 43 or GenBank Accession No. AF135024] and another form [referred to as the short KLK-L4 variant] that utilizes an upstream alternative splice donor site, located inside exon 3, thus creating an mRNA product that that is 214 bp shorter. This alternative splice site causes frame-shifting of the coding region that will generate a predicted stop codon at the beginning of exon 4, giving rise to a truncated protein product that does not contain the serine residue of the catalytic triad (FIGS. 24 and 25).

Alignment of the amino acid sequence of the KLK-L4 protein (long form) against the GenBank database and the known kallikreins, using the BLAST algorithm (37), indicated that KLK-L4 has 51% amino acid sequence identity with the TLSP and zyme genes, 49% identity with KLK-L2 and 47% and 45% identity with PSA and KLK2 genes, respectively. Multiple alignment study shows that the typical catalytic triad of serine proteases is conserved in the KLK-L4 gene ($H^{108}$, $D^{153}$, and $S^{245}$) and, as is the case with all other kallikreins, a well conserved peptide motif is found around the amino acid residues of the catalytic triad [i.e. histidine (WLLTAAHC SEQ ID NO: 91), serine (GDSGGP SEQ ID NO: 92), and aspartate (DLMLI SEQ ID NO: 93)] (FIG. 27) (1, 11, 13, 35). In addition, several other residues were found to be fully or partially conserved among the human kallikrein gene family, as further shown in FIG. 27. To predict the phylogenetic relatedness of the KLK-L4 gene with other serine proteases, the amino acid sequences of the kallikrein genes were aligned together using the "Clustal X" multiple alignment program and a distance matrix tree was predicted using the Neighbor-joining/UPGMA method (FIG. 29). Phylogenetic analysis separated the classical kallikreins (KLK1, KLK2, and PSA) and grouped KLK-L4 with zyme, TLSP, KLK-L3, neuropsin, and NES1 genes, consistent with previously published studies (41) and indicating that this group of genes probably arose from a common ancestral gene by duplication.

Structural Characterization of the KLK-L4 Gene and its Protein Product

The long form of the KLK-L4 gene is presented in FIG. 25 (SEQ.ID.NO. 43). KLC-L4 is formed of five coding exons and four intervening introns, spanning an area of 8,905 bp of genomic sequence on chromosome 19q13.3–q13.4. The lengths of the coding regions are 52, 187, 269, 137 and 189 bp, respectively. The predicted protein coding region of the gene is formed of 831 bp, encoding a deduced 277-amino acid protein with a predicted molecular mass of 30.6 kDa (FIG. 25). The intron/exon splice sites (mGT . . . AGm, where m is any base) and their flanking sequences are in agreement with the consensus splice site sequence. A potential translation initiation codon is present at position 45 of the predicted first exon [numbers refer to SEQ. ID. No. 43]. The cDNA extends at least 382 bp further downstream from the stop codon and a putative polyadenylation signal (TATAAA) is present at the end of this region (FIG. 25).

Hydrophobicity analysis revealed that the amino-terminal region is quite hydrophobic (FIG. 26), consistent with the possibility that this region may harbor a signal sequence, analogous to other serine proteases. FIG. 26 also shows the presence of several evenly distributed hydrophobic regions throughout the KLK-L4 polypeptide, which are consistent with a globular protein, similar to other serine proteases (13). Computer analysis of the amino acid sequence of KLK-L4 predicted a cleavage site between amino acids 20 and 21 (GVS-QE). Sequence homology with other serine proteases (FIG. 27) predicted another potential cleavage site (Lys25) in close proximity. Most other kallikreins are activated by cleavage after arginine or lysine. Thus, the protein product is very likely to be a secreted protein. The dotted region in FIG. 27 indicates an 11-amino acid loop characteristic of the classical kallikreins (PSA, KLK1, and KLK2) which is not found in KLK-L4 or other members of the kallikrein multi-gene family (11.13, 35).

Amino acid sequences for KLK-L4 proteins are shown in SEQ.ID.NO. 44 and 45.

Sequence analysis of eukaryotic serine proteases indicates the presence of twenty nine invariant amino acids (39). Twenty eight of them are conserved in the KLK-L4 protein and the remaining amino acid (Q182 instead of P) is not conserved among all other kallikreins (FIG. 27). Ten cysteine residues are present in the putative mature KLK-L4 protein. These are conserved in all the serine proteases that are aligned in FIG. 27, and would be expected to form disulphide bridges. The presence of aspartate (D) in position 239 suggests that KLK-L4 will possess a trypsin-like cleavage pattern, similarly to most of the other kallikreins [e.g., KLK1, KLK2, TLSP, neuropsin, zyme, prostase, and EMSP] but different from PSA which has a serine (S) residue in the corresponding position, and is known to have chymotrypsin like activity (FIG. 27) (2,40).

Mapping and Chromosomal Localization of the KLK-L4 Gene

Alignment of the KLK-L4 gene and the sequences of other known kallikrein genes within the 300 Kb area of interest [the human kallikrein gene family locus], enabled precise localization of all known genes and to determine the direction of transcription, as shown by the arrows in FIG. 28. The PSA gene lies between KLK1 and KLK2 genes and is separated by 13, 319 base pairs (bp) from KLK2, and both genes are transcribed in the same direction (centromere to telomere). All other kallikrein-like genes are transcribed in the opposite direction. KLK-L4 is 13 kb centromeric from KLK-L6 [SEQ.ID.NO. 65], and 21 kb more telomeric to KLK-L5 [SEQ. ID. NO. 56].

Homology With the Kallikrein Multi-Gene Family

Alignment of the amino acid sequence of the KLK-L4 protein (long form) against the GenBank database and the known kallikreins, using the BLAST algorithm (37), indicated that KLK-L4 has 51% amino acid sequence identity with the TLSP and zyme genes. 49% identity with KLK-L2 and 47% and 45% identity with PSA and KLK2 genes, respectively. Multiple alignment study shows that the typical catalytic triad of serine proteases is conserved in the KLK-L4 gene ($H^{108}$, $D^{153}$, and $S^{245}$) and, as is the case with all other kallikreins, a well conserved peptide motif is found around the amino acid residues of the catalytic triad [i.e. histidine (WLLTAAHC), serine (GDSGGP), and aspartate (DLMLI)] (FIG. 27) (1, 11, 13, 35). In addition, several other residues were found to be fully or partially conserved among the human kallikrein gene family, as further shown in FIG. 27. To predict the phylogenetic relatedness of the KLK-L4 gene with other serine proteases, the amino acid sequences of the kallikrein genes were aligned together using the "Clustal X" multiple alignment program and a distance matrix tree was predicted using the Neighbor joining/UPGMA method (FIG. 29). Phylogenetic analysis separated the classical kallikreins (KLK1, KLK2, and PSA) and grouped KLK-L4 with zyme, TLSP. KLK-L3, neuropsin, and NES1 genes, consistent with previously published studies (41) and indicating that this group of genes probably arose from a common ancestral gene by duplication.

Tissue Expression and Hormonal Regulation of the KLK-L4 Gene

As shown in FIG. 23, the KLK-L4 gene is primarily expressed in mammary gland, prostate, salivary gland and testis, but, as is the case with other kallikreins, lower levels of expression are found in many other tissues. In order to verify the RT-PCR specificity, the PCR products were cloned and sequenced.

A steroid hormone receptor-positive breast cancer cell line (BT-474) was used as a model, to verify whether the KLK-L4 gene is under steroid hormone regulation. PSA was used as a control gene, known to be up-regulated by androgens and progestins and pS2 as an estrogen up-regulated control gene in the same cell line. Preliminary results indicate that KLK-L4 is up-regulated by progestins and androgens and to a lower extent by estrogens (FIG. 30).

Expression of KLK-L4 in Breast Cancer Tissues and Cell Lines

To characterize the extent and frequency of expression of the KLK-L4 gene in breast tumors, cDNA derived from 3 normal and 19 malignant breast tissues and 3 breast cancer cell lines was used. The data were interpreted by comparison of band intensities. Out of the 19 tumors, KLK-L4 gene expression was undetectable in 7, lower than normal tissues in 9, comparable to the normal tissues in 1, and higher than normal tissues in 2 tumors. Without hormonal stimulation, the BT-474 and T-47D cell lines had no detectable KLK-L4 mRNA, while the MCF-7 cell line was positive. These preliminary results suggest that this gene is down-regulated in the majority (16/19) of breast tumors.

Discussion

The established kallikreins (KLK1, KLK2, and PSA), trypsinogen and chymotrypsinogen belong to a group that has: (1) an intron just downstream from the codon for the active site histidine residue, (2) a second intron downstream from the exon containing the codon for the active site aspartic acid residue, and (3) a third intron just upstream from the exon containing the codon for the active site serine residue. FIG. 31 shows that KLK-L4 meets the above mentioned criteria; moreover, is located in close proximity to other kallikrein genes on the chromosomal locus 19q13.3–q13.4 (FIG. 28).

The preliminary findings, supporting that the KLK-L4 gene may be down-regulated in a subset of breast cancers, is not surprising. There is now growing evidence that many of the kallikreins and kallikrein-like genes that are clustered in the same chromosomal region (FIG. 28) are related to malignancy. PSA is the best marker for prostate cancer so far (24). A recent report provided evidence that PSA has anti-angiogenic activity, and that this activity may be related to its function as a serine protease (49). This study suggested that other serine proteases, including new members of the kallikrein multigene family of enzymes, should also be evaluated for potential antiangiogenic activity (49). Recent reports suggest that hK2 (encoded by the KLK2 gene) could be another useful diagnostic marker for prostate cancer (57, 58). NES1 appears to be a tumor suppressor gene (29). The protease M gene was shown to be differentially expressed in primary breast and ovarian tumors (10), and the human stratum corneum chymotryptic enzyme has been shown to be expressed at abnormally high levels in ovarian cancer (59). Another recently identified kallikrein-like gene, located close to KLK-L4 and tentatively named tumor-associated, differentially expressed gene-14 (TADG14) [an alternatively spliced form of neuropsin, see FIG. 28] was found to be overexpressed in about 60% of ovarian cancer tissues (59). Also, prostase/KLK-L1, another newly discovered kallikrein-like gene, is speculated to be linked to prostate cancer (41). Thus, extensive new literature suggests multiple connections of many kallikrein genes to various forms of human cancer.

The removal of intervening RNA sequences (introns) from the pre-messenger RNA in eukaryotic nuclei is a major step in the regulation of gene expression (60). RNA splicing provides a mechanism whereby protein isoform diversity can be generated and the expression of particular proteins with specialized functions can be restricted to certain cell or tissue types during development (60). The sequence elements in the pre-mRNA at the 5' and 3' splice sites in metazoans have very loose consensus sequence; only the first and the last two bases (GT . . . AG) of the introns are highly conserved (Sambrook, supra). These sequences cannot be the sole determinants of splice site selection, since identical, but not ordinarily active, consensus sequences can be found within both exons and introns of many eukaryotic genes. Other protein factors and sequences downstream of the splice sites are also involved.

The existence of multiple splice forms is frequent among kallikreins. Distinct RNA species are transcribed from the PSA gene, in addition to the major 1.6-kb transcript (61). Several distinct PSA transcripts have been described by Reigman et al (7). Interestingly, one of these clones lacks the 3' untranslated region and the first 373 nucleotides of the open reading frame, and has an extended exon that contains a stop codon, a pattern that is comparable with some alternative forms of the KLK-L4 cDNA, as described here (FIG. 22). Heuze et al., reported the cloning of a full-length cDNA corresponding to a 2.1 kb PSA mRNA. This form results from the alternative splicing of intron 4 and lacks the serine residue that is essential for catalytic activity (61). Also, Reigman et al reported the identification of two alternatively spliced forms of the human glandular kallikrein 2 (KLK2) gene (62). A novel transcript of the tissue kallikrein gene (KLK1) was also isolated from the colon (63). Interestingly, this transcript lacks the first two exons of the tissue kallikrein gene, but the last three exons were fully conserved, a pattern that is similar to the findings with some ESTs containing parts of the KLK-L4 gene (FIG. 22). Neuropsin, a recently identified kallikrein-like gene, was found to have two alternatively spliced forms, in addition to the major form (59, 64). Here, the cloning of the KLK-L4 gene is described and the identification of a number of alternative mRNA forms. These forms may result from alternative-splicing (Sambrook, supra), retained intronic segment (7), or from the utilization of an alternative transcription initiation site (63). Because the long form of KLK-L4 and the major alternative splice variant [short KLK-L4 variant] (FIG. 24) have an identical 5' sequence required for translation, secretion and activation, it is possible to assume that both mRNAs encode for a secreted protein (61).

In order to investigate the relative predominance of the long KLK-L4 and related forms, cDNA from various tissues was amplified by PCR. Although, in general, it is difficult to use PCR for quantitative comparisons between mRNA species, in this experiment, [mRNAs of comparable sizes, using one set of primers under identical conditions], such a comparison is reasonable (62). In all five normal tissues examined [breast, prostate, testis, salivary gland and uterus] the long form of KLK-IA was the predominant, with minimal level of expression of the short form (FIG. 24).

The presence of alternatively spliced forms may be related to malignancy. Recent literature suggests that distinct molecular forms of PSA could be expressed differently by malignant versus benign prostate epithelium (65). Aberrant PSA mRNA splicing in benign prostatic hyperplasia, as opposed to prostate cancer, has been described by Henttu et al (66). In addition, it has been recently postulated that different prostatic tissues potentially harboring occult cancer could account for the presence of various forms of PSA (65).

Example 6

Materials and Methods

DNA Sequence on Chromosome 19

Sequencing data of approximately 300 Kb of nucleotides on chromosome 19q13.3–q13.4 was obtained from the web site of the Lawrence Livermore National Laboratory (LLNL) (http://www-bio.llnl.gov/genome/genome.html). This sequence was in the form of 9 contigs of different lengths. Restriction enzyme analysis, long PCR strategies, followed by DNA sequencing, BAC and PAC library screening and end sequencing of selected clones, were used to construct a contiguous genomic region, representing the complete human kallikrein gene locus.

New Gene Identification

A number of computer programs were used to predict the presence of putative new genes within the contiguous genomic area of interest. The ability of these programs for predicting new genes was first examined by using the genomic sequences of the known kallikreins as testing parameters. The most reliable computer programs; GeneBuilder (gene prediction) (http://125.itba.mi.cnr.it/~webgene/genebuilder.html), GeneBuilder (exon prediction) (http://125.itba.mi.cnr.it/~webgene/genebuilder.html), Grail 2 (http://compbio.ornl.gov), and GENEID-3 (http://apolo.imim.es/geneid.html) were selected for further use.

Expressed Sequence Tag (EST) Searching

The predicted exons of the putative new gene were subjected to homology search using the BLASTN algorithm (37) on the National Center for Biotechnology Information web server (http://www ncbi.nim.nih.gov/BLAST/) against the human EST database (dbEST). A clone with >95% homology was obtained from the I.M.A.G.E. consortium (38) through Research Genetics Inc, Huntsville, Ala. This clone was propagated, purified and sequenced from both directions with an automated sequencer, using insert-flanking vector primers.

Rapid Amplification of cDNA Ends (RACE)

According to the EST sequence and the predicted structure of the gene, two sets of gene-specific primers were designed for 5' and 3' RACE reactions. Two rounds of RACE reactions (nested PCR) were performed for each type of RACE with 5 µl Marathon Ready™ cDNA of human testis and prostate (Clontech, Palo Alto, Calif., USA) as templates. The reaction mix and PCR conditions were selected according to the manufacturer's recommendations. In brief, the initial denaturation was for 5 min at 94° C., followed by 94° C. for 5 s and 72° C. for 2 min. for 5 cycles; then, 94° C. for 5 s and 70° C. for 2 min, for 5 cycles; then, 94° C. for 5 s and 65° C. for 2 min for 30 cycles for the first reaction and 25 cycles for the nested PCR reaction.

Tissue Expression

Total RNA isolated from 26 different human tissues was purchased from Clontech, Palo Alto, Calif. cDNA was prepared as described below for the tissue culture experiments and used for PCR reactions. After aligning all known kallikrein genes, two primers (KLK-L5-R1 and KLK-L5-F1) (Table 17, SEQ.ID.NOs. 61–64, 9–12, and FIG. 32) were designed from areas with relatively low homology. Tissue cDNAs were amplified at various dilutions. Due to the high degree of homology between kallikreins, and to exclude non-specific amplification, PCR products were cloned and sequenced.

Normal and Malignant Breast Tissues

Normal breast tissues were obtained from women undergoing reduction mammoplasties. Breast tumor tissues were obtained from female patients at participating hospitals of the Ontario Provincial Steroid Hormone Receptor Program. The normal and tumor tissues were immediately frozen in liquid nitrogen after surgical resection and stored in this manner until extracted. The tissues were pulverized with a hammer under liquid nitrogen and RNA was extracted as described below, using Trizol reagent.

Breast and Prostate Cancer Cell Lines and Hormonal Stimulation Experiments

The breast cancer cell lines BT-474 and T47D, and the LNCaP prostate cancer cell line were purchased from the American Type Culture Collection (ATCC), Rockville, Md. Cells were cultured in RPMI media (Gibco BRL, Gaithersburg, Md.) supplemented with glutamine (200 mmol/L), bovine insulin (10 mg/L), fetal bovine serum (10%), antibiotics and antimycotics, in plastic flasks, to near confluency. The cells were then aliquoted into 24-well tissue culture plates and cultured to 50% confluency. 24 hours before the experiments, the culture media were changed into phenol red-free media containing 10% charcoal-stripped fetal bovine serum. For stimulation experiments, various steroid hormones dissolved in 100% ethanol were added into the culture media at a final concentration of $10^{-8}$ M. Cells stimulated with 100% ethanol were included as controls. The cells were cultured for 24 hours, then harvested for mRNA extraction.

Reverse Transcriptase Polymerase Chain Reaction (RT-PCR)

Total RNA was extracted from the cell lines or tissues using Trizol reagent (Gibco BRL) following the manufacturer's instructions. RNA concentration was determined spectrophotometrically. 2 µg of total RNA was reverse-transcribed into first strand cDNA using the Superscript™ preamplification system (Gibco BRL). The final volume was 20 µl. Based on the combined information obtained from the predicted genomic structure of the new gene and the EST sequences, two gene-specific primers were designed (KLK-L5-F1 and KLK-L5-R1) (Table 17) and PCR was carried out in a reaction mixture containing 1 µl of cDNA, 10 mM Tris-HCl (pH 8.3), 50 mM KCl, 1.5 mM $MgCl_2$, 200 µM dNTPs (deoxynucleoside triphosphates), 150 ng of primers and 2.5 units of AmpliTaq Gold DNA polymerase (Roche Molecular Systems, Branchburg, N.J., USA) on a Perkin-Elmer 9600 thermal cycler. The cycling conditions were 94° C. for 9 minutes to activate the Taq Gold DNA polymerase, followed by 43 cycles of 94° C. for 30 s, 63° C. for 1 minute and a final extension step at 63° C. for 10 min. Equal amounts of PCR products were electrophoresed on 2% agarose gels and visualized by ethidium bromide staining. All primers for RT-PCR spanned at least 2 exons to avoid contamination by genomic DNA.

To verify the identity of the PCR products, they were cloned into the pCR 2.1-TOPO vector (Invitrogen, Carlsbad, Calif., USA) according to the manufacturer's instructions. The inserts were sequenced from both directions using vector-specific primers, with an automated DNA sequencer.

Structure Analysis

Multiple alignment was performed using the Clustal X software package available at: ftp://ftp.ebi.ac.uk/pub/software/dos/clustalw/clustalx/ (clustalx1.64b.msw.exe) and the multiple alignment program available from the Baylor College of Medicine (BCM), Houston, Tex., USA (kiwi.imgen.bcm.tmc. edu:8808/search-L4 uncher/launcher/html). Phylogenetic studies were performed using the Phylip software package available at: http://evolution.genetics.washington.edu/phylip/getme.html. Distance matrix analysis was performed using the "Neighbor-Joining/UPGMA" program and parsimony analysis was done using the "Protpars" program. Hydrophobicity study was performed using the BCM search launcher programs (http://dot.imgen.bcm.tmc.edu:9331/seq-search/struc-predict.html). Signal peptide was predicted using the "SignalP" server (http://www.cbs.dtu.dk/services/signal). Protein structure analysis was performed by "SAPS" (structural analysis of protein sequence) program (http://dot.imgen.bcm.tmc.edu:9331/seq-search/struc-predict.html).

Results

Identification of the KLK-L5 Gene

Computer analysis of the genomic area of interest (300 Kb around chromosome 19q 13.3-q 13.4) predicted a putative gene comprised of at least three exons. Screening of the human expressed sequence tag (EST) database revealed an EST clone (GenBank Accession #394679) with 99% homology with the predicted exons. This clone was obtained, purified, and sequenced. The full-length sequence of the EST was compared with the genomic area containing the putative new gene and showed 100% homology with certain areas (exons), which were separated by introns. This alignment indicated that the new gene was comprised of 7 exons. Sequence homology comparisons and phylogenetic analysis revealed that this new gene is structurally similar to known kallikreins and other serine proteases (see below). Since four other new kallikrein-like genes were discovered in this area, this gene was named KLK-L5 (for kallikrein-like gene 5). Attempts to translate the coding region in all three possible reading frames indicated that only one reading frame will produce a full-length polypeptide chain without interrupting in-frame stop codons. Further support for the correctness of this reading frame was obtained by demonstrating that only this frame will preserve the three amino acid residues necessary for serine protease activity (catalytic triad) and the conserved motifs around them. An in-frame methionine start codon was found in the second exon. This start codon falls within a typical consensus Kozak sequence (CCACC<u>ATG</u>G) (33). Thus, the gene will have at least one 5' untranslated exon, similarly to other kallikrein-like genes [e.g. zyme, the normal epithelial cell-specific 1 gene (NES1) (14), and neuropsin (35)]. 5' and 3' RACE reactions were performed in order to obtain the 5' and 3' ends of the gene. No more sequence was obtained by 5' RACE. However, 3' RACE enabled identification of the 3' untranslated region of the gene. The additional sequence ends with a poly-A stretch that does not exist in the genomic structure, thus marking the 3' end of the gene and the start of the poly-A tail.

Splice Variants of the KLK-L5 Gene

Homology analysis of the KLK-L5 gene with other kallikreins revealed the presence of an additional 3' exon, an observation that has not been reported for any other member of the kallikrein multigene family. Furthermore, two different PCR bands were obtained with the 3' RACE. Sequencing of these bands revealed that this gene has at least two splice forms at its 3' end; one form in which the last exon is a single continuous fragment, and another form in which the last exon is split into two exons, with an intervening intron. In order to identify the full structure of other possible splice variants of the gene, PCR was performed using two primers (L5-F2 and L5-R2) (Table 17 and FIG. 32). cDNA from 26 different tissues were used as templates and the reaction was performed under different experimental conditions (annealing temperature, $MgCl_2$ concentration). Three distinct bands were observed in many tissues. These bands were excised, gel-purified, and sequenced. As shown in FIG. 32, the KLK-L5 gene was found to have 3 molecular forms:

1) One form (referred to, from now on, as the "classical" form) represents a typical kallikrein-like serine protease with five coding exons and four intervening introns (FIG. 32). As is the case with some other kallikreins, a 5' untranslated exon is also present, and the possibility of further upstream untranslated exon(s) could not be excluded. Exons 1, 2 and 3 were present at the aforementioned EST. The start codon is present in the second exon (numbers refer to SEQ.ID.NO. 56 or GenBank Accession # AF135025). The stop codon is located in the sixth exon, followed by a 3' untranslated region, and a typical polyadenylation signal (AATAAA) is located 16 bp before the poly-A tail (FIG. 33). This form of KLK-L5 spans a genomic length of 5,801 bp on chromosome 19q13.3–q13.4. The lengths of the coding regions of the exons are 37, 160, 260, 134, and 156 bp, respectively (FIGS. 33 and 34). The predicted protein-coding region is formed of 747 bp, encoding a deduced 248-amino acid protein with a predicted molecular mass of 26.7 kDa. The intron/exon splice sites (GT . . . AG) and their flanking sequences are in agreement with the consensus splice site sequence.

2) The second mRNA form, encoding the KLK-L5-related protein-1, is an alternatively spliced form in which the last exon is split into two separate exons with an additional intervening intron (FIG. 32). This splitting of the last exon results in the utilization of another stop codon at position 9,478, thus creating a deduced 254-amino acid protein that is 6 amino acids longer than the "classical" KLK-L5 form and its carboxyterminal end is different in sequence by 19 amino acids (FIG. 32). This variant has a predicted molecular mass of 27.1 kDa (for base numbering please see SEQ.ID.NO. 56 and GenBank Accession # AF135025).

3) The third mRNA form, encoding for KLK-L5-related protein-2, is similar to the classical form except that the fourth exon is missing (FIG. 32). This leads to frame shifting of the coding region, and an earlier in-frame stop codon will be encountered at position 9,180. The protein-coding region of this form consists of 336 bp, encoding for a predicted 111-amino acid protein with a molecular mass of 12 kDa. This protein will lack both the serine and aspartate residues characteristic of serine proteases.

Amino acid sequences for KLK-L5 proteins are shown in SEQ. ID. NOs. 57 to 60.

Structural Analysis of the Classical KLK-L5 Gene

FIG. 35 shows a comparative hydrophobicity analysis of the KLK-L5 and the prostate-specific antigen (PSA) proteins. The amino terminal regions of both genes are quite hydrophobic, indicating that this region of KLK-L5 is possibly harboring a signal peptide analogous to PSA. FIG. 35 also shows the presence of several evenly distributed hydrophobic regions throughout the KLK-L5 polypeptide, which are consistent with a globular protein, similar to other serine proteases (13). FIG. 36 shows the alignment of KLK-L5 protein with another 10 members of the same gene family. The dotted region in FIG. 36 indicates an 11-amino acid loop characteristic of the classical human kallikreins (PSA, hK1 and hK2) but not found in KLK-L5 protein or other members of the kallikrein multigene family (11, 13, 35). Sequence analysis of eukaryotic serine proteases indicates the presence of twenty nine invariant amino acids (39). Twenty eight of them are conserved in the KLK-L5 polypeptide and the remaining amino acid (S156 instead of P) is not conserved among all other kallikreins (FIG. 36). Twelve cysteine residues are present in the putative mature KLK-L5 protein, ten of them are conserved in all kallikreins, and the remaining two (C133, and C235) are present in most of the other kallikrein-like proteins but not in the classical kallikreins and they are expected to form an additional disulphide bridge (FIG. 36).

The presence of aspartate (D) at position 194 suggests that KLK-L5 will possess a trypsin-like cleavage pattern, similarly to most of the other kallikreins (e.g., hK1, hK2, TLSP, neuropsin, zyme, prostase, and EMSP) but different from PSA, which has a serine (S) residue in the corresponding position, and is known to have chymotrypsin like activity (FIG. 36) (54).

Homology with Other Members of the Kallikrein Multigene Family

Although the protein encoded by the KLK-L5 gene is unique, it has a high degree of homology with the other kallikrein-like genes. The KLK-L5 protein (classical form) has 48% amino acid sequence identity and 57% overall similarity with neuropsin, 46% identity with the normal epithelial cell-specific 1 gene product (NES1) and 38% identity with both PSA and hK2 proteins. Multiple alignment shows that the typical catalytic triad of serine proteases is conserved in the KLK-L5 protein ($H^{62}$, $D^{108}$, and $S^{200}$) (FIGS. 33 and 36). In addition, a well-conserved peptide motif is found around the amino acid residues of the catalytic triad as is the case with other serine proteases [i.e., histidine (VLTAAHC SEQ ID NO: 94), serine (GDSGGP SEQ ID NO: 92), and aspartate (DLRLL SEQ ID NO: 95)] (11, 12) (FIG. 36). FIG. 36 also shows other amino acid residues that are completely conserved between kallikreins and kallikrein-like proteins. To predict the phylogenetic relatedness of the KLK-L5 protein with other serine proteases, the amino acid sequences of the kallikrein proteins were aligned together using the "Clustal X" multiple alignment program and a distance matrix tree was predicted using the Neighbor-joining/UPGMA and Protpars parsimony methods. FIG. 37 shows the phylogenetic analysis which separated the classical kallikreins (hK1, hK2, and PSA) and clustered KLK-L5 with NES1 and neuropsin proteins in a separate group away from other serine proteases, consistent with previously published studies (27, 41) and indicating that this group of genes probably arose from a common ancestral gene, by gene duplication.

Tissue Expression and Hormonal Regulation of the KLK-L5 Gene

As shown in FIG. 38, the KLK-L5 gene is primarily expressed in the salivary gland, stomach, uterus, trachea, prostate, thymus, lung, colon, brain, breast and thyroid gland, but, as is the case with other kallikreins, lower levels of expression are found in some other tissues (testis, pancreas, small intestine, spinal cord). In order to verify the RT-PCR specificity, the PCR products were cloned and sequenced. The three splice forms of the gene were expressed in most of these tissues. However, the relative abundance of each form was different among tissues (FIG. 38).

In order to investigate whether the KLK-L5 gene is under steroid hormone regulation, two breast cancer cell lines (BT-474 and T-47D) and a prostate cancer cell line (LNCaP) were used as models. In LNCaP cells, the gene was up-regulated only by androgen and progestin. Only in this cell line all 3 isoforms were expressed. In BT-474 cells, KLK-L5 was found to be up-regulated, at the mRNA level, by estrogen and androgen, and to a lesser extent by the progestin. The rank of potency was estrogen>androgen>progestin. However, the rank of potency for the T-47D cell line was androgen>progestin>estrogen. In both of these cell lines, only the short isoform (related protein-2) was present (FIG. 39).

KLK-L5 is Down Regulated in Breast Cancer

Expression of the KLK-L5 gene, at the mRNA level, was compared between seventeen breast cancer tissues and one normal breast tissue, by RT-PCR. The gene is not expressed at all in 12 tumors (FIG. 40). In all breast tissues (normal and malignant) the short isoform (related protein-2) was predominant, with the exception of one tumor, which expressed only the classical form (FIG. 40, lane 8). These results should be interpreted as preliminary, since the number of tumors and normal tissues tested is relatively small.

Mapping and Chromosomal Localization of the KLK-L5 Gene

The knowledge of extensive genomic sequence on chromosome 19q13.3–q13.4 enabled the precise localization of 14 kallikrein-like genes and determination of the direction of transcription, as shown by the arrows in FIG. 28. Only PSA and KLK2 transcribe from centromere to telomere; the rest of the genes are transcribed in the reverse direction. The KLK1 gene was found to be the most centromeric, and the KLK-L6 gene the most telomeric (KLK-L6; SEQ.ID. NO.65). KLK-L5 is 21.3 Kb centromeric to KLK-L4 (SEQ.ID.NO. 43) and 1.6 kb more telomeric to the trypsin-like serine protease gene (TLSP) (FIG. 28).

Discussion

As shown in FIG. 34, kallikreins are characterized by the following common structural features: (a) All genes are formed of 5 coding exons and 4 intervening introns [some genes may have extra 5(untranslated exon(s)] (14, 35). (b) The exon lengths are usually comparable. (c) The intron phases are always conserved (I-II-I-O) (see legend of FIG. 34 for definition of intron phases). (d) These genes are clustered in the same chromosomal region, without any intervening non-kallikrein-like genes (FIG. 28). (e) The histidine residue of the catalytic triad of serine proteases is located near the end of the second coding exon; the aspartate residue in the middle of the third coding exon; and serine at the beginning of the fifth coding exon. As shown in FIG. 34, all these criteria apply to the newly identified KLK-L5 gene. Thus, KLK-L5 should be considered a new member of the kallikrein multigene family.

Serine proteases and kallikreins are synthesized as "pre-proenzymes" that contain an N-terminal signal peptide (prezymogen), followed by a short activation peptide and the enzymatic domain (41, 54). PreproPSA has 24 additional residues that constitute the pre-region (signal peptide, 17 residues), and the propeptide (7 residues) (67). The signal peptide directs the protein to and across the endoplasmic reticulum (ER). In the ER, the signal peptide is removed and the resulting proPSA is transported to the plasma membrane, where it is secreted. The hydrophobicity study (FIG. 35) indicates that the amino terminal region of the KLK-L5 protein is harboring a signal peptide. Also, computer analysis of the amino acid sequence of KLK-L5 predicted a cleavage site between amino acids 17 and 18 (SQA-AT). Thus, the protein product is very likely a secreted protein.

The presence of alternatively spliced forms is not a unique feature of the KLK-L5 gene; several other kallikreins are known to be expressed in various alternatively spliced forms. In addition to the major 1.6-kb transcript, several RNA species are transcribed from the PSA gene (61). Furthermore, others (69, 70) have described several PSA isoforms. Retained introns and loss of complete exons have been reported in some of these forms. In addition, Riegman et al. reported the identification of two alternatively spliced forms of the human glandular kallikrein (KLK2) gene (62) and Liu et al. isolated three alternative forms of the same gene (68). A novel transcript of the tissue kallikrein gene was isolated from the colon (63). Neuropsin, a recently identified kallikrein-like gene, was found to have two alternatively spliced forms in addition to the major form (35, 64). Here, the cloning of the classical kallikrein form and two unique splice forms of the KLK-L5 gene are described. Because the classical form and the splice forms all have the same 5' sequence required for translation, secretion and activation as do other kallikreins, i.e. a 5' leader sequence, a signal peptide, and a proregion, it is reasonable to assume that all three mRNA forms should produce a secreted protein. Preliminary findings identifying forms of KLK-L5 predominant in certain tissues are presented in FIGS. 35 and 40.

The preliminary results indicate that KLK-L5 is up-regulated by steroid hormones in breast and prostate cancer cell lines (FIG. 39). These results are not surprising, since many other kallikrein genes are also regulated by steroid hormones. The differences in the rank of potency of steroid hormones among different cell lines could be attributed to differences in the abundance of the steroid hormone receptors between them as described elsewhere.

In conclusion, a new member of the human kallikrein gene family, KLK-L5, has been characterized which maps to the human kallikrein locus (chromosome 19q13.3–q13.4). This gene has two related splice forms in addition to the main form. KLK-L5 is expressed in a variety of tissues, appears to be down-regulated in breast cancer and its expression is influenced by steroid hormones. Since a few other kallikreins are already used as valuable tumour markers, KLK-L5 may also find a similar clinical application.

Example 7

Using the Materials and Methods substantially as set out in Example 6, the present inventors identified another novel gene of the kallikrein multigen family referred to as KLK-L6. The full structure of the KLK-L6 gene is shown in FIG. 41. Exons 1, 2, 3, 4, 5, 6, and 7 are at nucleic acids 1172–1281; 2561–2695; 2781–2842, 3714–3885; 5715–5968; 6466–6602; and 7258–7520. The nucleic acid sequence of the KLK-L6 gene is also shown in SEQ.ID.NO. 65 and amino acid sequences for the KLK-L6 protein are shown in SEQ.ID. Nos. 66 and 67. (See also GenBank Accession # AF161221).

FIG. 42 shows a comparative hydrophobicity analysis of KLK-L6 and the prostate-specific antigen (PSA). The amino terminal regions of both genes are quite hydrophobic indicating that this region of KLK-L6 is possibly harboring a signal peptide analogous to PSA.

Multiple alignment of KLK-L6 was carried out using the Clustal X software program as described herein (FIG. 43).

To predict the phylogenetic relatedness of the KLK-L6 protein with other serine proteases, the amino acid sequences of the kallikrein proteins were aligned together using the "Clustal X" multiple alignment program and a distance matrix tree was predicted using the Neighbor-joining/UPGMA and Protpars parsimony methods. FIG. 44 shows the phylogenetic analysis which separated the classical kallikreins (hK1, hK2, and PSA) and placed KLK-L6 in a separate group.

Having illustrated and described the principles of the invention in a preferred embodiment, it should be appreciated to those skilled in the art that the invention can be modified in arrangement and detail without departure from such principles. All modifications coming within the scope of the following claims are claimed.

All publications, patents and patent applications referred to herein are incorporated by reference in their entirety to the same extent as if each individual publication, patent or patent application was specifically and individually indicated to be incorporated by reference in its entirety.

FULL CITATIONS FOR REFERENCES REFERRED TO IN THE SPECIFICATION

1. Evans B A E, Yun Z X, Close J A, Tregear G W, Kitamura N, Nakanishi S. et al. Structure and chromosomal localization of the human renal kallikrein gene. Biochemistry 1988; 27:3124–3129.
2. Clements J A. The glandular kallikrein family of enzymes: Tissue-specific and hormonal regulation. Endocr Rev 1989; 10:393–419.
3. Evans B A, Drinkwater C C, Richards R I. Mouse glandular kallikrein genes: Structure and partial sequence analysis of the kallikrein gene locus. J Biol Chem 1987; 262:8027–8034.
4. Drinkwater C C, Evans B A, Richards R I. Kallikreins, kinins and growth factor biosynthesis. Trends Biochem Sci 1988b; 13:169–172.
5. Ashley P L, MacDonald R J. Tissue-specific expression of kallikrein-related genes in the rat. Biochemistry 1985; 24:4520–5427.
6. Gerald W L, Chao J, Chao L. Sex dimorphism and hormonal regulation of rat tissue kallikrein mRNA. Biochim Biophys Acta 1986; 867:16–23.
7. Riegman P H I, Vlietstra R J, van der Korput J A G M, Romijn J C, Trapman J. Characterization of the prostate-specific antigen gene: A novel human kallikrein-like gene. Biochem Biophys Res Commun 1989; 159:95–102.
8. Schedlich L J, Bennetts B H, Morris B J. Primary structure of a human glandular kallikrein gene. DNA 1987; 6:429–437.
9. Riegman P H, Vlietstra R J, Suurmeijer L, Cleutjens C B J M, Trapman J. Characterization of the human kallikrein locus. Genomics 1992; 14:6–11.
10. Anisowicz A, Sotiropoulou G. Stenman G. Mok S C, Sager R. A novel protease homolog differentially expressed in breast and ovarian cancer. Mol Med 1996; 2:624–636.
11. Little S P, Dixon E P, Norris F, Buckley W, Becker G W, Johnson M, et al. Zyme, a novel and potentially amyloidogenic enzyme cDNA isolated from Alzheimer's disease brain. J Biol Chem 1997; 272:25135–25142.
12. Yamashiro K, Tsuruoka N. Kodama S, Tsujimoto M, Yamamura Y, Tanaka T, et al. Molecular cloning of a novel trypsin-like serine protease (neurosin) preferentially expressed in brain. Biochim Biophys Acta 1997; 1350:11–14.
13. Liu X L, Wazer D E, Watanabe K, Band V. Identification of a novel serine protease-like gene, the expression of which is down-regulated during breast cancer progression. Cancer Res 1996; 56:3371–3379.
14. Luo L, Herbrick J-A, Scherer S W, Beatty B. Squire J. Diamandis E P. Structural characterization and mapping of the normal epithelial cell-specific 1 gene. Biochem Biophys Res Commun 1998; 247:580–586.
15. Milanesi L, Kolchanov N, Rogozin I. Kel A, Titov I. Sequence functional inference. In: "Guide to human genome computing", ed. M. J. Bishop, Academic Press, Cambridge, 1994, 249–312.
16. Burset M, Guigo R. Evaluation of gene structure prediction programs. Genomics 1996; 34:353–367.
17. Nadeau J, Grant P, Kosowsky M. Mouse and human homology map. Mouse Genome 1991; 89:31–36.
18. Schachter M. Kallikreins (kininogenases)—a group of serine proteases with bioregulatory actions. Pharmacol Rev 1980; 31:1–17.
19. Morris B J, Catanzaro D F, Richards R I, Mason A J, Shine J. Kallikrein and renin: Molecular biology and biosynthesis. Clin Sci 1981; 61:351s–353s.
20. Richards R I, Catanzaro D F, Mason A J, Morris B J, Baxter J D, Shine J. Mouse glandular kallikrein genes. Nucleotide sequence of cloned cDNA coding for a member of the kallikrein arginyl estero-peptidase group of serine proteases. J Biol Chem 1982; 257:2758–2761.
21. Van Leeuwen B H, Evans B A, Tregear G W, Richards R I. Mouse glandular kallikrein genes. Identification, structure and expression of the renal kallikrein gene. J Biol Chem 1986; 261:5529–5535.
22. Evans B A, Richards R I. Genes for the α and γ subunits of mouse nerve growth factor. EMBO J 1985; 4:133–138.
23. Rogozin I B, Milanesi L, Kolchanov N A. Gene structure prediction using information on homologous protein sequence. Comput Applic Biosci 1996; 12:161–170.
24. Diamandis, E. P. Prostate specific antigen-its usefulness in clinical medicine. Trends Endocrinol. Metab., 9: 310–316, 1998.
25. Diamandis, E. P., Yu H., and Sutherland, D. J. Detection of prostate-specific antigen immunoreactivity in breast tumours. Breast Cancer Res. Treat., 32: 301–310, 1994
26. Ishikawa, T., Kashiwagi, H., Iwakami, Y., et al. Expression of alpha-fetoprotein and prostate specific antigen genes in several tissues and detection of mRNAs in normal circulating blood by reverse trancriptase-polymerase chain reaction. Jpn. J. Oncol., 28:723–728, 1998.
27. Irwin, D. M., Robertson, K. A., and MacGillivary, R. T. J. Mol. Biol. 212:3145, 1988.
28. Yoshida, S., Taniguchi, M. Hirata, A., and Shiosaka, S. Sequence bovine prothrombin gene. J. Mol. Biol., 212: 31–45, 1988.
29. Goyal, J., Smith, K. M., Cowan, J. M., et al. The role of NES 1 serine protease as a novel tumor suppressor. Cancer Res., 58: 4782–4786, 1998.
30. Diamandis, E. P., and Yu, H. New biological functions of prostate specific antigen? J. Clin. Endocrinol. Metab., 80: 1515–1517, 1995.
31. Reifenberger, J., reifenberger, G., Liu, L., James, C. D. et al. Molecular genetic analysis of oligodendroglial tumors shows preferential allelic deletions on 19q and 1p.Am. J. Pathol., 145: 1175–90, 1994.
32. Iida, Y. (1990). Quantification analysis of 5'-splice signal sequence in mRNA precursors. Mutations in 5'-splice signal sequence of human β-globin gene and β-thalassemia. J. Theor. Biol. 145: 523–533.
33. Kozak, M. (1991). An analysis of vertebrate mRNA sequences: Intimations of translational control. J. Cell Biol. 115: 887–892.
34. Clements, J. (1997). The molecular biology of the kallikreins and their roles in inflamation. In: S. Farmer (ed.), The kinin system, pp. 71–97. New York: Academic Press.
35. Yoshida, S. Taniguchi, M., Hirata, A., and Shiosaka, S. (1998). Sequence analysis and expression of human neuropsin cDNA and gene. Gene 213:9–16.
36. Takayama, T. K, Fujikawa, K., Davie, E. W. (1997). Characterization of the precursor of prostate-specific antigen. Activation by trypsin and by human glandular kallikrein. J. Biol. Chem. 272: 21582–21588.

37. Altschul, S. F. et al., Nucleic Acids Res. 25: 3389–3402, 1997.
38. Lennon, G. et al, Genomics 33: 151–152, 1996.
39. Dayhoff, M. O., Natl. Biomed. Res. Found. 5 (Suppl 3) 79–81, 1998.
40. Simmer, J. P., et al, J. Dent. Res. 77:377–386, 1998.
41. Nelson, P. S. et al, PNAS 96: 3114–3119, 1999.
42. Osoegawa, K. et al, Genomics 52: 1–8, 1999.
43. Kozak, M., Nucleic Acid Res. 15: 8125–8148, 1987.
44. Proudfoot, N. J. and Brownlee, C. G., Nature 263: 211–214, 1976.
45. Miyata, T. et al, J. Mol. Evol. 12: 219–236, 1979.
46. Mitelman, F., Catalog of Chromosome Aberrations in Cancer. 5th ed. Wiley-Liss, New York, pp. 3067–3198.
47. Yu, H. et al, Clin. Cancer res. 4: 1489–1497, 1998.
48. Sauter, E. R., Cancer Epidemol. Biomarkers Prev. 5:967–970, 1996.
49. Fortier, A. H. et al, J. Natl. Cancer Inst. 91: 1635–1640, 1999.
50. Kumar, A., 1998, Cancer res. 57: 3111–3114, 1997.
51. Lovgren, J. Biochem. Biophys. Res. Commun. 238: 549–555, 1987.
52. Lai, L. C. et al., Int. J. Cancer 66: 743–746, 1996.
53. Balbay, M. D. et al, Proc. Amer. Assoc. Cancer Res. 40: 225–226, 1999.
54. Rittenhouse, H. G. et al Crit. Rev. Clin. Lab. Sci. 35: 275–368, 1998.
55. Hansson, L et al, J. Biol. Chem. 269: 19420–19426, 1994.
56. Stephenson, S. et al J. Biol. Chem. 27: 23210–23214, 1999.
57. Stenman, U. H. Clin. Chem. 45: 753–754, 1999.
58. Black, M. H., Clin. Chem. 45: 790–799, 1999.
59. Underwood, L J. et al, Cancer Res. 59:4435–4439, 1999.
60. Adams, M. D. et al, Curr. Opin. Cell Biol. 8:331–339, 1996.
61. Heuze, N. et al, cancer Res. 59: 2820–2824, 1999.
62. Riegman, P. H., Mol. Cell Endocrinol. 76: 181–190.
63. Chen, L. M. Braz. J. Med. Biol Res. 27: 1829–1838, 1994.
64. Mitsui, S. et al, Eur. J. Biochem. 260:627–634.
65. Baffa, R., Urology, 47:795–800, 1996.
66. Hentiu. P. et al. nt. J. Cancer 45: 654–660, 1990.
67. McCormack. R. T. et al, Urology 45: 729–744, 1995.
68. Liu, X. F. et al, Biochem. Biophys. Res. Commun. 264:833–839, 1999.
69. Riegman. P. H. et al, Biochem. Biophys. Res. Commun. 155: 181–188, 1988.
70. Lundwall, A. and H. Lilja. FEBS Lett. 214: 317–322, 1987.
71. Zarghami, N. et al, Br. J. Cancer 75: 579–88, 1997.

TABLE 1

Predicted exons of the putative gene KLK-L1. The translated protein sequences of each exon (open reading frame) are shown.

| Exon No.[1] | Putative coding region[2] From(bp) | To(bp) | No. of bases | Translated protein sequence | EST match[3] | Intron phase[4] | Stop codon[5] | Catalytic triad[6] | Exon prediction program[7] |
|---|---|---|---|---|---|---|---|---|---|
| 2 | 2263 | 2425 | 163 | SLVSGSCSQIINGEDCSPHSQPWQAALVMENELFCSGV LVHPQWVLSAAHCFQ | + | II | − | H | A,B,D |
| 3 | 2847 | 3109 | 263 | NSYTIGLGLHSLEADQEPGSQMVEASLSVRHPEYNRPL LANDLMLIKLDESVSESDTIRSISIASQCPTAGNSCLVSG WGLLANGELT | + | I | − | D | A,B,C,D |
| 4 | 3180 | 3317 | 137 | GRMPTVLQCVNVSVVSEEVCSKLYDPLYHPSMFCAGG GQDQKDSCN | + | 0 | − |  | A,B,C,D |
| 5 | 4588 | 4737 | 150 | GDSGGPLICNGYLQGLVSFGKAPCGQVGVPGYYTNLC KFTEWIEKTVQAS | + | — | + | S | A,B,C |

[1]Conventional numbering of exons in comparison to the five coding exons of PSA, as described in Ref. 14.
[2]Nucleotide numbers refer to the related contig
[3](+) = >95% homology with published human EST sequences.
[4]Intron phase: 0 = the intron occurs between codons; I = the intron occurs after the first nucleotide of the codon; II = the intron occurs after the second nucleotide of the codon.
[5](+) denotes the exon containing the stop codon.
[6]H = histidine, D = aspartic acid, S = serine. The aminoacids of the catalytic triad are bold and underlined.
[7]A = GeneBuilder (gene analysis), B = GeneBuilder (exon analysis), C = Grail 2, D = GENEID-3

TABLE 2

Predicted exons of the putative gene KLK-L2. The translated protein sequences of each exon (open reading frame) are shown*

| Exon No.[1] | Putative coding sequence[2] From (bp) | To(bp) | No. of bases | Translated protein sequence | EST match[3] | Intron phase[4] | Stop codon[5] | Catalytic triad[6] | Exon prediction program[7] |
|---|---|---|---|---|---|---|---|---|---|
| 1 | 15,361 | 15,433 | 73 | MATARPPWMWVLCALITALLLGVT | + | I | − | — | — |
| 2 | 17,904 | 18,165 | 262 | EHVLANNDVSCDHPSNTVPSGSNQDLGAGAGEDARSDDSSSRIIN GSDCDMHTQPWQAALLLRPNQLYCGAVLVHPQWLLTAAHCRK K | + | II | − | H | A,B,C,D |
| 3 | 18,903 | 19,159 | 257 | VFRVRLGHYSLSPVYESGQQMFQGVKSIPHPGYSHPGHSNDLMLI KLNRRIRTKDVRPINVSSHCPSAGTKCLVSGWGTTKSPQ | + | I | − | D | C,D |

TABLE 2-continued

Predicted exons of the putative gene KLK-L2. The translated protein sequences of each exon (open reading frame) are shown*

| Exon No.[1] | Putative coding sequence[2] From (bp) | To(bp) | No. of bases | Translated protein sequence | EST match[3] | Intron phase[4] | Stop codon[5] | Cata-lytic triad[6] | Exon prediction program[7] |
|---|---|---|---|---|---|---|---|---|---|
| 4 | 19,245 | 19,378 | 134 | VHFPKVLQCLNISVLSQKRCEDAYPRQIDDTMFCAGDKAGRDSCQ | + | 0 | − | — | B,C |
| 5 | 24,232 | 24,384 | 153 | GDSGGPVVCNGSLQGLVSWGDYPCARPNRPGVTNLCKTTKWIQETIQANS | + | — | + | S | A,B,C |

*All footnotes same as Table 1

TABLE 3

Predicted exons of the putative gene KLK-L3. The translated protein sequences of each exon (open reading frame) are shown*

| Exon No.[1] | Putative coding region[2] From(bp) | To(bp) | No. of bases | Translated protein sequence | EST match[3] | Intron phase[4] | Stop codon[5] | Cata-lytic triad[6] | Exon prediction program[7] |
|---|---|---|---|---|---|---|---|---|---|
| 1 | 70,473 | 70,584 | 112 | VHFPTPINHRGGPMEEEGDGMAYHKEALDAGCTFQDP | − | I | − | — | A,B,C,D |
| 2 | 70,764 | 70,962 | 199 | ACSSLTPLSLIPTPGHGWADTRAIGAEECRPNSQPWQAGLFHLTRLFCGATLISDRWLLTAAHCRK | + | II | − | H | A,B,C,D |
| 3 | 73,395 | 73,687 | 293 | PLTSEACPSRYLWVRLGEHHLWKWEGPEQLFRVTDFFPHPGFNKDLSANDHNDDIMLIRLPRQARLSPAVQPLNLSQTCVSPGMQCLISGWGAVSSPK | + | I | − | D | A,B,C,D |
| 4 | 76,305 | 76,441 | 137 | ALFPVTLQCANISILENKLCHWAYPGHISDSMLCAGLWEGGRGSCQ | + | 0 | − | — | A,B,C,D |
| 5 | 76,884 | 77633 | 749 | GDSGGPLVCNGTLAGVVSGGAEPCSRPRRPAVYTSVCHYLDWIQEIMEN | − | — | + | S | A,B |

*All footnotes same as Table 1

TABLE 4

Predicted exons of the putative gene KLK-L4. The translated protein sequences of each exon (open reading frame) are shown*

| Exon No.[1] | Putative coding region[2] From(bp) | To(bp) | No. of bases | Translated protein sequence | EST match[3] | Intron phase[4] | Stop codon[5] | Cata-lytic triad[6] | Exon prediction program[7] |
|---|---|---|---|---|---|---|---|---|---|
| 2 | 24,945 | 25,120 | 176 | ESSKVLNTNGTSGFLPGGYTCFPHSQPWQAALLVQGRLLCGGVLVHPKWVLTAAHCLKE | + | II | − | H | C |
| 3 | 25,460 | 25,728 | 269 | GLKVYLGHALGRVEAGEQVREVVHSIPHPEYRRSPTHLNHDHDIMLLELQSPVQLTGYIQTLPLSHNNRLTPGTTCRVSGWGTTTSPQ | + | I | − | D | A,B,C,D |
| 4 | 26,879 | 27,015 | 137 | VNYPKTLQCANIQLRSDEECRQVYPGKITDNMLCAGTKEGGKDSCE | + | 0 | − | — | A,B,C,D |
| 5 | 28,778 | 28,963 | 189 | GDSGGPLVCNRTLYGIVSWGDFPCGQPDRPGVYTRVSRYVLWIRETIRKYETQQQKWLKGPQ | + | — | + | S | A,B,C |

*All footnotes same as Table 1

TABLE 5

Predicted exons of the putative gene KLK-L5. The translated protein sequences of each exon (open reading frame) are shown*

| Exon No.[1] | Putative coding region[2] From(bp) | To(bp) | No. of bases | Translated protein sequence | EST match[3] | Intron phase[4] | Stop codon[5] | Catalytic triad[6] | Exon prediction program[7] |
|---|---|---|---|---|---|---|---|---|---|
| 2 | 1588 | 1747 | 160 | LSQAATPKIFNGTECGRNSQPWQVGLFEGTSLRCGGVLIDHRWVLTAAHCSG | − | II | − | H | A,B,C |
| 3 | 3592 | 3851 | 260 | SRYWVRLGEHSLSQLDWTEQIRHSGFSVTHPGYLGASTSHEHDLRLLRLRLPVRVTSSVQPLPLPNDCATAGTECHVSGWGITNHPR | + | I | − | D | A,B,C,D |

TABLE 5-continued

Predicted exons of the putative gene KLK-L5. The translated protein sequences of each exon (open reading frame) are shown*

| Exon No.[1] | Putative coding region[2] From(bp) | Putative coding region[2] To(bp) | No. of bases | Translated protein sequence | EST match[3] | Intron phase[4] | Stop codon[5] | Catalytic triad[6] | Exon prediction program[7] |
|---|---|---|---|---|---|---|---|---|---|
| 4 | 4806 | 4939 | 134 | NPFPDLLQCLNLSIVSHATCHGVYPGRITSNMVCAGGVPGQDACQ | + | 0 | – | — | A,B,C,D |

*All footnotes same as Table 1

TABLE 6

Homology between the predicted amino acid sequences of the newly identified putative genes and protein sequences deposited in Genbank

| No. | Gene identity | Homologous known protein | Identity % (number of amino acids) |
|---|---|---|---|
| 1 | KLK-L1 | Human stratum corneum chymotryptic enzyme | 44 (101/227) |
|  |  | Rat kallikrein | 40 (96/237) |
|  |  | Mouse glandular kallikrein K22 | 39 (94/236) |
|  |  | Human glandular kallikrein | 38 (93/241) |
|  |  | Human prostatic specific antigen | 37 (91/241) |
|  |  | Human protease M | 37 (87/229) |
| 2 | KLK-L2 | Human neuropsin | 48 (106/219) |
|  |  | Human stratum corneum chymotryptic enzyme | 47 (103/216) |
|  |  | Human protease M | 45 (99/219) |
|  |  | Human trypsinogen I | 45 (100/221) |
|  |  | Rat trypsinogen | 44 (98/220) |
| 3 | KLK-L3 | Human neuropsin | 44 (109/244) |
|  |  | Rat trypsinogen 4 | 39 (95/241) |
|  |  | Human protease M | 38 (98/253) |
|  |  | Human glandular kallikrein | 37 (94/248) |
|  |  | Human prostatic specific antigen | 36 (89/242) |
| 4 | KLK-L4 | Human protease M | 52 (118/225) |
|  |  | Human neuropsin | 51 (116/225) |
|  |  | Mouse neuropsin | 51 (116/226) |
|  |  | Human glandular kallikrein | 48 (113/234) |
|  |  | Human prostatic specific antigen | 47 (108/227) |
| 5 | KLK-L5 | Human neuropsin | 44 (81/184) |
|  |  | Rat trypsinogen I | 42 (76/178) |
|  |  | Rat trypsinogen II | 42 (75/178) |
|  |  | Human protease M | 41 (73/178) |

TABLE 7

Expressed sequence tags with >95% homology to exons of the prostase/KLK-L1 gene.

| GenBank # | Source | Tissue | homologous exons |
|---|---|---|---|
| AA551449 | I.M.A.G.E. | prostate | 3, 4, 5 |
| AA533140 | I.M.A.G.E. | prostate | 4, 5 |
| AA503963 | I.M.A.G.E. | prostate | 5 |
| AA569484 | I.M.A.G.E. | prostate | 5 |
| AA336074 | TIGR | endometrium | 2, 3 |

TABLE 8

Primers used for reverse transcription-polymerase chain reaction (RT-PCR) analysis of various genes.

| Gene | Primer name | Sequence[1] | Product size (base pairs) |
|---|---|---|---|
| Prostase (KLK-L1) | RS | TGACCCGCTGTACCACCCCA | 278 |
|  | RAS | GAATTCCTTCCGCAGGATGT |  |
| pS2 | PS2S | GGTGATCTGCGCCCTGGTCCT | 328 |
|  | PS2AS | AGGTGTCCGGTGGAGGTGGCA |  |
| PSA | PSAS | TGCGCAAGTTCACCCTCA | 754 |
|  | PSAAS | CCCTCTCCTTACTTCATCC |  |
| Actin | ACTINS | ACAATGAGCTGCGTGTGGCT | 372 |
|  | ACTINAS | TCTCCTTAATGTCACGCACGA |  |

[1]All nucleotide sequences are given in the 5'→3' orientation.

TABLE 9

Tissue expression of prostase/KLK-L1 by RT-PCR analysis

Expression level

| High | medium | low | No Expression |
|---|---|---|---|
| Prostate | Mammary gland | Salivary glands | Stomach |
| Testis | Colon | Lung | Heart |
| Adrenals | Spinal cord | Brain | Spleen |
| Uterus |  | Bone marrow | Placenta |
| Thyroid |  | Thymus | Liver |
|  |  | Trachea | Pancreas |
|  |  | Cerebellum | Kidney |
|  |  |  | Fetal brain |
|  |  |  | Fetal liver |
|  |  |  | Skeletal muscle |
|  |  |  | Small intestine |

TABLE 10

EST clones with >95% homology to exons of KLK-L2

| GENBANK # | Tissue of Origin | I.M.A.GE. ID | Homologous exons |
|---|---|---|---|
| W73140 | Fetal heart | 344588 | 4, 5 |
| W73168 | Fetal heart | 344588 | 3, 4, 5 |
| AA862032 | Squamous cell carcinoma | 1485736 | 4, 5 |
| AI002163 | Testis | 1619481 | 3, 4, 5 |
| N80762 | Fetal lung | 300611 | 5 |
| W68361 | Fetal heart | 342591 | 5 |
| W68496 | Fetal heart | 342591 | 5 |
| AA292366 | Ovarian tumor | 725905 | 1, 2 |
| AA394040 | Ovarian tumor | 726001 | 5 |

TABLE 11

Primers used for reverse transcription polymerase chain reaction (RT-PCR) analysis.

| Gene | Primer name | Sequence[1] | Product size (base pairs) |
| --- | --- | --- | --- |
| KLK-L2 | KS | GGATGCTTACCCGAGACAGA | 342 |
|  | KAS | GCTGGAGAGATGAACATTCT |  |
| pS2 | PS2S | GGTGATCTGCGCCCTGGTCCT | 328 |
|  | PS2AS | AGGTGTCCGGTGGAGGTGGCA |  |
| PSA | PSAS | TGCGCAAGTTCACCCTCA | 754 |
|  | PSAAS | CCCTCTCCTTACTTCATCC |  |
| Actin | ACTINS | ACAATGAGCTGCGTGTGGCT | 372 |
|  | ACTINAS | TCTCCTTAATGTCACGCACGA |  |
| KLK-L2 | R1 | CCGAGACGGACTCTGAAAACTTTCTTCC |  |
|  | R2 | TGAAAACTTTCTTCCTGCAGTGGGCGGC |  |

[1]All nucleotide sequence are given in the 5' 3' orientation.

TABLE 12

Tissue expression of KLK-L2 by RT-PCR analysis.

sion level

| high | Medium | low | No Expression |
| --- | --- | --- | --- |
| Brain | Salivary gland | Uterus | Stomach |
| Mammary gland | Fetal brain | Lung | Adrenal gland |
| Testis | Thymus | Heart | Colon |
|  | Prostate | Fetal liver | Skeletal muscle |
|  | Thyroid | Spleen |  |
|  | Trachea | Placenta |  |
|  | Cerebellum | Liver |  |
|  | Spinal cord | Pancreas |  |
|  |  | Small intestine |  |
|  |  | Kidney |  |
|  |  | Bone marrow |  |

TABLE 13

Primers used for reverse transcription polymerase chain reaction (RT-PCR) analysis.

| Gene | Primer name | Sequence[1] |
| --- | --- | --- |
| KLK-L3 | L3-F1 | CATGCAGTGTCTCATCTCAG |
|  | L3-F2 | CATGGAGGAGGAAGGAGATG |
|  | L3-R1 | CTTCGGCCTCTCTTGGTCTT |
| PSA | PSAS | TGCGCAAGTTCACCCTCA |
|  | PSAAS | CCCTCTCCTTACTTCATCC |
| Actin | ACTINS | ACAATGAGCTGCGTGTGGCT |
|  | ACTINAS | TCTCCTTAATGTCACGCACGA |

[1]All nucleotide sequence are given in the 5'→3' orientation.

TABLE 14

Primers used for gene-specific PCR amplification of the kallikrein genes using DNA as a template.

| Primer name | Sequence[1] | Coordinates | GenBank accession # | Gene name |
| --- | --- | --- | --- | --- |
| Z1S | GACCCTGACATGTGACATCTA | 979–999 | U62801 | Zyme |
| Z1AS | GCCACTGCCTGATGGAGACTG | 1422–1402 |  |  |
| GL3-F1 | AACATCAGCATCCTGGAGAA | 7324–7343 | AF135026 | KLK-L3 |
| LL3-R1 | CTTCGGCCTCTCTTGGTCTT | 8051–8060 |  |  |
| L2-1 | GGGTCAGAGCTGCAGAGAAG | 11104–11123 | AF135028 | KLK-L2 |
| L2-2 | GGGCCTGTCGTCTGCAATGG | 11522–11541 |  |  |
| KLK-L1 | ATGGCCACAGCAGGAAATCC | 1411–1430 | AF113141 | KLK-L1 |
|  | GGTCACTTGTCTGCGCAGAC | 1990–2019 |  |  |
| PS | CCCAACCCTGTGTTTTTCTC | 3634–3653 | M33105 | PSA[2] |
| PAS | GGCCCTCCTCCCTCAGA | 4143–4118 |  |  |
| K1S | ATCCCTCCATTCCCATCTTT | 2–22 | M18157 | KLK1[3] |
| K1AS | CACATACAATTCTCTGGTTC | 324–30 |  |  |
| K2S | AGTGACACTGTCTCAGAATT | 131–150 | AF024605 | KLK2[4] |
| K2AS | CCCCAATCTCACCAGTGCAC | 580–561 |  |  |
| NS | GCTTCCCTACCGCTGTGCT | 552–570 | AF055481 | NES1[5] |
| NAS | CACTCTGGCAAGGGTCCTG | 763–744 |  |  |

TABLE 14-continued

Primers used for gene-specific PCR amplification of the kallikrein genes using DNA as a template.

| Primer name | Sequence[1] | Coordinates | GenBank accession # | Gene name |
|---|---|---|---|---|

[1]all nucleotide sequences are given in the 5'→3' orientation
[2]prostate specific antigen
[3]human renal kallikrein
[4]human glandular kallikrein
[5]normal epithelia cell-specific 1 gene.

TABLE 15

Primers used for reverse transcription polymerase chain reaction (RT-PCR) analysis.

| Gene | Primer name | Sequence[1] |
|---|---|---|
| KLK-L4 | L4-F1 | AACTCTACAATGTGCCAACA |
|  | L4-R1 | TTATTGTGGGCCCTTCAACC |
|  | L4-R3 | GGATGGTCCATTTATAGGAC |
|  | L4-A | AGGCTGCCCTACTAGTGCAA |
|  | L4-B | ATATTGCCTAGGTGGATGTG |
|  | L4-D | AAGACTTCAAGGAGCCAAGC |
|  | L4-E | GACCCTTCACCTCCCAAAAT |
|  | L4-X1 | CTAGTGATCGCCTCCCTGAC |
| pS2 | PS2S | GGTGATCTGCGCCCTGGTCCT |
|  | PS2AS | AGGTGTCCGGTGGAGGTGGCA |
| PSA | PSAS | TGCGCAAGTTCACCCTCA |
|  | PSAAS | CCCTCTCCTTACTTCATCC |
| Actin | ACTINS | ACAATGAGCTGCGTGTGGCT |
|  | ACTINAS | TCTCCTTAATGTCACGCACGA |

[1]All nucleotide sequence are given in the 5'→3' orientation.

TABLE 16

EST clones with >95% homology to exons of KLK-L4

| GenBank # | Tissue of origin | I.M.A.GE. ID |
|---|---|---|
| AA399955 | Testis | 743113 |
| AA401397 |  |  |
| AA846771 | Testis | 1392889 |
| AI002101 | Testis | 1619045 |
| AI032327 | Testis | 1644236 |

TABLE 17

Primers used for reverse transcription polymerase chain reaction (RT-PCR) analysis.

| Gene | Primer name | Sequence[1] |
|---|---|---|
| KLK-L5 | KLK-L5-F1 | TCAGCCAGGCAGCCACACCG |
|  | KLK-L5-R1 | TTGGTGATGCCCCAGCCTGA |
|  | L5-F2 | CCACACCGAAGATTTTCAAT |
|  | L5-R2 | GCCCCTCCTTCATTTATA |
| PSA | PSAS | TGCGCAAGTTCACCCTCA |
|  | PSAAS | CCCTCTCCTTACTTCATCC |
| Actin | ACTINS | ACAATGAGCTGCGTGTGGCT |
|  | ACTINAS | TCTCCTTAATGTCACGCACGA |

[1]All nucleotide sequence are given in the 5'→3' orientation.

What is claimed is:

1. A purified and isolated nucleic acid molecule comprising:
   (i) the sequence of SEQ ID NO: 13; or
   (ii) a nucleic acid sequence 100% complementary to (i).

2. The nucleic acid molecule of claim 1 which differs from any of the nucleic acid sequences of (i) to (ii) in codon sequences due to the degeneracy of the genetic code.

3. A vector comprising a nucleic acid molecule of claim 1.

4. A purified and isolated host cell comprising the vector of claim 3.

5. A probe comprising a nucleic acid molecule of claim 1.

6. A composition comprising a nucleic acid molecule of claim 1 and a pharmaceutically acceptable carrier, excipient, or diluent.

7. A method for preparing a protein encoded by a nucleic acid molecule comprising the sequence of SEQ ID NO:13, said method comprising the step of:
   (a) transferring the vector of claim 3 into a host cell, wherein the vector comprises a nucleic acid molecule of SEQ ID NO:13;
   (b) selecting transformed host cells from untransformed host cells;
   (c) culturing a selected transformed host cell under conditions which allow expression of said protein; and
   (d) isolate said protein.

8. A probe comprising a nucleic acid sequence of SEQ ID NO: 13.

* * * * *

UNITED STATES PATENT AND TRADEMARK OFFICE
CERTIFICATE OF CORRECTION

PATENT NO.         : 7,022,497 B1
APPLICATION NO. : 09/936271
DATED                  : April 4, 2006
INVENTOR(S)        : Yousef et al.

It is certified that error appears in the above-identified patent and that said Letters Patent is hereby corrected as shown below:

Col. 1, line 39, replace "45 Kb" with -- 4.5 Kb --;

Col. 1, line 57, replace "(1114)." with -- (10-14). --;

Col. 2, line 58, replace "KLK-L Proteins" with -- KLK-L. Proteins --;

Col. 8, line 28, delete "is";

Col. 10, line 29, replace "ant" with -- art --;

Col. 11, line 5, delete the second occurrence of "in";

Col. 16, line 58, replace "44384442," with -- 4438-4442, --;

Col. 21, line 8, replace "3H," with -- $^3$H --;

Col. 22, line 49, replace "dextran." with -- dextran, --;

Col. 24, line 11, delete the second occurrence of "ovarian,";

Col. 26, line 43, replace "doe" with -- does --;

Col. 26, line 46, replace "doe" with -- does --;

Col. 26, line 58, replace "an" with -- a --;

Col. 31, line 36, replace ".nim-" with -- .nlm --;

Col. 32, line 57, replace "klk-L2" with -- KLK-L2 --;

Col. 34, line 51, replace "KLK-1L" with -- KLK-L1 --;

Col. 35, line 14, replace ".com.cutter" with -- .com/cutter --;

Col. 35, line 31, replace "cnr.it~" with -- cnr.it/~ --;

Col. 35, line 39, replace "nim." with -- nlm. --;

UNITED STATES PATENT AND TRADEMARK OFFICE
CERTIFICATE OF CORRECTION

PATENT NO. : 7,022,497 B1
APPLICATION NO. : 09/936271
DATED : April 4, 2006
INVENTOR(S) : Yousef et al.

It is certified that error appears in the above-identified patent and that said Letters Patent is hereby corrected as shown below:

Col. 36, line 53, replace "moen.bcm.tmc. edu:8808/search-L4 uncher" with

-- mgen.bcm.tmc. edu:8808/search-L4 launcher --;

Col. 43, line 63, replace "GenBAnk" with -- GenBank --;

Col. 45, line 67, replace "prostas" with -- prostase/ --;

Col. 47, line 49, replace "(LA-F1" with -- (L4-F1 --;

Col. 48, line 13, replace ".ukl/pub" with -- .uk/pub --;

Col. 48, line 24, replace "933/seq-" with -- 9331/seq- --;

Col. 49, line 47, delete the second occurrence of "that";

Col. 50, line 18, replace "KLC-L4" with -- KLK-L4 --;

Col. 51, line 41, replace "TLSP." with -- TLSP, --;

Col. 53, line 43, replace "KLK-IA" with -- KLK-L4 --;

Col. 54, line 21, replace ".nim.nih." with -- .nlm.nih. --;

Col. 55, line 57, replace "uncher" with -- launcher --;

Col. 56, line 1, replace "(http.//" with -- (http:// --;

Col. 60, line 30, replace "tumour" with -- tumor --;

Col. 61, line 30, replace "P H I," with -- P H J. --;

Col. 62, line 32, replace "trancriptase" with -- transcriptase --;

Col. 62, line 45, replace "reifenberger" with -- Reifenberger --;

UNITED STATES PATENT AND TRADEMARK OFFICE
CERTIFICATE OF CORRECTION

PATENT NO. : 7,022,497 B1
APPLICATION NO. : 09/936271
DATED : April 4, 2006
INVENTOR(S) : Yousef et al.

It is certified that error appears in the above-identified patent and that said Letters Patent is hereby corrected as shown below:

Col. 64, line 28, Table 1, row "Exon No. 5" replace

"GD<u>S</u>GGPLICNGYLQGLVSFGKAPCGQVGVPGYYTNLC" with

-- GD<u>S</u>GGPLICNGYLQGLVSFGKAPCGQVGVPGVYTNLC --;

Col. 64, line 41, Table 2, row "Exon No. 3" replace

"KLNRRIRTKDVRPINVSSHCPSAGTKCLVSGWGTTKSPQ" with

-- KLNRRIRPTKDVRPINVSSHCPSAGTKCLVSGWGTTKSPQ --;

Col. 64, line 57, Table 2-continued, row "Exon No. 5" replace

"GD<u>S</u>GGPVVCNGSLQGLVSWGDYPCARPNRPGVTNLCKTTKWI" with

-- GD<u>S</u>GGPVVCNGSLQGLVSWGDYPCARPNRPGVYTNLCKTTKWI --;

Col. 65 & 66, line 50, Table 4, row "Exon No. 3" replace

"GLKVYLGHALGRVEAGEQVREVVHSIPHPEYRRSPTHL" with

-- GLKVYLGKHALGRVEAGEQVREVVHSIPHPEYRRSPTHL --;

Signed and Sealed this

Seventeenth Day of February, 2009

JOHN DOLL
*Acting Director of the United States Patent and Trademark Office*

SEQUENCE LISTING

```
<160> NUMBER OF SEQ ID NOS: 97

<210> SEQ ID NO 1
<211> LENGTH: 4740
<212> TYPE: DNA
<213> ORGANISM: Homo sapiens

<400> SEQUENCE: 1
tatctcatga gagagaataa gaacatgaaa agagaaagaa tgagagagag agagagaaag       60
aaaaaggaga gtggagtcta ggatctgggc aggggtctcc tccctgggtc cctagaccct      120
gctgccagcc ccttctgggc ccccaaccac tgcctggtca gagttgaggc agcctgagag      180
agttgagctg gaagtttgca gcacctgacc cctggaacac atcccctggg ggcaggccag      240
cccaggctga ggatgcttat aagccccaag gaggccctg cggaggcagc aggctggagc       300
tcagcccagc agtggaatcc aggagcccag aggtggccgg gtaagaggcc tggtggtccc      360
ccactaaaag cctgcagtgt tcatgatcca actctcccta cagctccatg tcgctggatt      420
ctcagcctct gtgccttctg tctccacatc tctctagaca gatctctcac tgtctctagt      480
```

-continued

| | |
|---|---|
| taggagtcac tgtctctagt tagggctctc tctgtctctc tgaatctata tctccatgtc | 540 |
| taactctcag actgtctctg aggatatctc tcaagcactc tgtctctccg gctctgattc | 600 |
| tctgtgtgtc ttccctccat gcttgtttgt gggtggctag acaccatctc tccccattca | 660 |
| cagatggcta gatgctttct ctaaactttc ctttctacct agttctctct ctctctcttt | 720 |
| tcccatctct ctctctcttt ttctctctca gtctctaaat ctgtctctct aggttctggg | 780 |
| tccatggatg ggagaggggg tagatggtct aggctcttgc ctacctaata acgtcccaga | 840 |
| gggaagaaag ggagggacaa agagagggat ggagagactt gggctgaaga tccccagaca | 900 |
| cggctaagtc tcagtcctca tccccaggtg ctgacgtgat ggccacagca ggaaatccct | 960 |
| ggggctggtt cctggggtac ctcatccttg tgtcgcagg tatctgagta tgcgtgtgtg | 1020 |
| tgtctgtccg tgcttggggg cacagtgttt gttaatgttc aggtgtgact cagtgtcctc | 1080 |
| ttgcttgtga ctgcaaagct gcctgtgaga cggtaccgtg ttatccgtcc gccatggctg | 1140 |
| tgcccctgca actccttgta tcgtggtaaa tttgtgtgtg gcagtgtgcc tgggtgtgtg | 1200 |
| gttgtacctg tgagactctg acagtttgtg cctctgaata tctggtggag tgacaacagt | 1260 |
| gtaatgatga tatggggaca ggggaagccg agggtgcagg agattgtgct tcctggggcg | 1320 |
| tgatccattg ctgggaatct gtgcctgctt cctgggtctt cagtcctgag atcccctct | 1380 |
| cccatcccca aggaactcac ctcacaggac tataaaacgg tgttttggtg tgcatgggct | 1440 |
| tgtggcttgg tgtgactgtg ggcaaggctg ggagaggata ggagtgactc ggcgcaggac | 1500 |
| cgactctttg agcatcagtc tgcgcagaca agtgacccga tccttgctcc cagcaacaac | 1560 |
| tccaccccct gagctttaat tcaccccgaa ggacccgatc ctaccgctat gagcctagac | 1620 |
| tcctctgttg aacccctcct gaccgtggct ttgcaccgcg atggcaccag tctcacctcc | 1680 |
| agagctcacc ccagagccct gactccgccc cagaagccct ggtcccacct tctgagactg | 1740 |
| cctctagcca taacccagct cttgaagcct tgatggcgcc cctgcgctgt aaccccaacc | 1800 |
| ctaggagcac tgatcccgcc ttctcagccc acccccatgc cctgactctc ctcccaggag | 1860 |
| ccctgactac cctgaatccc tgaccaggct cctgcaccgt gatcaccgcc cctgggagcc | 1920 |
| ctaggcctat atcctggacc agcccctgaa gctccgatca tgacccctgc accataaccc | 1980 |
| cacccccagg agccctgggt ccgccccctg ggcccgcccc cagccctgac tcggccccc | 2040 |
| aagagtcctg actgctcctg aagccctgac cacgcccctg ctcggtaacc cctcccccaa | 2100 |
| gagccctggg cccgcctcct gagcccgttc ccagccctga ctccgccccg aggagccctg | 2160 |
| actgctcctg aacctctgac cacgcccctg ctcggtaagc ccaccccccag gaaccctggg | 2220 |
| cccgcctcct ggtcccgatc ccatccctga ctccgccctc aggatctctc gtctctggta | 2280 |
| gctgcagcca aatcataaac ggcgaggact gcagcccgca ctcgcagccc tggcaggcgg | 2340 |
| cactggtcat ggaaaacgaa ttgttctgct cgggcgtcct ggtgcatccg cagtgggtgc | 2400 |
| tgtcagccgc acactgtttc cagaagtgag tgcagaggta gggggagtgg gcagggcctg | 2460 |
| ggtccggggg cggggcctaa tatcaggctc atcttggggt gctcaggggg aaacagcggt | 2520 |
| gaaggctctg gaggaggac ggaatgagcc tggatccggg gagcccagag ggaagggctg | 2580 |
| ggaggcggga atcttgcttc ggaaggactc agagagccct gacttgaaat ctcagcccag | 2640 |
| tgctgagtct ctagtgaact aaggcaagtt cttgtccctg aattttttgtg aatgaggatt | 2700 |
| tgagaccatg gttaagtagc tcttagggtg tttagcgaag agggtggggt tggggttagg | 2760 |
| agatggggat gggaatgggg ttgaagatga gaatggaggt aaggatgtag ttgccacaaa | 2820 |
| actgacctgc cctccgtggc ccacagctcc tacaccatcg ggctgggcct gcacagtctt | 2880 |

-continued

```
gaggccgacc aagagccagg gagccagatg gtggaggcca gcctctccgt acggcaccca   2940
gagtacaaca gaccccttgct cgctaacgac ctcatgctca tcaagttgga cgaatccgtg   3000
tccgagtctg acaccatccg gagcatcagc attgcttcgc agtgccctac cgcggggaac   3060
tcttgcctcg tttctggctg gggtctgctg gcgaacggtg agctcacggg tgtgtgtctg   3120
ccctcttcaa ggaggtcctc tgcccagtcg cggggggctga cccagagctc tgcgtcccag   3180
gcagaatgcc taccgtgctg cagtgcgtga acgtgtcggt ggtgtctgag gaggtctgca   3240
gtaagctcta tgacccgctg taccaccccca gcatgttctg cgccggcgga gggcaagacc   3300
agaaggactc ctgcaacgtg agagagggga aggggaggg caggcgactc agggaagggt   3360
ggagaagggg gagacagaga cacacagggc cgcatggcga gatgcagaga tggagagaca   3420
cacagggaga cagtgacaac tagagagaga aactgagaga aacagagaaa taaacacagg   3480
aataaagaga agcaaaggaa gagagaaaca gaaacagaca tggggaggca gaaacacaca   3540
cacatagaaa tgcagttgac cttccaacag catggggcct gagggcggtg acctccaccc   3600
aatagaaaat cctcttataa cttttgactc cccaaaaacc tgactagaaa tagcctactg   3660
ttgacgggga gccttaccaa taacataaat agtcgattta tgcatacgtt ttatgcattc   3720
atgatatacc tttgttggaa ttttttgata tttctaagct acacagttcg tctgtgaatt   3780
tttttaaatt gttgcaactc tcctaaaatt tttctgatgt gtttattgaa aaaatccaag   3840
tataagtgga cttgtgcagt tcaaaccagg gttgttcaag ggtcaactgt gtacccagag   3900
ggaaacagtg acacagattc atagaggtga aacacgaaga gaaacaggaa aaatcaagac   3960
tctacaaaga ggctgggcag ggtggctcat gcctgtaatc ccagcacttt gggaggcgag   4020
gcaggcagat cacttgaggt aaggagttca agaccagcct ggccaaaatg gtgaaatcct   4080
gtctgtacta aaaatacaaa agttagctgg atatggtggc aggcgcctgt aatcccagct   4140
acttgggagg ctgaggcagg agaattgctt gaatatggga ggcagaggtt gaagtgagtt   4200
gagatcacac cactatactc cagctgggc aacagagtaa gactctgtct caaaaaaaaa   4260
aaaaaaaaag actttacaaa gagatgcaga gacactgaga cagataaaca agccacaaag   4320
gagacaaagg agagacagac aaacagaaac agacagacca caagcccaag agaagcagcc   4380
agcattcagg acataggaca tcggaagca ggattagatg aagtcaggga tctggaatgg   4440
gacttccaac agatatgttg ctgggctatg ttgttattga tgatggttct gtctttgttt   4500
ctcagtctca tttagttcct ttctgagccc atatccattt ccacctctct gtgttttgaa   4560
ttctgactct ccctctcttc acaacagggt gactctgggg ggcccctgat ctgcaacggg   4620
tacttgcagg gccttgtgtc tttcggaaaa gccccgtgtg gccaagttgg cgtgccaggt   4680
gtctacacca acctctgcaa attcactgag tggatagaga aaaccgtcca ggccagttaa   4740
```

<210> SEQ ID NO 2
<211> LENGTH: 237
<212> TYPE: PRT
<213> ORGANISM: Homo sapiens

<400> SEQUENCE: 2

```
Ser Leu Val Ser Gly Ser Cys Ser Gln Ile Ile Asn Gly Glu Asp Cys
 1               5                  10                  15

Ser Pro His Ser Gln Pro Trp Gln Ala Ala Leu Val Met Glu Asn Glu
                20                  25                  30

Leu Phe Cys Ser Gly Val Leu Val His Pro Gln Trp Val Leu Ser Ala
            35                  40                  45
```

```
Ala His Cys Phe Gln Asn Ser Tyr Thr Ile Gly Leu Gly Leu His Ser
 50                  55                  60
Leu Glu Ala Asp Gln Glu Pro Gly Ser Gln Met Val Glu Ala Ser Leu
 65                  70                  75                  80
Ser Val Arg His Pro Glu Tyr Asn Arg Pro Leu Leu Ala Asn Asp Leu
                 85                  90                  95
Met Leu Ile Lys Leu Asp Glu Ser Val Ser Glu Ser Asp Thr Ile Arg
            100                 105                 110
Ser Ile Ser Ile Ala Ser Gln Cys Pro Thr Ala Gly Asn Ser Cys Leu
        115                 120                 125
Val Ser Gly Trp Gly Leu Leu Ala Asn Gly Glu Leu Thr Gly Arg Met
    130                 135                 140
Pro Thr Val Leu Gln Cys Val Asn Val Ser Val Val Ser Glu Glu Val
145                 150                 155                 160
Cys Ser Lys Leu Tyr Asp Pro Leu Tyr His Pro Ser Met Phe Cys Ala
                165                 170                 175
Gly Gly Gly Gln Asp Gln Lys Asp Ser Cys Asn Gly Asp Ser Gly Gly
            180                 185                 190
Pro Leu Ile Cys Asn Gly Tyr Leu Gln Gly Leu Val Ser Phe Gly Lys
        195                 200                 205
Ala Pro Cys Gly Gln Val Gly Val Pro Gly Val Tyr Thr Asn Leu Cys
    210                 215                 220
Lys Phe Thr Glu Trp Ile Glu Lys Thr Val Gln Ala Ser
225                 230                 235

<210> SEQ ID NO 3
<211> LENGTH: 254
<212> TYPE: PRT
<213> ORGANISM: Homo sapiens

<400> SEQUENCE: 3

Met Ala Thr Ala Gly Asn Pro Trp Gly Trp Phe Leu Gly Tyr Leu Ile
  1                   5                  10                  15
Leu Gly Val Ala Gly Ser Leu Val Ser Gly Ser Cys Ser Gln Ile Ile
                 20                  25                  30
Asn Gly Glu Asp Cys Ser Pro His Ser Gln Pro Trp Gln Ala Ala Leu
            35                  40                  45
Val Met Glu Asn Glu Leu Phe Cys Ser Gly Val Leu Val His Pro Gln
 50                  55                  60
Trp Val Leu Ser Ala Ala His Cys Phe Gln Asn Ser Tyr Thr Ile Gly
 65                  70                  75                  80
Leu Gly Leu His Ser Leu Glu Ala Asp Gln Glu Pro Gly Ser Gln Met
                 85                  90                  95
Val Glu Ala Ser Leu Ser Val Arg His Pro Glu Tyr Asn Arg Pro Leu
            100                 105                 110
Leu Ala Asn Asp Leu Met Leu Ile Lys Leu Asp Glu Ser Val Ser Glu
        115                 120                 125
Ser Asp Thr Ile Arg Ser Ile Ser Ile Ala Ser Gln Cys Pro Thr Ala
    130                 135                 140
Gly Asn Ser Cys Leu Val Ser Gly Trp Gly Leu Leu Ala Asn Gly Arg
145                 150                 155                 160
Met Pro Thr Val Leu Gln Cys Val Asn Val Ser Val Val Ser Glu Glu
                165                 170                 175
Val Cys Ser Lys Leu Tyr Asp Pro Leu Tyr His Pro Ser Met Phe Cys
```

```
                180             185             190
Ala Gly Gly Gln Asp Gln Lys Asp Ser Cys Asn Gly Asp Ser Gly
        195                 200                 205

Gly Pro Leu Ile Cys Asn Gly Tyr Leu Gln Leu Val Ser Phe Gly
    210                 215                 220

Lys Ala Pro Cys Gly Gln Val Gly Val Pro Gly Val Tyr Thr Asn Leu
225                 230                 235                 240

Cys Lys Phe Thr Glu Trp Ile Glu Lys Thr Val Gln Ala Ser
                245                 250

<210> SEQ ID NO 4
<211> LENGTH: 278
<212> TYPE: DNA
<213> ORGANISM: Homo sapiens

<400> SEQUENCE: 4
tgacccgctg taccacccca gcatgttctg cgccggcgga gggcaagacc agaaggactc      60
ctgcaacggt gactctgggg ggcccctgat ctgcaacggg tacttgcagg gccttgtgtc     120
tttcggaaaa gccccgtgtg ccaagttggg cgtgccaggt gcctacacca acctctgcaa     180
attcactgag tggatagaga aaaccgtcca ggccagttaa ctctggggac tgggaaccca     240
tgaaattgac ccccaaatac atcctgcgga aggaattc                             278

<210> SEQ ID NO 5
<211> LENGTH: 20
<212> TYPE: DNA
<213> ORGANISM: Artificial
<220> FEATURE:
<223> OTHER INFORMATION: primer

<400> SEQUENCE: 5
tgacccgctg taccacccca                                                  20

<210> SEQ ID NO 6
<211> LENGTH: 20
<212> TYPE: DNA
<213> ORGANISM: Artificial
<220> FEATURE:
<223> OTHER INFORMATION: primer

<400> SEQUENCE: 6
gaattccttc cgcaggatgt                                                  20

<210> SEQ ID NO 7
<211> LENGTH: 21
<212> TYPE: DNA
<213> ORGANISM: Artificial
<220> FEATURE:
<223> OTHER INFORMATION: primer

<400> SEQUENCE: 7
ggtgatctgc gccctggtcc t                                                21

<210> SEQ ID NO 8
<211> LENGTH: 21
<212> TYPE: DNA
<213> ORGANISM: Artificial
<220> FEATURE:
<223> OTHER INFORMATION: primer

<400> SEQUENCE: 8
aggtgtccgg tggaggtggc a                                                21
```

<210> SEQ ID NO 9
<211> LENGTH: 18
<212> TYPE: DNA
<213> ORGANISM: Artificial
<220> FEATURE:
<223> OTHER INFORMATION: primer

<400> SEQUENCE: 9
tgcgcaagtt caccctca                                                    18

<210> SEQ ID NO 10
<211> LENGTH: 19
<212> TYPE: DNA
<213> ORGANISM: Artificial
<220> FEATURE:
<223> OTHER INFORMATION: primer

<400> SEQUENCE: 10
ccctctcctt acttcatcc                                                   19

<210> SEQ ID NO 11
<211> LENGTH: 20
<212> TYPE: DNA
<213> ORGANISM: Artificial
<220> FEATURE:
<223> OTHER INFORMATION: primer

<400> SEQUENCE: 11
acaatgagct gcgtgtggct                                                  20

<210> SEQ ID NO 12
<211> LENGTH: 21
<212> TYPE: DNA
<213> ORGANISM: Artificial
<220> FEATURE:
<223> OTHER INFORMATION: primer

<400> SEQUENCE: 12
tctccttaat gtcacgcacg a                                                21

<210> SEQ ID NO 13
<211> LENGTH: 11570
<212> TYPE: DNA
<213> ORGANISM: Homo sapiens

<400> SEQUENCE: 13
gggcccagag tgaaggcaag agaaggagtt gagagctccc tctgcaaagt ggcttgagtc      60 tccctgcct aaaatgcagg gagagggagg cagaaagaca gggaagagga aggggtgggg      120
aagaaagaga gagagagaga gagacagaat aacacaacta cagaaacaca gagagaacac     180
acagagagcc tgggacacag ggacacacag agtcagagag aaaagagaag atagagaaag     240
acacaaatgg agacacagag gtgtaaagaa agagagatta acagagtccc agatacacgc     300 aaagggcag aagcacagtt ttcagggtgg tgtctatgat catcttcttt ttttttttt      360 tttttttt ttttgagac ggagtctcgc tctgtcgccc aggctggagt gcagtggcgg       420
gatctcggct cactgcaagc tccgcctccc gggttcacgc cattctcctg cctcagcctc     480
ccaagtagct gggactacag gcgcccgcca ctacgcccgg ctaatttttt tgtattttta     540
gtagagacgg ggtttcaccg ttttagccgg gatggcctcg atctcctgac ctcgtgatcc     600
gcccgcctcg gcctcccaaa gtgctgggat tacaggcgtg agccaccgcg cccggccatg     660

-continued

```
atcatcttct tgactatgct gatgtgacaa gtacctaaag ccatcagact ctacccttta    720
aatatgcagt ttgggccagg caccgtggct catgcctgta attccagcac tttgggaggc    780
agaggtgggt gaatcacttg aggccaggag tttgagacca gcctggccaa catggtgaaa    840
ctctgtcttt actaaaaaaa aaaaaaaaaa aaaaaaatc agccgggtgt cgtggggcac     900
acctgtaatc ccagctatgc tggaggctga ggcacgagag tcacttgaac cctggaggcg    960
gaggttgcag tgggccgaga tcacatcacc gccctccagc ctgggcgaca gagcaagact   1020
ctgtctcaaa taaataaata aacaaacgaa caagcagttt gttgtacctt agttatatct   1080
aaaaaaaaaa tgctgtcaac aaatagagca gaagtgaaat aaaggaaaat aaatgggcca   1140
agaactctaa ggtatatttg acaaatcatt cagaaccttt aaaaagaaa gaatcacaga    1200 ggcatagaaa gacagggagg aacagggaga cagaaacacc tgtggcccaa ggagaacaaa   1260
acaaggctcc taagacagac aggaggagag agagagagag tgagtgagag acagacagag   1320
aaaaagacag agagagagag acagagacag agagacagag aggcgagagg gatagaaaga   1380
gagagagggg tggagagaga cacgagatat tgagagagac tcagaaagat agccgaggga   1440
gaaccacaga gagatggaag aagactctga gaaaaaacca gagacaaaga tggaaagagg   1500
agtatcgagg gtgaacagac agtggtggaa tgagcaaaat gcagagaaga aagcaagcaa   1560
tccaggcgcc aagaatagtg acccagagtt ggtgagaagc cagatcctta aggctggggg   1620
aggcagggaa ggggctggcc tggcttccgg agacccctcc ccattctccg ggccagggag   1680
gtagggagtg acattccgga ctgggtgggg ggtgctctgg gggtggagat aggggagca    1740 ggaggagcta ttgctaaggc ccgataggca cctcattgcc cgggaatgtg ccccagggag   1800
cagtgggtgg ttataactca ggcccggtgc ccagagccca ggaggaggca gtggccagga   1860
aggcacaggc ctgagaagtc tgcggctgag ctgggagcaa atcccccacc ccctacctgg   1920
gggacagggc aagtgagacc tggtgagggt ggctcagcag gcaggaagg agaggtgtct    1980 gtgcgtcctg cacccacatc tttctctgtc ccctccttgc cctgtctgga ggctgctaga   2040
ctcctatctt ctgaattcta tagtgcctgg gtctcagcgc agtgccgatg gtggcccgtc   2100
cttgtggttc ctctctacct ggggaaataa ggtaggggag ggaggggaag tgggttaagg   2160
gctccccgga tcgcctgggc ctcccaaccc tctgacattc cccatccagg tgcagcggcc   2220
atggctacag caagaccccc ctggatgtgg gtgctctgtg ctctgatcac agccttgctt   2280 ctggggtca caggtaacca gaactctggg gtgggagggt tgtgggattg ggaggactgt    2340
ctctgcggca ctagagcgcc tgtcccctgg ggaactgtgt gagcctgggc atgactccgg   2400
gaccgggtga atgtgagtct ctgtctgtac ttgtggttgt gcgatcgtat gtggccctgt   2460
gactgccacg gtgtgtgtcg gggagggga tgccttttcc catatcaggt gactgtgcgg    2520
caggtggcac tgaccctttg aggctgtgtg tgtggttttg tgattgtgtg tgcatttaag   2580
attgtgtgtg gctccacagc tgtgtgggtg aatgcatgta gcactggggg tgttcactgt   2640
gtgtttggct gtgtgtggtg acttggcatt gtatatgact gcaggtatct gcagttcctg   2700
tccctgaggt cccgggattg cgtgcaacaa agtggtcat caccatggaa agctgtgact    2760
gtgtgctgct tgcaggcgat tatgtgattg tggctgagtg tgacgttatg gatgcccgta   2820
tttgtgaccg tgtgactacc tgaagctctg tgtaggggtg actgtatgtg actgtgtgtg   2880
tctgtgtgag gccgtgtaaa tgctactgta tgtgtgatgg tgcagctgtg tgtctggagt   2940
ttctgtctct gcctggaggg atagagggtg caggggtagc tatctctggg agatgggtgc   3000
caggtgactg acttgcagtg tgtgcctgtg tgcagaagag tatgtggcag tctgaacatc   3060
```

-continued

```
tgtgcacaca cggcatctgt gcgtggcact gagacactgt ggatgagggt gtgcgatccc    3120
gctaggctgc ccgggagcgt gtgtacctgg agacagagct gtatgttagc tgcacctgtg    3180
gaggcaacat gggcgtgtct gcagaactgc gtgcgtgctt ggctgttact gctgttgtgc    3240
gcgtggttct tggggtgagt tcgtgaatga tggtggtgcc agggccatca gcaagggtaa    3300
gaaccaggcc gggcgcggtg gctcacgcct gtaatcccag ccctttggga ggccgaggca    3360
ggcggatcac ctgaggtcgg gagatcgagg ccagcctgac caacatggag aaccccgtct    3420
ctactaaaaa tacaaaaaat tagctggtgt ggtggcgcgt gcctgtaatc ccagctactc    3480
gggagactgg ggcagaaaaa tcgcttgaac ccgggaggtg gaggttgcgg tgagccgaga    3540
tcgcgccatt gcactccagc ctgggcaaca agagcgaaac tccgtctcga agaaaaaaa    3600 gaaaaaaaaa agggtaagaa ccagtgaatg ggcacgggag gactgatgat ggagtggggc    3660
atgcatgtag tctgtaggtc tgtgtgtgag aggaggagat tgacaggatt gagaaggcat    3720
gttttcatct gagaattcag aaacctaggc ctgctcttcc cctccatgtg gcccctaag    3780 ctgagccctt ctttcctggt cctgctttcg gaacccctagc tccgcccatg agctctgacc    3840
ccacctcctt tcctcaacca cgcccctagg ccagactcta gtggaccccg cctaaggcca    3900 caccccttg ggccaggctc caccccctat tctgtgggta ccttctagaa ccccccttcaa    3960 agtcagagct ttttttttttt tttttttgga cacagtcttg ctctctctcc caggctggag    4020
tgcagtggcg tgatctcggc tcactgcaac ctctgcctcc caggttcaag tgattctcgt    4080
gcctccacct cctgagtagc tgggattaca ggtgcgcgcc accacgcctg gctaattttt    4140
gtgtctttag tagagacagg gttttcacctt gttggccagg ctggtctcaa actcccaacc    4200
tcaggtgatc cgcccacctc ggcctcccag agtgctgggg ttacaggcgt gagccaccgc    4260
ccccagccca aagtcagagc tctttatagg agactctaac atgtaaccct gaccctggcc    4320
ctaactaagt caattccaaa ccccttcctg cctccagccc tgaccccact cactgaggcc    4380
tgaccccact tcttgagacc agttccatcc ctaaagccct ggtctccctc ccatccccag    4440
gctccagccc ccacagcttt ggcactaccc ctgagcttgt ccaggaatcc tgtacccaat    4500
tttaccctca catgtagttc tagccaattc caggaatctg tgaggtccag ttagagtcca    4560 gtaacctac ctgagcctgg gctctgtcct tgagcttgag cctgggcttg agaggtgcca    4620
ctcttattct ccaggccctg cccctgcccc ctcagcatgt cagacaccca ccctctagct    4680
ggtctggcct cttgagtctg aaacccaccc ccagcccaag ccccgcctct gagccccgcc    4740
caacccattt tccgttccca gagcatgttc tcgccaacaa tgatgtttcc tgtgaccacc    4800
cctctaacac cgtgccctct gggagcaacc aggacctggg agctggggcc ggggaagacg    4860
cccggtcgga tgacagcagc agccgcatca tcaatggatc cgactgcgat atgcacaccc    4920
agccgtggca ggccgcgctg ttgctaaggc ccaaccagct ctactgcggg gcggtgttgg    4980
tgcatccaca gtggctgctc acggccgccc actgcaggaa gaagtgagtg ggagttccaa    5040
gaggagggtt ggtggggacg gggaagtggg ggtgggggtg gggaagtggg ggtgggggtg    5100
tcatggaggt gagggctggt ggggacgggg aagtgggtt gggggtgtca tggaaggtga    5160
gggttggtgg ggatgggttg gggatgtggg agcaggagga ggtcgagttg gggataggac    5220
taaggatgga gtttgcgggg ggagcaaggt gggaggatga ggttggagag gggagagtgt    5280
tgtggtaggg aatgggaagg agccaaggat gggttggatt tggggttagg agcatatatt    5340
tgttgaatgg tttgggatgg aggtggaatt gggattggct ttagaattgg gggtgggtga    5400
```

```
aaatcgggct ggggtggaaa tgaagatagc atggagatag ggttgagatt gggagcagat    5460
atagaatgaa ggatggggat tggagttttg ggtggggttg gagatggttg gatttgggct    5520
tgagaatgca tatggtgatg gcttctgggt agggaaagaa ttaggggttgg gaatgggatg    5580 ggtttggaat tgtgactggg atgggacag gcatgggatt ggagaccaag agggagttga    5640
ggatggtttg ggaccgggg gtggggatgg ggtggggct gggctgggt gtggggttgg    5700 gattggcgtt ggacgtggag atagagatca gggttggtgg tgacctgccc catcttcctc    5760
agagttttca gagtccgtct cggccactac tccctgtcac cagtttatga atctgggcag    5820
cagatgttcc agggggtcaa atccatcccc caccctggct actcccaccc tggccactct    5880
aacgacctca tgctcatcaa actgaacaga agaattcgtc ccactaaaga tgtcagaccc    5940
atcaacgtct cctctcattg tccctctgct gggacaaagt gcttggtgtc tggctggggg    6000
acaaccaaga gccccaagg tgagtgtcca ggttcttctt gataccgacc catctctgcc    6060
gccttccatc tttctccact tctcattgtg ttcctgtttg acagtgcact tccctaaggt    6120
cctccagtgc ttgaatatca gcgtgctaag tcagaaaagg tgcgaggatg cttacccgag    6180
acagatagat gacaccatgt tctgcgccgg tgacaaagca ggtagagact cctgccaggt    6240
gaggacacct ctctttattc agcagataca cactgagtgc caactcggta acatggagcg    6300
ttgccaaatt ctgagaatcc agcaattgcc aagacagtca ggaccctgt tctcacagag    6360 ctcataccct agagtagtgg tgtttagtag aaataatgct gagctgctta tgtcatttcc    6420
agttttttag tagccacatt aaaacaggta aaaaaggctg ggcgcagtgg ctcacacctg    6480
taatcccagc actttgggag gctgaggcag gcagatcacc tttggtcagg agtttgagac    6540
tagcctggcc aacatggcga aactctgtct ctaaaaaaaa atacaaaaat tagcctggca    6600
tggtggcggg cgcctgtaat ctcagctgct caggaggccg agacacaaga atcacttaaa    6660
cccaggaggt ggaggttgca gtgagctgag atcgtgccac tcactccaac ctgggagaca    6720
gagtgacact tttgtctcaa aaagaaaaaa aaaacaagt aaaaagaaa caggtgaagt    6780 taactttaat aacccaatgt atcccaaata caatcatttc aaagtgtaat taatataaaa    6840
caattatgaa tgagatactt tacattcttt tcttgttttc atattaagtc tttgaaagtg    6900
agtatatatg ttatgctgac agcacatctc aatttggact agctacattt caggtgctca    6960
gtagccacat gtggctagca gttactgtat tggatggcac ggatctagag ggaaagatca    7020
gggctgtttt gtatggttgg gcaggttgtg cactgcataa agataccata tctaataggg    7080
gcactccgtg ttacagatgt cagttttggc agttttcagg cgtgtggtag ttaagtgtct    7140
tgtttcaaca aaatctgtaa tatgacagtt ttctagcaag tgctggtaaa atatcttgag    7200
gaaggaaaag agaaatctgg taggtatttt tacaagagaa tatttaatac agggattaa    7260 ttgcaaagct gctggaaggg ctggaggaac aaagttaaaa aataaaaaac tctgtggtca    7320
agaatctgca taaataggc aatttcagag agtggtaaag gttaaccccca aaataaaaca    7380 tggttttagg atagtaaaca ataagggcca atattcaaaa aggtggtcag gggagcctcc    7440
ttggagaggt ggcatttgag cagagaatgg atgacacaaa gaagctaaac tcgtgaagtt    7500 taagggaaa gaaaaggcac gtgcaaaggc cctgaggcag taaggaattt ggctgattca    7560
aagaagaaga ggaaaccaat gcaactggag aacaaaagtg ggggcaacag tagaaagtga    7620
cgctggaggt gtaggcaggg gcgaatgctc tgcaagtatt tcttggtcac caacacagag    7680
cttccctatg ttctaatgga agctgtatct gttgaggaag acagaattta aaatcaaact    7740
gttacatcaa ccagcaccct tctctgtatt caggctccca agggatctag aaggacgtaa    7800
```

-continued

```
gttaacaagc tctcattagc agggtgtgtg tttcaacagt agttaggaag ctggggattc      7860
aggagtactc cagtcccatg gctatgaaaa gctcccccca aattgtacaa acctgacaaa      7920
tgcaacacct ccccagctct ccccatttct tctctgtgcc ctgggtgtgg gggggtgggt      7980
tgcgaggggg aaaactttta acagaagaaa gcacatctcg gccggcgtg gtggctcaca       8040 cctgtaatcc caacactttg ggaggccgag gcgggtggat cactaggtca ggagatggag      8100
accatcctgg ctgacacggt gaaaccctgt ctctactaaa aacacaaaaa attagccggg      8160
cgtggtggca ggcgcctgta gtcccagcta ctcgggaggc tgaggcagga gaatggcctg      8220
aacccgggag gcggaacttg cagtgagccg aggttgcacc actgcactcc agcctgggca      8280
acacagtgag actccgtctc aaaaaaaaaa aagaaaaga aagaaatca catctcattc        8340 aagtggtggc atttaaaact atttagcctt tctgtaggca aggttagtat cttgttttc       8400 cagacctcaa ggtgtttttt tgtttgtttt ttcataccgg tgtgtggtct gggtgtggcc      8460
actaaaagct acaagcaaga aataataaca actacaacaa tactaatacc aatagtataa      8520
aaataatagc atctggctaa ttgctggaca ctgttttaag tggtttgcat gcctcagctc      8580
attaactcat ttacctgtta ttattggccc tattttacaa acaaggagcc aaggctcaga      8640
gcagttaact aacagcctct caaaagaaac tctgcagaga tattaaattt aaaaaataat      8700
gagagaaatt aaaccacaag aaagttgaaa tttagaggta caggcagcta agcttgtttg      8760
ctttgaaaca gtgtctgcta ctgggaaaaa ggcaagtctt ggctttccta ataattgata      8820
ccaggactct gtaattcata ttttgcatgc atgtaagtaa gaaatgaagc cgggtgcaat      8880
ggcacatgcc agtaatccca gcactctggg agactgaagt gggaagatca cttgagctca      8940
ggagttcaag accagcctgg gcaactaaaa attaaaaaaa taaaaatact aattgttttt      9000
attttagtag attttattca taccacttac atcattattg tagtatgtac atatttattt      9060 cttttcttt cttttctttt ctttttgag acggagtctc gctctgtcac ccaggctgga        9120
gtgcaatggc accatatcag ctcactgcag catgcgcctc ctgggttcaa gcatttcttc      9180
cacctcagcc tcccaagtag ctgggataac aggcacccac caccatgcct ggctattttt      9240 tttttttccgt agagatgggg ttccaccatg ttggccaggc tggtcttgaa ctcctgacct     9300
ccagtgatct gcctgcctcg gcctcccaaa ttgctggtat tacaggtgtg agccaccgtg      9360
cccaggtggg agatagacat ttctctctac ctcaaacaga ggtccactca agctactttt      9420
cattttcttc ataaatatta gccgagtggc tattttgcac caggaatggt tccaggtgct      9480
gtggatatgg catcaggcaa aacagaccaa aaacttcctg ccgcgtggac ctcatgttcc      9540
ccaagtggaa gacaggcaat aaagagatag ataaatatgt agtaaattaa aaaaaaaaa      9600 aattagccgg gtgtggtggc ttgcacctgt agttccagct acttgggagg ctgaggtggg      9660
agaattgctt gagcccaaac gtttgaggct gcggtaagcc atgactgcac tgctgcactc      9720
cagacagcag cctgggtgac aaagcaagac gttttttgtca gaaagaaaaa aaaagagac      9780 gaagggagga aggagagaga aaggaaggaa ggaaggagaa agaaaggaag gaaggagaaa      9840
gaaaggaagg aaggaaggag aaagaaagga agaaagagaa agaaagaaaa agaaagaaag      9900
aaagaagaaa gaaagagag aggaaggaag gaaagaagga aaagagggaa aaaaatgact      9960
gttgaagagc agtgagtatt attataggag ggtaattata gggaggtatg gggaattgaa     10020
gacaggaaac acaaattagt ccaagcgaat ggatttctat tgggagtgat tctgcccta      10080 gaagacactg gcaataccag gagacatttt tggttgtcac aactatatgg aggggcatta     10140
```

```
ctggcaacta atggatagat gccaagtgtg ctgttcaaca tgctatgatg cacacggcag    10200
gcctccacaa caaaccatta tccagcttca gatgcccaca gtgcccagat cgaggaaccc    10260
tcatccaggg gctgagaacc gtattttgc agaagggagg tataaggatg ggttggtgga    10320
gaatggggaa ggaaggtgtg tgtccagtaa gagaaataag gcctgcacag gctggagggg    10380
agagtgagag agaaagggag gcggagagat acacgatgag ggagacaggc tggaacagaa    10440
agtagagacg aagattcgag atgtggagag gaagggtcac agacccccc gaaatgatgt    10500 gtggacaaca ggaatctgga agaggaagat ggagtggaga gtgacaaatg gggtctaaag    10560
gttgaacttg gaggccaggc atggtggctc acgcctgtaa tcccaacact ttggaggctg    10620
aggtgggcga atcacttgag gccaggagtt cgagaccagc ctggccaaca tggtgaaacc    10680
ccgtctctac aaaaaaata caaaaaatta gccgggtgtg gtgatggaca cctgtagtca    10740
cagctacttg ggaggctgag gcaggagaat tgcttgaacc cgggagatgg aggctgcagt    10800
gagctgaggt caggccactg cgctccaacc tgggcaacag agtaagactc catctcaaaa    10860 aaaaaaagc tggatttgga gtgaaatatt aataacattc ccctctctc tccttttgcc    10920 tgtgtctcca tctctgtctt tttctgcatt tcttcatctc tgtactttcc atctctgtgt    10980
gtctgttccc atctgcttct ccatctatgg gcatctctgg gtctctcatg tctccttctg    11040
cccactttgc cacatctctg cctctctcat gccccctttt ctctcctgca gggtgattct    11100 gggggggcctg tggtctgcaa tggctccctg cagggactcg tgtcctgggg agattaccct    11160
tgtgcccggc caacagacc gggtgtctac acgaacctct gcaagttcac caagtggatc    11220
caggaaacca tccaggccaa ctcctgagtc atcccaggac tcagcacacc ggcatcccca    11280
cctgctgcag ggacagccct gacactcctt tcagaccctc attccttccc agagatgttg    11340
agaatgttca tctctccagc ccctgacccc atgtctcctg gactcagggt ctgcttcccc    11400
cacattgggc tgaccgtgtc tctctagttg aaccctggga acaatttcca aaactgtcca    11460 gggcggggt tgcgtctcaa tctccctggg gcactttcat cctcaagctc agggcccatc    11520
ccttctctgc agctctgacc caaatttagt cccagaaata aactgagaag                 11570
```

<210> SEQ ID NO 14
<211> LENGTH: 293
<212> TYPE: PRT
<213> ORGANISM: Homo sapiens

<400> SEQUENCE: 14

```
Met Ala Thr Ala Arg Pro Pro Trp Met Trp Val Leu Cys Ala Leu Ile
1               5                   10                  15

Thr Ala Leu Leu Leu Gly Val Thr Glu His Val Leu Ala Asn Asn Asp
                20                  25                  30

Val Ser Cys Asp His Pro Ser Asn Thr Val Pro Ser Gly Ser Asn Gln
            35                  40                  45

Asp Leu Gly Ala Gly Ala Gly Glu Asp Ala Arg Ser Asp Asp Ser Ser
        50                  55                  60

Ser Arg Ile Ile Asn Gly Ser Asp Cys Asp Met His Thr Gln Pro Trp
65                  70                  75                  80

Gln Ala Ala Leu Leu Leu Arg Pro Asn Gln Leu Tyr Cys Gly Ala Val
                85                  90                  95

Leu Val His Pro Gln Trp Leu Leu Thr Ala Ala His Cys Arg Lys Lys
            100                 105                 110

Val Phe Arg Val Arg Leu Gly His Tyr Ser Leu Ser Pro Val Tyr Glu
        115                 120                 125
```

Ser Gly Gln Gln Met Phe Gln Gly Val Lys Ser Ile Pro His Pro Gly
    130                 135                 140

Tyr Ser His Pro Gly His Ser Asn Asp Leu Met Leu Ile Lys Leu Asn
145                 150                 155                 160

Arg Arg Ile Arg Pro Thr Lys Asp Val Arg Pro Ile Asn Val Ser Ser
                165                 170                 175

His Cys Pro Ser Ala Gly Thr Lys Cys Leu Val Ser Gly Trp Gly Thr
            180                 185                 190

Thr Lys Ser Pro Gln Val His Phe Pro Lys Val Leu Gln Cys Leu Asn
        195                 200                 205

Ile Ser Val Leu Ser Gln Lys Arg Cys Glu Asp Ala Tyr Pro Arg Gln
    210                 215                 220

Ile Asp Asp Thr Met Phe Cys Ala Gly Asp Lys Ala Gly Arg Asp Ser
225                 230                 235                 240

Cys Gln Gly Asp Ser Gly Gly Pro Val Val Cys Asn Gly Ser Leu Gln
                245                 250                 255

Gly Leu Val Ser Trp Gly Asp Tyr Pro Cys Ala Arg Pro Asn Arg Pro
            260                 265                 270

Gly Val Tyr Thr Asn Leu Cys Lys Phe Thr Lys Trp Ile Gln Glu Thr
        275                 280                 285

Ile Gln Ala Asn Ser
    290

<210> SEQ ID NO 15
<211> LENGTH: 20
<212> TYPE: DNA
<213> ORGANISM: Artificial
<220> FEATURE:
<223> OTHER INFORMATION: primer

<400> SEQUENCE: 15
ggatgcttac ccgagacaga                                            20

<210> SEQ ID NO 16
<211> LENGTH: 22
<212> TYPE: DNA
<213> ORGANISM: Artificial
<220> FEATURE:
<223> OTHER INFORMATION: primer

<400> SEQUENCE: 16
gctggagaga gatgaacatt ct                                         22

<210> SEQ ID NO 17
<211> LENGTH: 21
<212> TYPE: DNA
<213> ORGANISM: Artificial
<220> FEATURE:
<223> OTHER INFORMATION: primer

<400> SEQUENCE: 17
ggtgatctgc gccctggtcc t                                          21

<210> SEQ ID NO 18
<211> LENGTH: 21
<212> TYPE: DNA
<213> ORGANISM: Artificial
<220> FEATURE:
<223> OTHER INFORMATION: primer

<400> SEQUENCE: 18

```
aggtgtccgg tggaggtggc a                                              21

<210> SEQ ID NO 19
<211> LENGTH: 28
<212> TYPE: DNA
<213> ORGANISM: Artificial
<220> FEATURE:
<223> OTHER INFORMATION: primer

<400> SEQUENCE: 19
ccgagacgga ctctgaaaac tttcttcc                                       28

<210> SEQ ID NO 20
<211> LENGTH: 28
<212> TYPE: DNA
<213> ORGANISM: Artificial
<220> FEATURE:
<223> OTHER INFORMATION: primer

<400> SEQUENCE: 20
tgaaaacttt cttcctgcag tgggcggc                                       28

<210> SEQ ID NO 21
<211> LENGTH: 8622
<212> TYPE: DNA
<213> ORGANISM: Homo sapiens

<400> SEQUENCE: 21
cttgacccca ggaggcagag gttgcagtga gctgagatcg cgccactgta cttcagcctg      60
ggtgtcagag caatactccg ttttggaaaa caaacaaaca aacaaacaaa caaaaaacag     120
atggagcaac tgagagaggt cttgtgactt gcccaaagtc acacacctca tcactaatca     180
cacctaatca ttgagatttg gacacacatg gttcagttcc agagtccatg ctccaaacca     240
tgacgacaca gtgagagaac attcaagggg agcccagacc cagcttcata accaggcctg     300
tgagcaggag aaagtggaag ggatcgtaag tgcccagggg aggcaaagat ggactctgcc     360
tgaggatctc agagatttcc tggaggaggg agaattgagg ttgggtgttg aaggatgagt     420
gggagttcac caggaaaaga aggatatgga gaaagacatt cactcattca atgaacatct     480
cctgaggact tctgcaagcc ctgttccgcc tggaacgggg tgatgctggg acacagagat     540
gagtcagacc tgggcccagc cctccagaag ctgtccacct ggtgagaagg aatgatgagg     600
agagaggcag ggaggatggg gtgatggaag ggacaatggg gtgggggca gggagatgga     660 tgaaaaaaat atatagcaaa tgttctcagg atttggcaaa gatcaggatg tattaagaga     720
gagcacaggg cacttgctac ctggaaggtt gggcacctgg gtccttgggt ggtgagccg     780 tggggaaggg ggcaggttat gacaagagtg ggttaatcca gatggaacca gatttctcaa     840
cattctagga gagggccttg tccttgtggg aagaggccca atcccccagg gcagggaagg     900
ttctgcaagg tgtgtaaacc tgtgcagctg cctgtggtct ctgcctcact ccacctggat     960
ttccctcaat cttccccgtg ttctgtctcc tcctcccact cctcctctca tcttgggtcc    1020
ttctgtgcct gtacctccct ctctttgtat cttttgctct tgtgtctgag tcctgactct    1080
gtcttccacc cctcgcctcc tttctgggtg gtcccctgc acatcccctcc agcctgccgt    1140 gggaggttgg tctctgcaca ccactgcttt atccaaaata aacctgctgc accccaggac    1200
cttaggcttc aaggatctcc ctccttttcc aggacacaaa agattctgta tcttgtagcc    1260
taaggtgatg aggaatgagg tctcccactc tgaagacccc agaggaggtg cccacaacct    1320
```

```
ctccacaccc ccagcactcc tcctccattc agtcaagctc tggcccagca agccgccagt   1380
tcatcccaaa agggggtcc ccctgcactt acctcctctc ccaaggcccc tgtcacagcc   1440
ccagggcttc cccctcccc aggtacattt cccaacccg attaatcaca ggggcggccc   1500
catggaggag aaggagatg gcatggctta ccataaagaa gcactggacg ccgggtgcac   1560
gttccaggat ccaggtgccc aggggtcatg aagctgggac tcctctgtgc tctgctctct   1620
ctgctggcag gtgaggctcc caggctggct gcccttcac ggctgtacta aggtcacctt   1680
gctcttccct cccatcccag gcttctgcct cctgccctct aggcttctca gcatcctctc   1740
cctgccctcc cagcctgctc ttcgctgacc ctttgtccc tcatcccac cccagggcat   1800 ggctgggcag acaccgtgc catcggggcc gaggaatgtc gccccaactc ccagccttgg   1860
caggccggcc tcttccacct tactcggctc ttctgtgggg cgaccctcat cagtgaccgc   1920
tggctgctca cagctgccca ctgccgcaag ccgtgagtga cccaggctgg ccatgctggg   1980
gagggacaga ggctggggt caggagaggg tgagggtgc tttaggccag aagtgcggag   2040
cctccacttc tgataccaca agttcaactc ttagaagtag aagggtagc ctcccaaatc   2100 ctaaaattct agagaccagc aatatctcat ttgagaagtc taagattcga aacttaggct   2160
cttcgaatcc gagactgacc cagagaaatc cagaatcgta gaatcctaaa atcttgaatt   2220
tatgaaattc tgcaatagcc tcagcaaatt ttagaatcat agattcgcag actattagaa   2280
tcttagcagt ctgggtcagc actgcccaga ggaattatga tgccagccac atgtgtaagt   2340
ttaaatttct ggtggacaca tttaaaaaat aaggaatgag taaaattaat tctaatagat   2400
ttaacttgac atacccaaaa acttattttg acatgtaatc aattttaaa tacgtatgaa   2460 cgatacagtt tacttttgtt ttggtactaa gcctttgaaa tctgttctgt attttacaca   2520
catagcctgt tacaaaatgg actagccaca tttcaagtgt tcaatagcca taatggctag   2580
tgtgatccta gaatcttaaa ttcagagctt tctagattca ttgaatattg aaactcacag   2640
tactagaatc tttgattcac agtatcctag aatattgaga ttcagataat tctgtagtct   2700
taaactattt gaatcccaga ctcttaaatt tctaaggtta tagatttata gaatgatgac   2760
attctagtct ttcttttttt tttttttttt tttttttgag acagagtctc cctctatctc   2820
ccaggctgga gtgcagtggc acaatctcag ctcactgcaa cctctgcctc tcggttcaa   2880 gcaattctcc tgcctcagcc tcctgagtag ctgggattac aggtatgcac caccatgcca   2940 ggctatttt tttttttttt ttttttagt agagacgggg gtttcaccat attggccagg   3000
ctggtcttga actcctgacc ttgtgatctg cccgcctcgg cctcccaaag tgctgggatt   3060
acaggcgtga gccaccgcgc ccagccaaaa ttctagtctt tttgtcctag aacattaaaa   3120
ttctatgttc aaatcttaga tttaattcag ataatgttag aatcctggag ttttttttgat   3180 ccagggggaat ctggaatgtt agaatcttgg attcataaaa ctctaaacct tgagcctcta   3240
gattctagaa tcatggataa tagtgtgtcg gaatctgaga attctagaat cttaggttct   3300
gggcattcta atagtatcct ggaatccacc tgatgcagga atcctctctc cattgcctct   3360
gaaaagtgac catccatact gttccaattt tcttccctcc atgagtaaag cactgattgt   3420
ggtaagagat gctgtgtggg aatttcccat catgcattgc tccatgatgg aacctccttt   3480
aacttaagcc tatacatcag actggagaa cgatgttcag atttcagccg aaagtgaagc   3540
aggagaaatg cagagatatg aaggtggaag agagtgagag gcaggggaag ggtaggggga   3600
tgaagggatg taggggtgag gactactttt ccagatccag agccaagaca gcaagaatga   3660
cagagagaga cagacacaga tgttctggt tccccaaccc tgaattcgca gtcattagcc   3720
```

```
tgctgcctaa tgtcagaggt cagaggctgg ggaatggact tgtcatcccc gaaaggatcc    3780
cagctgtcta gggcatggac cagaaatgaa acaagtgcgc tgagactgtg gtgagggctt    3840
aaggttagac accaggaaga catgcattga agggtgaagg atatgataga caggaaaagc    3900
tgaggccaga gatgaccccc aatttgggga ttttccatat cccatcccct tcatacaca    3960 cgcacacgta tacacacaca ccacttagac atacagagcc gctcccacag aagccaccag    4020
acctgtgggg gcagggtgg ggcggttgtt atgtggtagg tggggtcccc cgtgcccaca    4080
ccgttcctag ggacccaagt caccaccaag gctccaggtg agtagggagg aaggtggctc    4140
actcagcctg ggactaggag cggggggcttt gtggggagag ctacaaagat ggagacacac    4200
aaaacatcag agtggggacc agggacccag aggaggtgtg tgcctcgctt aaaatcacag    4260
taccctgggc cagacataga tgatgagggt gcagagaggg tgtgtggctt gcagagggtc    4320
acacagcacc ctgatggaca ggaaaagagg gctggggctg aaaggacttt tacctttccc    4380
ccagcttgac ctctgaggcc tgtcccagca ggtatctgtg ggtccgcctt ggagagcacc    4440
acctctggaa atgggaggt ccggagcagc tgttccgggt tacggacttc ttcccccacc    4500
ctggcttcaa caaggacctc agcgccaatg accacaatga tgacatcatg ctgatccgcc    4560
tgcccaggca ggcacgtctg agtcctgctg tgcagcccct caacctcagc cagacctgtg    4620
tctccccagg catgcagtgt ctcatctcag gctgggggc cgtgtccagc cccaagggta    4680
tgacctggcc cagaactctc tctgaaactt gctccctcac ccctctgtct ctgccttttc    4740
atctctgtct tctccttttc tctctcctct ctctctctgt cagtctatct atctgccaat    4800
cgatatattt aaccaaatat aagatgctag cattttaag atgtgccatt atttcatgaa    4860
ctgcgaagaa gtggaagaag gaggaggagg agaagaaaaa aaggaggagg aggaaagatc    4920
ccattagatc ccattgatta tataacacca ttttctggaa gacacattct aatttcagag    4980
tgtttgtttg tttgtttgtt tgtttgtttt tgagacaggg tctcgctttg ttgctcaggc    5040
tggagtgcag cggtgtgatc acggctcatt gcagctttga actcctgggc tcaagtgatc    5100
ctctcgcctc aacctcccaa gtagctggga ttacagatat gcaccaccac atcccacacc    5160
ggggtcattt ttttattatt tattattatt attattatta tcttttttt tgtatttta    5220 gtagagacag aggtttcacc atattggcca ggctggtctc aaattcctga cctggtgatc    5280
tgcccgcctt ggactcccaa agtgctggga aaacaggcat gagccactgc acccagccaa    5340
aattctagtc tttttttaaat ctagtcatat cttagattta attcagataa tgttagaatc    5400
ctggagtttt tgatccagg ggaatctgga atgttagaat cttggattca taaaactcta    5460
aacgttgagc tctagattc tagaatcatg gatactagtg tgtcagaatc tgagaattct    5520
agaatcttag attctgggca ttctaatagt atcctggaat ccacctgatg caggaatcct    5580
ctctccattg cctctgaaaa gtgaccatcc atactgttcc aatttcttc cctccatgaa    5640 taaagcactg attctggtaa agatgctgg gtgggaattt cccatcatgc attgctccat    5700
gatgggacct cctttaactt aagccttatg ctaaaaattt ttattatttt tagcaaagat    5760
gaggtcttgc tatgttgtcc aggctagtct caaactcctg gcctcccaaa gtgctgagat    5820
tacaagtgtg agccactgta cctggcccag agatgtttaa atgtgaaatg cgttcatctt    5880
agaatgggaa taagaccatg tctctcagag tcacggatca ctgacccatt agccaaattg    5940
ggtcagtgga ttggaaaaac agtctgaatt tgttgctgcc aatatctaaa acttggaaag    6000
ttttatacaa aagccaggtt tctggattca cctgaaaaag tttgaagaac tcacattccc    6060
```

```
aaaatagcaa gcattgggct gagtcaatgg aggctgcccc cttcagccaa gataagttct     6120
ctgattcact ccaatggacc caaatggctc ctgtctccct gcacagcccc cgtccccgac     6180
ttctgtttac caattctgtt tatcatatcc cttgatgcat cggagcctgc acccatgtct     6240
tatatagatg cacatgtgta ttatatatcc atatccacat ctatactgac tacactgtat     6300
ctggtatctc tgtctatgtc tctgtctcca tcagtgacca tcttcctgca aatctctttc     6360
cttttatctc actgccttca ttccacccct tgaggtctgg gtcttttttct atttcttttt     6420 tttttttttt taagagactg agtcttgctc ttgttgccca ggctggagtg cagtggtgtg     6480
atctcggctc actgcaacct ccacctcctg gttttaagt gatcctcctg cctcagcctc     6540
ccgagtagct gggactacag gtgtgcaaca gcatgcccag ctgattttttt gtattttcag     6600 tagagacgga gtttcaccat gttggccagg atggtctcaa tctcttgacc ttgtgatccg     6660
cccgcctcag cctcccaaag tgctagggag ttatatatgc atctcctctt atctcttggc     6720
tctctgcatg catctttctg tttctcttcc ttcctttctt tttttttttt tttttttttt     6780
tttttttttt tttttgaga cggagtcttg ctctgtctcc caggctggag tgcagtgacc     6840
agtctcggct cactgcaacc tccacctccc aggttcaagt gattctcgtg cctcagcctc     6900
ccgagtagct gggattacag gcgcctgcca ccatgcctgg ctaatttttg tatatttagc     6960
agagatgggg tttcaccatg ttggctgggc tggtctcaaa ctcctgacct caagcgatcc     7020
gccggcctcg gcctccaaaa cactgggatt acaggcatga gccacggtgc ccggccagcc     7080
tctctctcta cttggccctc ttcctccttg tctccatttg tttctcttgt gtgctatgac     7140
tgtctgtctg tcactgtctc ttgtctctat ctttgagagt cctaaatgtg gctccattgg     7200
tcctttggaa aagctgcagg gaggactcag ggcagtgggg tgctgagtgt gttggagaca     7260
gttgcagatc cttgacagtt ctcttccctg acagcgctgt ttccagtcac actgcagtgt     7320
gccaacatca gcatcctgga gaacaaactc tgtcactggg catacccgtgg acacatctcg     7380 gacagcatgc tctgtgcggg cctgtgggag ggggccgag gttcctgcca ggtgagacct     7440
tactctgggg aaaatgaggc tgtcctgcca agttttctag gatttagggg agcagagggg     7500
tcggccccca gccttcctgg gtcaaaatga gaaggagact gggatacctg gttcctggga     7560
gaggacggga ccagggcctg gactccttag tgtaaaagag aaaaggtctg gaggtccaga     7620
cttctggatc tacaggagga gtgggctggg cgtccagagt ctgagtcctc ggggaggagg     7680
aggttaggtc ctgcggggag gtgggccctc tgagcttttta ctcctgggtc tgaggaagaa     7740
gaggctggag atggaggact ctcggatgtt ggaggaggaa ggggctgggg cctttctggg     7800
agggaggaag tggcccgtgt aattgtcatg aacagagtgg cctaacagtt cctctgccct     7860
tctctcgcgt acagggtgac tctgggggcc ccctggtttg caatgaaacc ttggcaggcg     7920
tggtgtctgg gggtgctgag ccctgctcca gaccccggcg ccccgcagtc tacaccagcg     7980
tatgccacta ccttgactgg atccaagaaa tcatggagaa ctgagcccgc gcgccacggg     8040
ggcaccttgg aagaccaaga gaggccgaag ggcacgggt aggggttct cgtagggtcc     8100 cagcctcaat ggttcccgcc ctggacctcc agctgccctg actccctctct ggacactaag     8160 actccgcccc tgaggctccg cccctcacg aggtcaagca agacacagtc gcgcccctc     8220 ggaacggagc agggacacgc ccttcagagc ccgtctctat gacgtcaccg acagccatca     8280
cctccttctt ggaacagcac agcctgtggc tccgcccaa ggaaccactt acacaaaata     8340
gctccgcccc tcggaacttt gcccagtggg acttcccctc gggactccac cccttgtggc     8400
cccgcctcct tcaccagaga tctcgcccct cgtgatgtca ggggcgcagt agctccgccc     8460
```

```
acgtggagct cgggcggtgt agagctcagc cccttgtggc cccgtcctgg gcgtgtgctg    8520
ggtttgaatc ctggcggaga cctgggggga aattgaggga gggtctggat acctttagag    8580
ccaatgcaac ggatgatttt tcagtaaacg cgggaaacct ca                       8622

<210> SEQ ID NO 22
<211> LENGTH: 296
<212> TYPE: PRT
<213> ORGANISM: Homo sapiens

<400> SEQUENCE: 22

Val His Phe Pro Thr Pro Ile Asn His Arg Gly Gly Pro Met Glu Glu
1               5                   10                  15

Glu Gly Asp Gly Met Ala Tyr His Lys Glu Ala Leu Asp Ala Gly Cys
            20                  25                  30

Thr Phe Gln Asp Pro Ala Cys Ser Ser Leu Thr Pro Leu Ser Leu Ile
        35                  40                  45

Pro Thr Pro Gly His Gly Trp Ala Asp Thr Arg Ala Ile Gly Ala Glu
    50                  55                  60

Glu Cys Arg Pro Asn Ser Gln Pro Trp Gln Ala Gly Leu Phe His Leu
65                  70                  75                  80

Thr Arg Leu Phe Cys Gly Ala Thr Leu Ile Ser Asp Arg Trp Leu Leu
                85                  90                  95

Thr Ala His Cys Arg Lys Pro Leu Thr Ser Glu Ala Cys Pro Ser
            100                 105                 110

Arg Tyr Leu Trp Val Arg Leu Gly Glu His His Leu Trp Lys Trp Glu
        115                 120                 125

Gly Pro Glu Gln Leu Phe Arg Val Thr Asp Phe Phe Pro His Pro Gly
    130                 135                 140

Phe Asn Lys Asp Leu Ser Ala Asn Asp His Asn Asp Asp Ile Met Leu
145                 150                 155                 160

Ile Arg Leu Pro Arg Gln Ala Arg Leu Ser Pro Ala Val Gln Pro Leu
                165                 170                 175

Asn Leu Ser Gln Thr Cys Val Ser Pro Gly Met Gln Cys Leu Ile Ser
            180                 185                 190

Gly Trp Gly Ala Val Ser Ser Pro Lys Ala Leu Phe Pro Val Thr Leu
        195                 200                 205

Gln Cys Ala Asn Ile Ser Ile Leu Glu Asn Lys Leu Cys His Trp Ala
    210                 215                 220

Tyr Pro Gly His Ile Ser Asp Ser Met Leu Cys Ala Gly Leu Trp Glu
225                 230                 235                 240

Gly Gly Arg Gly Ser Cys Gln Gly Asp Ser Gly Gly Pro Leu Val Cys
                245                 250                 255

Asn Gly Thr Leu Ala Gly Val Val Ser Gly Gly Ala Glu Pro Cys Ser
            260                 265                 270

Arg Pro Arg Arg Pro Ala Val Tyr Thr Ser Val Cys His Tyr Leu Asp
        275                 280                 285

Trp Ile Gln Glu Ile Met Glu Asn
    290                 295

<210> SEQ ID NO 23
<211> LENGTH: 250
<212> TYPE: PRT
<213> ORGANISM: Homo sapiens

<400> SEQUENCE: 23
```

Met Lys Leu Gly Leu Leu Cys Ala Leu Leu Ser Leu Leu Ala Gly His
1               5                   10                  15

Gly Trp Ala Asp Thr Arg Ala Ile Gly Ala Glu Glu Cys Arg Pro Asn
            20                  25                  30

Ser Gln Pro Trp Gln Ala Gly Leu Phe His Leu Thr Arg Leu Phe Cys
        35                  40                  45

Gly Ala Thr Leu Ile Ser Asp Arg Trp Leu Leu Thr Ala Ala His Cys
    50                  55                  60

Arg Lys Pro Tyr Leu Trp Val Arg Leu Gly Glu His His Leu Trp Lys
65                  70                  75                  80

Trp Glu Gly Pro Glu Gln Leu Phe Arg Val Thr Asp Phe Phe Pro His
                85                  90                  95

Pro Gly Phe Asn Lys Asp Leu Ser Ala Asn Asp His Asn Asp Asp Ile
            100                 105                 110

Met Leu Ile Arg Leu Pro Arg Gln Ala Arg Leu Ser Pro Ala Val Gln
            115                 120                 125

Pro Leu Asn Leu Ser Gln Thr Cys Val Ser Pro Gly Met Gln Cys Leu
130                 135                 140

Ile Ser Gly Trp Gly Ala Val Ser Ser Pro Lys Ala Leu Phe Pro Val
145                 150                 155                 160

Thr Leu Gln Cys Ala Asn Ile Ser Ile Leu Glu Asn Lys Leu Cys His
            165                 170                 175

Trp Ala Tyr Pro Gly His Ile Ser Asp Ser Met Leu Cys Ala Gly Leu
            180                 185                 190

Trp Glu Gly Gly Arg Gly Ser Cys Gln Gly Asp Ser Gly Gly Pro Leu
            195                 200                 205

Val Cys Asn Gly Thr Leu Ala Gly Val Val Ser Gly Gly Ala Glu Pro
            210                 215                 220

Cys Ser Arg Pro Arg Arg Pro Ala Val Tyr Thr Ser Val Cys His Tyr
225                 230                 235                 240

Leu Asp Trp Ile Gln Glu Ile Met Glu Asn
                245                 250

<210> SEQ ID NO 24
<211> LENGTH: 20
<212> TYPE: DNA
<213> ORGANISM: Artificial
<220> FEATURE:
<223> OTHER INFORMATION: primer

<400> SEQUENCE: 24
catgcagtgt ctcatctcag                                               20

<210> SEQ ID NO 25
<211> LENGTH: 20
<212> TYPE: DNA
<213> ORGANISM: Artificial
<220> FEATURE:
<223> OTHER INFORMATION: primer

<400> SEQUENCE: 25
catggaggag gaaggagatg                                               20

<210> SEQ ID NO 26
<211> LENGTH: 20
<212> TYPE: DNA
<213> ORGANISM: Artificial
<220> FEATURE:

```
<223> OTHER INFORMATION: primer

<400> SEQUENCE: 26
cttcggcctc tcttggtctt                                               20

<210> SEQ ID NO 27
<211> LENGTH: 21
<212> TYPE: DNA
<213> ORGANISM: Artificial
<220> FEATURE:
<223> OTHER INFORMATION: primer

<400> SEQUENCE: 27
gaccctgaca ttggacatct a                                             21

<210> SEQ ID NO 28
<211> LENGTH: 21
<212> TYPE: DNA
<213> ORGANISM: Artificial
<220> FEATURE:
<223> OTHER INFORMATION: primer

<400> SEQUENCE: 28
gccactgcct gatggagact g                                             21

<210> SEQ ID NO 29
<211> LENGTH: 20
<212> TYPE: DNA
<213> ORGANISM: Artificial
<220> FEATURE:
<223> OTHER INFORMATION: primer

<400> SEQUENCE: 29
aacatcagca tcctggagaa                                               20

<210> SEQ ID NO 30
<211> LENGTH: 20
<212> TYPE: DNA
<213> ORGANISM: Artificial
<220> FEATURE:
<223> OTHER INFORMATION: primer

<400> SEQUENCE: 30
cttcggcctc tcttggtctt                                               20

<210> SEQ ID NO 31
<211> LENGTH: 20
<212> TYPE: DNA
<213> ORGANISM: Artificial
<220> FEATURE:
<223> OTHER INFORMATION: primer

<400> SEQUENCE: 31
gggtcagagc tgcagagaag                                               20

<210> SEQ ID NO 32
<211> LENGTH: 20
<212> TYPE: DNA
<213> ORGANISM: Artificial
<220> FEATURE:
<223> OTHER INFORMATION: primer

<400> SEQUENCE: 32
gggcctgtcg tctgcaatgg                                               20
```

```
<210> SEQ ID NO 33
<211> LENGTH: 20
<212> TYPE: DNA
<213> ORGANISM: Artificial
<220> FEATURE:
<223> OTHER INFORMATION: primer

<400> SEQUENCE: 33
atggccacag caggaaatcc                                               20

<210> SEQ ID NO 34
<211> LENGTH: 20
<212> TYPE: DNA
<213> ORGANISM: Artificial
<220> FEATURE:
<223> OTHER INFORMATION: primer

<400> SEQUENCE: 34
ggtcacttgt ctgcgcagac                                               20

<210> SEQ ID NO 35
<211> LENGTH: 20
<212> TYPE: DNA
<213> ORGANISM: Artificial
<220> FEATURE:
<223> OTHER INFORMATION: primer

<400> SEQUENCE: 35
cccaaccctg tgtttttctc                                               20

<210> SEQ ID NO 36
<211> LENGTH: 17
<212> TYPE: DNA
<213> ORGANISM: Artificial
<220> FEATURE:
<223> OTHER INFORMATION: primer

<400> SEQUENCE: 36
ggccctcctc cctcaga                                                  17

<210> SEQ ID NO 37
<211> LENGTH: 20
<212> TYPE: DNA
<213> ORGANISM: Artificial
<220> FEATURE:
<223> OTHER INFORMATION: primer

<400> SEQUENCE: 37
atccctccat tcccatcttt                                               20

<210> SEQ ID NO 38
<211> LENGTH: 20
<212> TYPE: DNA
<213> ORGANISM: Artificial
<220> FEATURE:
<223> OTHER INFORMATION: primer

<400> SEQUENCE: 38
cacatacaat tctctggttc                                               20

<210> SEQ ID NO 39
<211> LENGTH: 20
<212> TYPE: DNA
<213> ORGANISM: Artificial
<220> FEATURE:
<223> OTHER INFORMATION: primer
```

-continued

```
<400> SEQUENCE: 39
agtgacactg tctcagaatt                                            20

<210> SEQ ID NO 40
<211> LENGTH: 20
<212> TYPE: DNA
<213> ORGANISM: Artificial
<220> FEATURE:
<223> OTHER INFORMATION: primer

<400> SEQUENCE: 40
ccccaatctc accagtgcac                                            20

<210> SEQ ID NO 41
<211> LENGTH: 19
<212> TYPE: DNA
<213> ORGANISM: Artificial
<220> FEATURE:
<223> OTHER INFORMATION: primer

<400> SEQUENCE: 41
gcttccctac cgctgtgct                                             19

<210> SEQ ID NO 42
<211> LENGTH: 19
<212> TYPE: DNA
<213> ORGANISM: Artificial
<220> FEATURE:
<223> OTHER INFORMATION: primer

<400> SEQUENCE: 42
cactctggca agggtcctg                                             19

<210> SEQ ID NO 43
<211> LENGTH: 10080
<212> TYPE: DNA
<213> ORGANISM: Homo sapiens

<400> SEQUENCE: 43
caggaggttg cacactgttc ctcccacctc gccactgcac ccccaccaag gatggaattg    60
gaggcggggg gcagattcca gggtcagggc tgtcaagagt gaatgaggcg aggagacatt   120
caggagcaga gaggtttcag acgcggaggt tccgggcacg ccctcaacac ccccttcacc   180
ttctcctcag gccccgcccg ccctgccctc ccctcccgat cccggagcca tgtggcccct   240
ggccctagtg atcgcctccc tgaccttggc cttgtcagga ggtaagaatg cgcggggtg    300 gaggcgcggc ggccattcgg gacaatggta ggaggggtca ggccggaggg ggaggggggcg  360 tgggagccgc gagctccgcc cccgcccac tcggggccgg gtccagtggg gacagctcag    420
agctcttcct gcttgtccct gggtgacctg gtttcccggc tgaggttggc cctccgaccc   480
cagacccttc acctcccaaa ataccctcgc agcagcccct cccgcgttca aggcttcctg   540
tcctctctgg aaagctgaaa gacatgggtt cgcgtcctga cgctgccgct ttgagccagt   600
agcctagcag ctgctttgtg cctaaattgt tttcatctgg aaaatgggct taatctataa   660
gtgcttacca gagaaggtca ctgtgaatat tgaaacgagg taatgcgtcg agccttcagt   720
atgtcgcagg tagaagggac ttgaaagtta gccacttagc cgttattact ttattagtag   780
tattcctttt tttttttttt ttttttttg agatggaacc ttgctctgtc tcccaggctg    840
gaaggcagtg gcacgatctt ggcttactga aacctcgcc tccgggttg aagcgattct     900 cctgcctcag cctcccgagt agctgggatt acaggcgccc gccaccacgc caactaatt   960
```

-continued

```
tttgtatttt cagcagagac ggggtttcgc catgttggtt aggctggtct cgaacttcta   1020
acttcaagta gcccgcgtca gcctcccaaa gtgccaggat tacaggcatg agccaccgag   1080
cccggcctct agtattctgt cttcatactc agccccttcc agaaccttct agattgttat   1140
tttaatcctt gggttgaccc caaacctatg tgacctcacc ccaaattggt agtccttaag   1200
atccttatgg atctttccca tctttccctg ccgttgtagg caggttctct ggaaccccg    1260 ttcatgaatc atttattcat tcaacaaaca gctattaaac accggccact gtgctgggtg   1320
ctgtacaagc agagacacag tccctgctct cagcacctgg agtctagcgg ggacagacgc   1380
agatgttatt caaacaatta tccaaataat tagttaataa ttatcttgac atgaggtgaa   1440
gacttcaagg agccaagcca ggggcctaga gatgtaatgg cggcttcccg accagaggcc   1500
ttcccaaagg gcttgaccct tgagccaaga cctgaaaaag gagggatctg tgggtgcctg   1560
gcacctggca ccatccttgg cctgaaggtg gggtggcttt tctcctctgg cgacactccc   1620
tggattcatg cccgtgccac tcctgagtgc cacaccctag gctaggagac ccacacgcta   1680
cgccttgtgg agtcctcaac aacctggcga ggtaggtgca ttgtaattac tccaatttca   1740
tggcagagaa acctaggact caaagacaga aggctcctgc tccaatgaca ccggcgatgc   1800
ctgagtcaga atcctaatca aggttgtttt ccctgtccat atcctggact tgaggctctg   1860
aaaaccattt ttataacttt tgacctaatc atttgcttaa agttagcttt ttttcttctt   1920
ttttcactca acaaaagca tgttcaactt tatattactg tcctgaatag agaatagaat    1980
tctttgtcat aaatagaagg taaggaagga aataaatcct gcacaatgaa agaaaaataa   2040
tatgtttatt gggttggacc acctgaaatt gctgatactt gacccttttt gaccttccta   2100
aaacaacttt tgcagatggt tcagtgtaat aaatgttagg tggcctgatg aggcttctgt   2160
gtcctcctgg ctttgaaaag tgagctcagt gaggattagg gaggtgttaa aaccatatta   2220
gcaccatcct gagactttat ccttgacaaa atcaggttta aaagagaact ggatgctggt   2280
tcagcgtctg agtgtgcgat ttaacgttac ttaaatctca tctctctacc atctaaaatg   2340
atcctgtgct caccgacaac ttctgtccct aactgcaaac cactgagcta atccaactgc   2400
ttgccctgta gttggggaaa ctagctaggg aggcagaggg acctcctgtt gtagctaata   2460
attaataata acatttccca ctgactgagt gctctccatg ccacctgctg tgctgcacgg   2520
tttgaaatgc aggatcatct tgaattcttc aactgcgcaa tgagagatga actattactt   2580
tttctacttg acagctgggg aaactgaggc tggtgatttg cataaggtca cacagtcaca   2640
aaatggcatg catgttcagg attggattct ccctgtccca cggacccctg ctgtgctttc   2700
aatgccagac acagtgcctg gcacacacag catttattta ttgagccccc attgtgtgcc   2760
aggcgctgtg ttaggtcctg ggaatatggt actgaataaa gcagttaagg tgcctgttgt   2820
caatggagct tacagtcaaa gtggagagat ttttaaaaac gaatacatac aaatgtgaag   2880
agaaatgaat agcaatcatt gttctgatga agaccaactg gaagaatgta atggggagg    2940 agtcgggacc aggagagtca acattagacc aggtggtcag ggaaggcctt tctgaagagg   3000
agacatttga gctgacctct cagaattaag aaggacccag acatacaacc tctaaattct   3060
gagggtcatc cagtagaata ttccatatat gtatatatga aatatcctat atctgtgctg   3120
tccaattatc cactagcccc ttcaggctat tgaacatttg aaatatggct ggtgtgactt   3180
aagaactgaa tttttaattt agttttactt cattttaatt agtttaaatt taaatagcca   3240
catgtagcta gtggctacca tattaaacaa cataggtctg gagaaaggac tgtgcagaga   3300
```

-continued

```
gaggaaatag caagtataaa atgtctagta tgggggcatc caagatgatt taaattcttc    3360
ttttctttaa atgcctggtg tgtttgaaga acaggcccat gaggctggac tagaggaagt    3420
cagaagaaag aggttggaga tggggtcaaa gaggctggca agggccagac agcacagagt    3480
cctgcacacc ttgggaaggc tttttggatt ttattttaaa gaaagttgag cctgggaaca    3540
acatctgact ttctttgttt gaagagtcct cagcctactt tgagaagact ggatcggagg    3600
gatgtaaaag tggaaggatt taggttaatg ttgtagtcat ttgggctaca gaagatgggg    3660
catggaccaa gatggtggca gaagtgtgga gataactgga tatttgggag ataaaaccaa    3720
taggaactgg ttgtgagtga tgaaggaaag aagagaagca aagatgactc ccaggtttgg    3780
ggctgagcac tgaggtggga aatactggag cgaacagttt tgattgagaa gaatcaagtt    3840
gggaatacaa agcttaagat gcctgtaagg catccaaatc aacagtgttt gagttttgag    3900
cttaaagaag agttcagggc tggagatgat tagcctatag ctggtattta aagccatgga    3960
ggcaaccagt atatatgcag tgaaggata gagagatggg tggaaagatg attggatgga    4020
tgcatggatg gatatatgga tagatggatg gatggatggt tggattggat ggatggatgg    4080
atggatggat ggatggatgg atggatggat ggatgaataa atggaccagt ggatggaggg    4140
acagatgagt ggatggatgg ttggatggat ggatggatgg atggatggat agatggttag    4200
atgactacct aaatggatga atggatagat ggatgagtag acggatggac aaatcaatag    4260
gatgaatggg ggatggatga ttggatagat tgatggatag atattgccta ggtggatgtg    4320
taggtcagtc tcacttctac ctcctgaaat ccatcttctg gtagaatgat ataaaaaatg    4380
catgtggaga gaaagtcagg ctcctgctta cctatcagca acatcctcat tttgtgaact    4440
cttctgttaa cccccagtgg aggatttggt acttcctgag aaaataatgt cacccctttg    4500
ccctaattca tctccacttg gtcaagaata gcaactgcca taggtcggca aattcatctt    4560
cagttcctgg tcacccaggg caataatccg acccttaccc caaacccaga accacaacc    4620 ccagggctcc tctgccccct ggatcccagt tttctaacaa tctctcttct ttaccaggtg    4680
tctcccagga gtcttccaag gttctcaaca ccaatgggac cagtgggttt ctcccaggtg    4740
gctacacctg cttcccccac tctcagccct ggcaggctgc cctactagtg caagggcggc    4800
tactctgtgg gggagtcctg gtccacccca aatgggtcct cactgccgca cactgtctaa    4860
aggagtatgt gggggccggg ggagcatggg gtagggatga gaatgggact gggattgtgg    4920
atggggtaga gttggatttg aggatggagt tggagttagg gttggggatg gacatgggag    4980
tgagaatgag gtttggggtt gagatatggg gattgggtat gggaatagaa tcaaagtagg    5040
ggatttggat gggattgaag ttgaggatgg gggagatgta tttggagatg aggaaggtag    5100 gatgagaag aagttaggtt ggggatggga agaggttggg gctgggatgg ggatggaaat    5160
gggctcatct tctttcctaa ccaccttctt tctgcaccca caggggctc aaagtttacc    5220 taggcaagca cgcccctaggg cgtgtggaag ctggtgagca ggtgagggaa gttgtccact    5280 ctatcccca ccctgaatac cggagaagcc ccacccacct gaaccacgac catgacatca    5340
tgcttctgga gctgcagtcc ccggtccagc tcacaggcta catccaaacc ctgccccttt    5400
cccacaacaa ccgcctaacc cctggcacca cctgtcgggt gtctggctgg ggcaccacca    5460
ccagccccca gggtatgcac ccacacaggt ggcctgaggc cccataggag tggctgggga    5520
aacaggggca gagatgggag ggaaggtctg aggtaggttc ctttatatat aaaaatataa    5580
ataagtaaat aaatatatat atttaaagtt agctgtatcc tttatataaa tataaattca    5640
tgaatatata aaaatatgag tatataaatt catgaatata tagaaatata aatagatcta    5700
```

-continued

```
atatatgaat atattatatg atgtatatta tgtattatat agtaatataa ttatatatta    5760
tacaaaaagt atacaaatta aatgtatttt ataaattata aaatttatca attatgtatt    5820
ttaaatatgt atttctgcat aatgtatata ttatatataa tctatattta aattatatat    5880
tataaatgta ttttataaat gtatacattt atatatttat atactgtaaa tgaattttat    5940
catttataat atataaatca tacatataaa atgtttatat ttctataatt tataaaatgt    6000
ttaatatatt aaatatggtt attaatgaaa tgtctaataa ttcaatgtaa taattaattc    6060
tatatcatta cttagtaagt ataatacatt atatatgtga atataaagtt gatgtatata    6120
ccgacaagag cccttttgcat ctccctagca atccctgact ctctcccagc ctcatgtttg    6180
tatctttctc ctcaacatgc cctgtctctc ttcctaccat tctatccaac tctcccgtaa    6240
ctcttcccat ccctgttcct gcttttccca tctttaattc tctatttctg accatctccc    6300
tattccaact ccctctctcc aactttctct ccccaccgct ggctccacca ctctccttat    6360
caaccttcca ttctcttgtc ccttccctcc ttgtccttcc ctccactttt ctcctcatct    6420
ctcccttcgc ctctctccca tgtccctcca tatttctgtc acttccgttg ctttacccag    6480
ataggtgctc atctcttctc ccatctttct cttcccatct caattttcta tctactcttt    6540
acccattcaa ctcgcctatt tcaccttcat cccatatcct atccaggtcg gatcccttag    6600
accttctctt tcttctcccc agtgaattac cccaaaactc tacaatgtgc caacatccaa    6660
cttcgctcag atgaggagtg tcgtcaagtc tacccaggaa agatcactga caacatgttg    6720
tgtgccggca caaagagggg tggcaaagac tcctgtgagg tgaggccggg aggctggtgg    6780
gtgccttgga caggatagaa agccagaatg gaagtgacag atgctgggga aaaagctttg    6840
tttccagcct taggggaacc aatctttata agatacaatg tcccctcaca taggaggtca    6900
agacaaaaag gggtacccag ggatggcagg aataattcat cataagcccc agctttgact    6960
gagtggctgc caagatccct gtgttgagat gcataaaggt tggtattctt tcacttgtga    7020
gtgatagaca accaactcaa actggcttaa acaaaatgca ggcttttgta actgaaaatc    7080
caggttgtct ggcttaggc acagatggat ccagtatgc aaattgtgtg tttggaattc    7140
tgtctttctt ttaactctca gctcttcttt attctgtttt ggcttcattc tcggttagat    7200
tcttcccatg acaagatggc cccagcagct ttgagcttac atcctaccct ctaggcaacc    7260
ctattagaaa gagaacctct cttttccaat agttcacaca aaagtcttaa gcatgattct    7320
cactaggctg acctaagtca tgtgtcttga gccatcactc caccagagct gtgggattct    7380
ctgatgggcc aagcctgagt cacatagtta actgtgggtg ctggagaggg gcagggacaa    7440
actgcatgga ttggaagtgg agaagggcag ttccccaaat gaaaaaatca ggagaggctg    7500
ttaccaaaat aagggggaaat ggccaagtac agtagttcat gcctgtaatc ccagcacttt    7560
gggaggctga ggtgagagga ttacttgagc ccaggagttt gagaccagcc tgggcaacat    7620
agtgagactc tgtctctaca aaaagaaaaa aaagttttta aattagccag gtgtggtgga    7680
gtacaactgc agtcctagtt actcgggagg ctgaggcaga aggactattt gaacccagga    7740
gttcaaggct gcagtgaggt atgatcatgc cactgcactc cagcctgggt gatagagcaa    7800
ggccctgtct ctaaaacaaa aagaaataaa tagagcaaga cactgtctct aataaataaa    7860
taaataaaaa tttaaaaatg aatgtttaat tttttaaaaa taagaggaaa tggatactac    7920
atgagcaaaa aatagccttc atcaataaag aagttgagat tggattcagt gagaaagagt    7980
atgatactat attaatgata tgtgccttga tcgattagtg atgtctgcct tgggcccagg    8040
```

```
aagagaaata gacttacacg tgtgttgcat accctgccca gatatgaatg ggttcactca    8100
atagtgagag acacaaatga gccttaaata ggagcagggt cagctggtgt ggggcagggg    8160
gtgatttagt accagggaaa caaaaatggg tatgaagtaa gttgttacca ttttaatgaa    8220
actgaggaac agagaaaaac acagaaattt ctctgtgtct ctctttctct gggcctatct    8280
ctgtctttct gtcccctattt ctgtctcttg ctgtctgtcc ctctgtgttt gtcttcttgt    8340
ctgtttctca ctgtcttcat tgctttctct cacactgtgt gtgtctgact ctgcctctct    8400
gagtctcctt ctctgtgtgt gtctctctcc atctttcact ctctccccac acctccctgt    8460
ccctgccttg tttagcccca gcaaggaccc acctctctct ctctttcttt ccccaactca    8520
gggtgactct gggggccccc tggtctgtaa cagaacactg tatggcatcg tctcctgggg    8580
agacttccca tgtgggcaac ctgaccggcc tggtgtctac acccgtgtct caagatacgt    8640
cctgtggatc cgtgaaacaa tccgaaaata tgaaacccag cagcaaaaat ggttgaaggg    8700
cccacaataa aagttgagaa atgtaccggc ttccatcctg tcaccatgac ttcctcacat    8760
ggtctgctta gcccttctct gctccttatt cccagtgttc catttgaacc agtgatccat    8820
gtcctgaaaa atgctcaatc tcagctaaca ttccatgttt cagaagcatt caggcactgc    8880
caggcttgca gtctcccaga tgttgcatcc ctgaaacatc tcaacaacct gaatgtccca    8940
acccagacaa tggcccaggt ctctcaactt catcagtgtg gcttctatga gcccagatca    9000
ccacctgaac gttctgtctg tggcacattc ttaaatattt ccatcagccc atctcaacaa    9060
tatatgtcct ataaatggac catccttgac aacatcctct aactcttcaa gtatttattc    9120
aatgccagta tcctagacct tctatttttt gcactcaaga aggctctaga ctcccatgat    9180
agttcatcct gaaatatttc tcttatgccc acaatcttct gccctgacaa cattctgtgt    9240
acctctgtga ctcaccacag ctaacattgg atcctcagaa tatttcattc tcacactgtt    9300
atgggtgtct cagaagtccc aacccaacct acatcccaca ttcttccaat accccacctc    9360
tgccaacatt ccctctctga atcaatggca ccctagtctc tagagttata gggttcagta    9420
taccaaaggg tcttcttgcc tgaactttat tgtctaccaa atattccgtc ttgtatcccc    9480
tccatgaaca tccttggtca gtgtcccttg ctgttacatc tttgtgcatg accctaaaat    9540
gtagtgcaaa tccttgcttt ggacaagtta taaaactcac agtctctgtg ctttctcatc    9600
tgtaaaatgg gttcataatt tttttaatt gtaacattat tacaagaata aatgtcaagc    9660
atttatcact attattattt gcatggttcc cataaaatat taccttagaa tgttaataac    9720
agcccttcga atttgcagag tgtccaaaaa aagtgttgca ctgatttatt ttcctcagga    9780
gacatttctt cagtgttgac tatgtgcaag cactctcctg ggtgttgtta aatatagttt    9840
atttactcaa caaatatttg tacctatcaa gagccaggca ctgttgcaga gacaagtgat    9900
aaccaatgag ttaaacagat aaaaacttct gcccttgtag aacttacatt cttttcaaga    9960
agtctccata acaatgaata aagaaatagg ctgtcaggtc gtgctgcaag ccatagcaag    10020
aaatgaaaca agggccatat gtggtagctc atgcctgtaa taccaacact gggaggccaa    10080
```

<210> SEQ ID NO 44
<211> LENGTH: 256
<212> TYPE: PRT
<213> ORGANISM: Homo sapiens

<400> SEQUENCE: 44

```
Glu Ser Ser Lys Val Leu Asn Thr Asn Gly Thr Ser Gly Phe Leu Pro
1               5                   10                  15
```

```
Gly Gly Tyr Thr Cys Phe Pro His Ser Gln Pro Trp Gln Ala Ala Leu
            20                  25                  30

Leu Val Gln Gly Arg Leu Leu Cys Gly Gly Val Leu Val His Pro Lys
        35                  40                  45

Trp Val Leu Thr Ala Ala His Cys Leu Lys Glu Gly Leu Lys Val Tyr
50                  55                  60

Leu Gly Lys His Ala Leu Gly Arg Val Glu Ala Gly Glu Gln Val Arg
65                  70                  75                  80

Glu Val Val His Ser Ile Pro His Pro Glu Tyr Arg Arg Ser Pro Thr
                85                  90                  95

His Leu Asn His Asp His Asp Ile Met Leu Leu Glu Leu Gln Ser Pro
            100                 105                 110

Val Gln Leu Thr Gly Tyr Ile Gln Thr Leu Pro Leu Ser His Asn Asn
        115                 120                 125

Arg Leu Thr Pro Gly Thr Thr Cys Arg Val Ser Gly Trp Gly Thr Thr
130                 135                 140

Thr Ser Pro Gln Val Asn Tyr Pro Lys Thr Leu Gln Cys Ala Asn Ile
145                 150                 155                 160

Gln Leu Arg Ser Asp Glu Glu Cys Arg Gln Val Tyr Pro Gly Lys Ile
                165                 170                 175

Thr Asp Asn Met Leu Cys Ala Gly Thr Lys Glu Gly Gly Lys Asp Ser
            180                 185                 190

Cys Glu Gly Asp Ser Gly Gly Pro Leu Val Cys Asn Arg Thr Leu Tyr
        195                 200                 205

Gly Ile Val Ser Trp Gly Asp Phe Pro Cys Gly Gln Pro Asp Arg Pro
210                 215                 220

Gly Val Tyr Thr Arg Val Ser Arg Tyr Val Leu Trp Ile Arg Glu Thr
225                 230                 235                 240

Ile Arg Lys Tyr Glu Thr Gln Gln Lys Trp Leu Lys Gly Pro Gln
                245                 250                 255

<210> SEQ ID NO 45
<211> LENGTH: 277
<212> TYPE: PRT
<213> ORGANISM: Homo sapiens

<400> SEQUENCE: 45

Met Trp Pro Leu Ala Leu Val Ile Ala Ser Leu Thr Leu Ala Leu Ser
1               5                   10                  15

Gly Gly Val Ser Gln Glu Ser Ser Lys Val Leu Asn Thr Asn Gly Thr
            20                  25                  30

Ser Gly Phe Leu Pro Gly Gly Tyr Thr Cys Phe Pro His Ser Gln Pro
        35                  40                  45

Trp Gln Ala Ala Leu Leu Val Gln Gly Arg Leu Leu Cys Gly Gly Val
50                  55                  60

Leu Val His Pro Lys Trp Val Leu Thr Ala Ala His Cys Leu Lys Glu
65                  70                  75                  80

Gly Leu Lys Val Tyr Leu Gly Lys His Ala Leu Gly Arg Val Glu Ala
                85                  90                  95

Gly Glu Gln Val Arg Glu Val Val His Ser Ile Pro His Pro Glu Tyr
            100                 105                 110

Arg Arg Ser Pro Thr His Leu Asn His Asp His Asp Ile Met Leu Leu
        115                 120                 125

Glu Leu Gln Ser Pro Val Gln Leu Thr Gly Tyr Ile Gln Thr Leu Pro
130                 135                 140
```

-continued

```
Leu Ser His Asn Asn Arg Leu Thr Pro Gly Thr Thr Cys Arg Val Ser
145                 150                 155                 160

Gly Trp Gly Thr Thr Thr Ser Pro Gln Val Asn Tyr Pro Lys Thr Leu
                165                 170                 175

Gln Cys Ala Asn Ile Gln Leu Arg Ser Asp Glu Glu Cys Arg Gln Val
            180                 185                 190

Tyr Pro Gly Lys Ile Thr Asp Asn Met Leu Cys Ala Gly Thr Lys Glu
        195                 200                 205

Gly Gly Lys Asp Ser Cys Glu Gly Asp Ser Gly Gly Pro Leu Val Cys
    210                 215                 220

Asn Arg Thr Leu Tyr Gly Ile Val Ser Trp Gly Asp Phe Pro Cys Gly
225                 230                 235                 240

Gln Pro Asp Arg Pro Gly Val Tyr Thr Arg Val Ser Arg Tyr Val Leu
                245                 250                 255

Trp Ile Arg Glu Thr Ile Arg Lys Tyr Glu Thr Gln Gln Lys Trp
            260                 265                 270

Leu Lys Gly Pro Gln
        275
```

<210> SEQ ID NO 46
<211> LENGTH: 19
<212> TYPE: DNA
<213> ORGANISM: Artificial
<220> FEATURE:
<223> OTHER INFORMATION: primer

<400> SEQUENCE: 46
aactctacaa tgtgccaca                                                19

<210> SEQ ID NO 47
<211> LENGTH: 20
<212> TYPE: DNA
<213> ORGANISM: Artificial
<220> FEATURE:
<223> OTHER INFORMATION: primer

<400> SEQUENCE: 47
ttattgtggg cccttcaacc                                               20

<210> SEQ ID NO 48
<211> LENGTH: 20
<212> TYPE: DNA
<213> ORGANISM: Artificial
<220> FEATURE:
<223> OTHER INFORMATION: primer

<400> SEQUENCE: 48
ggatggtcca tttataggac                                               20

<210> SEQ ID NO 49
<211> LENGTH: 20
<212> TYPE: DNA
<213> ORGANISM: Artificial
<220> FEATURE:
<223> OTHER INFORMATION: primer

<400> SEQUENCE: 49
aggctgccct actagtgcaa                                               20

<210> SEQ ID NO 50
<211> LENGTH: 20

```
<212> TYPE: DNA
<213> ORGANISM: Artificial
<220> FEATURE:
<223> OTHER INFORMATION: primer

<400> SEQUENCE: 50
atattgccta ggtggatgtg                                              20

<210> SEQ ID NO 51
<211> LENGTH: 20
<212> TYPE: DNA
<213> ORGANISM: Artificial
<220> FEATURE:
<223> OTHER INFORMATION: primer

<400> SEQUENCE: 51
aagacttcaa ggagccaagc                                              20

<210> SEQ ID NO 52
<211> LENGTH: 20
<212> TYPE: DNA
<213> ORGANISM: Artificial
<220> FEATURE:
<223> OTHER INFORMATION: primer

<400> SEQUENCE: 52
gacccttcac ctcccaaaat                                              20

<210> SEQ ID NO 53
<211> LENGTH: 20
<212> TYPE: DNA
<213> ORGANISM: Artificial
<220> FEATURE:
<223> OTHER INFORMATION: primer

<400> SEQUENCE: 53
ctagtgatcg cctccctgac                                              20

<210> SEQ ID NO 54
<211> LENGTH: 21
<212> TYPE: DNA
<213> ORGANISM: Artificial
<220> FEATURE:
<223> OTHER INFORMATION: primer

<400> SEQUENCE: 54
ggtgatctgc gccctggtcc t                                            21

<210> SEQ ID NO 55
<211> LENGTH: 21
<212> TYPE: DNA
<213> ORGANISM: Artificial
<220> FEATURE:
<223> OTHER INFORMATION: primer

<400> SEQUENCE: 55
aggtgtccgg tggaggtggc a                                            21

<210> SEQ ID NO 56
<211> LENGTH: 11820
<212> TYPE: DNA
<213> ORGANISM: Homo sapiens

<400> SEQUENCE: 56
attgaggggg gatcccagca ggtcccattt gttcagattc ttctgggcct ttctgtgttg   60
```

```
catttcttcc tctgcaggac acctgtcaca tgagggtctt caggggaaaa ggaattctag    120
tgtctgtgac tgcttcaaag gagaagtaag gggagaggag aggaaagcag gaggaggttg    180
gagagaacct cttgttcctg aggtcttcca atctccttca gctcaaagca ctcagcatgc    240
tgaagttcca gactctgggc tatcacgttc tgacatgcaa cacaggcaac accccagctc    300
catccacgtt tctccaaaag cacaggcatg acgtcatatg gtgacaaaca cccttgtcca    360
aaggaagccc ataggatacg ctaattctag attcacaaat actctagagg aactcacaca    420
atgggatggg ccagtgcccc acacagagta tgaggcctcc caccttggtt gaatatcttt    480 ttctttttt tcttttttt tttttttgag acggagtctc actctgtcac ccaggctgga    540
gtgcagtggc tcgatctcgg ctcactgcaa cctctgcctc ccaggttcaa gtgattctcc    600
tgcctcagcc tctggagtag ctggaattac aggtgcccac caccacaact ggctaatttt    660 tgtatttta gtagagacga gggtccacca tgttgaccag gcttgtctcg aactcctggt    720
ctcaagtgat ctgcccacct cggcctagtg ctgggattac agacgtgagt caccacgccc    780
ggccccacct tggttaaatt tctgaaaatc atttggtaaa gtgaggaccc ctccagctga    840
gacactgcca ggaaacagct attgagtctc ttagcaccca cagcattaaa acaaacccaa    900
aacattttag gcctcgttga gttctggagg caaaatattc ctcatctaca aatttatttt    960
attttatttt ttaataaaag ttattattat tttttttat agagagacag ggtcttgctc   1020
tgtgacccag actagagtgc agtggtgtga ccatggttca ctgcagcctc cacctcctgg   1080
gctcaagcga tcctcccacc tcagcctgcc aagtagctgg gaccacaggt atgcccctcc   1140
cccaggctaa cttttttta cttttgtgg agatgaggtc tcactatgtt gcccatgctg   1200 gtctttttt tttttttt tttttttgag acgggagtgc aggctggagt gcccaggctg   1260
gagtgcagtg gcacaatcat aactcactgc agcctcaaac tcctgggtc aagtgatcct   1320 cccacctcag cctcccacat aactaggact acaggcctgt gtcaccataa tgcctggtta   1380
atttttttag ttttgtttg tagaaacagg gtctcactat gttacccagg ctggcctcta   1440
actcctggcc tcaatccatc ctcccatctc aacctcccaa agtgctagga ttatagccac   1500
gagccaccat gcccggcccc atacttatat ttacttgtag tgagaacact taaaccctac   1560
tcggtcagta attttcaagt acacaataca ttgttactaa ctatatacat ggtatttta   1620 atttgcatga atgctcctta aaatcagcga gcccgcctta tttttgtat tcaattttat   1680 tggatataaa ttccacatca gtaaacctga ttctcttaaa aatctacaca gaaaaaaaaa   1740
aagagagaga ggttgagttg ggtagttgtt ggtattttg tttttgtttc tttgcttatt   1800
cagttgaggt ttattgtaaa acttgacacc agaaaaagga agaagtggcg tttttgtgct   1860
gtgagcgtgt gacgtgtgtc ctttccagag aaaggacagt catggtgctt ttttatcctc   1920
tctgcccaaa gaaggaaagc tcttaacagc cagcaggagg ctttgtaggg accagcgtta   1980
tcaacgccag tcgcgctgac caatgatgag ttaaagcagt taggtcgttt ctaagagcaa   2040
atcaaaagct aaggttctgt gattctgaaa atgagacacg gacagagact ggagacccag   2100
agagaaagtg aaggactaaa agacagtcat agggtgggag tttgctctcc tctgttttgt   2160
tctgggtttt tttgtttgtt tgtgcgctct gtctgaccgc ttttcttttt tttcttttc   2220 tttctttttt tttttttt tttgagatg gagtcttgct ctgccgccca ggctggagtg   2280
cggtggcaca atctcggctc actgcaagct ccgcctccca cgttcaaggg attctcctgc   2340
ctcagcctcc cgagcagctg ggattacagg catgcaccac cacactcagc taattttgt   2400 attttagta gagatggggt ttcaccatat tgaccaggct ggtcttgaac tctggcgtc   2460
```

-continued

```
aagtgacttg cccgcctcgg cctcccaaag tgttgggatt acaggcgtga gccaccgcgc    2520
ctggccctga ctgcttttct ccttggtttg tttgtcaatc ccccttcctc tgagccgaat    2580
tccctttttg ttctcatttt ctctctctgt cccctctctc tctccttctt tctctccttc    2640
cattcctcct agatgaagca aaaactcaga taaaccagca cagaggccag gtatggtggc    2700
tcacacctgt aatcccggca ctttgggaag ccaaggcagg caggttgctt gaggccagga    2760
gttcaagacc agcctggccc acatggtgaa accccgtctc tactaaaaat acaaaaatta    2820
gccggacatg gtggcacgtg cctgtaatcc caggtactca gaggtggag gttgcagtga     2880 gcggagatca cagccctgca ctccagcctg ggtgacagag cgagactcca tctcaaaacg    2940
aaaaacaaaa aacagcacaa agttcccttg tcctgtgact cattctctct ctctctttct    3000
accatttctc cttccctgtg tcttttttt ttctctctgt gggttttatt taagcaatag     3060
aagttcttag caaagaaaaa ctttatgaaa ttagattgat ccacttcata tgtacatata    3120
tgaactcagt tcagaaactc tcttctaccc ctgcctgatc acctatttgg aagtctgttc    3180
cttcaactct tcttctcttt ctgggactct ttctagcttg ggcttcctgc ccctcccgtc    3240
cactctcctg ctttcacagc ctctccttcc ccctgcccct cccctgcact gcatgggat     3300 gggcccagg tgtccaaggt ctccccaccc tcctttgtca ctggagtcag gattagaacc     3360
cagctcccta gtcaccttga gtcatcagtc ctggggctgc tgacgggctt gcagaggaga    3420
gagggagtgg ggctgggtct tcccaccctg ggtcctttcc tccttcccca ctccgtttag    3480
ctgtaaagct caattaagtg tgattagctg agaagagttt ctgcagaatt agagcacgcc    3540 ccaccctgt cttcgtggtc cccttccctt aacccggaaa ctggatgggc caggacaaag     3600
agagttaaga gctttgtcag tggtctgtct ggagcgacag atggaaggaa agggaccggt    3660
tgagcaacat gacaggtggc tgaggagcca ggtgcagagt ggtagagttg gctggcggag    3720
tggccagcac atgagaagac aggcaggtag gtggacggag agatagcagc gacgaggaca    3780
ggccaaacag tgacagccac gtagaggatc tggcagacaa agagacaagg tgagaaggag    3840
gtaggcgact gccaatgagg gagtgacaca caggggagca ggtagagaga ggacaagcag    3900
gtcatcccct tggtgaccctt caaagagaag cagagagggc agaggtgggg ggcacaggga   3960
aagggtgacc tctgagattc ccttttccc ccagactttg gaagtgaccc accatggggc     4020
tcagcatctt tttgctcctg tgtgttcttg gtgagttctc ccggagcagg gagagggcag    4080
gactgcgact ggatcccttc accccatga ggaggcccca ccaccctccc catctcagct     4140
ctggccccca gcctggtggt gaggaggaga ggggctttct ctgtgcctcc atttacctgc    4200
agctctcagg gtactgctca cctcggtctc ccctattttt tgatccctct tcccttctgt    4260
ccctctctga atctctgtct ctccatttcc ctcctatgtg taagcatctt tctccctggg    4320
tgtctttgat gtttcatggt cttttttctat cactgggtct ctctctcttt ctctctcttt   4380
ctcgtctctc tttctcctct ctctctcctg cctgtttctc tctctcactc tgtgtgtctc    4440
tccatctctg tatcttttct tcctctctct gacccatgcc cctgtctgtc tccagggctc    4500
agccaggcag ccacaccgaa gattttcaat ggcactgagt gtgggcgtaa ctcacagccg    4560
tggcaggtgg ggctgtttga gggcaccagc ctgcgctgcg ggggtgtcct tattgaccac    4620
aggtgggtcc tcacagcggc tcactgcagc ggcaggtaag tcccttcctg gggtgggcga    4680
agggaggact atgggaaggc aagcgctggg gtaggatca caaggagggg tggtgcccac     4740
tgggaagaag ctgatcctgc aacaagagag tctgaggtta gaccaggagt ggaacttcct    4800
```

-continued

```
tagcagtggg cctggggtgg tgctgggcag ggtgaggtat gttgggtgga gggccgggga    4860
gggtcctgga acctgccctc ctgcctctcc cattcctgca tgtacccttt ctttcctata    4920
tgacatctgc cactcacccc agccattcct tgacccagtc tgggcccggg gcccaggtct    4980
cacccaagct ctttttcttt ttcttttttt tattttttg agacagggtc tcgctctgtc     5040
gcccaggctg ctgtgcaatg gcgtgatcac agctcactgc tgtctctgcc tcccaggttc    5100
aagtgattct cctgccccag cctcctgagt agctgggatt acaggcaccc gccaccatgc    5160
ccagctaatt tttgtatttt ttgtagagac agggttttgc catgttggcc aggctggtct    5220
cgaactcctg gcctcaaatg acctgcccgt cttggcctcc caaagtgctg ggattacagg    5280
tgtgagccac tgcacccggc caacatgacc caaactcttt gtgcaacttc agaatctatg    5340
cctggcacct ctctgggcct cagtagactg atgttctgga attttttct ttttctttct     5400 tttttttttt ttttggagac agagtcttgc tctttctgtc atccaagctg gagtgcagtg    5460
atgctatctt ggctcactac agcctcaacc acctgggctc aagtgatcct cacacctcag    5520
cctcccaagg agctaagact acaggcctgc gccaccacac ctggctaatt tttaaatttt    5580
ttttgtagag acagggtttt gctatgttac ccaggctggt ctcaaactcc tcagctcaag    5640
caatcttcct gccttgacct cccaaagtgc tgggattaca ggcatgagcc actgtgcctg    5700
gcctggaact ttttttgtga aggggagat cagatgcaaa gaaacagaga ctcagggaga     5760
gagagggcca gcagcaggat gcagagaggc cattcatcaa cccactcgtt caatcatgaa    5820
cccactcgtc cacgcatgag catggagggc acatgtccg tgccaggcgg tgggaataag     5880
gcagtgaaca aggtccactg atgtccctgc cttcatgggc ttcaccagcc gagagaatca    5940
gaaagagagg cctggcgcgg tggctcacac ctgtaatccc agcactttgg gaggccgagg    6000
cgggcggatc acttgaggtc aggagtttga ccagcctg acacacatgg tgaaacctta      6060
tctctactaa aaatacaaaa attagctggg catggtggca tgcttctgta atcccagcta    6120
cttgggaggc tgaggcaggt gaattgcttg aacctgggag gtggaggttg tagtgagcca    6180
agatggtgcc actgcactcc agcctgggcg acagagcgag actcggtctt gaaaaaaaaa    6240 aaaaaaaaa aaaggagaga gagagacaca gatgcaggga catggtagga gaaacaggga    6300
acacccaaga tggaaagagg gtgatggagg ttgggaataa gagcctgtaa gagagactcg    6360
gagaatgaga gttgcgggtg agaggacaga cagtgagggg cagaacagtg gggagcggca    6420
ggagcgcctg agtgtccgtg gagggtgca aggtggggga ctgcgtgcct gccacccgct     6480
cagccgtcgc caccggcagc aggtactggg tgcgcctggg ggaacacagc ctcagccagc    6540
tcgactggac cgagcagatc cggcacagcg gcttctctgt gacccatccc ggctacctgg    6600
gagcctcgac gagccacgag cacgacctcc ggctgctgcg gctgcgcctg cccgtccgcg    6660
taaccagcag cgttcaaccc ctgcccctgc ccaatgactg tgcaaccgct ggcaccgagt    6720
gccacgtctc aggctgggc atcaccaacc acccacggag taaggggccc agggccaggg    6780 gtcagggtc aggatgggta caagtctggg atgcaggcg agaggtcgaa tcatgacacc      6840
tcagaggaag gatgggtaaa gggtcaggt gtgggatggg acatcaggat catggtttgg    6900
ggtcagagat tatggtggat tgggtcttg ggagccaaag gggttaaagg actgggtatg    6960
aagtcaggga tcagaggtca gaggtcagag tgtgtcagag gtcatcacac tggagcaaaa    7020
ggcatatata tatatatatg tatgtatagg atatgggcat tgtgggtcat gggtctgggg    7080
ttagaggtca ccgtagaatt aaggtcatgg gatccgagag ttgtacaatc tggtcaaaat    7140
ctgaggatgg aaattgggat tctatccaaa atcacatatc tgagattgga ggtcatagcg    7200
```

-continued

```
tttggggtgt ggggcccgaa gtttggggtc atggaggctg ggcccaata aactaggatc    7260 aggggacact ggcgttggaa gcagtgaggt ttggaagatg cagagctgag gttggaggtt    7320
aaggtaaaga cagggacatg gggtcaggag acagaagata tgagatcaag ctgggatcat    7380
aaggtaataa gacagaaggt caaagatcac agtagctggc attgaagagg gtcaggtctg    7440
gattcgttgt ctctgacgct ggagagacaa gaaagttctt gagttatgcc actcaaagtc    7500
aaatgtcaaa gatcaaagag accgtcaatc atctgggtc atgattcata tgaaattaag    7560
tcataaatat gtaacttgga ggtttcggga ttgtagtaca ggtcggtgag gggcaggggt    7620
attgacatgg atgggccaca tccagggaag agggacgtgg cctcaaagtg gggagattta    7680
ggggaccctg cagcacgcat gttctctctc cagacccatt cccggatctg ctccagtgcc    7740
tcaacctctc catcgtctcc catgccacct gccatggtgt gtatcccggg agaatcacga    7800
gcaacatggt gtgtgcaggc ggcgtcccgg ggcaggatgc ctgccaggtg agccagtgca    7860
ggcagcgtgc gtggtcacca ggacaggaag tgaagggggag gggctggaag caggagggga    7920
actgatggag gatgaatcag ggaaagggga tgctgcagag agacgggtc aaaaaggaag    7980 ggagaggctg gttacggagg ctcacacctg taatcccagc actttgggag gccgaggcgg    8040
gcggatcact tgaggtcagg agttcaagac aagcctggcc aacacggtga gactctgaat    8100
ctactaaaaa taccagaatt agccggggt ggtggtgcaa gcctgtggcc ccagctactt    8160
ggaaggctga ggcaggagaa tcgcttgatc ccgggaggcg gaggttgcag tgagctgaga    8220
tcacgccact gcactccagc ctgggcgaca gagccagact ctgtctcaaa acaaaataat    8280
taataataat aataataata ataataataa taatggagga gaggcccagg ataagggagg    8340
gagagagaca gggagtaaaa gggaggaccg gggaatggag gaggggagg ggcagggaga    8400 gagagggagg aagggaacag agaaggaaag atggggcagg ggttacagag agagacagca    8460
aaacagacgg agaggactgg gagcccagac agggaaccag ctgtttctgg ggctctaagt    8520 cttttcccata ccatcctcca gttggtgctg tcccagactg agagagattt gaggatggcg    8580
gtctctcccc tcattggtca gggccccagc cattgtcctt gagagaactc tgtgcttttg    8640
atggagtcct gcccaccttc cctgggattg gtcattttg atggcactct ctcccctcat    8700
tggtcagaac cccaggcatt gtccttgaga gaacctctat cctttatgga gtcccaccct    8760
cctcccctgg gattggtcat tgataatagt gttctctctc ctcattggtc agggcccag    8820 ccattgtcct tgagagaatg ctcgactctt tatgttgtct tgacagcctc ccctgagatt    8880
ggtcattaat gactgtgctc tctctcctca ttggtcaggg ccccagccat tgtccttgag    8940
agaacctctg tcctttatgg agttccaccc ttcttccctg ggattggccc ctagagacag    9000
tggttcttct cttttggtta gccattgcca ttgtcctccg ggaaagtgat tatactcttt    9060
tgtctaatga ccagacttgg agccctcccc aaggcccagg actgggttga agggttgggg    9120
aggaaaacag aaataagatg tctcccttgt tcagacagta cttctcttcc cttccagggt    9180
gattctgggg gcccctggt gtgtggggga gtccttcaag gtctggtgtc ctgggggtct    9240
gtggggccct gtggacaaga tggcatccct ggagtctaca cctatatttg caagtatgtg    9300
gactggatcc ggatgatcat gaggaacaac tgcctgtttt cctccacctc cacccccacc    9360
ccttaacttg ggtacccctc tggccctcag agcaccaata tctcctccat cacttcccct    9420
agctccactc ttgttggcct gggaacttct tggaaccttta actcctgcca gcccttctaa    9480
gacccacgag cggggtgaga gaagtgtgca atagtctgga ataaatataa atgaaggagg    9540
```

```
ggccatgtct gtccatttga agtcctcatg ctggttgaga ctggaagaag gactcagcag    9600
tttccctatc tcataggagt agaaacagag ctcaaataag gccaggcaca gtggctcaca    9660
cctgtaatcc catcactttg ggaagctgag gcaggtggat cacctgaggt caggaactcg    9720
ggaccagcct ggtcaacata gtgaaacccc aactctacta aaaatgcaaa aattagccag    9780
gcatggtggc gcatgcctgt aatcccagct actcaggagg ctgagacagg agaatagcat    9840
gaacccgtga ggcagaggct gcagcgagcc gagattgaac cattacactc cagcctgggc    9900
gacagagcga gactccatct caaaaacaaa caaacaaaaa acccagtgct caaataggat    9960
gagggtcttc cctgagtagt tactcagaaa tggagtagaa aaagttactt ttaataatat   10020
aggccgggtg cagtggccca cgcctgtaat cccagcactt tgggaggccg aggtgggagg   10080
atggcttgag ctcagatttc gagatcagcc tggcaacaca gtgaaatctt gtcactacaa   10140
aaacacaaaa aattagctgg gtgtggtggt gcgtgcctgt agtcccagct acttgggaag   10200
ctgaggtggg aggatcaccc gagccgggga ggtggaggct gcaaagagcc gagatcatgc   10260
cactgcactc cagcctgggc aataaagtga gaccttgtct caaaaacaaa acccagcaa    10320
tataaataag acacatgttt cttcatctgg cataatagaa atagtgccca gagcttataa   10380
gcttttcaag agtccacaaa agacccgaaa agaaaaaga aaattgttag ctccaaaata    10440
ccagatgaaa gctgcaaagt caacatttat gaccatttaa tccaatgtcc ataaaacgta   10500
gcattctttc cactagccaa ctgcagttta ctttcttgta atgaagcata cattgtatct   10560
ttaatgtggg acgtggcttt gttctaataa gacgaagggt ggagtgcagg cttggaaagc   10620
aggagagctc agcctacgtc tttaatcctc ctgcccaccc cttggattct gtctccactg   10680
ggactcaaga ggtgaggaga gaccatctcc ccaaatgcac tgaagggaaa ctggaggagg   10740
gagggagtga ggggtgatca taccagcgga ggcacatttg ctgagccccc ccgcagtctg   10800
ctctttccaa gtggaccctc ctggaagcct gatcccaacc tcccctgcaa gcaggtctgt   10860
cacccccatc tctcagatga agaaactgag ccttgcaggg gtggagtccc ttgtccccac   10920
gtcataaggg tagtcatagt agtaggaaga ggaagcacct aggtttgagg ccagggctgg   10980
ctgctgtcag aacctaggcc ctcccctgcc ttgctccaca cctggtcagg ggagagaggg   11040
gaggaaagcc aagggaaggg acctaactga aaacaaacaa gctgggagaa gcaggaatct   11100
gcgctcgggt tccgcagatg cagaggttga ggtggctgcg ggactggaag tcatcgggca   11160
gaggtctcac agcagccagt aagtgaacag ctggactcgg gctgcctggg cggcagggag   11220
aagcgggcag gggaagggtc agcagaggag cgaggccca gaggagccct ggggtggagc    11280
acagccaagg gctctgttcc ctttcctgga ctcggcttcc acaggccctg acctgcctcc   11340
cccaccctcc ggtcctgccc ctgtgcctgg cagcagcccc acctgtgtga catcccagca   11400
cacccccct ctccttgcaa aggagaaggg agcggcctag gggaggccag gggcccacct    11460
gggctggggc tgtggagagg gagtggctgg acgggagga aaaagagaga cggagattag    11520
atggaagaag agggatttca agacaaattg ccagagatgc agtcagagag actgactgag   11580
agacacaaaa atagaaggaa ttagagaaag gccacacag agccagacag agagagaaga    11640
gtggagatgg agacagggac gaggacagag aaaggcagac agacacatag ggacagaaag   11700
agaaaaatca cacaaagtca gaattactga atgacaggga atgacacata gaacgagaca   11760
cagattcaga gactcagggc agggaaagga aggctgcaga cagacagaca gacagaggga   11820
```

<210> SEQ ID NO 57
<211> LENGTH: 184

-continued

```
<212> TYPE: PRT
<213> ORGANISM: Homo sapiens

<400> SEQUENCE: 57

Leu Ser Gln Ala Ala Thr Pro Lys Ile Phe Asn Gly Thr Glu Cys Gly
1               5                   10                  15

Arg Asn Ser Gln Pro Trp Gln Val Gly Leu Phe Glu Gly Thr Ser Leu
            20                  25                  30

Arg Cys Gly Gly Val Leu Ile Asp His Arg Trp Val Leu Thr Ala Ala
        35                  40                  45

His Cys Ser Gly Ser Arg Tyr Trp Val Arg Leu Gly Glu His Ser Leu
    50                  55                  60

Ser Gln Leu Asp Trp Thr Glu Gln Ile Arg His Ser Gly Phe Ser Val
65                  70                  75                  80

Thr His Pro Gly Tyr Leu Gly Ala Ser Thr Ser His Glu His Asp Leu
                85                  90                  95

Arg Leu Leu Arg Leu Arg Leu Pro Arg Val Thr Ser Ser Val Gln
            100                 105                 110

Pro Leu Pro Leu Pro Asn Asp Cys Ala Thr Ala Gly Thr Glu Cys His
        115                 120                 125

Val Ser Gly Trp Gly Ile Thr Asn His Pro Arg Asn Pro Phe Pro Asp
    130                 135                 140

Leu Leu Gln Cys Leu Asn Leu Ser Ile Val Ser His Ala Thr Cys His
145                 150                 155                 160

Gly Val Tyr Pro Gly Arg Ile Thr Ser Asn Met Val Cys Ala Gly Gly
                165                 170                 175

Val Pro Gly Gln Asp Ala Cys Gln
            180

<210> SEQ ID NO 58
<211> LENGTH: 111
<212> TYPE: PRT
<213> ORGANISM: Homo sapiens

<400> SEQUENCE: 58

Met Gly Leu Ser Ile Phe Leu Leu Leu Cys Val Leu Gly Leu Ser Gln
1               5                   10                  15

Ala Ala Thr Pro Lys Ile Phe Asn Gly Thr Glu Cys Gly Arg Asn Ser
            20                  25                  30

Gln Pro Trp Gln Val Gly Leu Phe Glu Gly Thr Ser Leu Arg Cys Gly
        35                  40                  45

Gly Val Leu Ile Asp His Arg Trp Val Leu Thr Ala Ala His Cys Ser
    50                  55                  60

Gly Arg Pro Ile Pro Gly Ser Ala Pro Val Pro Gln Pro Leu His Arg
65                  70                  75                  80

Leu Pro Cys His Leu Pro Trp Cys Val Ser Arg Glu Asn His Glu Gln
                85                  90                  95

His Gly Val Cys Arg Arg Pro Gly Ala Gly Cys Leu Pro Gly
            100                 105                 110

<210> SEQ ID NO 59
<211> LENGTH: 254
<212> TYPE: PRT
<213> ORGANISM: Homo sapiens

<400> SEQUENCE: 59

Met Gly Leu Ser Ile Phe Leu Leu Leu Cys Val Leu Gly Leu Ser Gln
```

```
            1               5                  10                 15
Ala Ala Thr Pro Lys Ile Phe Asn Gly Thr Glu Cys Gly Arg Asn Ser
                    20                  25                  30

Gln Pro Trp Gln Val Gly Leu Phe Glu Gly Thr Ser Leu Arg Cys Gly
                35                  40                  45

Gly Val Leu Ile Asp His Arg Trp Val Leu Thr Ala Ala His Cys Ser
        50                  55                  60

Gly Ser Arg Tyr Trp Val Arg Leu Gly Glu His Ser Leu Ser Gln Leu
65                  70                  75                  80

Asp Trp Thr Glu Gln Ile Arg His Ser Gly Phe Ser Val Thr His Pro
                85                  90                  95

Gly Tyr Leu Gly Ala Ser Thr Ser His Glu His Asp Leu Arg Leu Leu
                100                 105                 110

Arg Leu Arg Leu Pro Val Arg Val Thr Ser Ser Val Gln Pro Leu Pro
            115                 120                 125

Leu Pro Asn Asp Cys Ala Thr Ala Gly Thr Glu Cys His Val Ser Gly
        130                 135                 140

Trp Gly Ile Thr Asn His Pro Arg Asn Pro Phe Pro Asp Leu Leu Gln
145                 150                 155                 160

Cys Leu Asn Leu Ser Ile Val Ser His Ala Thr Cys His Gly Val Tyr
                165                 170                 175

Pro Gly Arg Ile Thr Ser Asn Met Val Cys Ala Gly Val Pro Gly
                180                 185                 190

Gln Asp Ala Cys Gln Gly Asp Ser Gly Gly Pro Leu Val Cys Gly Gly
            195                 200                 205

Val Leu Gln Gly Leu Val Ser Trp Gly Ser Val Gly Pro Cys Gly Gln
        210                 215                 220

Asp Gly Ile Pro Gly Val Tyr Thr Tyr Ile Cys Asn Ser Thr Leu Val
225                 230                 235                 240

Gly Leu Gly Thr Ser Trp Asn Phe Asn Ser Cys Gln Pro Phe
                245                 250

<210> SEQ ID NO 60
<211> LENGTH: 248
<212> TYPE: PRT
<213> ORGANISM: Homo sapiens

<400> SEQUENCE: 60

Met Gly Leu Ser Ile Phe Leu Leu Leu Cys Val Leu Gly Leu Ser Gln
1               5                   10                  15

Ala Ala Thr Pro Lys Ile Phe Asn Gly Thr Glu Cys Gly Arg Asn Ser
                20                  25                  30

Gln Pro Trp Gln Val Gly Leu Phe Glu Gly Thr Ser Leu Arg Cys Gly
            35                  40                  45

Gly Val Leu Ile Asp His Arg Trp Val Leu Thr Ala Ala His Cys Ser
        50                  55                  60

Gly Ser Arg Tyr Trp Val Arg Leu Gly Glu His Ser Leu Ser Gln Leu
65                  70                  75                  80

Asp Trp Thr Glu Gln Ile Arg His Ser Gly Phe Ser Val Thr His Pro
                85                  90                  95

Gly Tyr Leu Gly Ala Ser Thr Ser His Glu His Asp Leu Arg Leu Leu
                100                 105                 110

Arg Leu Arg Leu Pro Val Arg Val Thr Ser Ser Val Gln Pro Leu Pro
            115                 120                 125
```

```
Leu Pro Asn Asp Cys Ala Thr Ala Gly Thr Glu Cys His Val Ser Gly
    130                 135                 140
Trp Gly Ile Thr Asn His Pro Arg Asn Pro Phe Pro Asp Leu Leu Gln
145                 150                 155                 160
Cys Leu Asn Leu Ser Ile Val Ser His Ala Thr Cys His Gly Val Tyr
                165                 170                 175
Pro Gly Arg Ile Thr Ser Asn Met Val Cys Ala Gly Val Pro Gly
            180                 185                 190
Gln Asp Ala Cys Gln Gly Asp Ser Gly Gly Pro Leu Val Cys Gly Gly
        195                 200                 205
Val Leu Gln Gly Leu Val Ser Trp Gly Ser Val Gly Pro Cys Gly Gln
    210                 215                 220
Asp Gly Ile Pro Gly Val Tyr Thr Tyr Ile Cys Lys Tyr Val Asp Trp
225                 230                 235                 240
Ile Arg Met Ile Met Arg Asn Asn
                245
```

<210> SEQ ID NO 61
<211> LENGTH: 20
<212> TYPE: DNA
<213> ORGANISM: Artificial
<220> FEATURE:
<223> OTHER INFORMATION: primer

<400> SEQUENCE: 61
tcagccaggc agccacaccg                                         20

<210> SEQ ID NO 62
<211> LENGTH: 20
<212> TYPE: DNA
<213> ORGANISM: Artificial
<220> FEATURE:
<223> OTHER INFORMATION: primer

<400> SEQUENCE: 62
ttggtgatgc cccagcctga                                         20

<210> SEQ ID NO 63
<211> LENGTH: 20
<212> TYPE: DNA
<213> ORGANISM: Artificial
<220> FEATURE:
<223> OTHER INFORMATION: primer

<400> SEQUENCE: 63
ccacaccgaa gattttcaat                                         20

<210> SEQ ID NO 64
<211> LENGTH: 18
<212> TYPE: DNA
<213> ORGANISM: Artificial
<220> FEATURE:
<223> OTHER INFORMATION: primer

<400> SEQUENCE: 64
gccctccctt catttata                                           18

<210> SEQ ID NO 65
<211> LENGTH: 8280
<212> TYPE: DNA
<213> ORGANISM: Homo sapiens

<400> SEQUENCE: 65

-continued

```
atcgtgtaat caccgccaca tccagtgcaa agctgattcg tcaccacaga gcagctccct    60
cctgccaccc catccctggg tcccaagaga acctttctt aaaagaggga gttcttgacg    120
ggtgtggtgg ctcatgcctg taatccttgc actttgggag gccaaggagg gtggatcatt   180
tgaggtcagg agtttgagac cagactggcc aacatggtga aaccctgtct ttactaaaaa   240
tacaaaaaaa tgagcgggc atggtggtgg gtgcctatag ccccagctac tcaggaggct    300
gaggcaggag aatcgcttga acccaggagg cagaggttgc agtgagccga gattgagcca   360
ctgcactcca gccggggcta agagtgaga ctctgtctca aaaaaaaaa aagaaaaag     420 aaaaaagaa aaaaaataa aataaataaa taaataaaat aaatttaaaa atttaaaaat    480
aaagaggggg ttcttgtgtt gatgccgagc ctgaaccaag gcagaggagg ccgggaaggc   540
ttcccaaggc cttcagctca agcagggag gcccatagtt aaacagaaac agttcaggaa    600
tcacagaaag gcacctgggg agagatgggt gtgtggctcc agatgcaggt gcccagacag   660
tgcgtcccca ggtgtacaga cagacccagg ccaagctcca gctcaaagag ccagcctagg   720
ggggtgccga ggtggaggga ggctgagtca ggctgaggcc ggggaacagt tggggtagcc   780
aagggaggca agcagcctcc tgagtcacca cgtggtccag gtacggggct gcccaggccc   840
agagacggac acaagcactg gggaatttaa ggggctaggg gaggggctga ggagggtagg   900
ccctccccca aatgaggatg aaccccccc aactccagaa ccccctgca ggctggccag    960 aatccttccc catctcattc actctgtctc tcctgtctct tgccgtctcc tattttgaat  1020
ttccaacccc gtctgttaag actgtccttc tgtctctgaa tctctgtccc cttctctttc  1080
tgggtctctc tccctctccc tctgggtctc tgtcccccctc tctgggtctc tgtcactctc 1140
tctttgcatc tccagctctc actttgtctc tgcacctagc agatcccaag ctggggaatg  1200
ccagttctgg caccaacctt cctgctccct gctgggcct ctgctcccccc atctctcagg  1260 agtcgaaagt gagaaagcaa ggtgggcagc tctgctccag gtccaggtat ctcccgccca  1320
cctcctgccc gtcctctatc ccacccctcc tctccatctc tccctggcgc tgccatctct  1380
catctaggcc tccgtctcct ctgtcattgt ccccatcccc tgtaggtgcc catccttccc  1440
gtctcccctc tgccatcggc ctgcctgtcc catcctcttt ctcccaccat gtcccgttct  1500 cttcacgtc tcatgcccgc actgccttca tcatcatcgc tgttgttctg tgtgtgtttg    1560
tggtgagtgc cgcatggtgg gggcgtctcg gcctctctcc tctctctcca ctgtttttctc 1620 tttctgtgtg tctgttttcca ttctatctcc accttcttcc ctccgtcttt tgcttttcta 1680
tctccacttc tccacacccc tctctccctg cgtctctgtg tctccctctt cctctgtctt  1740
gtttttttcc caccgtctgc ctcttctgtt ccctgtcaca tccaacttcc accggtttct  1800
ccagctctct cctcagttcc ttctctcatg agcacacctg cctctgtgct cgtattcctg  1860
gactcctctc tctccactgt catatcttct cattcatttt cccagtctct ctctgtctct  1920
tgctctcccc ctctctgtca ctctgtctct gtctctctct ttctctctct ctctctgtgt  1980
ctctctgtct ggctctctct ctgtctctct tccatctctc tctctctct ccccccgtc    2040 accctgtctc tgtctctctc tgtctgtgtg tctctctgtc tttctctctc tccatctctc  2100
tctgtctctc tctctctctc tctctctctc cctctctccc tctcccgtg actccctctc   2160 tcagtccatc tcttcctccc tctctcagcc ccttcgtgcc ctttcctctg acactcccca  2220
ccctggtttc ctgactccac cactagatcc accacctcca gcaactggga accctccct    2280 gcccacccctg ccctgggtc ccctcccagg attccttcta gattatagca tcttccctgg  2340
```

-continued

```
gcgggttctc atgaacaatt gtggctgctt ttttggccag acaggggagg gagggggatgg    2400 gatcaggag tcctggaatg ggaactaggc aataaaaaaa aaaaaatgtc agaagcaggg      2460 cggcggagg tggggcagg gccagctgtc cttaccaggg ataaaaggct ttgccagtgt       2520
gactaggaag agagacacct cccctccttc cttcatcaag acatcaagga gggacctgtg    2580
ccctgctcca catcctccca cctgccgccc gcagagcctg caggccccgc cccctcgtc     2640 tctggtccct acctctctgc tgtgtcttca tgtccctgag ggtcttgggc tctgggtaag    2700 tgcccttgc tgtctctgcc tctcagcccc cggttctgtt gaaggttcct tctctctcac     2760
tttttctctg catttgacag gacctggccc tcagccccta aaatgttcct cctgctgaca    2820
gcacttcaag tcctggctat aggtaagaga acggttgggt atgacacaag ggggtcccct    2880
ggagactctg agaagagatg gggatgggtc cttggggccc ctggatgctc atggtgacct    2940
cataagaaag agcagggagt ggtttggggg tcatggtggg ggaacgtgct ggaggcctaa    3000
attcctagtt gtggaggtgc tagggaattg tgggccgggg gagagaggtg tttataaggt    3060
ctggtgcaaa atacataagg aatcttaggg aactattagg tcctgagtgg gtcatagcag    3120
aaagatcacg gggctctacc tgactgtgtt aggaaagaaa caatgtcaga aagatgtttt    3180
gttgtcagag ggaaggtgga gaaggatgat gggatggcgg gatcgtggca tggggtggcg    3240
ggatcgtggc atgggtgtgt gaggtggatg ggggcaagtg tggggcaaga gatggcggat    3300
ccttggggtc ccactgagtg ggaacgttgg ggaggagaca gggaggtcct tgaatgtgtt    3360
ggggaaggac tcattgggg gaaatgtggc atatttcgag aagtgatcac agaaattatg     3420
ggagcataga gctaagggtc gtagatgtag caaggccctg gataaggtgg ccacggcaca    3480
aaataagaga tgctacggag gtgacttggg aggtgagtca gaaagctctc cgtgctgggg    3540
caataacggg gtcaatattg ggcatgtctc accctgggtg ggacagatag aggcgggcag    3600
tttaggggtt agaccaaaag gaaggggatt tgtcagtttt ggaatcctac aaacttgtgg    3660
agtggagagt gttttgctcat ctactttccc cacccaatcc tgtccactcc tagccatgac   3720
acagagccaa gaggatgaga acaagataat tggtggccat acgtgcaccc ggagctccca    3780
gccgtggcag gcggccctgc tggcgggtcc caggcgccgc ttcctctgcg gaggcgccct    3840
gctttcaggc cagtgggtca tcactgctgc tcactgcggc cgcccgtaag tgaccccctc    3900
ccctgtccct gtaccagtg aattccagag tctaaagccc tagagctgag ctgagaacct     3960
ggatctctgt atagaaccca atgtagtggc tggctcctgg tttgaggtct agagaagagc    4020
ctggaacaaa aacacagctc gggatgtggg ctcctccata aatctcgaac tcagcatagg    4080
ttctgaaagc agatgggcag cttggaaccc atggacctgc tgagaaccga acatctgatc    4140
cagtgattct tccagaggcc acacattaca tcgagaccaa gcttagccca ttccagattg    4200
gtggctgaat tcaggacccc gtctacattc agaaactcag gacactacgt agaactcaga    4260
gcccagttca ggacctgcag tctagccata aatccagaac tagaacgctg ctcacagctg    4320
gaacatacaa ctctaagaat agaggcaaaa cctggaggct gtttcacacc caaggtttag    4380
ttcagagtct agtctatagc tccgctatga gcagacttca acccagtgtt tgaatcccag    4440
aatgtggcgg gtgcggtggc tcatgcctat aatcctagca cttgggatg ctgaggcagg     4500 cagatcacct gaggtcagga gttcgagacc agcctgagca acatagagaa accctgtctc    4560
tactaaaaat gcaaaattag ccaggcatgg tggcacatgc ctgtaatccc agccactcgg    4620
gaggctgagg caggagaatc acttgaacct gggaggcgga ggttgcagtg agtcaagatc    4680
gcaccattgc actccaggct aggcaacaag agcgaaactc catatcaatc aatcaatcaa    4740
```

```
taaatcccag aatgcagatc ctaatcagaa gccccatata aaacctagac ccctcctaaa   4800
ttctagatct gaacttacaa cccagacccc agccaagagg tcaaaatgcc tataagccat   4860
atctatgcca taaacaggtc agtctagaac ctagagatca aagctcaggc cagagtctag   4920
aatataaagg ccagaatgca aaccagactc tagaatcttg gatccgggcc ataacctaga   4980
gctccaacta gaacccagag cccaacctga ggtcaagggc tagggccaga gtccagaacc   5040
aagagcccta taatccaata tgaaacagac ctgtagaggc tgggtgcggt ggctcacgcc   5100
tgtaatccca gcactttggg aggctgaggc gggagaatca cttgaactgg gagttggagg   5160
tcgagagtga gctgagatcg tgccactgca ctccagccta ggtgacagag cgagactcca   5220
tcacaaaaaa aaaataaata aataaatcaa gtcataatcc aggttcgatc tagaatcctg   5280
atcttagcat agagtcaaaa gtttaagatg tctagaactc agaacccagg ctagaaacag   5340
aatggtgcct actccggaat atcagttccg atttagagcc tagactcata acgcagtttc   5400
gcttaggact caatgcaccg agcccagcac agaccctggc acggagccaa gctctcccaa   5460
tcatcaccct cttcccaagc caggagctgg agcccagccc aagagcggaa ggagaggcag   5520
ctggggctgg gccgagagaa tgccctggcc atggggaagg gcacaggagg ccaagaatgc   5580
tcggcctgca gttagtgaga agcaggctag acctcgggga agactcgtca cccgccaggg   5640
gaaccgggct ggagggtggg gaggagtctc tggctcagac cctgagcagc gcttctcttg   5700
ggggtcgtgg ccaggatcct tcaggttgcc ctgggcaagc acaacctgag gaggtgggag   5760
gccacccagc aggtgctgcg cgtggttcgt caggtgacgc accccaacta caactcccgg   5820
acccacgaca acgacctcat gctgctgcag ctacagcagc ccgcacggat cgggagggca   5880
gtcaggccca ttgaggtcac ccaggcctgt gccagccccg ggacctcctg ccgagtgtca   5940
ggctggggaa ctatatccag ccccatcggt gaggactcct gcgtcttgga aagcagggga   6000
ctgggcctgg gctcctgggt ctccaggagg tggagctggg gggactgggg ctcctgggtc   6060
tgagggagga ggggctgggc ctggactcct gggtctgagg gaggaggggg ctgaggcctg   6120
gactcctggg tctcaaggag gaggagctgg gcctggactc atacgtctga gggaggaggg   6180
gctggagcct ggactcctgg gtctcaagga ggagggggctg ggcctggact tctgggtctg   6240
agggaggagg ggctggggac ctggactccc gggtctgagg gaggagggac tggggtctg   6300
gactcctggg tctgagggag gagggggctgg gggcctggac tcctgggtct gagggaggag   6360
gtgctggggc tggactcctg gtcggaagg aggaggggct ggggggcctgg acccttgggt   6420
cttatgggag ggtagaccca gttataaccc tgcagtgtcc cccagccagg tacccccgcct   6480
ctctgcaatg cgtgaacatc aacatctccc cggatgaggt gtgccagaag gcctatccta   6540
gaaccatcac gcctggcatg gtctgtgcag gagttcccca gggcgggaag gactcttgtc   6600
aggtaaggcc caggatggga gctgtggtag ggattatttg ggactgggat ttaagcaaat   6660
gatgtcagga gcatggaagt ctgcagaggt cttcagaaga gagtgaaccg caggcacaga   6720
gagattccga tagccaggcc accctgcttc ctagccctgt gcccctggg taatggactc   6780
agagcattca tgcctcagtt tcctcatctg tcaggtggga gtaaccctct tagggtagtt   6840
ggtggaatgg gatgaggcag gttggggaaa gatcgcagag tggcctctgc tcatatgggt   6900
ctgggaaagg ctgtgctgag gcttctagaa atcttaatgc atccttgagg gaggcagaga   6960
tggggaaata gaaaagaga gacacacaaa tgttctacag ttggagcgaa cagagagggg   7020
cctggtgaga ttcaagggac aggcaggtgc acacagagac agagccagac ccagcggaga   7080
```

```
gggaaggaag tgccccgacc tccggggctg agacctcaga gctggggcag gactgtgtcc    7140
ctaactgtcc accagtgtct ctgcctgtct ccctgtgtct gcttctcggg ttctctgtgc    7200
catggtggct ctggctacct gtccatcagt gtctccattt ctgttcctcc ccctcagggt    7260
gactctgggg gacccctggt gtgcagagga cagctccagg gcctcgtgtc ttggggaatg    7320
gagcgctgcg ccctgcctgg ctaccccggt gtctacacca acctgtgcaa gtacagaagc    7380
tggattgagg aaacgatgcg ggacaaatga tggtcttcac ggtgggatgg acctcgtcag    7440
ctgcccaggc cctcctctct ctactcagga cccaggagtc caggcccag ccctcctcc     7500 ctcagaccca ggagtccagg cccccagccc ctcctccctc agacccggga gtccaggccc    7560
ccagcccctc ctccctcaga cccaggagtc caggccccag ccctcctcc ctcagacccg     7620 ggagtccagg cccccagccc ctcctccctc agacccagga gtccaggccc cagtccctcc    7680
tccctcagac ccaggagtcc aggcccccag ccctcctcc ctcagaccca ggaatccagg    7740
cccagcccct cctccctcag acccaggagc cccagtcccc cagcccctcc tccttgagac    7800
ccaggagtcc aggcccagcc cctcctccct cagacccagg agcccagtc ccagcatcc      7860 tgatctttac tccggctctg atctctcctt cccagagca gttgcttcag gcgttttctc     7920
cccaccaagc ccccacccct gctgtgtcac catcactact caagaccgga ggcacagagg     7980
gcaggagcac agacccctta aaccggcatt gtattccaaa gacgcaatt tttaacacgc      8040 ttagtgtctc taaaaaccga ataaataatg acaataaaaa tggaatcatc ctaaattgta    8100
ttcattcatc catgtgttta cttttttattt tttgagacaa ggtcttgctc agtctcctgg    8160
tgaaatgctg taacgcaatc atagctcact gcaaccgtga cctcctgggc tccagtgatc     8220
ctcttacctc agcctcccga gtagctggga ccacaggtgc ccgtcaccat gccccgctac     8280
```

<210> SEQ ID NO 66
<211> LENGTH: 237
<212> TYPE: PRT
<213> ORGANISM: Homo sapiens

<400> SEQUENCE: 66

```
Met Thr Gln Ser Gln Glu Asp Glu Asn Lys Ile Ile Gly Gly His Thr
1               5                   10                  15

Cys Thr Arg Ser Ser Gln Pro Trp Gln Ala Ala Leu Leu Ala Gly Pro
            20                  25                  30

Arg Arg Arg Phe Leu Cys Gly Gly Ala Leu Leu Ser Gly Gln Trp Val
        35                  40                  45

Ile Thr Ala Ala His Cys Gly Arg Pro Ile Leu Gln Val Ala Leu Gly
    50                  55                  60

Lys His Asn Leu Arg Arg Trp Glu Ala Thr Gln Gln Val Leu Arg Val
65                  70                  75                  80

Val Arg Gln Val Thr His Pro Asn Tyr Asn Ser Arg Thr His Asp Asn
                85                  90                  95

Asp Leu Met Leu Leu Gln Leu Gln Gln Pro Ala Arg Ile Gly Arg Ala
            100                 105                 110

Val Arg Pro Ile Glu Val Thr Gln Ala Cys Ala Ser Pro Gly Thr Ser
        115                 120                 125

Cys Arg Val Ser Gly Trp Gly Thr Ile Ser Ser Pro Ile Ala Arg Tyr
    130                 135                 140

Pro Ala Ser Leu Gln Cys Val Asn Ile Asn Ile Ser Pro Asp Glu Val
145                 150                 155                 160

Cys Gln Lys Ala Tyr Pro Arg Thr Ile Thr Pro Gly Met Val Cys Ala
```

```
                165                 170                 175
Gly Val Pro Gln Gly Lys Asp Ser Cys Gln Gly Asp Ser Gly Gly
            180                 185                 190

Pro Leu Val Cys Arg Gly Gln Leu Gln Gly Leu Val Ser Trp Gly Met
            195                 200                 205

Glu Arg Cys Ala Leu Pro Gly Tyr Pro Gly Val Tyr Thr Asn Leu Cys
            210                 215                 220

Lys Tyr Arg Ser Trp Ile Glu Glu Thr Met Arg Asp Lys
225                 230                 235

<210> SEQ ID NO 67
<211> LENGTH: 251
<212> TYPE: PRT
<213> ORGANISM: Homo sapiens

<400> SEQUENCE: 67

Met Phe Leu Leu Leu Thr Ala Leu Gln Val Leu Ala Ile Ala Met Thr
1               5                   10                  15

Gln Ser Gln Glu Asp Glu Asn Lys Ile Ile Gly Gly His Thr Cys Thr
            20                  25                  30

Arg Ser Ser Gln Pro Trp Gln Ala Ala Leu Leu Ala Gly Pro Arg Arg
        35                  40                  45

Arg Phe Leu Cys Gly Gly Ala Leu Leu Ser Gly Gln Trp Val Ile Thr
    50                  55                  60

Ala Ala His Cys Gly Arg Pro Ile Leu Gln Val Ala Leu Gly Lys His
65                  70                  75                  80

Asn Leu Arg Arg Trp Glu Ala Thr Gln Gln Val Leu Arg Val Val Arg
                85                  90                  95

Gln Val Thr His Pro Asn Tyr Asn Ser Arg Thr His Asp Asn Asp Leu
            100                 105                 110

Met Leu Leu Gln Leu Gln Gln Pro Ala Arg Ile Gly Arg Ala Val Arg
        115                 120                 125

Pro Ile Glu Val Thr Gln Ala Cys Ala Ser Pro Gly Thr Ser Cys Arg
    130                 135                 140

Val Ser Gly Trp Gly Thr Ile Ser Ser Pro Ile Ala Arg Tyr Pro Ala
145                 150                 155                 160

Ser Leu Gln Cys Val Asn Ile Asn Ile Ser Pro Asp Glu Val Cys Gln
                165                 170                 175

Lys Ala Tyr Pro Arg Thr Ile Thr Pro Gly Met Val Cys Ala Gly Val
            180                 185                 190

Pro Gln Gly Gly Lys Asp Ser Cys Gln Gly Asp Ser Gly Gly Pro Leu
        195                 200                 205

Val Cys Arg Gly Gln Leu Gln Gly Leu Val Ser Trp Gly Met Glu Arg
    210                 215                 220

Cys Ala Leu Pro Gly Tyr Pro Gly Val Tyr Thr Asn Leu Cys Lys Tyr
225                 230                 235                 240

Arg Ser Trp Ile Glu Glu Thr Met Arg Asp Lys
                245                 250

<210> SEQ ID NO 68
<211> LENGTH: 249
<212> TYPE: PRT
<213> ORGANISM: Homo sapiens

<400> SEQUENCE: 68

Met Ala Thr Ala Gly Asn Pro Trp Gly Trp Phe Leu Gly Tyr Leu Ile
```

```
                1               5                   10                  15
Leu Gly Val Ala Gly Ser Leu Val Ser Gly Ser Cys Ser Gln Ile Ile
                    20                  25                  30

Asn Gly Glu Asp Cys Ser Pro His Ser Gln Pro Trp Gln Ala Ala Leu
                35                  40                  45

Val Met Glu Asn Glu Leu Phe Cys Ser Gly Val Leu Val His Pro Gln
            50                  55                  60

Trp Val Leu Ser Ala Ala His Cys Phe Gln Asn Ser Tyr Thr Ile Gly
65                  70                  75                  80

Leu Gly Leu His Ser Leu Glu Ala Asp Gln Glu Pro Gly Ser Gln Met
                85                  90                  95

Val Glu Ala Ser Leu Ser Val Arg His Pro Glu Tyr Asn Arg Pro Leu
                100                 105                 110

Leu Ala Asn Asp Leu Met Leu Ile Lys Leu Asp Glu Ser Val Ser Glu
            115                 120                 125

Ser Asp Thr Ile Arg Ser Ile Ser Ile Ala Ser Gln Cys Pro Thr Ala
    130                 135                 140

Gly Asn Ser Cys Leu Val Ser Gly Trp Gly Leu Leu Ala Asn Gly Arg
145                 150                 155                 160

Met Pro Thr Val Leu Gln Cys Val Asn Val Ser Val Val Ser Glu Glu
                165                 170                 175

Val Cys Ser Lys Leu Tyr Asp Pro Leu Tyr His Pro Ser Met Phe Cys
                180                 185                 190

Ala Gly Gly Gly His Asp Gln Lys Asp Ser Cys Asn Gly Asp Ser Gly
            195                 200                 205

Gly Pro Leu Ile Cys Asn Gly Tyr Leu Gln Gly Leu Val Ser Phe Gly
    210                 215                 220

Lys Ala Pro Cys Gly Gln Val Gly Val Pro Gly Val Tyr Thr Asn Leu
225                 230                 235                 240

Cys Lys Phe Thr Glu Trp Ile Glu Lys
                245

<210> SEQ ID NO 69
<211> LENGTH: 253
<212> TYPE: PRT
<213> ORGANISM: Homo sapiens

<400> SEQUENCE: 69

Met Ala Thr Ala Gly Asn Pro Trp Gly Trp Phe Leu Gly Tyr Leu Ile
1               5                   10                  15

Leu Gly Val Ala Gly Ser Leu Val Ser Gly Glu Met Ser Pro Ser Cys
                20                  25                  30

Ser Gln Ile Ile Asn Gly Glu Asp Cys Ser Pro His Ser Gln Pro Trp
            35                  40                  45

Gln Ala Ala Leu Val Met Glu Asn Glu Leu Phe Cys Ser Gly Val Leu
        50                  55                  60

Val His Pro Gln Trp Val Leu Ser Ala Ala His Cys Phe Gln Asn Ser
65                  70                  75                  80

Tyr Thr Ile Gly Leu Gly Leu His Ser Leu Glu Ala Asp Gln Glu Pro
                85                  90                  95

Gly Ser Gln Met Val Glu Ala Ser Leu Ser Val Arg His Pro Glu Tyr
                100                 105                 110

Asn Arg Pro Leu Leu Ala Asn Asp Leu Met Leu Ile Lys Leu Asp Glu
            115                 120                 125
```

```
Ser Val Ser Glu Ser Asp Thr Ile Arg Ser Ile Ser Ile Ala Ser Gln
    130                 135                 140

Cys Pro Thr Ala Gly Asn Ser Cys Leu Val Ser Gly Trp Gly Leu Leu
145                 150                 155                 160

Ala Asn Gly Arg Met Pro Thr Val Leu Gln Cys Val Asn Val Ser Val
                165                 170                 175

Val Ser Glu Glu Val Cys Ser Lys Leu Tyr Asp Pro Leu Tyr His Pro
            180                 185                 190

Ser Met Phe Cys Ala Gly Gly His Asp Gln Lys Asp Ser Cys Asn
        195                 200                 205

Gly Asp Ser Gly Gly Pro Leu Ile Cys Asn Gly Tyr Leu Gln Gly Leu
    210                 215                 220

Val Ser Phe Gly Lys Ala Pro Cys Gly Gln Val Gly Val Pro Gly Val
225                 230                 235                 240

Tyr Thr Asn Leu Cys Lys Phe Thr Glu Trp Ile Glu Lys
                245                 250

<210> SEQ ID NO 70
<211> LENGTH: 287
<212> TYPE: PRT
<213> ORGANISM: Homo sapiens

<400> SEQUENCE: 70

Met Ala Thr Ala Arg Pro Pro Trp Met Trp Val Leu Cys Ala Leu Ile
1               5                   10                  15

Thr Ala Leu Leu Leu Gly Val Thr Glu His Val Leu Ala Asn Asn Asp
                20                  25                  30

Val Ser Cys Asp His Pro Ser Asn Thr Val Pro Ser Gly Ser Asn Gln
            35                  40                  45

Asp Leu Gly Ala Gly Ala Gly Glu Asp Ala Arg Ser Asp Asp Ser Ser
    50                  55                  60

Ser Arg Ile Ile Asn Gly Ser Asp Cys Asp Met His Thr Gln Pro Trp
65                  70                  75                  80

Gln Ala Leu Leu Leu Arg Pro Asn Gln Leu Tyr Cys Gly Ala Val
                85                  90                  95

Leu Val His Pro Gln Trp Leu Leu Thr Ala Ala His Cys Arg Lys Lys
            100                 105                 110

Val Phe Arg Val Arg Leu Gly His Tyr Ser Leu Ser Pro Val Tyr Glu
        115                 120                 125

Ser Gly Gln Gln Met Phe Gln Gly Val Lys Ser Ile Pro His Pro Gly
    130                 135                 140

Tyr Ser His Pro Gly His Ser Asn Asp Leu Met Leu Ile Lys Leu Asn
145                 150                 155                 160

Arg Arg Ile Arg Pro Thr Lys Asp Val Arg Pro Ile Asn Val Ser Ser
                165                 170                 175

His Cys Pro Ser Ala Gly Thr Lys Cys Leu Val Ser Gly Trp Gly Thr
            180                 185                 190

Thr Lys Ser Pro Gln Val His Phe Pro Lys Val Leu Gln Cys Leu Asn
        195                 200                 205

Ile Ser Val Leu Ser Gln Lys Arg Cys Glu Asp Ala Tyr Pro Arg Gln
    210                 215                 220

Ile Asp Asp Thr Met Phe Cys Ala Gly Asp Lys Ala Gly Arg Asp Ser
225                 230                 235                 240

Cys Gln Gly Asp Ser Gly Gly Pro Val Val Cys Asn Gly Ser Leu Gln
                245                 250                 255
```

-continued

Gly Leu Val Ser Trp Gly Asp Tyr Pro Cys Ala Arg Pro Asn Arg Pro
            260                 265                 270

Gly Val Tyr Thr Asn Leu Cys Lys Phe Thr Lys Trp Ile Gln Glu
        275                 280                 285

<210> SEQ ID NO 71
<211> LENGTH: 239
<212> TYPE: PRT
<213> ORGANISM: Homo sapiens

<400> SEQUENCE: 71

Met Lys Lys Leu Met Val Val Leu Ser Leu Ile Ala Ala Trp Ala
1               5                   10                  15

Glu Glu Gln Asn Lys Leu Val His Gly Gly Pro Cys Asp Lys Thr Ser
                20                  25                  30

His Pro Tyr Gln Ala Ala Leu Tyr Thr Ser Gly His Leu Leu Cys Gly
            35                  40                  45

Gly Val Leu Ile His Pro Leu Trp Val Leu Thr Ala Ala His Cys Lys
    50                  55                  60

Lys Pro Asn Leu Gln Val Phe Leu Gly Lys His Asn Leu Arg Gln Arg
65                  70                  75                  80

Glu Ser Ser Gln Glu Gln Ser Ser Val Val Arg Ala Val Ile His Pro
                85                  90                  95

Asp Tyr Asp Ala Ala Ser His Asp Gln Asp Ile Met Leu Leu Arg Leu
            100                 105                 110

Ala Arg Pro Ala Lys Leu Ser Glu Leu Ile Gln Pro Leu Pro Leu Glu
        115                 120                 125

Arg Asp Cys Ser Ala Asn Thr Thr Ser Cys His Ile Leu Gly Trp Gly
    130                 135                 140

Lys Thr Ala Asp Gly Asp Phe Pro Asp Thr Ile Gln Cys Ala Tyr Ile
145                 150                 155                 160

His Leu Val Ser Arg Glu Glu Cys Glu His Ala Tyr Pro Gly Gln Ile
                165                 170                 175

Thr Gln Asn Met Leu Cys Ala Gly Asp Glu Lys Tyr Gly Lys Asp Ser
            180                 185                 190

Cys Gln Gly Asp Ser Gly Gly Pro Leu Val Cys Gly Asp His Leu Arg
        195                 200                 205

Gly Leu Val Ser Trp Gly Asn Ile Pro Cys Gly Ser Lys Glu Lys Pro
    210                 215                 220

Gly Val Tyr Thr Asn Val Cys Arg Tyr Thr Asn Trp Ile Gln Lys
225                 230                 235

<210> SEQ ID NO 72
<211> LENGTH: 275
<212> TYPE: PRT
<213> ORGANISM: Homo sapiens

<400> SEQUENCE: 72

Met Gly Arg Pro Arg Pro Arg Ala Ala Lys Thr Trp Met Phe Leu Leu
1               5                   10                  15

Leu Leu Gly Gly Ala Trp Ala Gly His Ser Arg Ala Gln Glu Asp Lys
                20                  25                  30

Val Leu Gly Gly His Glu Cys Gln Pro His Ser Gln Pro Trp Gln Ala
            35                  40                  45

Ala Leu Phe Gln Gly Gln Gln Leu Leu Cys Gly Gly Val Leu Val Gly
        50                  55                  60

-continued

```
Gly Asn Trp Val Leu Thr Ala Ala His Cys Lys Lys Pro Lys Tyr Thr
 65                  70                  75                  80

Val Arg Leu Gly Asp His Ser Leu Gln Asn Lys Asp Gly Pro Glu Gln
                 85                  90                  95

Glu Ile Pro Val Val Gln Ser Ile Pro His Pro Cys Tyr Asn Ser Ser
            100                 105                 110

Asp Val Glu Asp His Asn His Asp Leu Met Leu Gln Leu Arg Asp
        115                 120                 125

Gln Ala Ser Leu Gly Ser Lys Val Lys Pro Ile Ser Leu Ala Asp His
130                 135                 140

Cys Thr Gln Pro Gly Gln Lys Cys Thr Val Ser Gly Trp Gly Thr Val
145                 150                 155                 160

Thr Ser Pro Arg Glu Asn Phe Pro Asp Thr Leu Asn Cys Ala Glu Val
                165                 170                 175

Lys Ile Phe Pro Gln Lys Lys Cys Glu Asp Ala Tyr Pro Gly Gln Ile
            180                 185                 190

Thr Asp Gly Met Val Cys Ala Gly Ser Ser Lys Gly Ala Asp Thr Cys
        195                 200                 205

Gln Gly Asp Ser Gly Gly Pro Leu Val Cys Asp Gly Ala Leu Gln Gly
210                 215                 220

Ile Thr Ser Trp Gly Ser Asp Pro Cys Gly Arg Ser Asp Lys Pro Gly
225                 230                 235                 240

Val Tyr Thr Asn Ile Cys Arg Tyr Leu Asp Trp Ile Lys Lys Thr Leu
                245                 250                 255

Ser Pro Met Arg Ile Leu Gln Leu Ile Leu Leu Ala Leu Ala Thr Gly
            260                 265                 270

Leu Val Gly
        275

<210> SEQ ID NO 73
<211> LENGTH: 228
<212> TYPE: PRT
<213> ORGANISM: Homo sapiens

<400> SEQUENCE: 73

Gly Glu Thr Arg Ile Ile Lys Gly Phe Glu Cys Lys Pro His Ser Gln
 1               5                  10                  15

Pro Trp Gln Ala Ala Leu Phe Glu Lys Thr Arg Leu Leu Cys Gly Ala
                20                  25                  30

Thr Leu Ile Ala Pro Arg Trp Leu Leu Thr Ala Ala His Cys Leu Lys
            35                  40                  45

Pro Arg Tyr Ile Val His Leu Gly Gln His Asn Leu Gln Lys Glu Glu
        50                  55                  60

Gly Cys Glu Gln Thr Arg Thr Ala Thr Glu Ser Phe Pro His Pro Gly
 65                  70                  75                  80

Phe Asn Asn Ser Leu Pro Asn Lys Asp His Arg Asn Asp Ile Met Leu
                 85                  90                  95

Val Lys Met Ala Ser Pro Val Ser Ile Thr Trp Ala Val Arg Pro Leu
            100                 105                 110

Thr Leu Ser Ser Arg Cys Val Thr Ala Gly Thr Ser Cys Leu Ile Ser
        115                 120                 125

Gly Trp Gly Ser Thr Ser Ser Pro Gln Leu Arg Leu Pro His Thr Leu
130                 135                 140

Arg Cys Ala Asn Ile Thr Ile Ile Glu His Gln Lys Cys Glu Asn Ala
```

-continued

```
            145                 150                 155                 160
Tyr Pro Gly Asn Ile Thr Asp Thr Met Val Cys Ala Ser Val Gln Glu
                165                 170                 175

Gly Gly Lys Asp Ser Cys Gln Gly Asp Ser Gly Gly Pro Leu Val Cys
            180                 185                 190

Asn Gln Ser Leu Gln Gly Ile Ile Ser Trp Gly Gln Asp Pro Cys Ala
            195                 200                 205

Ile Thr Arg Lys Pro Gly Val Tyr Thr Lys Val Cys Lys Tyr Val Asp
            210                 215                 220

Trp Ile Gln Glu
225

<210> SEQ ID NO 74
<211> LENGTH: 255
<212> TYPE: PRT
<213> ORGANISM: Homo sapiens

<400> SEQUENCE: 74

Met Trp Val Pro Val Val Phe Leu Thr Leu Ser Val Thr Trp Ile Gly
1               5                   10                  15

Ala Ala Pro Leu Ile Leu Ser Arg Ile Val Gly Gly Trp Glu Cys Glu
                20                  25                  30

Lys His Ser Gln Pro Trp Gln Val Leu Val Ala Ser Arg Gly Arg Ala
            35                  40                  45

Val Cys Gly Gly Val Leu Val His Pro Gln Trp Val Leu Thr Ala Ala
        50                  55                  60

His Cys Ile Arg Asn Lys Ser Val Ile Leu Leu Gly Arg His Ser Leu
65                  70                  75                  80

Phe His Pro Glu Asp Thr Gly Gln Val Phe Gln Val Ser His Ser Phe
                85                  90                  95

Pro His Pro Leu Tyr Asp Met Ser Leu Leu Lys Asn Arg Phe Leu Arg
            100                 105                 110

Pro Gly Asp Asp Ser Ser His Asp Leu Met Leu Leu Arg Leu Ser Glu
        115                 120                 125

Pro Ala Glu Leu Thr Asp Ala Val Lys Val Met Asp Leu Pro Thr Gln
    130                 135                 140

Glu Pro Ala Leu Gly Thr Thr Cys Tyr Ala Ser Gly Trp Gly Ser Ile
145                 150                 155                 160

Glu Pro Glu Glu Phe Leu Thr Pro Lys Lys Leu Gln Cys Val Asp Leu
                165                 170                 175

His Val Ile Ser Asn Asp Val Cys Ala Gln Val His Pro Gln Lys Val
            180                 185                 190

Thr Lys Phe Met Leu Cys Ala Gly Arg Trp Thr Gly Gly Lys Ser Thr
        195                 200                 205

Cys Ser Gly Asp Ser Gly Gly Pro Leu Val Cys Asn Gly Val Leu Gln
    210                 215                 220

Gly Ile Thr Ser Trp Gly Ser Glu Pro Cys Ala Leu Pro Glu Arg Pro
225                 230                 235                 240

Ser Leu Tyr Thr Lys Val Val His Tyr Arg Lys Trp Ile Lys Asp
                245                 250                 255

<210> SEQ ID NO 75
<211> LENGTH: 255
<212> TYPE: PRT
<213> ORGANISM: Homo sapiens
```

```
<400> SEQUENCE: 75

Met Trp Asp Leu Val Leu Ser Ile Ala Leu Ser Val Gly Cys Thr Gly
1               5                   10                  15

Ala Val Pro Leu Ile Gln Ser Arg Ile Val Gly Gly Trp Glu Cys Glu
            20                  25                  30

Lys His Ser Gln Pro Trp Gln Val Ala Val Tyr Ser His Gly Trp Ala
                35                  40                  45

His Cys Gly Gly Val Leu Val His Pro Gln Trp Val Leu Thr Ala Ala
        50                  55                  60

His Cys Leu Lys Lys Asn Ser Gln Val Trp Leu Gly Arg His Asn Leu
65                  70                  75                  80

Phe Glu Pro Glu Asp Thr Gly Gln Arg Val Pro Val Ser His Ser Phe
                85                  90                  95

Pro His Pro Leu Tyr Asn Met Ser Leu Leu Lys His Gln Ser Leu Arg
            100                 105                 110

Pro Asp Glu Asp Ser Ser His Asp Leu Met Leu Leu Arg Leu Ser Glu
        115                 120                 125

Pro Ala Lys Ile Thr Asp Val Val Lys Val Leu Gly Leu Pro Thr Gln
130                 135                 140

Glu Pro Ala Leu Gly Thr Thr Cys Tyr Ala Ser Gly Trp Gly Ser Ile
145                 150                 155                 160

Glu Pro Glu Glu Phe Leu Arg Pro Arg Ser Leu Gln Cys Val Ser Leu
                165                 170                 175

His Leu Leu Ser Asn Asp Met Cys Ala Arg Ala Tyr Ser Glu Lys Val
            180                 185                 190

Thr Glu Phe Met Leu Cys Ala Gly Leu Trp Thr Gly Gly Lys Asp Thr
        195                 200                 205

Cys Gly Gly Asp Ser Gly Gly Pro Leu Val Cys Asn Gly Val Leu Gln
210                 215                 220

Gly Ile Thr Ser Trp Gly Pro Glu Pro Cys Ala Leu Pro Glu Lys Pro
225                 230                 235                 240

Ala Val Tyr Thr Lys Val Val His Tyr Arg Lys Trp Ile Lys Asp
                245                 250                 255

<210> SEQ ID NO 76
<211> LENGTH: 256
<212> TYPE: PRT
<213> ORGANISM: Homo sapiens

<400> SEQUENCE: 76

Met Trp Phe Leu Val Leu Cys Leu Ala Leu Ser Leu Gly Gly Thr Gly
1               5                   10                  15

Ala Ala Pro Pro Ile Gln Ser Arg Ile Val Gly Gly Trp Glu Cys Glu
            20                  25                  30

Gln His Ser Gln Pro Trp Gln Ala Ala Leu Tyr His Phe Ser Thr Phe
                35                  40                  45

Gln Cys Gly Gly Ile Leu Val His Arg Gln Trp Val Leu Thr Ala Ala
        50                  55                  60

His Cys Ile Ser Asp Asn Tyr Gln Leu Trp Leu Gly Arg His Asn Leu
65                  70                  75                  80

Phe Asp Asp Glu Asn Thr Ala Gln Phe Val His Val Ser Glu Ser Phe
                85                  90                  95

Pro His Pro Gly Phe Asn Met Ser Leu Leu Glu Asn His Thr Arg Gln
            100                 105                 110
```

```
Ala Asp Glu Asp Tyr Ser His Asp Leu Met Leu Leu Arg Leu Thr Glu
            115                 120                 125

Pro Ala Asp Thr Ile Thr Asp Ala Val Lys Val Glu Leu Pro Thr
130                 135                 140

Glu Glu Pro Glu Val Gly Ser Thr Cys Leu Ala Ser Gly Trp Gly Ser
145                 150                 155                 160

Ile Glu Pro Glu Asn Phe Ser Phe Pro Asp Asp Leu Gln Cys Val Asp
                165                 170                 175

Leu Lys Ile Leu Pro Asn Asp Glu Cys Lys Lys Ala His Val Gln Lys
            180                 185                 190

Val Thr Asp Phe Met Leu Cys Val Gly His Leu Glu Gly Gly Lys Asp
        195                 200                 205

Thr Cys Val Gly Asp Ser Gly Gly Pro Leu Met Cys Asp Gly Val Leu
    210                 215                 220

Gln Gly Val Thr Ser Trp Gly Tyr Val Pro Cys Gly Thr Pro Asn Lys
225                 230                 235                 240

Pro Ser Val Ala Val Arg Val Leu Ser Tyr Val Lys Trp Ile Glu Asp
                245                 250                 255

<210> SEQ ID NO 77
<211> LENGTH: 241
<212> TYPE: PRT
<213> ORGANISM: Homo sapiens

<400> SEQUENCE: 77

Met Asn Pro Leu Leu Ile Leu Thr Phe Val Ala Ala Leu Ala Ala
1               5                   10                  15

Pro Phe Asp Asp Asp Lys Ile Val Gly Gly Tyr Asn Cys Glu Glu
            20                  25                  30

Asn Ser Val Pro Tyr Gln Val Ser Leu Asn Ser Gly Tyr His Phe Cys
        35                  40                  45

Gly Gly Ser Leu Ile Asn Glu Gln Trp Val Val Ser Ala Gly His Cys
    50                  55                  60

Tyr Lys Ser Arg Ile Gln Val Arg Leu Gly Glu His Asn Ile Glu Val
65                  70                  75                  80

Leu Glu Gly Asn Glu Gln Phe Ile Asn Ala Ala Lys Ile Ile Arg His
                85                  90                  95

Pro Gln Tyr Asp Arg Lys Thr Leu Asn Asn Asp Ile Met Leu Ile Lys
            100                 105                 110

Leu Ser Ser Arg Ala Val Ile Asn Ala Arg Val Ser Thr Ile Ser Leu
        115                 120                 125

Pro Thr Ala Pro Pro Ala Thr Gly Thr Lys Cys Leu Ile Ser Gly Trp
130                 135                 140

Gly Asn Thr Ala Ser Ser Gly Ala Asp Tyr Pro Asp Glu Leu Gln Cys
145                 150                 155                 160

Leu Asp Ala Pro Val Leu Ser Gln Ala Lys Cys Glu Ala Ser Tyr Pro
                165                 170                 175

Gly Lys Ile Thr Ser Asn Met Phe Cys Val Gly Phe Leu Glu Gly Gly
            180                 185                 190

Lys Asp Ser Cys Gln Gly Asp Ser Gly Gly Pro Val Val Cys Asn Gly
        195                 200                 205

Gln Leu Gln Gly Val Val Ser Trp Gly Asp Gly Cys Ala Gln Lys Asn
    210                 215                 220

Lys Pro Gly Val Tyr Thr Lys Val Tyr Asn Tyr Val Lys Trp Ile Lys
225                 230                 235                 240
```

Asn

<210> SEQ ID NO 78
<211> LENGTH: 261
<212> TYPE: PRT
<213> ORGANISM: Homo sapiens

<400> SEQUENCE: 78

```
Met Trp Val Pro Val Phe Leu Thr Leu Ser Val Thr Trp Ile Gly
1               5                   10                  15

Ala Ala Pro Leu Ile Leu Ser Arg Ile Val Gly Gly Trp Glu Cys Glu
            20                  25                  30

Lys His Ser Gln Pro Trp Gln Val Leu Val Ala Ser Arg Gly Arg Ala
            35                  40                  45

Val Cys Gly Gly Val Leu Val His Pro Gln Trp Val Leu Thr Ala Ala
        50                  55                  60

His Cys Ile Arg Asn Lys Ser Val Ile Leu Leu Gly Arg His Ser Leu
65                  70                  75                  80

Phe His Pro Glu Asp Thr Gly Gln Val Phe Gln Val Ser His Ser Phe
                85                  90                  95

Pro His Pro Leu Tyr Asp Met Ser Leu Leu Lys Asn Arg Phe Leu Arg
            100                 105                 110

Pro Gly Asp Asp Ser Ser His Asp Leu Met Leu Leu Arg Leu Ser Glu
            115                 120                 125

Pro Ala Glu Leu Thr Asp Ala Val Lys Val Met Asp Leu Pro Thr Gln
        130                 135                 140

Glu Pro Ala Leu Gly Thr Thr Cys Tyr Ala Ser Gly Trp Gly Ser Ile
145                 150                 155                 160

Glu Pro Glu Glu Phe Leu Thr Pro Lys Lys Leu Gln Cys Val Asp Leu
                165                 170                 175

His Val Ile Ser Asn Asp Val Cys Ala Gln Val His Pro Gln Lys Val
            180                 185                 190

Thr Lys Phe Met Leu Cys Ala Gly Arg Trp Thr Gly Gly Lys Ser Thr
        195                 200                 205

Cys Ser Gly Asp Ser Gly Gly Pro Leu Val Cys Asn Gly Val Leu Gln
210                 215                 220

Gly Ile Thr Ser Trp Gly Ser Glu Pro Cys Ala Leu Pro Glu Arg Pro
225                 230                 235                 240

Ser Leu Tyr Thr Lys Val Val His Tyr Arg Lys Trp Ile Lys Asp Thr
                245                 250                 255

Ile Val Ala Asn Pro
            260
```

<210> SEQ ID NO 79
<211> LENGTH: 261
<212> TYPE: PRT
<213> ORGANISM: Homo sapiens

<400> SEQUENCE: 79

```
Met Trp Asp Leu Val Leu Ser Ile Ala Leu Ser Val Gly Cys Thr Gly
1               5                   10                  15

Ala Val Pro Leu Ile Gln Ser Arg Ile Val Gly Gly Trp Glu Cys Glu
            20                  25                  30

Lys His Ser Gln Pro Trp Gln Val Ala Val Tyr Ser His Gly Trp Ala
            35                  40                  45
```

```
His Cys Gly Gly Val Leu Val His Pro Gln Trp Val Leu Thr Ala Ala
 50                  55                  60

His Cys Leu Lys Lys Asn Ser Gln Val Trp Leu Gly Arg His Asn Leu
 65                  70                  75                  80

Phe Glu Pro Glu Asp Thr Gly Gln Arg Val Pro Val Ser His Ser Phe
                 85                  90                  95

Pro His Pro Leu Tyr Asn Met Ser Leu Leu Lys His Gln Ser Leu Arg
                100                 105                 110

Pro Asp Glu Asp Ser Ser His Asp Leu Met Leu Arg Leu Ser Glu
                115                 120                 125

Pro Ala Lys Ile Thr Asp Val Val Lys Val Leu Gly Leu Pro Thr Gln
    130                 135                 140

Glu Pro Ala Leu Gly Thr Thr Cys Tyr Ala Ser Gly Trp Gly Ser Ile
145                 150                 155                 160

Glu Pro Glu Glu Phe Leu Arg Pro Arg Ser Leu Gln Cys Val Ser Leu
                165                 170                 175

His Leu Leu Ser Asn Asp Met Cys Ala Arg Ala Tyr Ser Glu Lys Val
                180                 185                 190

Thr Glu Phe Met Leu Cys Ala Gly Leu Trp Thr Gly Gly Lys Asp Thr
                195                 200                 205

Cys Gly Gly Asp Ser Gly Gly Pro Leu Val Cys Asn Gly Val Leu Gln
210                 215                 220

Gly Ile Thr Ser Trp Gly Pro Glu Pro Cys Ala Leu Pro Glu Lys Pro
225                 230                 235                 240

Ala Val Tyr Thr Lys Val Val His Tyr Arg Lys Trp Ile Lys Asp Thr
                245                 250                 255

Ile Ala Ala Asn Pro
            260

<210> SEQ ID NO 80
<211> LENGTH: 262
<212> TYPE: PRT
<213> ORGANISM: Homo sapiens

<400> SEQUENCE: 80

Met Trp Phe Leu Val Leu Cys Leu Ala Leu Ser Leu Gly Gly Thr Gly
 1                   5                  10                  15

Ala Ala Pro Pro Ile Gln Ser Arg Ile Val Gly Gly Trp Glu Cys Glu
                 20                  25                  30

Gln His Ser Gln Pro Trp Gln Ala Ala Leu Tyr His Phe Ser Thr Phe
             35                  40                  45

Gln Cys Gly Gly Ile Leu Val His Arg Gln Trp Val Leu Thr Ala Ala
 50                  55                  60

His Cys Ile Ser Asp Asn Tyr Gln Leu Trp Leu Gly Arg His Asn Leu
 65                  70                  75                  80

Phe Asp Asp Glu Asn Thr Ala Gln Phe Val His Val Ser Glu Ser Phe
                 85                  90                  95

Pro His Pro Gly Phe Asn Met Ser Leu Leu Glu Asn His Thr Arg Gln
                100                 105                 110

Ala Asp Glu Asp Tyr Ser His Asp Leu Met Leu Leu Arg Leu Thr Glu
                115                 120                 125

Pro Ala Asp Thr Ile Thr Asp Ala Val Lys Val Val Glu Leu Pro Thr
    130                 135                 140

Glu Glu Pro Glu Val Gly Ser Thr Cys Leu Ala Ser Gly Trp Gly Ser
145                 150                 155                 160
```

```
Ile Glu Pro Glu Asn Phe Ser Phe Pro Asp Asp Leu Gln Cys Val Asp
                165                 170                 175
Leu Lys Ile Leu Pro Asn Asp Glu Cys Lys Lys Ala His Val Gln Lys
            180                 185                 190
Val Thr Asp Phe Met Leu Cys Val Gly His Leu Glu Gly Gly Lys Asp
        195                 200                 205
Thr Cys Val Gly Asp Ser Gly Gly Pro Leu Met Cys Asp Gly Val Leu
    210                 215                 220
Gln Gly Val Thr Ser Trp Gly Tyr Val Pro Cys Gly Thr Pro Asn Lys
225                 230                 235                 240
Pro Ser Val Ala Val Arg Val Leu Ser Tyr Val Lys Trp Ile Glu Asp
                245                 250                 255
Thr Ile Ala Glu Asn Ser
            260

<210> SEQ ID NO 81
<211> LENGTH: 254
<212> TYPE: PRT
<213> ORGANISM: Homo sapiens

<400> SEQUENCE: 81

Met Ala Thr Ala Gly Asn Pro Trp Gly Trp Phe Leu Gly Tyr Leu Ile
1               5                   10                  15
Leu Gly Val Ala Gly Ser Leu Val Ser Gly Ser Cys Ser Gln Ile Ile
                20                  25                  30
Asn Gly Glu Asp Cys Ser Pro His Ser Gln Pro Trp Gln Ala Ala Leu
            35                  40                  45
Val Met Glu Asn Glu Leu Phe Cys Ser Gly Val Leu Val His Pro Gln
        50                  55                  60
Trp Val Leu Ser Ala Ala His Cys Phe Gln Asn Ser Tyr Thr Ile Gly
65                  70                  75                  80
Leu Gly Leu His Ser Leu Glu Ala Asp Gln Glu Pro Gly Ser Gln Met
                85                  90                  95
Val Glu Ala Ser Leu Ser Val Arg His Pro Glu Tyr Asn Arg Pro Leu
                100                 105                 110
Leu Ala Asn Asp Leu Met Leu Ile Lys Leu Asp Glu Ser Val Ser Glu
            115                 120                 125
Ser Asp Thr Ile Arg Ser Ile Ser Ile Ala Ser Gln Cys Pro Thr Ala
        130                 135                 140
Gly Asn Ser Cys Leu Val Ser Gly Trp Gly Leu Leu Ala Asn Gly Arg
145                 150                 155                 160
Met Pro Thr Val Leu Gln Cys Val Asn Val Ser Val Val Ser Glu Glu
                165                 170                 175
Val Cys Ser Lys Leu Tyr Asp Pro Leu Tyr His Pro Ser Met Phe Cys
            180                 185                 190
Ala Gly Gly Gly His Asp Gln Lys Asp Ser Cys Asn Gly Asp Ser Gly
        195                 200                 205
Gly Pro Leu Ile Cys Asn Gly Tyr Leu Gln Gly Leu Val Ser Phe Gly
    210                 215                 220
Lys Ala Pro Cys Gly Gln Val Gly Val Pro Gly Val Tyr Thr Asn Leu
225                 230                 235                 240
Cys Lys Phe Thr Glu Trp Ile Glu Lys Thr Val Gln Ala Ser
                245                 250
```

```
<210> SEQ ID NO 82
<211> LENGTH: 247
<212> TYPE: PRT
<213> ORGANISM: Homo sapiens

<400> SEQUENCE: 82

Met Asn Pro Leu Leu Ile Leu Thr Phe Val Ala Ala Leu Ala Ala
1               5                   10                  15

Pro Phe Asp Asp Asp Lys Ile Val Gly Gly Tyr Asn Cys Glu Glu
            20                  25                  30

Asn Ser Val Pro Tyr Gln Val Ser Leu Asn Ser Gly Tyr His Phe Cys
        35                  40                  45

Gly Gly Ser Leu Ile Asn Glu Gln Trp Val Val Ser Ala Gly His Cys
    50                  55                  60

Tyr Lys Ser Arg Ile Gln Val Arg Leu Gly Glu His Asn Ile Glu Val
65                  70                  75                  80

Leu Glu Gly Asn Glu Gln Phe Ile Asn Ala Ala Lys Ile Ile Arg His
                85                  90                  95

Pro Gln Tyr Asp Arg Lys Thr Leu Asn Asn Asp Ile Met Leu Ile Lys
            100                 105                 110

Leu Ser Ser Arg Ala Val Ile Asn Ala Arg Val Ser Thr Ile Ser Leu
        115                 120                 125

Pro Thr Ala Pro Pro Ala Thr Gly Thr Lys Cys Leu Ile Ser Gly Trp
    130                 135                 140

Gly Asn Thr Ala Ser Ser Gly Ala Asp Tyr Pro Asp Glu Leu Gln Cys
145                 150                 155                 160

Leu Asp Ala Pro Val Leu Ser Gln Ala Lys Cys Glu Ala Ser Tyr Pro
                165                 170                 175

Gly Lys Ile Thr Ser Asn Met Phe Cys Val Gly Phe Leu Glu Gly Gly
            180                 185                 190

Lys Asp Ser Cys Gln Gly Asp Ser Gly Gly Pro Val Val Cys Asn Gly
        195                 200                 205

Gln Leu Gln Gly Val Val Ser Trp Gly Asp Gly Cys Ala Gln Lys Asn
    210                 215                 220

Lys Pro Gly Val Tyr Thr Lys Val Tyr Asn Tyr Val Lys Trp Ile Lys
225                 230                 235                 240

Asn Thr Ile Ala Ala Asn Ser
            245

<210> SEQ ID NO 83
<211> LENGTH: 260
<212> TYPE: PRT
<213> ORGANISM: Homo sapiens

<400> SEQUENCE: 83

Met Gly Arg Pro Arg Pro Arg Ala Ala Lys Thr Trp Met Phe Leu Leu
1               5                   10                  15

Leu Leu Gly Gly Ala Trp Ala Gly His Ser Arg Ala Gln Glu Asp Lys
            20                  25                  30

Val Leu Gly Gly His Glu Cys Gln Pro His Ser Gln Pro Trp Gln Ala
        35                  40                  45

Ala Leu Phe Gln Gly Gln Gln Leu Leu Cys Gly Gly Val Leu Val Gly
    50                  55                  60

Gly Asn Trp Val Leu Thr Ala Ala His Cys Lys Lys Pro Lys Tyr Thr
65                  70                  75                  80

Val Arg Leu Gly Asp His Ser Leu Gln Asn Lys Asp Gly Pro Glu Gln
```

-continued

```
                85                  90                  95
Glu Ile Pro Val Val Gln Ser Ile Pro His Pro Cys Tyr Asn Ser Ser
            100                 105                 110

Asp Val Glu Asp His Asn His Asp Leu Met Leu Leu Gln Leu Arg Asp
            115                 120                 125

Gln Ala Ser Leu Gly Ser Lys Val Lys Pro Ile Ser Leu Ala Asp His
        130                 135                 140

Cys Thr Gln Pro Gly Gln Lys Cys Thr Val Ser Gly Trp Gly Thr Val
145                 150                 155                 160

Thr Ser Pro Arg Glu Asn Phe Pro Asp Thr Leu Asn Cys Ala Glu Val
                165                 170                 175

Lys Ile Phe Pro Gln Lys Lys Cys Glu Asp Ala Tyr Pro Gly Gln Ile
            180                 185                 190

Thr Asp Gly Met Val Cys Ala Gly Ser Ser Lys Gly Ala Asp Thr Cys
        195                 200                 205

Gln Gly Asp Ser Gly Gly Pro Leu Val Cys Asp Gly Ala Leu Gln Gly
    210                 215                 220

Ile Thr Ser Trp Gly Ser Asp Pro Cys Gly Arg Ser Asp Lys Pro Gly
225                 230                 235                 240

Val Tyr Thr Asn Ile Cys Arg Tyr Leu Asp Trp Ile Lys Lys Ile Ile
                245                 250                 255

Gly Ser Lys Gly
            260

<210> SEQ ID NO 84
<211> LENGTH: 244
<212> TYPE: PRT
<213> ORGANISM: Homo sapiens

<400> SEQUENCE: 84

Met Lys Lys Leu Met Val Val Leu Ser Leu Ile Ala Ala Ala Trp Ala
1               5                   10                  15

Glu Glu Gln Asn Lys Leu Val His Gly Gly Pro Cys Asp Lys Thr Ser
            20                  25                  30

His Pro Tyr Gln Ala Ala Leu Tyr Thr Ser Gly His Leu Leu Cys Gly
        35                  40                  45

Gly Val Leu Ile His Pro Leu Trp Val Leu Thr Ala Ala His Cys Lys
    50                  55                  60

Lys Pro Asn Leu Gln Val Phe Leu Gly Lys His Asn Leu Arg Gln Arg
65                  70                  75                  80

Glu Ser Ser Gln Glu Gln Ser Ser Val Val Arg Ala Val Ile His Pro
                85                  90                  95

Asp Tyr Asp Ala Ala Ser His Asp Gln Asp Ile Met Leu Leu Arg Leu
            100                 105                 110

Ala Arg Pro Ala Lys Leu Ser Glu Leu Ile Gln Pro Leu Pro Leu Glu
        115                 120                 125

Arg Asp Cys Ser Ala Asn Thr Thr Ser Cys His Ile Leu Gly Trp Gly
    130                 135                 140

Lys Thr Ala Asp Gly Asp Phe Pro Asp Thr Ile Gln Cys Ala Tyr Ile
145                 150                 155                 160

His Leu Val Ser Arg Glu Glu Cys Glu His Ala Tyr Pro Gly Gln Ile
                165                 170                 175

Thr Gln Asn Met Leu Cys Ala Gly Asp Glu Lys Tyr Gly Lys Asp Ser
            180                 185                 190
```

```
Cys Gln Gly Asp Ser Gly Gly Pro Leu Val Cys Gly Asp His Leu Arg
        195                 200                 205
Gly Leu Val Ser Trp Gly Asn Ile Pro Cys Gly Ser Lys Glu Lys Pro
    210                 215                 220
Gly Val Tyr Thr Asn Val Cys Arg Tyr Thr Asn Trp Ile Gln Lys Thr
225                 230                 235                 240
Ile Gln Ala Lys

<210> SEQ ID NO 85
<211> LENGTH: 258
<212> TYPE: PRT
<213> ORGANISM: Homo sapiens

<400> SEQUENCE: 85

Met Ala Thr Ala Gly Asn Pro Trp Gly Trp Phe Leu Gly Tyr Leu Ile
1               5                   10                  15
Leu Gly Val Ala Gly Ser Leu Val Ser Gly Glu Met Ser Pro Ser Cys
            20                  25                  30
Ser Gln Ile Ile Asn Gly Glu Asp Cys Ser Pro His Ser Gln Pro Trp
        35                  40                  45
Gln Ala Ala Leu Val Met Glu Asn Glu Leu Phe Cys Ser Gly Val Leu
    50                  55                  60
Val His Pro Gln Trp Val Leu Ser Ala Ala His Cys Phe Gln Asn Ser
65                  70                  75                  80
Tyr Thr Ile Gly Leu Gly Leu His Ser Leu Glu Ala Asp Gln Glu Pro
                85                  90                  95
Gly Ser Gln Met Val Glu Ala Ser Leu Ser Val Arg His Pro Glu Tyr
            100                 105                 110
Asn Arg Pro Leu Leu Ala Asn Asp Leu Met Leu Ile Lys Leu Asp Glu
        115                 120                 125
Ser Val Ser Glu Ser Asp Thr Ile Arg Ser Ile Ser Ile Ala Ser Gln
    130                 135                 140
Cys Pro Thr Ala Gly Asn Ser Cys Leu Val Ser Gly Trp Gly Leu Leu
145                 150                 155                 160
Ala Asn Gly Arg Met Pro Thr Val Leu Gln Cys Val Asn Val Ser Val
                165                 170                 175
Val Ser Glu Glu Val Cys Ser Lys Leu Tyr Asp Pro Leu Tyr His Pro
            180                 185                 190
Ser Met Phe Cys Ala Gly Gly His Asp Gln Lys Asp Ser Cys Asn
        195                 200                 205
Gly Asp Ser Gly Gly Pro Leu Ile Cys Asn Gly Tyr Leu Gln Gly Leu
    210                 215                 220
Val Ser Phe Gly Lys Ala Pro Cys Gly Gln Val Gly Val Pro Gly Val
225                 230                 235                 240
Tyr Thr Asn Leu Cys Lys Phe Thr Glu Trp Ile Glu Lys Thr Val Gln
                245                 250                 255
Ala Ser

<210> SEQ ID NO 86
<211> LENGTH: 250
<212> TYPE: PRT
<213> ORGANISM: Homo sapiens

<400> SEQUENCE: 86

Met Arg Ile Leu Gln Leu Ile Leu Leu Ala Leu Ala Thr Gly Leu Val
1               5                   10                  15
```

-continued

Gly Gly Glu Thr Arg Ile Ile Lys Gly Phe Glu Cys Lys Pro His Ser
             20                  25                  30

Gln Pro Trp Gln Ala Ala Leu Phe Glu Lys Thr Arg Leu Leu Cys Gly
         35                  40                  45

Ala Thr Leu Ile Ala Pro Arg Trp Leu Leu Thr Ala Ala His Cys Leu
 50                  55                  60

Lys Pro Arg Tyr Ile Val His Leu Gly Gln His Asn Leu Gln Lys Glu
 65                  70                  75                  80

Glu Gly Cys Glu Gln Thr Arg Thr Ala Thr Glu Ser Phe Pro His Pro
                 85                  90                  95

Gly Phe Asn Asn Ser Leu Pro Asn Lys Asp His Arg Asn Asp Ile Met
             100                 105                 110

Leu Val Lys Met Ala Ser Pro Val Ser Ile Thr Trp Ala Val Arg Pro
         115                 120                 125

Leu Thr Leu Ser Ser Arg Cys Val Thr Ala Gly Thr Ser Cys Leu Ile
 130                 135                 140

Ser Gly Trp Gly Ser Thr Ser Ser Pro Gln Leu Arg Leu Pro His Thr
145                 150                 155                 160

Leu Arg Cys Ala Asn Ile Thr Ile Ile Glu His Gln Lys Cys Glu Asn
                 165                 170                 175

Ala Tyr Pro Gly Asn Ile Thr Asp Thr Met Val Cys Ala Ser Val Gln
             180                 185                 190

Glu Gly Gly Lys Asp Ser Cys Gln Gly Asp Ser Gly Gly Pro Leu Val
         195                 200                 205

Cys Asn Gln Ser Leu Gln Gly Ile Ile Ser Trp Gly Gln Asp Pro Cys
 210                 215                 220

Ala Ile Thr Arg Lys Pro Gly Val Tyr Thr Lys Val Cys Lys Tyr Val
225                 230                 235                 240

Asp Trp Ile Gln Glu Thr Met Lys Asn Asn
                 245                 250

<210> SEQ ID NO 87
<211> LENGTH: 257
<212> TYPE: PRT
<213> ORGANISM: Homo sapiens

<400> SEQUENCE: 87

Met Ala Arg Ser Leu Leu Pro Leu Gln Ile Leu Leu Leu Ser Leu
1               5                   10                  15

Ala Leu Glu Thr Ala Gly Glu Glu Ala Gln Gly Asp Lys Ile Ile Asp
             20                  25                  30

Gly Ala Pro Cys Ala Arg Gly Ser His Pro Trp Gln Val Ala Leu Leu
         35                  40                  45

Ser Gly Asn Gln Leu His Cys His Ser Cys Cys Glu Gly Gly Val Leu
 50                  55                  60

Val Asn Glu Arg Trp Val Leu Thr Ala Ala His Cys Lys Met Asn Glu
 65                  70                  75                  80

Tyr Thr Val His Leu Gly Ser Asp Thr Leu Gly Asp Arg Arg Ala Gln
                 85                  90                  95

Arg Ile Lys Ala Ser Lys Ser Phe Arg His Pro Gly Tyr Ser Thr Gln
             100                 105                 110

Thr His Val Asn Asp Leu Met Leu Val Lys Leu Asn Ser Gln Ala Arg
         115                 120                 125

Leu Ser Ser Met Val Lys Lys Val Arg Leu Pro Ser Arg Cys Glu Pro

```
            130                 135                 140
Pro Gly Thr Thr Cys Thr Val Ser Gly Trp Gly Thr Thr Ser Pro
145                 150                 155                 160

Asp Val Thr Phe Pro Asp Leu Met Cys Val Asp Val Lys Leu Ile Ser
                165                 170                 175

Pro Gln Asp Cys Thr Lys Val Tyr Lys Asp Leu Leu Glu Asn Ser Met
            180                 185                 190

Leu Cys Ala Gly Ile Pro Asp Ser Lys Lys Asn Ala Cys Asn Gly Asp
        195                 200                 205

Ser Gly Gly Pro Leu Val Cys Arg Gly Thr Leu Gln Gly Leu Val Ser
    210                 215                 220

Trp Gly Thr Phe Pro Cys Gly Gln Pro Asn Asp Pro Gly Val Tyr Thr
225                 230                 235                 240

Gln Val Cys Lys Phe Thr Lys Trp Ile Asn Asp Thr Met Lys Lys His
                245                 250                 255

Arg

<210> SEQ ID NO 88
<211> LENGTH: 276
<212> TYPE: PRT
<213> ORGANISM: Homo sapiens

<400> SEQUENCE: 88

Met Arg Ala Pro His Leu His Leu Ser Ala Ser Gly Ala Arg Ala
1               5                   10                  15

Leu Ala Lys Leu Leu Pro Leu Leu Met Ala Gln Leu Trp Ala Ala Glu
                20                  25                  30

Ala Ala Leu Leu Pro Gln Asn Asp Thr Arg Leu Asp Pro Glu Ala Tyr
            35                  40                  45

Gly Ala Pro Cys Ala Arg Gly Ser Gln Pro Trp Gln Val Ser Leu Phe
        50                  55                  60

Asn Gly Leu Ser Phe His Cys Ala Gly Val Leu Val Asp Gln Ser Trp
65                  70                  75                  80

Val Leu Thr Ala Ala His Cys Gly Asn Lys Pro Leu Trp Ala Arg Val
                85                  90                  95

Gly Asp Asp His Leu Leu Leu Gln Gly Glu Gln Leu Arg Arg Thr
            100                 105                 110

Thr Arg Ser Val Val His Pro Lys Tyr His Gln Gly Ser Gly Pro Ile
        115                 120                 125

Leu Pro Arg Arg Thr Asp Glu His Asp Leu Met Leu Leu Lys Leu Ala
    130                 135                 140

Arg Pro Val Val Pro Gly Pro Arg Val Arg Ala Leu Gln Leu Pro Tyr
145                 150                 155                 160

Arg Cys Ala Gln Pro Gly Asp Gln Cys Gln Val Ala Gly Trp Gly Thr
                165                 170                 175

Thr Ala Ala Arg Arg Val Lys Tyr Asn Lys Gly Leu Thr Cys Ser Ser
            180                 185                 190

Ile Thr Ile Leu Ser Pro Lys Glu Cys Glu Val Phe Tyr Pro Gly Val
        195                 200                 205

Val Thr Asn Asn Met Ile Cys Ala Gly Leu Asp Arg Gly Gln Asp Pro
    210                 215                 220

Cys Gln Ser Asp Ser Gly Gly Pro Leu Val Cys Asp Glu Thr Leu Gln
225                 230                 235                 240

Gly Ile Leu Ser Trp Gly Val Tyr Pro Cys Gly Ser Ala Gln His Pro
```

```
                      245                 250                 255
Ala Val Tyr Thr Gln Ile Cys Lys Tyr Met Ser Trp Ile Asn Lys Val
            260                 265                 270

Ile Arg Ser Asn
        275
```

<210> SEQ ID NO 89
<211> LENGTH: 10
<212> TYPE: DNA
<213> ORGANISM: Homo sapiens

<400> SEQUENCE: 89
gcggccatgg                                                              10

<210> SEQ ID NO 90
<211> LENGTH: 10
<212> TYPE: DNA
<213> ORGANISM: Artificial
<220> FEATURE:
<223> OTHER INFORMATION: Kozak consensus sequence

<400> SEQUENCE: 90 gccvccatgg                                                              10

<210> SEQ ID NO 91
<211> LENGTH: 8
<212> TYPE: PRT
<213> ORGANISM: Homo sapiens

<400> SEQUENCE: 91

Trp Leu Leu Thr Ala Ala His Cys
1               5

<210> SEQ ID NO 92
<211> LENGTH: 6
<212> TYPE: PRT
<213> ORGANISM: Homo sapiens

<400> SEQUENCE: 92

Gly Asp Ser Gly Gly Pro
1               5

<210> SEQ ID NO 93
<211> LENGTH: 5
<212> TYPE: PRT
<213> ORGANISM: Homo sapiens

<400> SEQUENCE: 93

Asp Leu Met Leu Ile
1               5

<210> SEQ ID NO 94
<211> LENGTH: 7
<212> TYPE: PRT
<213> ORGANISM: Homo sapiens

<400> SEQUENCE: 94

Val Leu Thr Ala Ala His Cys
1               5

<210> SEQ ID NO 95
<211> LENGTH: 5
<212> TYPE: PRT
<213> ORGANISM: Homo sapiens

-continued

<400> SEQUENCE: 95

Asp Leu Arg Leu Leu
1               5

<210> SEQ ID NO 96
<211> LENGTH: 882
<212> TYPE: DNA
<213> ORGANISM: Homo sapiens

<400> SEQUENCE: 96

| | | | | | |
|---|---|---|---|---|---|
| atggctacag | caagaccccc | ctggatgtgg | gtgctctgtg | ctctgatcac | agccttgctt | 60 |
| ctggggtca | cagagcatgt | tctcgccaac | aatgatgttt | cctgtgacca | cccctctaac | 120 |
| accgtgccct | ctgggagcaa | ccaggacctg | ggagctgggg | ccggggaaga | cgcccggtcg | 180 |
| gatgacagca | gcagccgcat | catcaatgga | tccgactgcg | atatgcacac | ccagccgtgg | 240 |
| caggccgcgc | tgttgctaag | gcccaaccag | ctctactgcg | gggcggtgtt | ggtgcatcca | 300 |
| cagtggctgc | tcacggccgc | ccactgcagg | aagaaagttt | tcagagtccg | tctcggccac | 360 |
| tactccctgt | caccagttta | tgaatctggg | cagcagatgt | tccagggggt | caaatccatc | 420 |
| ccccaccctg | gctactccca | ccctggccac | tctaacgacc | tcatgctcat | caaactgaac | 480 |
| agaagaattc | gtcccactaa | agatgtcaga | cccatcaacg | tctcctctca | ttgtccctct | 540 |
| gctgggacaa | agtgcttggt | gtctggctgg | gggacaacca | agagccccca | agtgcacttc | 600 |
| cctaaggtcc | tccagtgctt | gaatatcagc | gtgctaagtc | agaaaaggtg | cgaggatgct | 660 |
| tacccgagac | agatagatga | caccatgttc | tgcgccggtg | acaaagcagg | tagagactcc | 720 |
| tgccaggtg | attctggggg | gcctgtggtc | tgcaatggct | ccctgcaggg | actcgtgtcc | 780 |
| tggggagatt | acccttgtgc | ccggcccaac | agaccgggtg | tctacacgaa | cctctgcaag | 840 |
| ttcaccaagt | ggatccagga | aaccatccag | gccaactcct | ga | | 882 |

<210> SEQ ID NO 97
<211> LENGTH: 10080
<212> TYPE: DNA
<213> ORGANISM: Homo sapiens

<400> SEQUENCE: 97

| | | | | | |
|---|---|---|---|---|---|
| atcgtgtaat | caccgccaca | tccagtgcaa | agctgattcg | tcaccacaga | gcagctccct | 60 |
| cctgccaccc | catccctggg | tcccaagaga | acccttctt | aaaagaggga | gttcttgacg | 120 |
| ggtgtggtgg | ctcatgcctg | taatccttgc | actttgggag | gccaaggagg | gtggatcatt | 180 |
| tgaggtcagg | agtttgagac | cagactggcc | aacatggtga | aaccctgtct | ttactaaaaa | 240 |
| tacaaaaaaa | tgagcgggc | atggtggtgg | gtgcctatag | ccccagctac | tcaggaggct | 300 |
| gaggcaggag | aatcgcttga | acccaggagg | cagaggttgc | agtgagccga | gattgagcca | 360 |
| ctgcactcca | gccggggcta | aagagtgaga | ctctgtctca | aaaaaaaaa | aagaaaaag | 420 |
| aaaaaagaa | aaaaaaataa | aataaataaa | taaataaaat | aaatttaaaa | atttaaaaat | 480 |
| aaagagggg | ttcttgtgtt | gatgccgagc | ctgaaccaag | gcagaggagg | ccggaaggc | 540 |
| ttcccaaggc | cttcagctca | aagcagggag | gcccatagtt | aaacagaaac | agttcaggaa | 600 |
| tcacagaaag | gcacctgggg | agagatgggt | gtgtggctcc | agatgcaggt | gcccagacag | 660 |
| tgcgtcccca | ggtgtacaga | cagacccagg | ccaagctcca | gctcaaagag | ccagcctagg | 720 |
| gggtgccga | ggtggaggga | ggctgagtca | ggctgaggcc | gggaacagt | tggggtagcc | 780 |
| aagggaggca | agcagcctcc | tgagtcacca | cgtggtccag | gtacggggct | gcccaggccc | 840 |

-continued

```
agagacggac acaagcactg gggaatttaa ggggctaggg gagggctga ggagggtagg      900
ccctccccca aatgaggatg aaccccccc aactccagaa ccccctgca ggctggccag      960
aatccttccc catctcattc actctgtctc tcctgctctc tgccgtctcc tattttgaat   1020
ttccaacccc gtctgttaag actgtccttc tgtctctgaa tctctgtccc cttctctttc   1080
tgggtctctc tccctctccc tctgggtctc tgtcccctc tctgggtctc tgtcactctc    1140
tctttgcatc tccagctctc actttgtctc tgcacctagc agatcccaag ctggggaatg   1200
ccagttctgg caccaacctt cctgctccct gctgggcct ctgctccccc atctctcagg    1260
agtcgaaagt gagaaagcaa ggtgggcagc tctgctccag gtccaggtat ctcccgccca   1320
cctcctgccc gtcctctatc ccaccctcc tctccatctc tccctggcgc tgccatctct    1380
catctaggcc tccgtctcct ctgtcattgt ccccatcccc tgtaggtgcc catccttccc   1440
gtctcccctc tgccatcggc ctgcctgtcc catcctcttt ctccaccat gtcccgttct    1500
cttccacgtc tcatgcccgc actgccttca tcatcatcgc tgttgttctg tgtgtgtttg   1560
tggtgagtgc cgcatggtgg gggcgtctcg gcctctctcc tctctctcca ctgttttctc   1620
tttctgtgtg tctgtttcca ttctatctcc accttcttcc ctccgtcttt tgcttttcta   1680
tctccacttc tccacacccc tctctccctg cgtctctgtg tctccctctt cctctgtctt   1740
gttttttttcc caccgtctgc ctcttctgtt ccctgtcaca tccaacttcc accggtttct   1800
ccagctctct cctcagttcc ttctctcatg agcacacctg cctctgtgct cgtattcctg   1860
gactcctctc tctccactgt catatcttct cattcattt cccagtctct ctctgtctct    1920
tgctctcccc ctctctgtca ctctgtctct gtctctctct ttctctctct ctctctgtgt   1980
ctctctgtct ggctctctct ctgtctctct ctccatctct ctctctctct ccccccgtc    2040
accctgtctc tgtctctctc tgtctgtgtg tctctctgtc tttctctctc tccatctctc   2100
tctgtctctc tctctctctc tctctctctc cctctctccc tcctcccgtg actccctctc   2160
tcagtccatc tcttcctccc tctctcagcc ccttcgtgcc cttttcctctg acactcccca   2220
ccctggtttc ctgactccac cactagatcc accacctcca gcaactggga accctccct    2280
gcccaccctg ccctggggtc ccctcccagg attccttcta gattatagca tcttccctgg   2340
gcgggttctc atgaacaatt gtggctgctt ttttggccag acaggggagg gaggggatgg   2400
gatcagggag tcctggaatg ggaactaggc aataaaaaaa aaaaatgtc agaagcaggg    2460
cggcgggagt gggggcagg gccagctgtc cttaccaggg ataaaaggct ttgccagtgt    2520
gactaggaag agagacacct ccctccttc cttcatcaag acatcaagga gggacctgtg    2580
ccctgctcca catcctccca cctgccgccc gcagagcctg caggcccgc cccctcgtc     2640
tctggtccct acctctctgc tgtgtcttca tgtccctgag ggtcttgggc tctgggtaag   2700
tgccccttgc tgtctctgcc tctcagcccc cggttctgtt gaaggttcct tctctctcac   2760
ttttttctctg catttgacag gacctggccc tcagccccta aaatgttcct cctgctgaca   2820
gcacttcaag tcctggctat aggtaagaga acggttgggt atgacacaag ggggtcccct   2880
ggagactctg agaagagatg gggatgggtc cttgggcc ctggatgctc atggtgacct    2940
cataagaaag agcaggagt ggtttgggg tcatggtggg ggaacgtgct ggaggcctaa     3000
attcctagtt gtggaggtgc tagggaattg tggggccggg gagagaggtg tttataaggt   3060
ctggtgcaaa atacataagg aatcttaggg aactattagg tcctgagtgg gtcatagcag   3120
aaagatcacg gggctctacc tgactgtgtt aggaaagaaa caatgtcaga aagatgtttt   3180
```

-continued

```
gttgtcagag ggaaggtgga gaaggatgat gggatggcgg gatcgtggca tggggtggcg    3240
ggatcgtggc atgggtgtgt gaggtggatg ggggcaagtg tggggcaaga gatggcggat    3300
ccttggggtc ccactgagtg ggaacgttgg ggaggagaca gggaggtcct tgaatgtgtt    3360
ggggaaggac tcattggggg gaaatgtggc atatttcgag aagtgatcac agaaattatg    3420
ggagcataga gctaagggtc gtagatgtag caaggccctg gataaggtgg ccacggcaca    3480
aaataagaga tgctacggag gtgacttggg aggtgagtca gaaagctctc cgtgctgggg    3540
caataacggg gtcaatattg gcatgtctc accctgggtg ggacagatag aggcgggcag    3600
tttaggggtt agaccaaaag gaaggggatt tgtcagtttt ggaatcctac aaacttgtgg    3660
agtggagagt gtttgctcat ctactttccc cacccaatcc tgtccactcc tagccatgac    3720
acagagccaa gaggatgaga acaagataat tggtggccat acgtgcaccc ggagctccca    3780
gccgtggcag gcggccctgc tggcgggtcc caggcgccgc ttcctctgcg gaggcgccct    3840
gctttcaggc cagtgggtca tcactgctgc tcactgcggc cgcccgtaag tgaccccctc    3900
ccctgtccct gtacctagtg aattccagag tctaaagccc tagagctgag ctgagaacct    3960
ggatctctgt atagaaccca atgtagtggc tggctcctgg tttgaggtct agagaagagc    4020
ctggaacaaa aacacagctc gggatgtggg ctcctccata aatctcgaac tcagcatagg    4080
ttctgaaagc agatgggcag cttggaaccc atggacctgc tgagaaccga acatctgatc    4140
cagtgattct tccagaggcc acacattaca tcgagaccaa gcttagccca ttccagattg    4200
gtggctgaat tcaggacccc gtctacattc agaaactcag gacactacgt agaactcaga    4260
gcccagttca ggacctgcag tctagccata aatccagaac tagaacgctg ctcacagctg    4320
gaacatacaa ctctaagaat agaggcaaaa cctggaggct gtttcacacc caaggtttag    4380
ttcagagtct agtctatagc tccgctatga gcagacttca acccagtgtt tgaatcccag    4440
aatgtggcgg gtgcggtggc tcatgcctat aatcctagca cttgggatg ctgaggcagg    4500 cagatcacct gaggtcagga gttcgagacc agcctgagca acatagagaa accctgtctc    4560
tactaaaaat gcaaaattag ccaggcatgg tggcacatgc ctgtaatccc agccactcgg    4620
gaggctgagg caggagaatc acttgaacct gggaggcgga ggttgcagtg agtcaagatc    4680
gcaccattgc actccaggct aggcaacaag agcgaaactc catatcaatc aatcaatcaa    4740
taaatcccag aatgcagatc ctaatcagaa gccccatata aaacctagac ccctcctaaa    4800
ttctagatct gaacttacaa cccagacccc agccaagagg tcaaaatgcc tataagccat    4860
atctatgcca taaacaggtc agtctagaac ctagagatca aagctcaggc cagagtctag    4920
aatataaagg ccagaatgca aaccagactc tagaatcttg gatccgggcc ataacctaga    4980
gctccaacta gaacccagag cccaacctga ggtcaagggc tagggccaga gtccagaacc    5040
aagagcccta taatccaata tgaaacagac ctgtagaggc tgggtgcggt ggctcacgcc    5100
tgtaatccca gcactttggg aggctgaggc gggaagaatca cttgaactgg gagttggagg    5160
tcgagagtga gctgagatcg tgccactgca ctccagccta ggtgacagag cgagactcca    5220
tcacaaaaaa aaaataaata aataaatcaa gtcataatcc aggttcgatc tagaatcctg    5280
atcttagcat agagtcaaaa gtttaagatg tctagaactc agaacccagg ctagaaacag    5340
aatggtgcct actccggaat atcagttccg atttagagcc tagactcata acgcagtttc    5400
gcttaggact caatgcaccg agcccagcac agaccctggc acggagccaa gctctcccaa    5460 tcatcaccctt cttcccaagc caggagctgg agcccagccc aagagcggaa ggagaggcag    5520
ctggggctgg gccgagagaa tgccctggcc atggggaagg gcacaggagg ccaagaatgc    5580
```

```
                                            -continued tcggcctgca gttagtgaga agcaggctag acctcgggga agactcgtca cccggccagg   5640
gaaccgggct ggagggtggg gaggagtctc tggctcagac cctgagcagc gcttctcttg   5700
ggggtcgtgg ccaggatcct tcaggttgcc ctgggcaagc acaacctgag gaggtgggag   5760
gccacccagc aggtgctgcg cgtggttcgt caggtgacgc accccaacta caactcccgg   5820
acccacgaca acgacctcat gctgctgcag ctacagcagc ccgcacggat cgggagggca   5880
gtcaggccca ttgaggtcac ccaggcctgt gccagccccg ggacctcctg ccgagtgtca   5940
ggctggggaa ctatatccag ccccatcggt gaggactcct gcgtcttgga aagcagggga   6000
ctgggcctgg gctcctgggt tccaggagg tggagctggg gggactgggg ctcctgggtc   6060
tgagggagga gggctgggc ctggactcct gggtctgagg gaggagggg ctgaggcctg     6120 gactcctggg tctcaaggag gaggagctgg gcctggactc atacgtctga gggaggaggg   6180
gctggagcct ggactcctgg gtctcaagga ggaggggctg ggcctggact tctgggtctg   6240
agggaggagg ggctggggac ctggactccc gggtctgagg gaggagggac tgggggtctg   6300
gactcctggg tctgagggag gaggggctgg gggcctggac tcctgggtct gagggaggag   6360
gtgctggggc tggactcctg ggtcggaagg aggaggggct ggggcctgg accttgggt    6420 cttatgggag ggtagaccca gttataaccc tgcagtgtcc cccagccagg taccccgcct   6480
ctctgcaatg cgtgaacatc aacatctccc cggatgaggt gtgccagaag gcctatccta   6540
gaaccatcac gcctggcatg gtctgtgcag gagttcccca gggcgggaag gactcttgtc   6600
aggtaaggcc caggatggga gctgtggtag ggattatttg ggactgggat ttaagcaaat   6660
gatgtcagga gcatggaagt ctgcagaggt cttcagaaga gagtgaaccg caggcacaga   6720
gagattccga tagccaggcc accctgcttc ctagccctgt gcccctggg taatggactc     6780 agagcattca tgcctcagtt tcctcatctg tcaggtggga gtaaccctct tagggtagtt   6840
ggtggaatgg gatgaggcag gttggggaaa gatcgcagag tggcctctgc tcatatgggt   6900
ctgggaaagg ctgtgctgag gcttctagaa atcttaatgc atccttgagg gaggcagaga   6960
tgggaaaata gaaaagaga gacacacaaa tgttctacag ttggagcgaa cagagagggg    7020
cctggtgaga ttcaagggac aggcaggtgc acacagagac agagccagac ccagcggaga   7080
gggaaggaag tgccccgacc tccggggctg agacctcaga gctggggcag gactgtgtcc   7140
ctaactgtcc accagtgtct ctgcctgtct ccctgtgtct gcttctcggg ttctctgtgc   7200
catggtggct ctggctacct gtccatcagt gtctccatt ctgttcctcc ccctcagggt    7260
gactctgggg gaccoctggt gtgcagagga cagctccagg gcctcgtgtc ttggggaatg    7320
gagcgctgcg ccctgcctgg ctaccccggt gtctacacca acctgtgcaa gtacagaagc   7380
tggattgagg aaacgatgcg ggacaaatga tggtcttcac ggtgggatgg acctcgtcag   7440
ctgcccaggc cctcctctct ctactcagga cccaggagtc caggcccag ccctcctcc     7500 ctcagaccca ggagtccagg ccccagccc ctcctccctc agacccggga gtccaggccc    7560
ccagcccctc ctccctcaga cccaggagtc caggcccag cccctcctcc ctcagacccg    7620
ggagtccagg ccccagccc ctcctccctc agacccagga gtccaggccc cagtccctcc    7680
tccctcagac ccaggagtcc aggccccag cccctcctcc ctcagaccca ggaatccagg    7740
cccagcccct cctccctcag acccaggagc ccagtcccc cagcccctcc tccttgagac    7800
ccaggagtcc aggcccagcc cctcctccct cagacccagg agcccagtc cccagcatcc    7860 tgatctttac tccggctctg atctctcctt tcccagagca gttgcttcag gcgttttctc   7920
```

-continued

```
cccaccaagc ccccacccct gctgtgtcac catcactact caagaccgga ggcacagagg    7980
gcaggagcac agacccctta aaccggcatt gtattccaaa gacgcacaatt tttaacacgc    8040 ttagtgtctc taaaaaccga ataaataatg acaataaaaa tggaatcatc ctaaattgta    8100
ttcattcatc catgtgttta cttttattt tttgagacaa ggtcttgctc agtctcctgg     8160
tgaaatgctg taacgcaatc atagctcact gcaaccgtga cctcctgggc tccagtgatc    8220
ctcttacctc agcctcccga gtagctggga ccacaggtgc ccgtcaccat gccccgctac    8280
tttttaaatt ttgtgtagag atgaggtttc cctgtgttgc tcaggctggt ctcgaacacc    8340 tgacccccaag caatccgcct acgtcggttt cccaaagtgc cgggattgca ggcgtgagct    8400
gccgcgccca gccttatcca tccaattaat gacttcaaga aacatgtaca cagtggcccc    8460
accatgccaa gccaggagct gtgtactgac aagtggctgc ctccctcttt gcgtgttttt    8520
ccttgggagt cccccgtcca ccccactgta tcaggtttct agacggaaac acctcagccc    8580
tgcagagtga ccttgagcat gactgccttc taccagcctc ctccctggag ccctgtggt    8640 ccagggtagg gaactaagtg ccttgtttcc tggaaaattc tatgcaaatg aagatgtcct    8700
cattttccta atcagatctc aggtgaggag agttgagtta atcacaggct tcagttcctg    8760
cccaggcaaa gccttctctc cattttatta atttatttcc actcttcatc tctggctctg    8820 ctccctccc tccccacagg caccgacata aatggctttg agtgccctgc atccttggaa    8880
aacaaggcag tgtcacagtg tactgttct aatttacatg aaaccattgt gttaggaatc     8940
tcattctctt tcttactttc actcatcaac agctattgag cacctactac gggccaggca    9000
ttggtctatt tattaggcac ctgctataca ccaggcattg ttctgggtgc tggaggaaga    9060
actgtgagca agccagtcag aatccctgcc ctcacagaac ttatattcta gcaggagatg    9120
acagacaaga agccataaac ataattttaa aataaagcag agtccctatg agtaacgagg    9180
tcaataaact tgggctgggc ggcaggccca atgtgtgcca gggccagctc atacatgctc    9240
gcaagagtct accagcaaat tttcaggaat ttcgagaacc agttgctaaa tgcagccatc    9300
attaaaaatt aaattacata agcgtataat tacataattg attaaaaaaa ttgtcagtaa    9360
atactcaaaa ctcaactgtt gctaattatt tcaactaata cctatgcttg ggagtgagat    9420
atgtctcttg tactacgtct gtaatgatga gtttctgcac acctctttcc aactccccaa    9480
ctctgtctgc accagtagct tgacaatagc caaagaagaa gtatttactg cactgaaatt    9540
gaaaaacact atagataggg ctttgccgga cagtcattgc taaaccttta ccaggcaccc    9600
ttggatgggt ctgcctggga atgacctcat gatcttagtg tctgtcttct caaagttctg    9660
tgcttggata ctgcagagta tagctaaaat agaatgttgt actcaccttta tgttctatgg    9720 ggacagcaca gtattgggga accctaaggt ggcaggtctg ggacatgcac gaaagattgc    9780
tgggaagtag aggctccctc cttttcctca tcctcccacc ccatcctcca gtgtctggta    9840
accaccattc tactctctgc ttctaagagt ctgagttttt tagatttcac atgtaagtga    9900
gatcatgcag taattgtcat tctgtgtctg acctatttca cttaacacag tgtcctcccg    9960
gtccatccat gttgtcacaa atgacaggat ttctttcttt tataaggcag aataatatta   10020
aattatactg atactaatat attacatttc ctttatccat tcatccatca acagacacat   10080
```